(12) United States Patent
Gawand et al.

(10) Patent No.: US 11,060,079 B2
(45) Date of Patent: Jul. 13, 2021

(54) METHODS AND MICROORGANISMS FOR PRODUCING FLAVORS AND FRAGRANCE CHEMICALS

(71) Applicant: ARDRA INC., Toronto (CA)

(72) Inventors: Pratish Gawand, Toronto (CA); Jonas Ernst Norbert Muller, Toronto (CA)

(73) Assignee: ARDRA INC., Toronto (CA)

( * ) Notice: Subject to any disclaimer, the term of this patent is extended or adjusted under 35 U.S.C. 154(b) by 0 days.

(21) Appl. No.: 16/225,611

(22) Filed: Dec. 19, 2018

(65) Prior Publication Data

US 2019/0177713 A1 Jun. 13, 2019

Related U.S. Application Data

(63) Continuation of application No. PCT/US2017/040019, filed on Jun. 29, 2017.

(60) Provisional application No. 62/415,363, filed on Oct. 31, 2016, provisional application No. 62/357,337, filed on Jun. 30, 2016.

(51) Int. Cl.
| | |
|---|---|
| *C12N 9/88* | (2006.01) |
| *C12N 15/52* | (2006.01) |
| *C12P 7/24* | (2006.01) |
| *C12P 17/04* | (2006.01) |
| *C12P 17/06* | (2006.01) |

(52) U.S. Cl.
CPC ............... *C12N 9/88* (2013.01); *C12N 15/52* (2013.01); *C12P 7/24* (2013.01); *C12P 17/04* (2013.01); *C12P 17/06* (2013.01); *C12Y 401/02004* (2013.01)

(58) Field of Classification Search
None
See application file for complete search history.

(56) References Cited

U.S. PATENT DOCUMENTS

| | | |
|---|---|---|
| 2007/0117191 A1 | 5/2007 | Kamachi et al. |
| 2007/0254341 A1 | 11/2007 | Raemakers-Franken et al. |
| 2008/0289056 A1 | 11/2008 | Greenberg et al. |
| 2011/0014669 A1 | 1/2011 | Madden et al. |
| 2012/0142081 A1 | 6/2012 | Yoshikuni et al. |
| 2016/0060635 A1 | 3/2016 | Liao et al. |

FOREIGN PATENT DOCUMENTS

| | | | |
|---|---|---|---|
| WO | WO-2005118794 A2 | 12/2005 | |
| WO | WO-2006134482 A1 | 12/2006 | |
| WO | WO-2007068498 A1 | 6/2007 | |
| WO | WO-2015042201 A2 | 3/2015 | |
| WO | WO-2017011815 A2 * | 1/2017 | ......... C12N 15/8279 |
| WO | WO-2018005806 A2 | 1/2018 | |

OTHER PUBLICATIONS

Genbank Q9X1P5.1.2014. Genbank. p. 1-8 (Year: 2014).*
Genbank Q6QBS4. 2006. Genbank. p. 1-2 (Year: 2006).*
Kizer L et al. Application of Functional Genomics to Pathway Optimization for Increased Isoprenoid Production. Applied and Environmental Microbiology, May 2008, p. 3229-3241. (Year: 2008).*
Prather KLJ et al. De novo biosynthetic pathways: rational design of microbial chemical factories. Current Opinion in Biotechnology 2008, 19:468-474. (Year: 2008).*
Dobritzsch D et al. High Resolution Crystal Structure of Pyruvate Decarboxylase from Zymomonas mobilis. 1998. The Journal of Biological Chemistry. vol. 273, No. 32, Issue 7. p. 20196-20204. (Year: 1998).*
Hasson MS et al. Purification and crystallization of benzoylformate decarboxylase. 1995. Protein Science. 955-959. (Year: 1995).*
Atsumi et al. Non-fermentative pathways for synthesis of branched-chain higher alcohols as biofuels. Nature 451:86-89 (2008).
Baba et al. Construction of *Escherichia coli* K-12 in-frame, single-gene knockout mutants: the Keio collection. Mol Syst Biol 2006. 0008 (2006).
Baker et al. Rational approaches for engineering novel functionalities in carbon-carbon bond forming enzymes. Comput Struct Biotechnol J 2:e201209003 (2012).
Billman-Jacobe. Expression in bacteria other than *Escherichia coli*. Current Opinion in Biotechnology 7:500-4 (1996).
Bitter et al. Expression and secretion vectors for yeast. Methods Enzymol 153:516-544 (1987).
Boros et al. Expression vectors based on the rac fusion promoter. Gene 42:97-100 (1986).
Buckholz. Yeast systems for the commercial production of heterologous proteins. BioTechnology 9:1067-1072 (1991).
Bussineau et al. Genetic stability of protein expression systems in yeast. Developments in Biological Standardization 83:13-19 (1994).
Candy et al. Expression of active yeast pyruvate decarboxylase has also been studied. Journal of General Microbiology 137:2811-2815 (1991).
Candy et al. The role of residues glutamate-50 and phenylalanine-496 in *Zymomonas mobilis* pyruvate decarboxylase, the promoter and nucleotide sequences of the *Zymomonas mobilis* pyruvate decarboxylase, and the active site mutants of pyruvate decarboxylase from *Zymomonas mobilis* have been studied. The Biochemical Journal 315(Pt 3):745-51 (1998).
Conway et al. Promoter and nucleotide sequences of the *Zymomonas mobilis* pyruvate decarboxylase. Journal of Bacteriology 169(3):949-54 (1987).

(Continued)

*Primary Examiner* — Paul J Holland
(74) *Attorney, Agent, or Firm* — Wilson Sonsini Goodrich & Rosati

(57) ABSTRACT

The present disclosure relates to biosynthetic pathways for producing flavor and fragrance chemicals, such as green notes including trans-2-unsaturated aldehydes and lactones. The present disclosure provides methods for producing trans-2-unsaturated aldehydes, delta-lactones, and gamma-lactones. The present disclosure provides pathways for the preparation of trans-2-unsaturated aldehydes, delta-lactones, and gamma-lactones by reacting aldehydes in the presence of aldolases.

10 Claims, 11 Drawing Sheets

Specification includes a Sequence Listing.

(56) References Cited

OTHER PUBLICATIONS

Datsenko et al. One-step inactivation of chromosomal genes in *Escherichia coli* K-12 using PCR products. PNAS USA 97(12):6640-6645 (2000).
Deboer et al. Promoters, Structure and Function. Edited by Rodriguez and Chamberlin (Eds). Praeger, New York, pp. 462-481 (1982).
Deboer et al. The tac promoter: a functional hybrid derived from the trp and lac promoters PNAS USA 80:21-25 (1983).
Diamond et al. Method of RNA sequence analysis. Methods in Enzymology 100:431-453 (1983).
Finn et al. Pfam: the protein families database. Nucl Acids Res 42(D1):D222-D230 (Jan. 1, 2014).
Fleer. Engineering yeast for high level expression. Current Opinion in Biotechnology 3:486-496 (1992).
Gellissen et al. Heterologous protein production in yeast. Antonie van Leuwenhoek 62:79-93 (1992).
Gigot et al. The lipoxygenase metabolic pathway in plants: potential for industrial production of natural green leaf volatiles. Biotechnol Agron soc Environ 14(3):451-460 (2010) (English Abstract).
Gijsen et al. Unprecedented Asymmetric Aldol Reactions with Three Aldehyde Substrates Catalyzed by 2-Deoxyribose-5-phosphate Aldolase. J Am Chem Soc 116(18):8422-8423 (1994).
Gocke et al. Comparative characterisation of thiamine diphosphate-dependent decarboxylases. Journal of Molecular Catalysis B: Enzymatic 61(1-2):30-35 (2009).
Griffiths et al. Production of heterologous proteins using the baculovirus/insect expression system. Methods Mol Biol 75:427-440 (1997).
Gruez et al. Crystal structure and kinetics identify *Escherichia coli* YdcW gene product as a medium-chain aldehyde dehydrogenase J Mol Biol 343(1):29-41 (2004).
Hensing et al. Physiological and technological aspects of large-scale heterologous-protein production with yeasts. Antonie van Leuwenhoek 67:261-279 (1995).
Hockney. Recent developments in heterologous protein production in *Escherichia coli*. Trends in Biotechnology 12:456-463 (1994).
Hummel et al. Dehydrogenases for the synthesis of chiral compounds. Eur J Biochem 184:1-13 (1989).
Killenberg-Jabs et al. Purification and characterisation of the pyruvate decarboxylase from a haploid strain of *Saccharomyces cerevisiae*. Biological Chemistry Hoppe-Seyler 377(5):313-317 (1996).
Lee et al. Engineering of NADPH regenerators in *Escherichia coli* for enhanced biotransformation. Applied Microbiology and Biotechnology 97(7):2761-72 (2013).
Mak et al. Integrative genomic mining for enzyme function to enable engineering of a non-natural biosynthetic pathway. Nat Commun 6:10005 (2015).
McPherson et al. PCR a Practical Approach. Oxford University Press pp. 200-209 (1991).
Nobuhara. Syntheses of Unsaturated Lactones: Part I. Some Lactones of 5-Substituted-5-hydroxy-2-enoic Acids as a Synthetic Butter or Butter Cake Flavor Agr. Biol. Chem 32(8):1016-1020 (1968).
Oxford Dictionary of Biochemistry and Molecular Biology, Revised Edition, A D. Smith, Ed., New York: Oxford University Press (1997) pp. 161, 476, 477, and 560.
PCT/US2017/040019 International Preliminary Report on Patentability dated Jan. 10, 2019.
PCT/US2017/040019 International Search Report and Written Opinion dated Dec. 21, 2017.
PCT/US2017/040019 Invitation to Pay Additional Fees dated Oct. 3, 2017.
Pohl et al. Active site mutants of pyruvate decarboxylase from *Zymomonas mobilis*—a site-directed mutagenesis study of L112,I472,I476, E473, and N482. Eur J Biochem 257:538-546 (1998).
Ramachandran et al. Asymmetric synthesis of goniothalamin, hexadecanolide, massoia lactone, and parasorbic acid via sequential allylboration-esterification ring-closing metathesis reactions. Tetrahedron Letters 41:583-586 (2000).
Ricardo et al. Bioactive pyrones and flavonoids from *Cryptocarya ashersoniana* seedlings. ARKIVOC Available at< http://hdl.handle.net/11449/32714> pp. 127-136 (2004).
Rodriguez et al. Toward aldehyde and alkane production by removing aldehyde reductase activity in *Escherichia coli*. Metab Eng 25:227-237 (2014).
Sawers et al. Alternative regulation principles for the production of recombinant proteins in *Escherichia coli*. Applied Microbiology and Biotechnology 46:1-9 (1996).
Siegert et al. Exchanging the substrate specificities of pyruvate decarboxylase from Zymomonas mobilis and benzoylformate decarboxylase from *Pseudomonas putida*. Protein Engineering, Design & Selection 18(7):345-57 (2005).
Studier et al. Use of T3 RNA polymerase to direct expression of cloned genes. Methods Enzymol. 185:60-89 (1990).
Vedvick. Gene expression in yeast: *Pichia pastoris*. Current Opinion in Biotechnology 2:742-745 (1991).
Webb. Enzyme Nomenclature. Orlando, Fl. pp. 20-141 (1984).
Yu et al. Cosmid cloning and walking to map human CD1 leukocyte differentiation antigen genes. Meth. Enzymol. 217:378-398 (1993).
Zhang et al. Expanding metabolism for biosynthesis of nonnatural alcohols. PNAS USA 105(52):20653-20658 (2008).
Zoller et al. Oligonucleotide-directed mutagenesis using M13-derived vectors: an efficient and general procedure for the production of point mutations in any fragment of DNA. Nucleic Acid Res. 10:6487-6500 (1982).

* cited by examiner

Fatty acid lipoxygenase pathway for trans-2-hexenal production

Fatty acid oxidation pathway for gamma-decalactone production

Fatty acid oxidation pathway for production of delta-decalactone

Current industrial process for making trans-2-hexenal and cis-3-hexenol where, R = H or $C_nH_{2n+1}$ and n = 1 - 10

General pathway for producing trans-2-unsaturated aldehydes

General pathway for producing various delta-lactones using aldolases

General pathway for producing various gamma-lactones using aldolases

Pathway for producing trans-2-hexenal

Pathway for producing massoia lactone

Pathway for producing gamma-decalactone

Production of trans-2-hexanal by feeding acetaldehyde and butyraldehyde

METHODS AND MICROORGANISMS FOR PRODUCING FLAVORS AND FRAGRANCE CHEMICALS

CROSS-REFERENCE

This application is a continuation of International Application No. PCT/US2017/040019, filed Jun. 29, 2017, which claims the benefit of U.S. Provisional Application No. 62/357,337, filed Jun. 30, 2016 and U.S. Provisional application No. 62/415,363, filed Oct. 31, 2016, each of which is entirely incorporated herein by reference.

BACKGROUND

Trans-2-unsaturated aldehydes such as trans-2-hexenal, gamma-lactones such as gamma-deltalactone, and delta-lactones such as delta-decalactone are important flavor and aroma constituents and are found in many natural products. These compounds can be used either directly or as intermediates in the flavor, fragrance, pharmaceutical, and cosmetic industries. Most flavors are provided by extraction from natural sources or by traditional methods as chemical synthesis. The problem with chemical synthesis is that the resulting compounds are non-natural and products containing them need to be labelled accordingly. On the other hand, extracting the compounds from natural sources is complicated, expensive, non-sustainable and the supply is often limited. For example, natural trans-2-hexenal, which is used in apple flavors, is currently produced using a fatty acid lipoxygenase pathway with very low yields and *massoia* lactone ((R)-5,6-dihydro-6-pentyl-2H-pyran-2-one) is extracted from the bark of the *Massoia* tree at great expense for its conversion to delta-decalactone.

Chemical synthesis of food aroma starts from petroleum derived chemicals and the resulting products are considered non-natural. Driven by consumer preference for products without artificial flavors, demand for alternative, sustainable ways to produce these compounds has increased over the last years. Chemical synthesis also has drawbacks such as poor reactions selectivity leading to undesirable side reactions, low yields, pollution, and, in some cases, high manufacturing costs. Additionally, resolution of racemic mixtures is usually difficult to achieve chemically. This leads to the reduction of process efficiency and to the increase of downstream costs. Extraction of natural products is also subject to various problems. These raw materials may contain low concentrations of the desired compounds and are subject to weather and plant diseases, making the extraction expensive. Natural sources become insufficient to cover the increasing demand of the market.

SUMMARY

A large interest has been focused on producing flavor compounds from biological origin. The present disclosure relates to high-yield, cost-effective methods of producing trans-2-unsaturated aldehydes, gamma-lactones, and delta-lactones and applications thereof in the industry of, e.g., flavors, fragrances, pharmaceuticals and/or cosmetics.

In one embodiment, the present disclosure relates to a non-naturally occurring microorganism having a trans-2-unsaturated aldehyde pathway, wherein the non-naturally occurring microorganism comprises at least one of the following trans-2-unsaturated aldehyde pathway enzymes: an aldolase that catalyzes condensation of two aldehydes to produce 3-hydroxy aldehyde; and a dehydratase that dehydrates the 3-hydroxy aldehyde to trans-2-unsaturated aldehyde; wherein the non-naturally occurring microorganism comprises at least one exogenous nucleic acid encoding an enzyme from the trans-2-unsaturated aldehyde pathway; and optionally wherein the non-naturally occurring microorganism comprises an increased enzymatic activity of at least one enzyme in the trans-2-unsaturated aldehyde pathway in comparison with the enzymatic activity of the same enzyme in a corresponding unmodified or wild-type microorganism.

In one embodiment, the present disclosure relates to a non-naturally occurring microorganism having a delta-lactone pathway, wherein the non-naturally occurring microorganism comprises at least one of the following delta-lactone pathway enzymes:
  i. an aldolase (a first aldolase) that catalyzes condensation of two aldehydes to produce 3-hydroxy aldehyde;
  ii. an aldolase (a second aldolase) that catalyzes condensation of the 3-hydroxy aldehyde and an aldehyde to a 5,3-dihydroxy aldehyde, which undergoes cyclization to form tetrahydro-2H-pyran-2,4-diol;
  iii. an oxidase enzyme that transforms the tetrahydro-2H-pyran-2,4-diol to a tetrahydro-4-hydroxy-2H-pyran-2-one;
  iv. a dehydratase that dehydrates the tetrahydro-4-hydroxy-2H-pyran-2-one to a 5,6-dihydro-2H-pyran-2-one; and
  v. a reductase that reduces the 5,6-dihydro-2H-pyran-2-one to a delta-lactone;

wherein the non-naturally occurring microorganism comprises at least one exogenous nucleic acid encoding an enzyme from the delta-lactone pathway; optionally wherein the aldolase in i. is different from the aldolase in ii.; and optionally wherein the non-naturally occurring microorganism comprises an increased enzymatic activity of at least one enzyme in the delta-lactone pathway in comparison with the enzymatic activity of the same enzyme in a corresponding unmodified or wild-type microorganism.

In one embodiment, the present disclosure relates to a non-naturally occurring microorganism having a delta-lactone pathway, wherein the non-naturally occurring microorganism comprises at least one of the following delta-lactone pathway enzymes:
  i. an aldolase (a first aldolase) that catalyzes condensation of two aldehydes to produce 3-hydroxy aldehyde;
  ii. an aldolase (a second aldolase) that catalyzes condensation of the 3-hydroxy aldehyde and an aldehyde to a 5,3-dihydroxy aldehyde, which undergoes cyclization to form tetrahydro-2H-pyran-2,4-diol;
  iii. an oxidase enzyme that transforms the tetrahydro-2H-pyran-2,4-diol to a tetrahydro-4-hydroxy-2H-pyran-2-one;
  iv. a dehydratase that dehydrates the tetrahydro-4-hydroxy-2H-pyran-2-one to a 5,6-dihydro-2H-pyran-2-one; and
  v. a reductase that reduces the 5,6-dihydro-2H-pyran-2-one to a delta-lactone, wherein the non-naturally occurring microorganism comprises at least one exogenous nucleic acid encoding an enzyme from the delta-lactone pathway; optionally wherein the aldolase in i. is different from the aldolase in ii.; and optionally wherein the non-naturally occurring microorganism comprises an increased enzymatic activity of at least one enzyme in the delta-lactone pathway in comparison with the enzymatic activity of the same enzyme in a corresponding unmodified or wild-type microorganism.

In one embodiment, the present disclosure relates to a non-naturally occurring microorganism having a gamma-lactone pathway, wherein the non-naturally occurring microorganism comprises at least one of the following gamma-lactone pathway enzymes:
  i. an aldolase that catalyzes condensation of an aldehyde molecule and a pyruvic acid to a 4-hydroxy-2-oxo carboxylic acid;
  ii. a dehydrogenase or a keto-reductase that reduces the 4-hydroxy-2-oxo carboxylic acid to 2,4-dihydroxy carboxylic acid;
  iii. a lactonization enzyme that transforms the 2,4-dihydroxy carboxylic acid to a 3-hydroxydihydro-2-(3H)-furanone;
  iv. a dehydratase that dehydrates the 3-hydroxydihydro-2-(3H)-furanone to 2-(5H)-furanone; and
  v. a reductase that reduces the 2-(5H)-furanone to a gamma-lactone:
wherein the non-naturally occurring microorganism comprises at least one exogenous nucleic acid encoding an enzyme from the gamma-lactone pathway; and optionally wherein the non-naturally occurring microorganism comprises an increased enzymatic activity of at least one enzyme in the gamma-lactone pathway in comparison with the enzymatic activity of the same enzyme in a corresponding unmodified or wild-type microorganism.

In one embodiment, the present disclosure relates to a non-naturally occurring microorganism having a delta-lactone pathway, wherein the non-naturally occurring microorganism comprises at least one of the following delta-lactone pathway enzymes:
  i. an aldolase (a first aldolase) that catalyzes condensation of an acetaldehyde and an aldehyde to 3-hydroxy aldehyde;
  ii. an aldolase (a second aldolase) that catalyzes condensation of the 3-hydroxy aldehyde and an acetaldehyde to 5,3-dihydroxy aldehyde, which undergoes cyclization to form tetrahydro-2H-pyran-2,4-diol;
  iii. an oxidase enzyme that transforms the tetrahydro-2H-pyran-2,4-diol to a tetrahydro-4-hydroxy-2H-pyran-2-one; and
  iv. a dehydratase enzyme that dehydrates the tetrahydro-4-hydroxy-2H-pyran-2-one to a 5,6-dihydro-2H-pyran-2-one;
wherein the non-naturally occurring microorganism comprises at least one exogenous nucleic acid encoding an enzyme from the delta-lactone pathway; optionally wherein the aldolase in i. is different from the aldolase in ii.; and optionally wherein the non-naturally occurring microorganism comprises an increased enzymatic activity of at least one enzyme in the delta-lactone pathway in comparison with the enzymatic activity of the same enzyme in a corresponding unmodified or wild-type microorganism.

In one embodiment, the present disclosure relates to a non-naturally occurring microorganism having a gamma-lactone pathway, wherein the non-naturally occurring microorganism comprises at least one of the following gamma-lactone pathway enzymes:
  i. an aldolase that catalyzes condensation of an aldehyde molecule and a pyruvate to a 4-hydroxy-2-oxo carboxylic acid;
  ii. a dehydrogenase or a keto-reductase that reduces the 4-hydroxy-2-oxo carboxylic acid to 2,4-dihydroxy acid;
  iii. dehydration of the 2,4-dihydroxy acid to 4-hydroxy-2-ene-acid;
  iv. a lactonization enzyme that transforms the 4-hydroxy-2-ene acid to 2(5H)-furanone; and
  v. a reductase that reduces the 2(5H)-furanone to a gamma-lactone:
wherein the non-naturally occurring microorganism comprises at least one exogenous nucleic acid encoding an enzyme from the gamma-lactone pathway; and optionally wherein the non-naturally occurring microorganism comprises an increased enzymatic activity of at least one enzyme in the gamma-lactone pathway in comparison with the enzymatic activity of the same enzyme in a corresponding unmodified or wild-type microorganism.

In one embodiment, the present disclosure relates to a process comprising reacting acetaldehyde and an aldehyde of formula R—CHO, wherein R is hydrogen or $C_nH_{2n+1}$, and each 'n' is independently 1, 2, 3, 4, 5, 6, 7, 8, 9, or 10, in the presence of an aldolase enzyme, to form the 3-hydroxy aldehyde compound of formula II

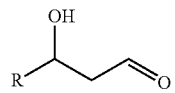

wherein R is hydrogen or $C_nH_{2n+1}$, and each 'n' is independently 1, 2, 3, 4, 5, 6, 7, 8, 9, or 10; wherein, the aldolase enzyme is specific for the condensation of an acetaldehyde and an aldehyde molecule; and optionally wherein the aldolase enzyme is a modified aldolase enzyme comprising an increased enzymatic activity in comparison with a corresponding unmodified or wild-type aldolase enzyme.

In some embodiments, the process further comprises a dehydration step to dehydrate the compound of formula II to form a trans-2-unsaturated aldehyde compound of formula III

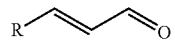

wherein R is hydrogen or $C_nH_{2+1}$, and each 'n' is independently 1, 2, 3, 4, 5, 6, 7, 8, 9, or 10.

In some embodiments, the process further comprises reacting the trans-2-unsaturated aldehyde compound of formula III with an alcohol dehydrogenase or an enzyme having alcohol dehydrogenase activity to form trans-2-unsaturated alcohols. In some embodiments, the process further comprises reacting the trans-2-unsaturated aldehyde compound of formula III with oxidoreductases to form trans-2-unsaturated carboxylic acids.

In some embodiments, the trans-2-unsaturated aldehyde comprises 2-propenal, trans-2-butenal, trans-2-pentenal, trans-2-hexenal, trans-2-heptenal, trans-2-octenal, trans-2-nonenal, trans-2-decenal, trans-2-undecenal, trans-2-dodecenal, trans-2-tridecenal, and any combination thereof. In some embodiments, the trans-2-unsaturated alcohol comprises prop-2-enol, trans-2-butenol, trans-2-pentenol, trans-2-hexenol, trans-2-heptenol, trans-2-octenol, trans-2-nonenol, trans-2-decenol, trans-2-undecenol, trans-2-dodecenol, trans-2-tridecenol, and any combination thereof. In some embodiments, the trans-2-unsaturated carboxylic acid comprises prop-2-enoic acid, trans-2-butenoic acid, trans-2-pentenoic acid, trans-2-hexenoic acid, trans-2-heptenoic acid, trans-2-octenoic acid, trans-2-nonenoic acid, trans-2-decenoic acid, trans-2-undecenoic acid, trans-2-dodecenoic acid, trans-2-tridecenoic acid, and any combination thereof.

In some embodiments, the process further comprises:
(a) condensation of the 3-hydroxy aldehyde compound of formula II and an acetaldehyde molecule in the presence of an aldolase enzyme to form a 5,3-dihydroxy aldehyde compound of formula IV

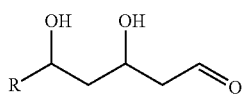

wherein R is hydrogen or $C_nH_{2n+1}$, and each 'n' is independently 1, 2, 3, 4, 5, 6, 7, 8, 9, or 10; wherein the aldolase enzyme is specific for the condensation of the compound of formula II and an acetaldehyde molecule; optionally wherein the aldolase enzyme specific for the condensation of the compound of formula II and an acetaldehyde molecule is different from the aldolase enzyme that is specific for the condensation of an acetaldehyde and an aldehyde molecule; and optionally wherein the aldolase enzyme is a modified aldolase enzyme comprising an increased enzymatic activity in comparison with a corresponding unmodified or wild-type aldolase enzyme;
(b) cyclization of the 5,3-dihydroxyaldehyde compound of formula IV to a tetrahydro-2H-pyran-2,4-diol compound of formula IV(b)

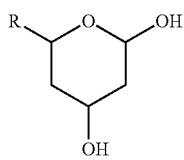

wherein R is hydrogen or $C_nH_{2n+1}$, and each 'n' is independently 1, 2, 3, 4, 5, 6, 7, 8, 9, or 10;
(c) oxidation of the tetrahydro-2H-pyran-2,4-diol compound of formula IV(b) to a tetrahydro-4-hydroxy-2H-pyran-2-one compound of formula V

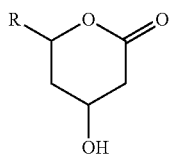

wherein R is hydrogen or $C_nH_{2n+1}$, and each 'n' is independently 1, 2, 3, 4, 5, 6, 7, 8, 9, or 10; optionally wherein the oxidation comprises an enzymatic oxidation;
(d) dehydration of the tetrahydro-4-hydroxy-2H-pyran-2-one compound of formula V to a 5,6-dihydro-2H-pyran-2-one compound of formula VI

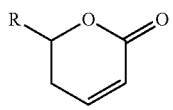

wherein R is hydrogen or $C_nH_{2n+1}$, and each 'n' is independently 1, 2, 3, 4, 5, 6, 7, 8, 9, or 10; optionally wherein the dehydration comprises dehydratase; and optionally, (e) reduction of the 5,6-dihydro-2H-pyran-2-one compound of formula VI in the presence of a reductase to form a delta-lactone compound of formula VII

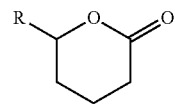

wherein R is hydrogen or $C_nH_{2n+1}$, and each 'n' is independently 1, 2, 3, 4, 5, 6, 7, 8, 9, or 10; and optionally wherein at least one enzyme of any one of (a)-(e) is partially purified, purified, or is a modified enzyme.

In some embodiments, the compound of formula VI comprises massoia lactone, C-10 massoia lactone (5,6-dihydro-6-pentyl-2H-pyran-2-one), C-12 massoia lactone (5,6-dihydro-6-heptyl-2H-pyran-2-one), C-14 massoia lactone (5,6-dihydro-6-nonyl-2H-pyran-2-one), 5,6-dihydro-2H-pyran-2-one, 5,6-dihydro-6-methyl-2H-pyran-2-one, 5,6-dihydro-6-hexyl-2H-pyran-2-one, 5,6-dihydro-6-ethyl-2H-pyran-2-one, 5,6-dihydro-6-propyl-2H-pyran-2-one, 5,6-dihydro-6-butyl-2H-pyran-2-one, 5,6-dihydro-6-decyl-2H-pyran-2-one, 5,6-dihydro-6-octyl-2H-pyran-2-one, and any combination thereof.

In some embodiments, the compound of formula VII comprises delta-valerolactone, delta-hexalactone, delta-heptalactone, delta-octalactone, delta-nonalactone, delta-decalactone, delta-undecalactone, delta-dodecalactone, delta-tridecalactone, delta-tetradecalactone, delta-pentadecalactone, and any combination thereof.

In one embodiment, the present disclosure relates to a process of producing a gamma-lactone compound, comprising:
(a) condensing an aldehyde molecule and a pyruvic acid in the presence of an aldolase enzyme to form a 4-hydroxy-2-oxo carboxylic acid compound of formula VIII

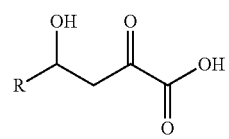

wherein R is hydrogen or $C_nH_{2n+1}$, and each 'n' is independently 1, 2, 3, 4, 5, 6, 7, 8, 9, or 10; wherein the aldolase enzyme is specific for the condensation of the pyruvic acid and an aldehyde molecule; and optionally wherein the aldolase enzyme is a modified aldolase enzyme comprising an increased enzymatic activity in comparison with a corresponding unmodified or wild-type aldolase enzyme;
(b) reduction of the 4-hydroxy-2-oxo carboxylic acid compound of formula VIII in the presence of a dehydrogenase or a keto-reductase to form a 2,4-dihydroxy carboxylic acid compound of formula IX

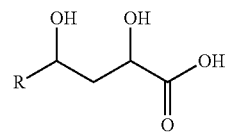

wherein R is hydrogen or $C_nH_{2n+1}$, and each 'n' is independently 1, 2, 3, 4, 5, 6, 7, 8, 9, or 10;

(c) lactonization of the 2,4-dihydroxy carboxylic acid compound of formula IX to a 3-hydroxydihydro-2-(3H)-furanone compound of formula X

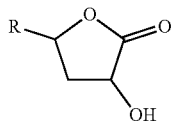

wherein R is hydrogen or $C_nH_{2n+1}$, and each 'n' is independently 1, 2, 3, 4, 5, 6, 7, 8, 9, or 10;
(d) dehydration of the 3-hydroxydihydro-2-(3H)-furanone compound of formula X to a 2(5H)-furanone compound of formula XI

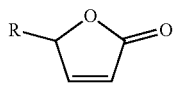

wherein R is hydrogen or $C_nH_{2n+1}$, and each 'n' is independently 1, 2, 3, 4, 5, 6, 7, 8, 9, or 10; optionally wherein the dehydration comprises dehydratase; and
(e) reduction of 2(5H)-furanone compound of formula XI in the presence of reductase to a gamma-lactone compound of formula XII

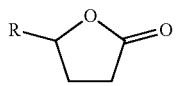

wherein R is hydrogen or $C_nH_{2n+1}$, and each 'n' is independently 1, 2, 3, 4, 5, 6, 7, 8, 9, or 10; optionally wherein the reduction comprises reductase.

In some embodiments, the gamma-lactone compound of formula XII comprises gamma-valerolactone, gamma-hexalactone, gamma-heptalactone, gamma-octalactone, gamma-nonalactone, gamma-decalactone, gamma-undecalactone, gamma-dodecalactone, gamma-tridecalactone, gamma-tetradecalactone, gamma-butyrolactone, and any combination thereof. In some embodiments, the lactone is in enantiomeric excess. In some embodiments, the gamma-lactone compound of formula XII comprises (R)-gamma-valerolactone, (R)-gamma-hexalactone, (R)-gamma-heptalactone, (R)-gamma-octalactone, (R)-gamma-nonalactone, (R)-gamma-decalactone, (R)-gamma-undecalactone, (R)-gamma-dodecalactone, (R)-gamma-tridecalactone, (R)-gamma-tetradecalactone, (R)-gamma-butyrolactone, and any combination thereof. In some embodiments, the compound of formula VII comprises (R)-delta-hexalactone, (R)-delta-heptalactone, (R)-delta-octalactone, (R)-delta-nonalactone, (R)-delta-decalactone, (R)-delta-undecalactone, (R)-delta-dodecalactone, (R)-delta-tridecalactone, (R)-delta-tetradecalactone, (R)-delta-pentadecalactone, and any combination thereof. In some embodiments, the compound of formula VI comprises (R)-massoia lactone, (R)-5,6-dihydro-6-pentyl-2H-pyran-2-one, (R)-5,6-dihydro-6-heptyl-2H-pyran-2-one, (R)-5,6-dihydro-6-nonyl-2H-pyran-2-one, (R)-5,6-dihydro-2H-pyran-2-one, (R)-5,6-dihydro-6-methyl-2H-pyran-2-one, (R)-5,6-dihydro-6-hexyl-2H-pyran-2-one, (R)-5,6-dihydro-6-ethyl-2H-pyran-2-one, (R)-5,6-dihydro-6-propyl-2H-pyran-2-one, (R)-5,6-dihydro-6-butyl-2H-pyran-2-one, (R)-5,6-dihydro-6-decyl-2H-pyran-2-one, (R)-5,6-dihydro-6-octyl-2H-pyran-2-one, and any combination thereof.

In some embodiments, the dehydration is spontaneous and/or chemically catalyzed. In some embodiments, the dehydration comprises dehydratase. In some embodiments, the lactonization is spontaneous, chemical, enzymatic, non-enzymatic, or any combination thereof.

In some embodiments, the 3-hydroxy aldehyde compound of formula I comprises 3-hydroxy-propanal, 3-hydroxy-butanal, 3-hydroxy-pentanal, 3-hydroxy-hexanal, 3-hydroxy-heptanal, 3-hydroxy-octanal, 3-hydroxy-nonanal, 3-hydroxy-decanal, 3-hydroxy-undecanal, 3-hydroxy-dodecanal, 3-hydroxy-tridecanal, and any combination thereof. In some embodiments, the compound of formula II is in enantiomeric excess. In some embodiments, the compound of formula II comprises (R)-3-hydroxy-propanal, (R)-3-hydroxy-butanal, (R)-3-hydroxy-pentanal, (R)-3-hydroxy-hexanal, (R)-3-hydroxy-heptanal, (R)-3-hydroxy-octanal, (R)-3-hydroxy-nonanal, (R)-3-hydroxy-decanal, (R)-3-hydroxy-undecanal, (R)-3-hydroxy-dodecanal, (R)-3-hydroxy-tridecanal, and any combination thereof.

In some embodiments, the compound of formula III comprises 2-propenal, trans-2-butenal, trans-2-pentenal, trans-2-hexenal, trans-2-heptenal, trans-2-octenal, trans-2-nonenal, trans-2-decenal, trans-2-undecenal, trans-2-dodecenal, trans-2-tridecenal, or any combination thereof.

In some embodiments, the non-naturally occurring microorganism comprises an exogenous nucleic acid that encodes an aldolase. In some embodiments, the aldolase is a pyruvate dependent aldolase. In some embodiments, the aldolase is a pyruvate class II aldolase. In some embodiments, the pyruvate class II aldolase is HpaI, BphI, Eda or a homolog, or a mutant, or any combination thereof. In some embodiments, the aldolase is or comprises deoxyribose-5-phosphate aldolase (DERA), or a variant, or a homologue thereof. In some embodiments, the aldolase comprises an amino acid sequence of SEQ ID NO: 11, 12, 13, 14, 15, 16, 17, 18, 19, or 20, or an active fragment, or a homologue thereof. In some embodiments, the aldolase comprises at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% amino acid sequence identity to any one of SEQ ID NOs: 11, 12, 13, 14, 15, 16, 17, 18, 19, or 20.

In some embodiments, the aldolase enzyme comprises the following conserved amino acid residues in the active site of the enzyme: lysine167, lysine 201, aspartic acid 16 and aspartic acid 102, where the number associated with each residue refers to the residue number in the amino acid sequence of *E. coli* DERA of SEQ ID NO: 16.

In some embodiments, the exogenous nucleic acid comprises a nucleotide sequence of SEQ ID NO: 1, 2, 3, 4, 5, 6, 7, 8, 9, or 10. In some embodiments, the exogenous nucleic acid comprises a nucleotide sequence that is at least about 50%, at least about 55%, at least about 60%, at least about 65%, at least about 70%, at least about 75%, at least about 80%, at least about 85%, at least about 90%, at least about 95%, or at least about 99% nucleotide sequence identity to any one of SEQ ID NOs: 1, 2, 3, 4, 5, 6, 7, 8, 9, or 10.

In some embodiments, the non-naturally occurring microorganism comprises an exogenous nucleic acid that encodes a ketoreductase, oxidoreductase, aldehyde reductase, enoate reductase, dehydratase, lactonization enzyme, or alcohol dehydrogenase. In some embodiments, the non-naturally occurring microorganism further comprises a decarboxylase capable of the decarboxylation of pyruvate to yield acetaldehyde and carbon dioxide.

In some embodiments, the decarboxylase is pyruvate decarboxylase (PDC), benzoylformate decarboxylase (BFD), or alpha-ketoacid decarboxylase (KDC). In some embodiments, the decarboxylase comprises an amino acid sequence of SEQ ID NO: 71 or an active fragment or homologue thereof. In some embodiments, the BFD comprises an amino acid sequence of SEQ ID NO: 76 or an active fragment or homologue thereof. In some embodiments, the KDC comprises an amino acid sequence of SEQ ID NO: 68 or 77 or an active fragment or homologue thereof.

In some embodiments, the non-naturally occurring microorganism expresses an enzyme identified in table 10 or table 9. In some embodiments, one or more genes encoding an enzyme that utilizes pyruvate is deleted from the non-naturally occurring microorganism as compared to wild-type. In some embodiments, one or more genes encoding an enzyme capable of catalyzing a reaction involving an acetaldehyde molecule, a pyruvate, or an aldehyde precursor is deleted from the non-naturally occurring microorganism as compared to wild-type. In some embodiments, the one or more genes that is deleted from the non-naturally occurring microorganism as compared to wild-type comprises one or more genes encoding an alcohol dehydrogenase, a lactate dehydrogenase, or a pyruvate formate lyase.

In some embodiments, the process comprises fermentation. In some embodiments, the fermentation is partially anaerobic, substantially, or fully anaerobic. In some embodiments, the process is a sugar based fermentation process. In some embodiments, the sugar based fermentation process comprises feeding sugar, or feeding at least one aldehyde precursor, or feeding sugar and an aldehyde precursor, or feeding only aldehyde precursors, or feeding pyruvate and/or pyruvic acid, or any combination thereof. In some embodiments, the sugar based fermentation process provides a higher yield of the trans-2-aldehyde than a fatty acid based process. In some embodiments, the fermentation is carried out in a single vessel. In some embodiments, the fermentation is a two-phase process; optionally wherein the two-phase process comprises a strain growth phase and/or a production phase. In some embodiments, the sugar based fermentation process comprises glucose, xylose, arabinose, glycerol, galactose, mannose, fructose, starch, and any combination thereof.

In some embodiments, the non-naturally occurring microorganism or the process of the present disclosure comprises a host microorganism, wherein the host is selected from a bacteria, yeast, algae, cyanobacteria, fungi, or a plant cell, or any combination thereof.

In some embodiments, the compound of formula III, and/or the compound of formula VII, and/or the compound of formula VI, and/or the compound of formula XII is at least about 50% pure. In some embodiments, the compound of formula II, and/or the compound of formula VI, and/or the compound of formula VII, and/or the compound of formula XII is in enantiomeric excess of the (R)-configuration.

In one embodiment, the present disclosure relates to method of producing trans-2-unsaturated aldehyde from aldehydes and aldolases comprising at least one of the following trans-2-unsaturated aldehyde pathway enzymes:
  i. an aldolase enzyme that catalyzes condensation of two aldehyde molecules to produce 3-hydroxy aldehyde; and
  ii. a dehydratase that dehydrates the 3-hydroxy aldehyde to trans-2-unsaturated aldehyde;

wherein at least one of the trans-2-unsaturated aldehyde pathway enzymes is partially purified, is purified, is a modified enzyme, or any combinations thereof.

In one embodiment, the present disclosure relates to a method of producing trans-2-unsaturated aldehyde from aldehydes and aldolases comprising an aldolase enzyme that catalyzes condensation of two aldehyde molecules to produce 3-hydroxy aldehyde; and optionally, a dehydratase that dehydrates the 3-hydroxy aldehyde to trans-2-unsaturated aldehyde: optionally wherein the aldolase enzyme and/or the dehydratase is partially purified, is purified, is a modified enzyme, or any combinations thereof.

In one embodiment, the present disclosure relates to a method of producing delta-lactones from aldehydes and aldolases comprising at least one of the following delta-lactone pathway enzymes
  i. an aldolase enzyme that catalyzes condensation of two aldehyde molecules to produce a 3-hydroxy aldehyde;
  ii. an aldolase enzyme that catalyzes condensation of the 3-hydroxy aldehyde and an aldehyde molecule to a 5,3-dihydroxy aldehyde;
  iii. an oxidase that oxidizes of tetrahydro-2H-pyran-2,4-diol to a tetrahydro-4-hydroxy-2H-pyran-2-one;
  iv. a dehydratase that dehydrates the tetrahydro-4-hydroxy-2H-pyran-2-one to a 5,6-dihydro-2H-pyran-2-one; and
  v. a reductase that reduces the 5,6-dihydro-2H-pyran-2-one to a delta-lactone;
optionally wherein the aldolase in i. is different from the aldolase in ii; and wherein at least one of the delta-lactone pathway enzymes is partially purified, is purified, is a modified enzyme, or any combinations thereof.

In one embodiment, the present disclosure relates to method of producing delta-lactones from aldehydes and aldolases comprising the following delta-lactone pathway enzymes:
  i. an aldolase (first aldolase) enzyme that catalyzes condensation of two aldehyde molecules to produce a 3-hydroxy aldehyde;
  ii. an aldolase (second aldolase) enzyme that catalyzes condensation of the 3-hydroxy aldehyde and an aldehyde molecule to a 5,3-dihydroxy aldehyde; optionally wherein the aldolase in i. is different from the aldolase in ii.; and optionally wherein the method further comprises at least one of the following delta-lactone pathway enzymes.
  iii. an oxidase that oxidizes tetrahydro-2H-pyran-2,4-diol to a tetrahydro-4-hydroxy-2H-pyran-2-one;
  iv. a dehydratase that dehydrates the tetrahydro-4-hydroxy-2H-pyran-2-one to a 5,6-dihydro-2H-pyran-2-one; and
  v. a reductase that reduces the 5,6-dihydro-2H-pyran-2-one to a delta-lactone:
optionally wherein at least one of the delta-lactone pathway enzymes of i. to v. is partially purified, is purified, is a modified enzyme, or any combinations thereof.

In one embodiment, the present disclosure relates to a method of producing gamma-lactones from an aldehyde molecule, a carboxylic acid, and aldolase comprising at least one of the following gamma-lactone pathway enzymes:
  i. an aldolase enzyme that catalyzes condensation of an aldehyde molecule and a pyruvic acid to a 4-hydroxy-2-oxo carboxylic acid;
  ii. a dehydrogenase or a keto-reductase that reduces the 4-hydroxy-2-oxo carboxylic acid to 2,4-dihydroxy carboxylic acid;

iii. a lactonization enzyme that transforms the 2,4-dihydroxy carboxylic acid to a 3-hydroxydihydro-2-(3H)-furanone;

iv. a dehydratase that dehydrates the 3-hydroxydihydro-2-(3H)-furanone to 2(5H)-furanone; and v. a reductase that reduces the 2(5H)-furanone to a gamma-lactone;

wherein at least one of the gamma-lactone pathway enzymes is partially purified, is purified, is a modified enzyme, or any combinations thereof.

In one embodiment, the present disclosure relates to a method of producing gamma-lactones from an aldehyde molecule, a carboxylic acid, and aldolase comprising an aldolase enzyme that catalyzes condensation of an aldehyde molecule and a pyruvic acid to a 4-hydroxy-2-oxo carboxylic acid; and optionally wherein the method further comprises at least one of the following gamma-lactone pathway enzymes:

i. a dehydrogenase or a keto-reductase that reduces the 4-hydroxy-2-oxo carboxylic acid to 2,4-dihydroxy carboxylic acid;

ii. a lactonization enzyme that transforms the 2,4-dihydroxy carboxylic acid to a 3-hydroxydihydro-2-(3H)-furanone;

iii. a dehydratase that dehydrates the 3-hydroxydihydro-2-(3H)-furanone to 2(5H)-furanone; and iv. a reductase that reduces the 2(5H)-furanone to a gamma-lactone;

wherein at least one of the enzymes is partially purified, is purified, is a modified enzyme, or any combinations thereof.

In one embodiment, the present disclosure relates to a method of producing gamma-lactones from an aldehyde, a pyruvate, and aldolase comprising at least one of the following gamma-lactone pathway enzymes:

i. an aldolase that catalyzes condensation of an aldehyde molecule and a pyruvate to a 4-hydroxy-2-oxo carboxylic acid;

ii. a dehydrogenase or a keto-reductase that reduces the 4-hydroxy-2-oxo carboxylic acid to 2,4-dihydroxy carboxylic acid;

iii. a dehydratase that dehydrates 2,4-dihydroxy carboxylic acid to 4-hydroxy-2-ene acid;

iv. a lactonization enzyme that transforms the 4-hydroxy-2-ene acid to 2(5H)-furanone; and v. a reductase that reduces the 2(5H)-furanone to a gamma-lactone;

wherein at least one of the gamma-lactone pathway enzymes is partially purified, is purified, is a modified enzyme, or any combinations thereof.

In one embodiment, the present disclosure relates to a method of producing gamma-lactones from an aldehyde, a pyruvate, and aldolase comprising an aldolase that catalyzes condensation of an aldehyde molecule and a pyruvate to a 4-hydroxy-2-oxo carboxylic acid; and optionally wherein the method further comprises at least one of the following gamma-lactone pathway enzymes:

i. a dehydrogenase or a keto-reductase that reduces the 4-hydroxy-2-oxo carboxylic acid to 2,4-dihydroxy carboxylic acid;

ii. a dehydratase that dehydrates 2,4-dihydroxy carboxylic acid to 4-hydroxy-2-ene acid;

iii. a lactonization enzyme that transforms the 4-hydroxy-2-ene acid to 2(5H)-furanone; and iv. a reductase that reduces the 2(5H)-furanone to a gamma-lactone;

wherein at least one of the enzymes is partially purified, is purified, is a modified enzyme, or any combinations thereof.

In some embodiments, the method, or the non-naturally occurring microorganism, or the process of the present disclosure comprises an aldolase wherein the aldolase is a deoxyribose-5-phosphate aldolase DERA enzyme. In some embodiments, the DERA enzyme is modified. In some embodiments, the aldolase comprises an amino acid sequence of SEQ ID NO: 11, 12, 13, 14, 15, 16, 17, 18, 19, or 20, or an active fragment, or a homologue thereof. In some embodiments, the aldolase comprises at least about 50%, at least about 60%, at least about 70%, at least about 80%, at least about 85%, at least about 90%, at least about 95%, at least about 96%, at least about 97%, at least about 98%, or at least about 99% amino acid sequence identity to any one of SEQ ID NOs: 11, 12, 13, 14, 15, 16, 17, 18, 19, or 20.

In some embodiments, the present disclosure provides for an exogenous nucleic acid encoding the aldolase comprising a nucleotide sequence of SEQ ID NO: 1, 2, 3, 4, 5, 6, 7, 8, 9, or 10. In some embodiments, the exogenous nucleic acid encoding the aldolase comprises a nucleotide sequence that is at least about 50%, at least about 60%, at least about 70%, at least about 80%, at least about 85%, at least about 90%, at least about 95%, or at least about 99% nucleotide sequence identity to any one of SEQ ID NOs: 1, 2, 3, 4, 5, 6, 7, 8, 9, or 10.

In some embodiments, the modified DERA enzyme comprises at least one mutation, wherein the at least one mutation corresponds to or is at an amino acid position selected from R190, T12, and S238 of SEQ ID NO: 18. In some embodiments, the DERA enzyme comprises at least one mutation selected from R190K, R190I, R190F, R190A, R190L, R190M, T12A, and S238A of SEQ ID NO: 18. In some embodiments, the modified DERA enzyme comprises mutations corresponding to each or at each amino acid position selected from R190, T12, and S238 of SEQ ID NO: 18. In some embodiments, the modified DERA enzyme comprises mutations at each amino acid position corresponding to or selected from R190, T12, and S238 of SEQ ID NO: 18. In some embodiments, the modified DERA enzyme comprises mutations at all of the amino acid positions corresponding to R190, T12, and S238 of SEQ ID NO: 18.

In some embodiments, the method or the process of the present disclosure is performed in a culture, wherein the culture is a microbial culture. In some embodiments, the aldehyde molecules are fed to the culture. In some embodiments, the aldehyde molecules are produced from glucose. In some embodiments, at least one aldehyde molecule is produced from glucose and the other aldehyde molecule is fed to the culture.

In some embodiments, at least one enzyme is in the form of and/or is included in and/or is derived from a microbial cell, a permeabilized microbial cell, a microbial cell extract, a partially purified enzyme, or a purified enzyme; optionally wherein the at least one enzyme is aldolase; optionally wherein the aldolase is DERA, or a variant, or homologue thereof.

In some embodiments, the method comprises expressing at least one of the enzymes in a host cell. In some embodiments, the host cell is a microbial cell. In some embodiments, the host cell is a fungal or bacterial cell. In some embodiments, the microbial host cell is a transformed microbial host cell selected from the group consisting of *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yar-* rowia sp., *Zygosaccharomyces* sp., *Pichia* sp., *Kluyveromyces* sp., *Candida* sp., *Hansenula* sp., *Dunaliella Debaryonyes* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. In some embodiments, the transformed microbial host cell is selected from the group consisting of *Bacillus* sp., *Pseudomonas* sp., and *Escherichia* sp. In some embodiments, the transformed microbial host cell is *Escherichia coli*.

In some embodiments, the microbial cell is a viable cell. In some embodiments, the microbial cell produces a crude cell lysate. In some embodiments, the crude cell lysate is purified.

In some embodiments, the microbial cell and/or the non-naturally occurring microorganism comprises one or more gene deletions to increase the availability of aldehyde and/or pyruvate. In some embodiments, the microbial cell and/or the non-naturally occurring microorganism comprises one or more gene deletions encoding an alcohol dehydrogenase gene, a lactate dehydrogenase gene, or a pyruvate formate lyase gene. In some embodiments, the non-naturally occurring microorganism comprises one or more gene deletions compared to a corresponding unmodified or wild-type microorganism. In some embodiments, the one or more deleted genes encode enzyme(s) that consume aldehyde and/or pyruvate.

In some embodiments, the one or more genes that is deleted corresponds to one or more genes selected from pflB, ldhA, adhE, yqhD, eutG, adhP, and yjgB in *E. coli*. In some embodiments, the one or more genes that is deleted corresponds to one or more genes selected from aldB, poxB, ybbO, yahK, deoC, paoAB/C (yagT/S/R), adhE, yqhD, eutG adhP, and yjgB in *E. coli*. In some embodiments, the one or more genes that is deleted corresponds to one or more genes selected from ilvD, rhtA, aldB, poxB, ybbO, yahK, deoC, paoA/B/C (yagT/S/R), pflB, ldhA, adhE, yqhD, eutG, adhP, and yjgB in *E. coli*. In some embodiments, the one or more genes that is deleted corresponds to one or more genes selected from dkgA aldB poxB ybbO yahK deoC paoA/B/C (yagT/S/R) adhE yqhD eutG adhP and yjgB in *E. coli*. In some embodiments, the one or more genes that is deleted corresponds to one or more genes selected from ilvD, rhtA, dkgA, aldB, poxB, ybbO, yahK, deoC, paoA/B/C (yagT/S/R), pflB, ldhA, adhE, yqhD, eutG, adhP, and yjgB in E col. In some embodiments, the one or more genes that is deleted corresponds to one or more genes selected from dkgA, aldB, ybbO, yahK, deoC, paoAB/C (yagTS/R), adhE, yqhD, eutG, adhP, and, yjgB in *E. coli*. In some embodiments, the one or more genes that is deleted corresponds to one or more genes selected from ilvD, rhtA, dkgA, a1 dB, ybbO, yahK, deoC, paoA/B/C (yagT/S/R), pflB ldhA, adhE, yqhD, eutG, adhP and yjgB in *E. coli*. In some embodiments, the one or more genes that is deleted corresponds to one or more genes selected from pflB, ldhA, adhE in *E. coli*. In some embodiments, the one or more gene(s) that is deleted increase the availability of aldehyde and/or pyruvate.

In one embodiment, the present disclosure relates to a method of producing delta-lactone comprising adding or mixing at least one aldolase and/or at least one (precursor) aldehyde, with a non-naturally occurring microorganism to produce a delta-lactone from precursor aldehyde molecules, wherein the non-naturally occurring microorganism comprises an increased enzymatic activity of at least one enzyme in the delta-lactone pathway in comparison with the enzymatic activity of the same enzyme in a corresponding unmodified or wild-type microorganism.

In one embodiment, the present disclosure relates to a method of producing gamma-lactone comprising adding or mixing at least one aldolase and/or at least one (precursor) aldehyde, with a non-naturally occurring microorganism to produce gamma-lactone from a precursor aldehyde molecule, wherein the non-naturally occurring microorganism comprises an increased enzymatic activity of at least one enzyme in the gamma-lactone pathway in comparison with the enzymatic activity of the same enzyme in a corresponding unmodified or wild-type microorganism.

In one embodiment, the present disclosure relates to a method of producing trans-2-unsaturated aldehyde comprising adding or mixing at least one aldolase and/or at least one (precursor) aldehyde, with a non-naturally occurring microorganism to produce trans-2-unsaturated aldehyde from precursor aldehyde molecules, wherein the non-naturally occurring microorganism comprises an increased enzymatic activity of at least one enzyme in the trans-2-unsaturated aldehyde pathway in comparison with the enzymatic activity of the same enzyme in a corresponding unmodified or wild-type microorganism.

In some embodiments, the aldolases are two aldolases, wherein one aldolase is specific for the condensation of an acetaldehyde and an aldehyde molecule: optionally wherein the other aldolase is specific for the condensation of 3-hydroxy aldehyde and an acetaldehyde molecule, and optionally wherein the two aldolases are two different aldolases.

In some embodiments, the precursor aldehyde molecules are two aldehyde molecules. In some embodiments, the two aldehyde molecules are fed to a microbial culture. In some embodiments, at least one of the aldehyde molecule, the pyruvate, or pyruvic acid is fed to a microbial culture. In some embodiments, the aldehyde molecule is produced from glucose via an aldehyde producing pathway. In some embodiments, at least one of the two aldehyde molecules is produced from glucose and at least one of the two aldehyde molecules is fed to a microbial culture. In some embodiments, at least one of the two aldehyde molecules is acetaldehyde. In some embodiments, the acetaldehyde is produced from glucose via decarboxylation of pyruvate by pyruvate decarboxylase.

In some embodiments, the non-naturally occurring microorganism comprises at least one modified aldolase enzyme, wherein the modified aldolase enzyme comprises an increased activity towards an aldehyde condensation reaction in comparison to an unmodified aldolase enzyme. In some embodiments, the method or process of the present disclosure relates to a modified enzyme comprising at least one modified aldolase enzyme. In some embodiments, the modified aldolase enzyme comprises an increased activity towards an aldehyde condensation reaction in comparison to an unmodified aldolase enzyme. In some embodiments, the modified aldolase enzyme is a modified deoxyribose-5-phosphate aldolase (DERA) enzyme. In some embodiments, the modified DERA enzyme comprises at least one mutation corresponding to or at an amino acid position selected from R190, T12, and S238 of SEQ ID NO: 18.

In one embodiment, the present disclosure relates to a non-naturally occurring microorganism capable of synthesizing delta-lactone from aldehydes and aldolases, wherein the non-naturally occurring microorganism is derived from a wild-type or unmodified microorganism and the non-naturally occurring microorganism comprises an increased enzymatic activity of at least one enzyme in the delta-lactone pathway, in comparison with the enzymatic activity of the same enzyme in the wild-type microorganism In one embodiment, the present disclosure relates to a non-naturally occurring microorganism capable of synthesizing gamma-lactone from an aldehyde, a pyruvate, and aldolases, wherein the non-naturally occurring microorganism is derived from a wild-type or unmodified microorganism and the non-naturally occurring microorganism comprises an increased enzymatic activity of at least one enzyme in the gamma-lactone pathway, in comparison with the enzymatic activity of the same enzyme in the wild-type microorganism.

In one embodiment, the present disclosure relates to a non-naturally occurring microorganism capable of synthesizing trans-2-unsaturated aldehyde from aldehydes and aldolases, wherein the non-naturally occurring microorganism is derived from a wild-type or unmodified microorganism and the non-naturally occurring microorganism comprises an increased enzymatic activity of at least one enzyme in the trans-2-unsaturated aldehyde pathway, in comparison with the enzymatic activity of the same enzyme in the wild-type microorganism.

In some embodiments, the present disclosure relates to a recombinant vector comprising a gene encoding any DERA enzyme, and/or encoding any KDC, and/or encoding any BFD, and/or encoding any decarboxylase of the present disclosure.

In some embodiments, the present disclosure relates to an expression vector comprising any nucleic acid sequence disclosed in the present disclosure. In some embodiments, a host cell comprises the expression vector. In some embodiments, the cell is a microbial cell.

In some embodiments, the present disclosure relates to an isolated non-naturally occurring microorganism comprising a gene encoding any DERA enzyme, and/or encoding any KDC, and/or encoding any BFD, and/or encoding any decarboxylase of the present disclosure.

In some embodiments, a non-naturally occurring microorganism is obtained by introducing a recombinant vector into a host microorganism.

In one embodiment, the present disclosure relates to a method of producing an aldolase, comprising: a) culturing a host cell that expresses a modified aldolase enzyme under conditions that allow for aldolase production, wherein the modified aldolase enzyme is encoded by a nucleic acid molecule with a sequence at least about 85%, or at least about 90% identical to any one of SEQ ID NOs: 11, 12, 13, 14, 15, 16, 17, 18, 19, or 20; and b) isolating the aldolase from the culture: optionally wherein the aldolase is DERA.

In one embodiment, the present disclosure relates to a method of preparing a modified enzyme, comprising: (a) subjecting a deoxyribonucleic acid (DNA) sequence encoding the enzyme to random or site directed mutagenesis: (b) expressing the modified DNA sequence obtained in (a) in a host cell; and (c) screening for host cells expressing the modified enzyme wherein the enzyme has improved aldehyde condensation activity; optionally wherein the enzyme is an aldolase; optionally wherein the aldolase is DERA; and optionally wherein DERA comprises SEQ ID NO: 1, 2, 3, 4, 5, 6, 7, 8, 9, or 10. In some embodiments, the host cells screened in (c) are subjected to a second mutagenesis treatment, to rescreening, to reisolation and to recloning.

In some embodiments, the modified DNA sequence is expressed by transforming a suitable host cell with the modified DNA sequence and culturing the host cell obtained in (b) under suitable conditions for expressing the modified DNA sequence. In some embodiments, the host cell is a microbial cell. In some embodiments, the host cell is a fungal or bacterial cell.

Advantages of the present disclosure include a high yield single-step fermentation process, as opposed to a multistep enzyme catalysis process, otherwise used for bio-based production of chemicals. The pathways disclosed herein are based on sugars and/or precursor aldehydes, which provides a higher yield than currently used pathways for the production of trans-2-unsaturated aldehydes, delta-lactones and gamma-lactones. Fatty acids may pose problems of insolubility, toxicity, and contacts with enzymes. Current pathways used in the industry for making trans-2-unsaturated aldehydes, delta-lactones, and gamma-lactones involve fatty acid-based pathways such as lipoxygenase pathway and beta-oxidation pathway. Fatty acids used in lactone processes are very expensive. The present disclosure uses glucose instead, which is a cheap precursor, thus making the production of the trans-2-unsaturated aldehydes, the delta-lactones, and the gamma-lactones more cost effective.

Current methods, for example for the production of trans-2-hexenal, involve expression of plant-based enzymes such as 13-hydroperoxide lyase (HPL), which is not well expressed in industrial hosts as it is a membrane-bound enzyme found in chloroplasts. The pathways of the present disclosure are based on microbial enzymes that are easily expressed in industrial hosts, such as in *E. coli* and *S. cerevisiae*. The pathways disclosed herein use carbon-carbon bond forming aldolase enzymes. Aldolases may have broad substrate specificity thus, the same pathway may be extended to make different products, by changing the chain length of the precursor molecules. For example, the same pathway may be used to make trans-2-pental, trans-2-hexenal, and trans-2-heptenal, trans-2-octenal, or trans-2-nonenal, all of which are aroma chemicals.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "FIGURE" and "FIG." herein), of which:

DETAILED DESCRIPTION

Figure 1:
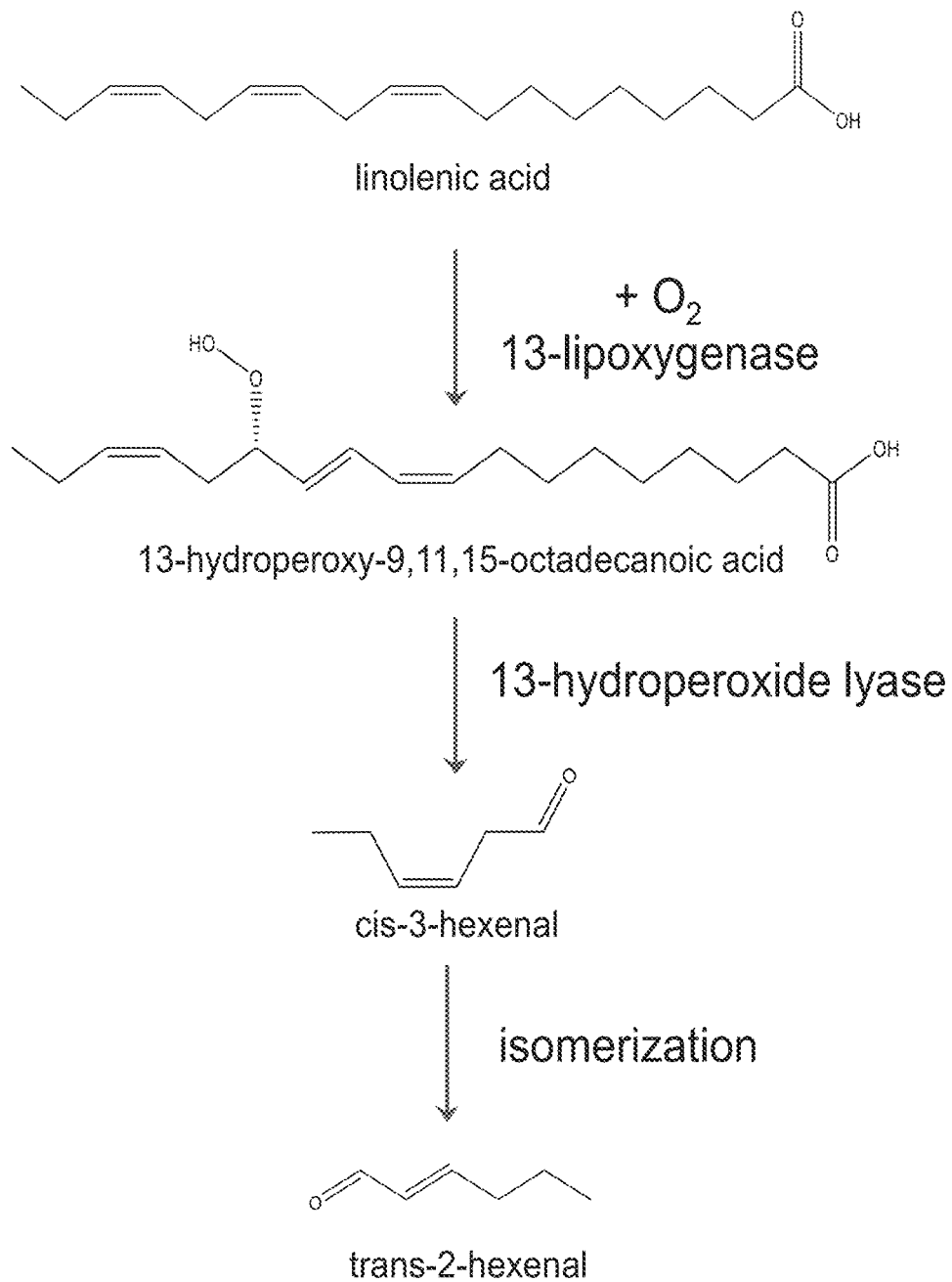
FIG. 1 exemplifies the fatty acid lipoxygenase pathway of trans-2-hexenal production.
Figure 2:
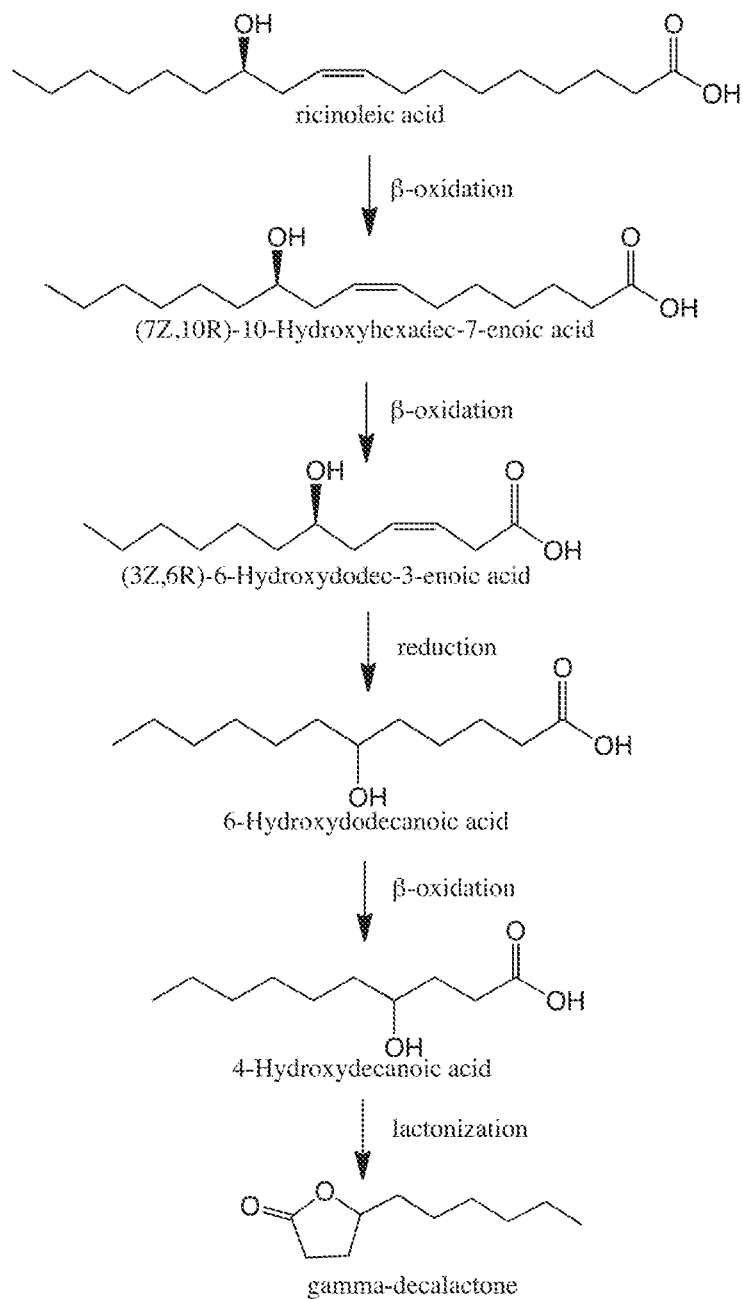
FIG. 2 exemplifies the fatty acid oxidation pathway of gamma-lactone production.
Figure 3:
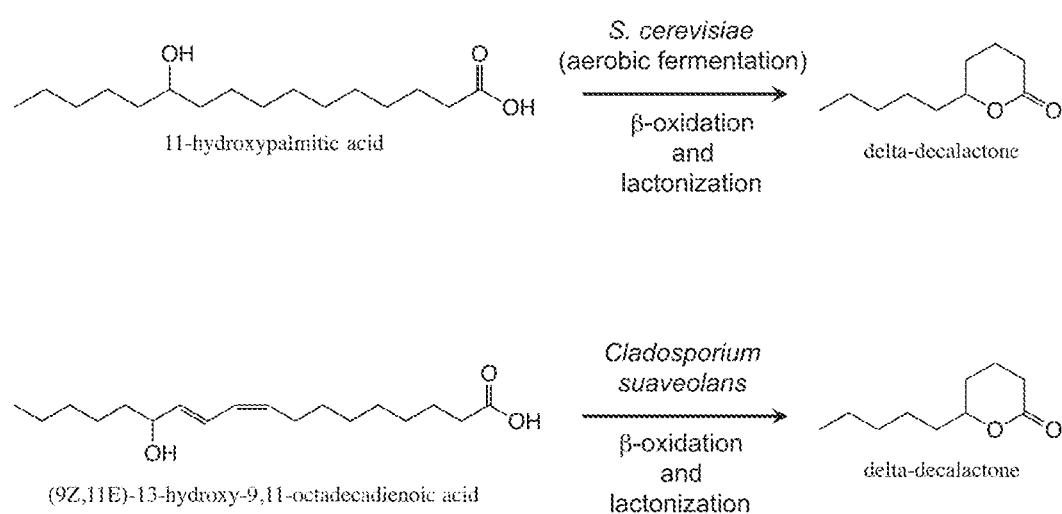
FIG. 3 exemplifies the fatty acid oxidation pathway of delta-lactone production.

While various embodiments of the disclosure have been shown and described herein, it will be obvious to those skilled in the art that such embodiments are provided by way of example only. Numerous variations, changes, and substitutions may occur to those skilled in the art without departing from the present disclosure. It should be understood that various alternatives to the embodiments of the disclosure described herein may be employed.

Unless defined otherwise, all technical and scientific terms used herein have the same meaning as commonly understood by one of ordinary skill in the art to which the present disclosure belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

The present disclosure describes non-naturally occurring microorganisms that are engineered by expressing genes encoding enzymes involved in biochemical pathways for producing trans-2-unsaturated aldehydes or lactones, such as delta-lactones and gamma-lactones, by using aldolases. The present disclosure also describes additional genetic modifications that may be used to improve the performance of the trans-2-unsaturated aldehyde pathway and the lactones (e.g, delta-lactone or gamma-lactone) production pathways. The genetic modifications may be towards optimizing the expression system or to the non-natural organism for improvement of production metrics including yield, titre, and productivity. Additionally, genetic modifications may be aimed at improving the non-natural microorganism's characteristics including but not limited to tolerance to inhibitors found in the feedstocks, product tolerance, osmotolerance, and efficient product secretion.

In order to further define the present disclosure, the following terms, abbreviations and definitions are provided.

As used herein, the term "about" modifying the quantity of an ingredient or reactant of the present disclosure employed refers to variations in the numerical quantity that may occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In some embodiments, the term "about" means within 10% of the reported numerical value, or within 5% of the reported numerical value, or within 20% of the reported numerical value.

The indefinite articles "a" and "an" preceding an element or component of the present disclosure are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

As used herein, "synergistic" refers to a greater-than-additive effect produced by a combination (i.e., an effect that is greater than the sum of individual effects) or an additive effect when the individual effects are not expected to be additive. The term also refers to the addition of one compound which results in less of another compound being required.

The term "polynucleotide" is intended to encompass a singular nucleic acid as well as plural nucleic acids, and may refer to a nucleic acid molecule or construct, e.g., messenger RNA (mRNA) or plasmid DNA (pDNA). A polynucleotide may contain the nucleotide sequence of the full-length cDNA sequence, or a fragment thereof, including the untranslated 5' and 3' sequences and the coding sequences. The polynucleotide may be composed of any polyribonucleotide or polydeoxyribonucleotide, which may be unmodified RNA or DNA or modified RNA or DNA. For example, polynucleotides may be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |

-continued

| Amino Acid | Three-Letter Abbreviation | One-Letter Abbreviation |
|---|---|---|
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The term "gene" refers to a nucleic acid fragment that is capable of being expressed as a specific protein, optionally including regulatory sequences preceding (5' non-coding sequences) and following (3' non-coding sequences) the coding sequence. The term "gene" refers to a linear sequence of nucleotides along a segment of DNA that provides the coded instructions for synthesis of RNA. In some instances, a gene provides coded instructions for translation into protein. In some instances, a gene provides coded instructions for the synthesis of non-coding RNA, which does not lead to translation into protein.

As used herein, the term "protein" comprises at least one polypeptide comprising amino acid residues bound together by peptide bonds.

As used herein, the terms "variant," "modified," and "mutant" are synonymous and refer to a polypeptide differing from a specifically recited polypeptide by one or more amino acid insertions, deletions, mutations, and substitutions, created using, e.g., recombinant DNA techniques, such as mutagenesis. Guidance in determining which amino acid residues may be replaced, added, or deleted without abolishing activities of interest, may be found by comparing the sequence of the particular polypeptide with that of homologous polypeptides, e.g., yeast or bacterial, and minimizing the number of amino acid sequence changes made in regions of high homology (conserved regions) or by replacing amino acids with consensus sequences.

The mutants of the present disclosure may be generated in accordance with any suitable method, including, but not limited to, methods described and exemplified herein. Mutations, such as substitutions, insertions, deletions, and/or side chain modifications, may be introduced into the nucleotide and amino acid sequences of the gene of interest using any suitable technique, including site-directed mutagenesis (Wu, ed., Meth. Enzymol. 217, Academic Press (1993)) or random mutagenesis, or a combination. The lambda red recombinase method may be used to "knock out" genes (Datsenko et al., PNAS USA 97: 6640-6645 (2000)). Permanent, marker-free, multiple gene disruptions may be created. Non-naturally occurring nucleotides and amino acids also may be used.

Random Mutagenesis

The random mutagenesis of the DNA sequence encoding an enzyme of the present disclosure may conveniently be performed by using any method known in the art. For instance, the random mutagenesis may be performed by using a suitable physical or chemical mutagenizing agent, by using a suitable oligonucleotide, or by subjecting the DNA sequence to PCR generated mutagenesis. In some embodiments, the random mutagenesis may be performed by using any combination of these mutagenizing agents.

In some embodiments, the mutagenizing agent may, e.g., be one which induces transitions, transversions, inversions, scrambling, deletions, and/or insertions. Examples of a physical or chemical mutagenizing agent suitable for the present purpose include, but is not limited to, ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used the mutagenesis is typically performed by incubating the DNA sequence encoding the unmodified or wild-type enzyme to be mutagenized in the presence of the mutagenizing agent of choice under suitable conditions for the mutagenesis to take place, and selecting for mutated DNA having the desired properties. When the mutagenesis is performed by using an oligonucleotide, the oligonucleotide may be doped or spiked with the non-parent or non wild-type nucleotides during the synthesis of the oligonucleotide at the positions wanted to be changed. The doping or spiking may be done so that codons for unwanted amino acids are avoided. The doped or spiked oligonucleotide can be incorporated into the DNA encoding the enzyme (e.g., DERA) by any published technique using e.g., PCR. LCR or any DNA polymerase and ligase. When PCR generated mutagenesis is used either a chemically treated or non-treated gene encoding a parent lipolytic enzyme is subjected to PCR under conditions that increases the misincorporation of nucleotides (Deshler 1992, Leung et al. 1989).

A mutator strain of *E. coli* (Fowler et al. 1974), *S. cereviciae* or any other microbial organism may be used for the random mutagenesis of the DNA encoding the enzyme (e.g., DERA) by e.g., transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent or wild-type enzyme (e.g., DERA). Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some embodiments, it may be convenient to amplify the mutated DNA sequence prior to expression in a host cell or screening. Such amplification may be performed in accordance with methods known in the art. In some embodiments, the method comprises PCR generated amplification using oligonucleotide primers prepared on the basis of the DNA or amino acid sequence of the parent or wild type enzyme.

Subsequent to the incubation with or exposure to the mutagenizing agent, the mutated DNA is expressed by culturing a suitable host cell carrying the DNA sequence under conditions allowing expression to take place. The host cell may be one which has been transformed with the mutated DNA sequence, optionally present on a vector, or one which carried the DNA sequence encoding the parent enzyme during the mutagenesis treatment. The mutated DNA sequence may further comprise a DNA sequence encoding functions permitting expression of the mutated DNA sequence.

As used herein, "homologue" refers to a protein that is functionally equivalent i.e. has the same enzymatic activity as an enzyme having an amino acid sequence of the specified sequence identification number, but may have a limited number of amino acid substitutions, deletions, insertions or additions in the amino acid sequence. In order to maintain the function of the protein, the substitutions may be conservative substitutions, replacing an amino acid with one having similar properties.

In various aspects, a homologue of each enzyme refers to a protein which has an identity of at least 25%, at least 50%, at least 60%, at least 70%, at least 80%, at least 85%, at least 90%, at least 95% or at least 99% with the amino acid sequence of SEQ ID NO corresponding to the enzyme and retains enzymatic activity. Algorithms for determining sequence identity are publicly available and include e.g. BLAST available through the National Center for Biotechnology Information (NCBI). One skilled in the art may determine if the sequences are similar to a degree that indicates homology and thus similar or identical function.

A polynucleotide encoding a homologue of each enzyme may be obtained by appropriately introducing substitution, deletion, insertion, and/or addition to the DNA of the enzyme which is composed of a nucleotide sequence disclosed herein, using methods such as site-specific mutagenesis (Nucleic Acid Res. 10, pp. 6487 (1982). Methods in Enzymol. 100, pp. 448 (1983). Molecular Cloning 2nd Edt., Cold Spring Harbor Laboratory Press (1989). PCR A Practical Approach IRL Press pp. 200 (1991)). The polynucleotide encoding a homologue of each enzyme may be introduced and expressed in a host to obtain the homologue.

As used herein, term "microbial cell" is intended to include whole microorganism cells, and/or fragmented cells, and/or homogenized cells. The term microbial cell preparation may include whole microorganism cells as well as cell mass particulate forms of immobilized intracellular enzymes. In some embodiments, the microbial cell is a viable cell. In some embodiments, the microbial cell produces a crude cell lysate. In some embodiments, the crude cell lysate is purified. In some embodiments, the crude cell lysate is unpurified. In some embodiments, the crude cell lysate is a combination of purified and unpurified crude cell lysate. In some embodiments, the microbial cell comprises one or more gene deletions to increase the availability of aldehyde and/or pyruvate. In some embodiments, the microbial cell comprises one or more gene deletions encoding an alcohol dehydrogenase, a lactate dehydrogenase, and/or a pyruvate formate lyase. In some embodiments, a deleted gene may be an alcohol dehydrogenase gene, a lactate dehydrogenase gene, and/or a pyruvate formate lyase gene.

As used herein, "enzyme" includes proteins produced by a cell capable of catalyzing biochemical reactions. Further, unless context dictates otherwise, as used herein "enzyme" includes protein fragments that retain the relevant catalytic activity, and may include artificial enzymes synthesized to retain the relevant catalytic activity. In some embodiments, at least one enzyme (e.g., aldolase, DERA) of the present disclosure may be in the form of a whole microbial cell, a microbial cell, a permeabilized microbial cell, a microbial cell extract, one or more cell components of a microbial cell extract, a partially purified enzyme, a purified enzyme, or combinations thereof.

Each of the enzymes described herein may be attached to an additional amino acid sequence as long as it retains an activity functionally equivalent to that of the enzyme. As mentioned above, it is understood that each enzyme or a homologue thereof may be a (poly)peptide fragment as long as it retains an activity functionally equivalent to that of the enzyme.

In some embodiments, at least one enzyme (e.g., aldolase, DERA) is expressed in a host cell. In some embodiments, the at least one enzyme is an unmodified or wild type enzyme. In some embodiments, the at least one enzyme is a modified or a variant enzyme. In some embodiments, the host cell is a microbial cell. In some embodiments, the host cell is a fungal or a bacteria cell. In some embodiments, the microbial host cell is a transformed microbial host cell. In some embodiments, the microbial or transformed microbial host cell may be selected from *Comamonas* sp., *Corynebacterium* sp., *Brevibacterium* sp., *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yarrowia* sp., *Zygosaccharomyces* sp., *Pichia* sp., *Kluveromyces* sp., *Candida* sp., *Hansenula* sp., *Dunaliella Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. In some embodiments, the microbial host cell may be *Bacillus* sp., *Pseudomonas* sp., or *Escherichia* sp.

As used herein, the term "enzymatic activity" describes the ability of an enzyme to convert a substrate (e.g., aldehyde molecule) into a product or an intermediate. For example, an enzymatic activity may be described as the ability of an enzyme to catalyze condensation of aldehyde molecules, such as the ability of an aldolase (e.g., DERA or a modified DERA) to catalyze condensation of two aldehyde molecules or one aldehyde and pyruvic acid to produce 3-hydroxy aldehyde or 4-hydroxy-2-oxo carboxylic acid, respectively. In some embodiments, both the natural substrate of the enzyme and a synthetic modified analog of the natural substrate can be used. The enzymatic activity can be determined in what is known as an activity assay via the increase in the product or intermediate, the decrease in the starting material, the decrease or increase in a specific cofactor, or a combination of at least two of the aforementioned parameters as a function of a defined period of time. If the enzyme catalyzes a reversible reaction, both the starting material and the product may be employed as substrate in the activity assay in question.

As used herein, the term "microorganism" is intended to mean any organism that exists as a microscopic cell and encompasses prokaryotic or eukaryotic cells or organisms having a microscopic size and includes bacteria, archaea and eubacteria of all species as well as eukaryotic microorganisms such as yeast and fungi. The term also includes cell cultures of any species (including e.g, plant and mammalian cells) that may be cultured for the production of a biochemical.

As used herein, the term "non-naturally occurring" when used in reference to a microorganism refers to a microorganism that has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. In some embodiments, the non-naturally occurring microorganism comprises an exogenous nucleic acid that encodes an aldolase enzyme. In some embodiments, the non-naturally occurring microorganism comprises an exogenous nucleic acid that encodes a pyruvate dependent aldolase. In some embodiments, the non-naturally occurring microorganism comprises an exogenous nucleic acid that encodes a pyruvate class II aldolase (e.g., HpaI, BphI, Eda, or a homologue, or a mutant, or any combination thereof). In some embodiments, the non-naturally occurring microorganism comprises an exogenous nucleic acid that encodes a ketoreductase, oxidoreductase, aldehyde reductase, enoate reductase, dehydratase, lactonization enzyme, or alcohol dehydrogenase, or any combination thereof.

The term "endogenous" refers to a referenced molecule or activity that originates in a host microorganism. Similarly, the term when used in reference to expression of an encoding nucleic acid refers to expression of an encoding nucleic acid contained within the microorganism.

As used herein the term "exogenous" refers to molecules or activity that is introduced into a host microorganism. The molecule may be introduced, for example, by introduction of an encoding nucleic acid into the host genetic material such as by integration into a host chromosome or as non-chromosomal genetic material such as a plasmid. In reference to expression of an encoding nucleic acid the term refers to introduction of the encoding nucleic acid in an expressible form into the microorganism. When used in reference to a biosynthetic activity, the term refers to an activity that is introduced into a reference host organism. The source may be, for example, an encoding nucleic acid that expresses the activity following introduction into the host microorganism.

The term "heterologous" refers to a molecule or activity derived from a source other than the referenced species whereas "homologous" refers to a molecule or activity derived from the host microbial organism. Accordingly, exogenous expression of an encoding nucleic acid of the present disclosure may use either or both a heterologous or homologous encoding nucleic acid.

The term "oxidoreductase" is defined as any enzyme that facilitates the oxidation or reduction of a substrate. The term oxidoreductase includes "oxidases," which facilitate oxidation reactions in which molecular oxygen is the electron acceptor; "reductases," which facilitate reduction reactions in which the analyte is reduced and molecular oxygen is not the analyte; and "dehydrogenases," which facilitate oxidation reactions in which molecular oxygen is not the electron acceptor. See, for example, Oxford Dictionary of Biochemistry and Molecular Biology, Revised Edition, A. D. Smith, Ed., New York: Oxford University Press (1997) pp. 161, 476, 477, and 560. Non-limiting examples of oxidoreductases include a reductase, an oxidase, a dehydrogenase, a ketoreductase, an alcohol dehydrogenase, a carbonyl reductase, an aldehyde dehydrogenase, an amino acid dehydrogenase, an amine oxidase, a disulfide reductase, an enoate reductase, and a mixed function oxidase. A listing of such enzymes may be found in Enzyme Nomenclature: Webb, E. C., Ed. Academic: Orlando 1984; pp 20-141.

As used herein, the term "operably linked" refers to a linkage between one or more expression control sequences and the coding region in a polynucleotide to be expressed in such a way that expression is achieved under conditions compatible with the expression control sequence.

The expression "derived from" in relation to an enzyme or (poly)peptide denotes that the enzyme or poly(peptide) was isolated from a (micro)organism or that it includes all or a biologically active part of the amino acid sequence of an enzyme or (poly)peptide isolated or characterized from such a (micro)organism.

In some embodiments, the processes/pathways disclosed herein is a process comprising, consisting of, or consisting essentially of condensing two aldehyde molecules using an aldolase enzyme as described herein.

The aldolases catalyze aldol condensation by stereo-controlled addition of a nucleophilic donor onto an electrophilic aldehyde acceptor. Due to the mechanistic requirements aldolases are quite specific for the nucleophilic donor component but show large flexibility in the acceptor range. Hence aldolases are categorized based on their nucleophilic donors. Different classes of aldolases are 1) acetaldehyde dependent aldolase, 2) pyruvate/phosphoenolpyruvate-dependent aldolases, 3) dihydroxyacetone phosphate/dihydroxyacetone-dependent aldolases, and 4) glycine dependent aldolases.

In some embodiments, aldolases may be acetaldehyde dependent aldolases. In some embodiments, aldolases may be pyruvate dependent aldolases. In some embodiments, the aldehydes may be donors or acceptors.

In some embodiments, the donors may include one or more of acetaldehyde (ethanal), propanal, 2-methylpropanal, methylglyoxal, lactaldehyde, glycolaldehyde, acrolein, formaldehyde, acetaldehyde, propionaldehyde, n-butyraldehyde, iso-butyraldehyde, hexanal, n-pentanal (valeraldehyde), caproaldehyde, crotonaldehyde, n-heptaldhyde, n-octanal, n-nonylaldehyde, phenylacetaldehyde, benzaldehyde, p-tolualdehyde, salicylaldehyde, vanillin, piperonal, 2-ethyl-2-hex-enal and 2-ethylhexaldehyde, undecaldehyde, decaldehyde, nonaldehyde, octaldehyde, heptaldehyde, hexaldehyde, pentaldehyde, or butyraldehyde.

In some embodiments, the donors may be non-aldehydes including pyruvate, propanone (acetone), glyoxylic acid, or 3-propenol.

In some embodiments, the acceptors may include one or more of acetaldehyde (ethanal), propanal, butanal, isobutanal, 2-methyl-1-butanal, 3-methyl-1-butanal, pentanal, hexanal, 3-methyl-1-pentanal, 4-methyl-1-pentanal, succinate semialdehyde, lactaldehyde, glycoldehyde, glyceraldehyde, 2-phenylacetaldehyde, cinnamaldehyde, glyoxal, glyoxylic acid, methyl glyoxal, acrolein, succindialdehyde, glutaraldehyde, adipaldehyde, malondialdehyde, malonic semialdehyde (3-oxopropionic acid), muconate semialdehyde, 2-hydroxymuconate semialdehyde, formaldehyde, acetaldehyde, propionaldehyde, n-butyraldehyde (butanal), iso-butyraldehyde, tert-butanal, hexanal (n-hexaldehyde), n-pentanal (valeraldehyde, pentaldehyde), caproaldehyde, crotonaldehyde, n-heptaldhyde (heptaldehyde, heptanal), n-octanal (octaldehyde), n-nonylaldehyde (nonaldehyde), n-decaldehyde, 3-hydroxypropanal, 3-hydroxybutanal, 3-hydroxypentanal, 3-hydroxyhexanal, 3-hydroxyheptanal, 3-hydroxy-octanal, 3-hydroxynonanal, 3-hydroxydecanal, phenylacetaldehyde, benzaldehyde, p-tolualdehyde, salicylaldehyde, vanillin, piperonal, 2-ethyl-2-hex-enal and 2-ethylhexaldehyde, undecaldehyde.

As used herein, the term DERA refers to the enzyme deoxyribose-5-phosphate aldolase belonging to the class aldolases, the term AKR refers to the class aldo-ketoreductase, the term ADH refers to the enzyme alcohol dehydrogenase, the term PDC refers to the enzyme pyruvate decarboxylase, the term BFD refers to the enzyme benzoylformate decarboxylase, the term KDC refers to the enzyme alpha-ketoacid decarboxylase, the term KRED refers to ketoreductase, the term G6PD refers to the enzyme glucose-6-phosphate 1-dehydrogenase (hemi-acetal oxidase), the term AKHD refers to the enzyme aspartokinase/homoserine dehydrogenase, the term HSK refers to the enzyme homoserine kinase, the term TS refers to the enzyme threonine synthase, the term IMDH refers to the enzyme isopropylmalate dehydrogenase, the term IPMI refers to the enzyme isopropylmalate dehydratase, the term NADH refers to reduced nicotinamide adenine dinucleotide, the term NADPH refers to reduced nicotinamide adenine dinucleotide phosphate, the term NAD refers to nicotinamide adenine dinucleotide, and the term NADP refers to nicotinamide adenine dinucleotide phosphate.

In some embodiments, the trans-2-unsaturated aldehyde pathway or the delta-lactone pathway disclosed herein comprise the condensation of two aldehyde molecules to 3-hydroxy acetaldehyde using enzyme from class aldolases. In some embodiments, the condensation of an aldehyde and a 3-hydroxy acetaldehyde molecule may be performed using an enzyme from class aldolases. In some embodiments, the enzyme from the class aldolases is a deoxyribose-5-phosphate aldolase (DERA) (EC 4.1.2.4.).

In some embodiments, DERA enzymes may be described as class I aldolases that form covalent Schiff base intermediates. In all studied structures, DERA adopts the classical eight-bladed TIM barrel fold. The oligomerisation state of DERA seems to depend on the temperature of the organism. For example, DERA from *E. coli* is a homodimer, whereas DERA from *Thermotoga maritima* is a homotetramer. The degree of oligomerization does not seem to affect catalysis but may affect stability under various conditions.

In some embodiments, the DERA is an enzyme comprising an amino acid sequence encoded by a DNA which comprises the nucleotide sequence of SEQ ID NO: 1, 2, 3, 4, 5, 6, 7, 8, 9, or 10. In some embodiments, the aldolase (e.g., DERA) is an enzyme comprising an amino acid sequence encoded by a DNA which comprises at least about 50%, at least about 55%, at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% nucleotide sequence identity to any one of SEQ ID NOs: 1, 2, 3, 4, 5, 6, 7, 8, 9, or 10.

In some embodiments, DERAs as described herein are derived from microorganisms of the genus *Bacillus, Escherichia, Thermotoga Deinococcus, Listeria, Staphylococcus, Streptococcus*, and *Methanothermobacter*. In some embodiments, the DERA is derived from *Bacillus halodurans, Bacillus cereus. Bacillus subtilis, Escherichia coli, Thermotoga maritima, Deinococcus radiodurans, Listeria monocytogenes, Staphylococcus aureus, Streptococcus pneumonia*, and *Methanothermobacter thermautotrophicus*. In some embodiments, a DERA as used in a process described herein comprises an amino acid sequence of SEQ ID NOs: 11, 12, 13, 14, 15, 16, 17, 18, 19, or 20 or active fragments or homologues thereof. In some embodiments, the DERA is an enzyme comprising an amino acid sequence which comprises at least about 50%, at least about 55%, at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to any one of SEQ ID NOs: 11, 12, 13, 14, 15, 16, 17, 18, 19, or 20.

In some embodiments, the aldolase enzyme comprises the following conserved amino acid residues in the active site of the enzyme: lysine 167, lysine 201, aspartic acid 16 and aspartic acid 102, where the number associated with each residue refers to the residue number in the amino acid sequence of *E. coli* DERA of the SEQ ID NO: 16 and corresponding codons in the nucleotide sequence of SEQ ID NO: 2.

In some embodiments, the DERA enzyme is specifically modified to increase activity towards an alkyl aldehyde. In some embodiments, the DERA enzyme is specifically modified to increase activity towards hexanal. In some embodiments, the DERA enzyme is modified to increase activity towards propanal, butanal, pentanal, hexanal, heptanal, octanal, nonanal, decanal, undecanal, dodecanal, tridecanal, and any combination thereof. In some embodiments, the DERA enzyme is modified to increase activity towards condensation of an acetaldehyde and an acetaldehyde, propanal, butanal, pentanal, hexanal, heptanal, octanal, nonanal, decanal, undecanal, dodecanal, or a tridecanal. In some embodiments, the DERA enzyme is modified to increase activity towards condensation of an acetaldehyde and a 3-hydroxy aldehyde (e.g., 3-hydroxy-propanal, 3-hydroxy-butanal, 3-hydroxy-pentanal, 3-hydroxy-hexanal, 3-hydroxy-heptanal, 3-hydroxy-octanal, 3-hydroxy-nonanal, 3-hydroxy-decanal, 3-hydroxy-undecanal, 3-hydroxy-dodecanal, 3-hydroxy-tridecanal). In some embodiments, the DERA enzyme used for the condensation of an acetaldehyde and an aldehyde is different from the DERA enzyme used for the condensation of an acetaldehyde and a 3-hydroxy aldehyde. In some embodiments, an aldolase enzyme (e.g., pyruvate-dependent aldolase) is modified to increase activity towards condensation of a pyruvic acid and an aldehyde (e.g., acetaldehyde, propanal, butanal, pentanal, hexanal, heptanal, octanal, nonanal, decanal, undecanal, dodecanal, or tridecanal).

In some embodiments, the DERA enzyme is modified to increase activity towards a 3-hydroxy aldehyde. In some embodiments, the DERA enzyme is modified to increase activity towards 3-hydroxy-propanal, 3-hydroxy-butanal, 3-hydroxy-pentanal, 3-hydroxy-hexanal, 3-hydroxy-heptanal, 3-hydroxy-octanal, 3-hydroxy-nonanal, 3-hydroxy-decanal, 3-hydroxy-undecanal, 3-hydroxy-dodecanal, 3-hydroxy-tridecanal, and any combination thereof. In some embodiments, the DERA enzyme is specifically modified to increase activity towards 3-hydroxy octanal.

In some embodiments, the DERA enzyme comprises one or more of the following mutations: R190K, R190I, R190F, R190A, R190L, R190M, T12A, and S238A. In some embodiments, the DERA enzyme comprises, but is not limited to, one or more of the following mutations: RI90K, R190I, R190F, TI2A, and S238A. In some embodiments, the DERA enzyme comprises, but is not limited to, one or more of the following mutations: R190A or R90L or RI90M, T12A and S238A. In some embodiments, the number associated with amino acids R190, T12, and S238 corresponds to the amino acid residue numbers in BH1352 DERA, represented in SEQ ID NO: 18. In some embodiments, all residues R190, T12, and S238 are mutated or modified. In some embodiments, only one of R190, T12, and S238 is mutated or modified. In some embodiments, the amino acid R190 is mutated or modified. In some embodiments, the DERA enzyme from another organism may comprise one or more amino acid mutations that correspond to the amino acid mutations R190K, R190I, R190F, R190A, R190L, R190M, T12A, and S238A (e.g., of SEQ ID NO: 18), wherein the amino acids R190, T12 and S238 correspond to the amino acid residue numbers in SEQ ID NO: 18. In some embodiments, one or more amino acid(s) is mutated to a hydrophobic amino acid. In some embodiments, one or more amino acid(s) is mutated to a nonpolar amino acid. In some embodiments, one or more amino acid(s) is mutated to a charged amino acid. In some embodiments, one or more amino acid(s) is mutated to a basic amino acid.

In some embodiments, enzymes belong to the Pfam database [Finn R. D. et al., Pfam: the protein families database Nucl. Acids Res. (1 Jan. 2014) 42 (Dl): D222-D230] group PF01791 (DeoC/LacD family aldolase) include deoxyribose-5-phosphate aldolases, which also belong to the InterPro family IPR002915, IPR013785, IPRO11343, and IPR028581. Protein sequences that belong to the InterPro and Pfam family of proteins may be obtained, such that they are homologues of DERA described herein.

In some embodiments, the 5,3-dihydroxy aldehyde product of the DERA catalyzed reaction spontaneously forms a hemi-acetal.

In some embodiments the hemi-acetal is oxidized to form a lactone by a hemi-acetal specific oxidase. TABLE 1 lists hemi-acetal specific oxidases.

TABLE 1

| Protein | Genbank ID | GI number | Organism | SEQ ID NO |
|---|---|---|---|---|
| Zwf | NP_416366.1 | 16129805 | Escherichia coli K-12 MG1655 | 21 |
| G6PD | P37986.1 | 585164 | Dickeya dadantii 3937 | 22 |
| G6PD | Q9Z8U6.1 | 6225396 | Chlamydia pneumoniae | 23 |

In some embodiments, hemi-acetal oxidases as described herein are derived from microorganisms of the genus Escherichia In some embodiments, the hemi-acetal oxidase is derived from Escherichia coli K-12 MG1655. In some embodiments, a hemi-acetal oxidase as used in a process described herein comprises an amino acid sequence of SEQ ID NO: 21 or active fragments or homologues thereof.

In some embodiments, the hemi-acetal oxidase is an enzyme comprising an amino acid sequence encoded by a DNA which comprises the nucleotide sequence of SEQ ID NO: 24.

In some embodiments, the gamma-lactone pathway disclosed herein comprises the condensation of one aldehyde molecule to pyruvate using enzyme from class aldolases. In some embodiments, the condensation of an aldehyde and a pyruvate molecule may be performed using an enzyme from class aldolases. In some embodiments, the enzyme from the class aldolases is a pyruvate dependent aldolase (PDA).

In some embodiments, sources of encoding nucleic acids for the pathway enzymes described herein are not particularly restricted and may include any species where the encoded gene product may catalyze the relevant reaction. The enzymes may be derived from, but not limited to, the following species: *Paraburkholderia xenovorans* LB400, *Agrobacterium tumefaciens, Bacillus cereus, Bacillus halodurans, Bacillus subtilis, Helicobacter pylori, Lactobacillus brevis, Pseudomonas aeruginosa, Pseudomonas putida, Pseudomonas synringae, Rhodopseudomonas palustris, Salmonella typhimurium, Saccharomyces cerevisiae, Clostridium acetobutylicum*. TABLE 2 illustrates exemplary pyruvate dependent aldolase enzymes.

TABLE 2

| Protein | Genbank ID | GI number | Organism | SEQ ID NO |
|---|---|---|---|---|
| EDA | NP_416364 | 16129803 | Escherichia coli K-12 MG1655 | 25 |
| MphE | NP_414886 | 16128337 | Escherichia coli K-12 MG1655 | 26 |
| BphI | ABE37049 | 91693852 | Paraburkholderia xenovorans LB400 | 27 |

In some embodiments, enzymes described herein may belong to the InterPro superfamily family IPR000887 and IPRO17629, which describe the pyruvate dependent aldolase family of enzymes.

In some embodiments, pyruvate dependent aldolase as described herein are derived from microorganisms of the genus Escherichia. In some embodiments, the pyruvate dependent aldolase is derived from Escherichia coli K-12 MG1655. In some embodiments, a pyruvate dependent aldolase as used in a process described herein comprises an amino acid sequence of SEQ ID Nos: 25 or 26, or active fragments or homologues thereof.

In some embodiments, the pyruvate dependent aldolase is an enzyme comprising an amino acid sequence encoded by a DNA which comprises the nucleotide sequence of SEQ ID NO: 28 or 29.

In some embodiments, sources of encoding nucleic acids for the pathway enzymes described herein are not particularly restricted and may include any species where the encoded gene product may catalyze the relevant reaction. The enzymes may be derived from, but not limited to, the following species: *Agrobacterium tumefaciens, Bacillus cereus, Bacillus halodurans, Bacillus subtilis. Helicobacter pylori. Lactobacillus brevis. Pseudomonas aeruginosa. Pseudomonas putida, Pseudomonas synringae, Rhodopseudomonas palustris. Salmonella typhimurium, Saccharomyces cerevisiae, Clostridium acetobutylicum*. TABLE 3 illustrates exemplary aldo-keto reductase enzymes.

TABLE 3

| Protein | Genebank ID | GI number | Organism | SEQ ID NO |
|---|---|---|---|---|
| AKR11B | CAB12792.1 | 2633288 | Bacillus subtilis | 30 |
| PA1127 | NP_249818.1 | 15596324 | Pseudomonas aeruginosa | 31 |
| AKR | WP_010898315 | 499200775 | Bacillus halodurans | 32 |
| AKR | NP_790200 | 28867581 | Pseudomonas syringae | 33 |

In some embodiments, enzymes described herein may belong to the InterPro superfamily family IPR023210, IPR001395, IPR018170, and IPRO20471, which describes the aldo-keto reductase family of enzymes that possess a beta-alpha-beta fold which comprises a parallel 8 beta/alpha barrel which contains the NADP binding motif.

In some embodiments, there is provided an alcohol dehydrogenase, aldo-keto reductases (AKR), oxidoreductase, or aldehyde reductase capable of selectively reducing trans-2-unsaturated aldehydes to trans-2-unsaturated alcohols or to trans-2-unsaturated carboxylic acids. In some embodiments, there is provided alcohol dehydrogenases, aldo-keto reductases (AKR), oxidoreductases, or aldehyde reductases capable of selectively reducing 2-keto-4-hydroxy aldehydes to 2,4-dihydroxy aldehydes. In some embodiments, there is provided alcohol dehydrogenases, aldo-keto reductases (AKR), oxidoreductases, or aldehyde reductases capable of selectively reducing 4-hydroxy-2-oxo carboxylic acid to 2,4-dihydroxy carboxylic acid. In some embodiments, the source of this enzyme is not particularly restricted.

In some embodiments, aldo-keto reductases (AKRs) as described herein are derived from microorganisms of the genus *Pseudomonas*. In some embodiments, an AKR as provided herein is derived from *Pseudomonas aeruginosa*. In some embodiments, an AKR as used in a process described herein comprises an amino acid sequence of SEQ ID NO: 31 or active fragments or homologues thereof.

In some embodiments, the AKR is an enzyme comprising an amino acid sequence encoded by a DNA which comprises the nucleotide sequence of SEQ ID NO: 34.

In some embodiments, L-threonine is the starting metabolite for the production of 2-ketobutyrate by pathways disclosed herein. It is a common metabolite but it may be produced by a sequence of reactions starting from L-aspartate.

In some embodiments, L-threonine is produced from L-aspartate by sequential reactions catalyzed by aspartate kinase/homoserine dehydrogenase (ThrA) (EC 2.7.2.4), homoserine kinase (ThrB) (EC 2.7.1.39) and threonine synthase (ThrC) (EC 4.2.3.1). The reaction proceeds via L-aspatyl-4-phosphate, L-aspartate semialdehyde, L-homoserine and O-phospho-L-homoserine. Over expression of aspartate kinase/homoserine dehydrogenase, homoserine kinase and threonine synthase leads to increased levels of L-threonine [Mak. W. S., et al., *Integrative genomic mining for enzyme function to enable engineering of a non-natural biosynthetic pathway*. Nat Commun, 2015, 6: p. 10005.; Rodriguez, G. M, and S. Atsumi, *Toward aldehdle and alkane production by removing aldehyde reductase activity in Escherichia coli*. Metab Eng, 2014, 25: p. blast.ncbi.nlm.nih.gov/Blast.cgi227-37.; Zhang, K., et al., *Expanding metabolism for biosynthesis of nonnatural alcohols*. Proc Natl Acad Sci USA, 2008, 105(52): p. 20653-8.1. TABLE 4 illustrates examples of isopropylmalate synthases, isopropylmalate dehydratases and 3-isopropylmalate dehydrogenases.

TABLE 4

| Protein | Genbank ID | GI number | Organism | SEQ ID NO |
|---|---|---|---|---|
| ThrA | NP_414543.1 | 16127996 | *Escherichia coli* K-12 MG1655 | 35 |
| ThrA | P27725.1 | 113540 | *Serratia marcescens* | 36 |
| ThrA | Q89AR4.1 | 38372169 | *Buchnera aphidicola* str. Bp (*Baizongia pistaciae*) | 37 |
| ThrB | NP_414544.1 | 16127997 | *Escherichia coli* K-12 MG1655 | 38 |
| ThrB | Q8DEP3.1 | 32129677 | *Vibrio vulnificus* CMCP6 | 39 |
| ThrB | Q057U7.1 | 122285538 | *Buchnera aphidicola* BCc | 40 |
| ThrC | NP_414545.1 | 16127998 | *Escherichia coli* K-12 MG1655 | 41 |
| ThrC | P44503.1 | 1174691 | *Haemophilus influenzae* Rd KW20 | 42 |
| ThrC | P29363.3 | 12231046 | *Pseudomonas aeruginosa* PAO1 | 43 |

In some embodiments, aspartate kinases/homoserine dehydrogenases as described herein are derived from microorganisms of the genus *Escherichia*. In some embodiments, the aspartate kinase/homoserine dehydrogenase is derived from *Escherichia coli* K-12 MG655. In some embodiments, an aspartate kinase/homoserine dehydrogenase as used in a process described herein comprises an amino acid sequence of SEQ ID NO: 35 or active fragments or homologues thereof.

In some embodiments, the aspartate kinase/homoserine dehydrogenase is an enzyme comprising an amino acid sequence encoded by a DNA which comprises the nucleotide sequence of SEQ ID NO: 44.

In some embodiments, homoserine kinases as described herein are derived from microorganisms of the genus *Escherichia*. In some embodiments, the homoserine kinase is derived from *Escherichia coli* K-12MG1655. In some embodiments, a homoserine kinase as used in a process described herein comprises an amino acid sequence of SEQ ID NO: 38 or active fragments or homologues thereof.

In some embodiments, the homoserine kinase is an enzyme comprising an amino acid sequence encoded by a DNA which comprises the nucleotide sequence of SEQ ID NO: 45.

In some embodiments, threonine synthases as described herein are derived from microorganisms of the genus *Escherichia*. In some embodiments, the threonine synthase is derived from *Escherichia coli* K-12MG1655. In some embodiments, a threonine synthase used in a process as described herein comprises an amino acid sequence of SEQ ID NO: 41 or active fragments or homologues thereof.

In some embodiments, the threonine synthase is an enzyme comprising an amino acid sequence encoded by a DNA which comprises the nucleotide sequence of SEQ ID NO: 46.

In some embodiments, 2-ketobutyrate is the starting metabolite for the production of longer chain precursor 2-ketoacids by pathways disclosed herein. In some embodiments, 2-ketobutyrate is produced by dehydration of L-threonine.

In some embodiments, 2-ketobutyrate is produced by dehydration of L-threonine by threonine dehydratase (IlvA) (EC 4.3.1.19) to yield water and 2-aminobut-2-enoate, which spontaneously converts into 2-ketobutyrate. Over expression of threonine dehydratase leads to increased levels of 2-ketobutyrate [Mak, W. S., et al., *Integrative genomic mining for enzyme function to enable engineering of a non-natural biosynthetic pathway*. Nat Commun. 2015, 6: p. 10005.; Rodriguez, G. M, and S. Atsumi, *Toward aldehyde and alkane production by removing aldehyde reductase activity in Escherichia coli*. Metab Eng, 2014, 25: p. blast.ncbi.nlm.nih.gov/Blast.cgi227-37.; Zhang, K., et al., *Expanding metabolism for biosynthesis of nonnatural alcohols*. Proc Natl Acad Sci USA, 2008, 105(52): p. 20653-8.]. TABLE 5 illustrates exemplary threonine dehydratases.

TABLE 5

| Protein | Genebank ID | GI number | Organism | SEQ ID NO |
|---|---|---|---|---|
| IlvA | NP_418220 | 16131630 | *Escherichia coli* K-12 MG1655 | 47 |
| IlvA | Q9CKJ2.1 | 20140770 | *Pasteurella multocida* subsp. *multocida* str. Pm70 | 48 |
| IlvA | P53607.1 | 1729930 | *Burkholderia multivorans* ATCC 17616 | 49 |

In some embodiments, threonine dehydratase as described herein are derived from microorganisms of the genus *Escherichia*. In some embodiments, the threonine dehydratase is derived from *Escherichia coli* K-12 MGI655. In some embodiments, a threonine dehydratase as used in a process described herein comprises an amino acid sequence of SEQ ID NO: 47 or active fragments or homologues thereof.

In some embodiments, the threonine dehydratase is an enzyme comprising an amino acid sequence encoded by a DNA which comprises the nucleotide sequence of SEQ ID NO: 50.

In some embodiments, 2-ketoacids of different chain length are the starting metabolites for the production of longer chain precursor aldehydes by pathways disclosed herein. In some embodiments, 2-ketoacids are produced by multiple reactions starting from 2-ketobutyrate.

In some embodiments, 2-ketoacids such as 2-ketovalerate, 2-ketoheptanoic acid and 2-ketooctanoic acid are produced from 2-ketobutyrate by sequential reactions catalyzed by 2-isopropylmalate synthase (LeuA) (EC 2.3.3.13), isopropylmalate dehydratase (LeuC) (EC 4.2.1.33; 4.2.1.35) and/or 3-isopropylmalate dehydrogenase (LeuB) (EC1.1.1.85). Each cycle requires one acetyl-CoA and leads to chain elongation. In some embodiments, longer chains are produced by passing the cycle several times. Over expression of the enzymes (e.g., 2-isopropylmalate synthase, isopropylmalate dehydratase, and/or 3-isopropylmalate) dehydrogenase can lead to increased levels of 2-ketoacid production [Mak, W. S., et al., *Integrative genomic mining for enzyme function to enable engineering of a non-natural biosynthetic pathway.* Nat Commun, 2015, 6: p. 10005.; Rodriguez. G. M, and S. Atsumi, *Toward aldehyde and alkane production by removing aldehyde reductase activity in Escherichia coli.* Metab Eng, 2014, 25: p. blast.ncbi.nlm-.nih.gov/Blast.cgi 227-37.; Zhang, K., et al., *Expanding metabolism for biosynthesis of nonnatural alcohols.* Proc Natl Acad Sci USA, 2008, 105(52): p. 20653-8.]. TABLE 6 illustrates examples of isopropylmalate synthases, isopropylmalate dehydratases and 3-isopropylmalate dehydrogenases.

In some embodiments, 2-isopropylmalate synthases as described herein are derived from microorganisms of the genus *Escherichia*. In some embodiments, the 2-isopropylmalate synthase is derived from *Escherichia coli* K-12 MG1655. In some embodiments, a 2-isopropylmalate synthase as used in a process described herein comprises an amino acid sequence of SEQ ID NO: 51 or active fragments or homologues thereof.

In some embodiments, the 2-isopropylmalate synthase is an enzyme comprising an amino acid sequence encoded by a DNA which comprises the nucleotide sequence of SEQ ID NO: 63.

In some embodiments, 3-isopropylmalate dehydrogenases as described herein are derived from microorganisms of the genus *Escherichia*. In some embodiments, the 3-isopropylmalate dehydrogenase is derived from *Escherichia coli* K-12 MG1655. In some embodiments, a 3-isopropylmalate dehydrogenase as used in a process described herein comprises an amino acid sequence of SEQ ID NO: 54 or active fragments or homologues thereof.

In some embodiments, the 3-isopropylmalate dehydrogenase is an enzyme comprising an amino acid sequence encoded by a DNA which comprises the nucleotide sequence of SEQ ID NO: 64.

In some embodiments, 3-isopropylmalate dehydratases as described herein are derived from microorganisms of the genus *Escherichia*. In some embodiments, the 3-isopropylmalate dehydratase is derived from *Escherichia coli* K-12 MG655. In some embodiments, a 3-isopropylmalate dehydratase as used in a process described herein comprises an amino acid sequence of SEQ ID NO: 57 or active fragments or homologues thereof. In some embodiments, a isopropylmalate dehydratase as used in a process described herein comprises an amino acid sequence of SEQ ID NO: 60 or active fragments or homologues thereof.

In some embodiments, the isopropylmalate dehydratases is an enzyme comprising an amino acid sequence encoded by a DNA which comprises the nucleotide sequence of SEQ ID NO: 65.

In some embodiments, the starting aldehyde of any one of the pathways disclosed herein is butyraldehyde. In some embodiments, the butyraldehyde is a natural metabolite. In some embodiments, the butyraldehyde is produced by decarboxylation of 2-ketovalerate.

In some embodiments, butyraldehyde is produced by the decarboxylation of 2-ketovalerate by alpha-ketoacid decarboxylase (KDC) (EC 4.1.1.74) to yield butyraldehyde and carbon dioxide. KDC (KivD) from *Lactococcus lactis lactis* KF147 has broad substrate specificity, ranging from ketopropionic acid to keto-octonoic acid, with highest activity observed for keto-valerate. [Mak, W. S., et al., *Integrative genomic mining for enzyme function to enable engineering of a non-natural biosynthetic pathway.* Nat Commun. 2015, 6: p. 10005.]. TABLE 7 illustrates examples of alpha-ketoacid decarboxylases.

TABLE 6

| Protein | Genebank ID | GI number | Organism | SEQ ID NO |
|---|---|---|---|---|
| LeuA | NP_414616.1 | 16128068 | *Escherichia coli* K-12 MG1655 | 51 |
| LeuA | Q9ZEY8.3 | 11182435 | *Buchnera aphidicola* str. APS | 52 |
| LeuA | Q47BI0.1 | 123626799 | *Dechloromonas aromatica* RCB | 53 |
| LeuB | NP_414615.4 | 90111082 | *Escherichia coli* K-12 MG1655 | 54 |
| LeuB | Q4QLS3.1 | 81335999 | *Haemophilus influenzae* 86-028NP | 55 |
| LeuB | Q8PH05.1 | 24211902 | *Xanthomonas axonopodis* pv. *citri* str. 306 | 56 |
| LeuC | NP_414614.1 | 16128066 | *Escherichia coli* K-12 MG1655 | 57 |
| LeuC | B1KKZ2.1 | 226736001 | *Shewanella woodyi* ATCC 51908 | 58 |
| LeuC | A6WXG4.1 | 166989645 | *Ochrobactrum anthropi* ATCC 49188 | 59 |
| LeuD | NP_414613.1 | 16128065 | *Escherichia coli* K-12 MG1655 | 60 |
| LeuD | C4LAV4.1 | 259494466 | *Tolumonas auensis* DSM 9187 | 61 |
| LeuD | C0ZCK0.1 | 254809060 | *Brevibacillus brevis* NBRC 100599 | 62 |

TABLE 7

| Protein | Genebank ID | GI number | Organism | SEQ ID NO |
|---|---|---|---|---|
| KivD | ADA65057.1 | 281375551 | *Lactococcus lactis lactis* KF147 | 66 |
| Indolepyruvate decarboxylase | P23234.1 | 118333 | *Enterobacter cloacae* | 67 |
| KDC | A0R480.1 | 189028401 | *Mycobacterium smegmatis* str. MC2 155 | 68 |

In some embodiments, alpha-ketoacid decarboxylases as described herein are derived from microorganisms of the genus *Lactococcus*. In some embodiments, the alpha-ketoacid decarboxylase is derived from *Lactococcus lactis lactis* KF147. In some embodiments, a alpha-ketoacid decarboxylase as used in a process described herein comprises an amino acid sequence of SEQ ID NO: 66 or active fragments or homologues thereof.

In some embodiments, the alpha-ketoacid decarboxylase a is an enzyme comprising an amino acid sequence encoded by a DNA which comprises the nucleotide sequence of SEQ ID NO: 69.

In some embodiments, butyraldehyde is obtained by the decarboxylation of 2-ketovalerate by KDC. In some embodiments, butyraldehyde is (alternatively or additionally) obtained by one or more of the reaction pathways identified in TABLE 8.

TABLE 8

| Kegg reaction ID | Enzyme Name | EC number | Reaction |
| --- | --- | --- | --- |
| R01172 | butanal: NAD+ oxidoreductase (CoA-acylating) | 1.2.1.10; 1.2.1.57; 1.2.1.87 | Butanal + CoA + NAD+ <=> Butanoyl-CoA + NADH + H+ |
| R01173 | butanal: NADP+ oxidoreductase (CoA-acylating | 1.2.1.57 | Butanal + CoA + NADP+ <=> Butanoyl-CoA + NADPH + H+ |
| R01172 | butanal: NAD+ oxidoreductase (CoA-acylating) | 1.2.1.10; 1.2.1.57; 1.2.1.87 | Butanal + CoA + NAD+ <=> Butanoyl-CoA + NADH + H+ |
| R03544 | butanol dehydrogenase | 1.1.1.- | Butanal + NADH + H+ <=> 1-Butanol + NAD+ |
| R03545 | butanol dehydrogenase | 1.1.1.- | Butanal + NADPH + H+ <=> 1-Butanol + NADP+ |

In some embodiments, hexanal is produced by the decarboxylation of 2-ketoheptanal by a mutated alpha-ketoacid decarboxylase (KDC) (EC 4.1.1.74) to yield hexanal and carbon dioxide. Three mutations G402V. M538L and F542V in KDC (KivD) from *Lactococcus lactis lactis* KF147 changes substrate specificity towards longer chain alpha-ketoacids, ranging from keto-hexanoic acid to keto-octonoic acid, with highest activity observed for keto-heptanoic acid. [Mak, W. S., et al., *Integrative genomic mining for enzyme function to enable engineering of a non-natural biosynthetic pathway*. Nat Commun. 2015, 6: p. 10005.].

In some embodiments, mutated KDCs showing high homology to KivD from *Lactococcus lactis lactis* KF147 might be used. Mutations include the following: G402V. M538L and F542. Amino acid positions are based on SEQ ID NO: 66.

In some embodiments, mutated alpha-ketoacid decarboxylases as described herein are derived from microorganisms of the genus *Lactococcus*. In some embodiments, the mutated alpha-ketoacid decarboxylase is derived from *Lactococcus lactis lactis* KF147. In some embodiments, a mutated alpha-ketoacid decarboxylase as used in a process described herein comprises an amino acid sequence of SEQ ID NO: 68 or active fragments or homologues thereof.

In some embodiments, the mutated alpha-ketoacid decarboxylase is an enzyme comprising an amino acid sequence encoded by a DNA which comprises the nucleotide sequence of SEQ ID NO: 70 or 79.

In some embodiments, the starting aldehyde of any one of the pathways disclosed herein is acetaldehyde which is a common central metabolite, or may be produced by decarboxylation of pyruvate.

In some embodiments, acetaldehyde is produced by the decarboxylation of pyruvate by pyruvate decarboxylase (PDC) (EC 4.1.1.1) to yield acetaldehyde and carbon dioxide. In some embodiments, the non-naturally occurring microorganism comprises a decarboxylase capable of the decarboxylaion of pyruvate to yield acetaldehyde and carbon dioxide. PDC from *S. cerevisiae* has a broad substrate range for aliphatic 2-keto acids. It has been extensively studied, engineered, and expressed in *E. coli* [Candy, J. M., Duggleby, R. G., & Mattick. J. S. (1991). Expression of active yeast pyruvate decarboxylase has also been studied. *Journal of General* Microbiology, (137), 5-9; Killenberg-Jabs, M., König, S., Hohmann, S., & Hübner, G. (1996). Purification and characterization of the pyruvate decarboxylase from a haploid strain of *S. cerevisiae* has been reported. [Biological Chemistry Hoppe-Seyler, 377(5), 313-7]. PDC from *Zymomonas mobilis* also has a broad substrate range for 2-keto acids, and has been extensively studied and expressed in *Escherichia coli* [Pohl, M., Siegert, P., Mesch, K., Bruhn, H., & Grotzinger, J. (1998). The role of residues glutamate-50 and phenylalanine-496 in *Zynomonas mobilis* pyruvate decarboxylase, the promoter and nucleotide sequences of the *Zymomonas mobilis* pyruvate decarboxylase, and the active site mutants of pyruvate decarboxylase from *Zymomonas mobilis* have been studied. [The Biochemical Journal, 315, Pt 3, 745-51. Conway. T., Osman, Y. a, Konnan, J. I., Hoffmann, E. M., & Ingram, L. O. (1987); *Journal of Bacteriology*, 169(3), 949-54. Siegert, P., Mesch, K., & Bruhn. H. (1998). *Eur. J. Biochem.*, 257, 538-546; Candy, J. M., Koga, J., Nixon, P. F., & Duggleby, R. G. (19%)]. The sequence identifiers for the exemplary PDC described herein may be found in TABLE 9 and searched for using the GenBank accession number (GI number).

TABLE 9

| Protein | Genebank ID | GI number | Organism | SEQ ID NO |
| --- | --- | --- | --- | --- |
| PDC | WP_011241152 | 499560369 | *Zymomonas mobilis* | 71 |
| PDC | P06169.7 | 30923172 | *Saccharomyces cerevisiae* | 72 |
| PDC | AEE86169 | 332660769 | *Arabidopsis thaliana* | 73 |
| PDC | KLA18896 | 821638028 | *Bacillus cereus* | 74 |

In some embodiments, PDCs as described herein are derived from microorganisms of the genus *Zymomonas*. In some embodiments, the PDC is derived from *Zymomonas mobilis*. In some embodiments, a PDC as used in a process described herein comprises an amino acid sequence of SEQ ID NO: 71 or active fragments or homologues thereof.

In some embodiments, the PDC is an enzyme comprising an amino acid sequence encoded by a DNA which comprises the nucleotide sequence of SEQ ID NO: 75.

Pyruvate decarboxylases have also been shown to act on pyruvate for the production of acetaldehyde may include, but are not limited to, benzoylformate decarboxylase (BFD) (EC 4.1.1.7) derived from *Pseudomonas putida* and branched chain alpha-ketoacid decarboxylase (KDC) derived from *Lactococcus lactis* [Gocke, D., Graf, T., Brosi, H., Frindi-Wosch, I., Walter, L., Möller, M., & Pohl, M. (2009). Comparative characterisation of thiamine diphosphate-dependent decarboxylases. Journal of Molecular Catalysis B: Enzymatic, 61(1-2), 30-35]. In addition, mutants of PDC and BFD that have been generated by site-directed mutagenesis including but not limited to: PDC 1472A, PDC I476F, PDC 1472A/I476F, BFD A460I, BFD F464I, and BFD A460I/F464I, have also shown activity on pyruvate towards acetaldehyde formation [Siegert, P., McLeish, M. J., Baumann, M., Iding, H., Kneen, M. M., Kenyon, G. L., & Pohl, M. (2005). Exchanging the substrate specificities of pyruvate decarboxylase from *Zymomonas mobilis* and benzoylformate decarboxylase from *Pseudomonas putida*. *Protein Engineering. Design & Selection*: PEDS, 18(7), 345-57].

In some embodiments, the non-naturally occurring microorganism further includes: a decarboxylase capable of the decarboxylation of pyruvate to yield acetaldehyde and carbon dioxide. In some embodiments, the decarboxylase comprises a pyruvate decarboxylase (PDC), which may comprise an amino acid sequence of SEQ ID NO: 71 or an active fragment or homologue thereof benzoylformate decarboxylase (BFD), which may comprise an amino acid sequence or SEQ ID NO: 76 or active fragment or homologue thereof, or alpha-detoacid decarboxylase (KDC), which may comprise an amino acid sequence of SEQ ID NO: 68 or 77 or active fragment or homologue thereof. The microorganism may alternatively or further express an enzyme identified in TABLE 9, and/or TABLE 10.

In some embodiments, the BFD described herein comprises an amino acid sequence of SEQ ID NO: 76 or active fragment or homologue thereof, and that of the KDC of SEQ ID NO: 68 or 77 or active fragments or homologues thereof.

In some embodiments, the BFD is an enzyme comprising an amino acid sequence encoded by a DNA which comprises the nucleotide sequence of SEQ ID NO: 78. In some embodiments, the KDC is an enzyme comprising an amino acid sequence encoded by a DNA which comprises the nucleotide sequence of SEQ ID NO: 79 or 70. In some embodiments, the processes as described herein are carried out with live cells. In some embodiments, the processes are carried out in vitro with lysed cells or with partially, or with substantially completely purified enzyme, or with purified enzyme. In some embodiments, the processes are carried out with permeabilized cells. In some embodiments, methods are carried out in vitro and the enzyme is immobilized. For example, the enzyme may be immobilized on a support (e.g., solid array) using a linker, such as using a biotin-(strept) avidin complex.

In some embodiments, the non-naturally occurring microorganism expresses at least one enzyme identified in TABLE 10. In some embodiments, acetaldehyde is obtained by the decarboxylation of pyruvate by PDC In some embodiments, acetaldehyde is (alternatively or additionally) obtained by one or more of the reaction pathways identified in TABLE 10 below.

TABLE 10

| KEGG REACTION ID | ENZYME NAME | EC NUMBER | REACTION |
|---|---|---|---|
| R00025 | ethylnitronate: oxygen 2-oxidoreductase (nitrite-forming) | 1.13.12.16 | Ethylnitronate + Oxygen + Reduced FMN <=> Acetaldehyde + Nitrite + FMN + H2O |
| R00224 | pyruvate carboxy-lyase (acetaldehyde-forming) | 4.1.1.1 | Pyruvate <=> Acetaldehyde + CO2 |
| R00228 | acetaldehyde: NAD+ oxidoreductase (CoA-acetylating) | 1.2.1.10 | Acetaldehyde + CoA + NAD+ <=> Acetyl-CoA + NADH + H+ |
| R00326 | acetaldehyde: acceptor oxidoreductase | 1.2.99.6 | Acetaldehyde + Acceptor + H2O <=> Acetate + Reduced acceptor |
| R00710 | Acetaldehyde: NAD+ oxidoreductase | 1.2.1.3, 1.2.1.5 | Acetaldehyde + NAD+ + H2O <=> Acetate + NADH + H+ |
| R00711 | Acetaldehyde: NADP+ oxidoreductase | 1.2.1.4, 1.2.1.5, 1.2.1.- | Acetaldehyde + NADP+ + H2O <=> Acetate + NADPH + H+ |
| R00746 | Ethanol: NADP+ oxidoreductase | 1.1.1.2, 1.1.1.71 | Ethanol + NADP+ <=> Acetaldehyde + NADPH + H+ |
| R00747 | 2-Phosphonoacetaldehyde phosphonohydrolase | 3.11.1.1 | Phosphonoacetaldehyde + H2O <=> Acetaldehyde + Orthophosphate |
| R00748 | ethanolamine-phosphate phosphate-lyase (deaminating; acetaldehyde-forming) | 4.2.3.2 | Ethanolamine phosphate + H2O <=> Acetaldehyde + Ammonia + Orthophosphate |
| R00749 | ethanolamine ammonia-lyase (acetaldehyde-forming) | 4.3.1.7 | Ethanolamine <=> Acetaldehyde + Ammonia |
| R00750 | 4-hydroxy-2-oxopentanoate pyruvate-lyase (acetaldehyde-forming) | 4.1.3.39 | Acetaldehyde + Pyruvate <=> 4-Hydroxy-2-oxopentanoate |
| R00751 | L-threonine acetaldehyde-lyase (glycine-forming) | 4.1.2.5 | L-Threonine <=> Glycine + Acetaldehyde |
| R00753 | (S)-lactate acetaldehyde-lyase (formate-forming) | 4.1.2.36 | (S)-Lactate <=> Formate + Acetaldehyde |
| R00754 | ethanol: NAD+ oxidoreductase | 1.1.1.1, 1.1.1.71 | Ethanol + NAD+ <=> Acetaldehyde + NADH + H+ |
| R00755 | Pyruvate decarboxylase, TPP dependent reaction | 4.1.1.1 | Acetaldehyde + Thiamin diphosphate <=> 2-(alpha-Hydroxyethyl)thiamine diphosphate |
| R00799 | Nitroethane: oxygen oxidoreductase | 1.7.3.1 | Nitrite + Acetaldehyde + Hydrogen peroxide <=> Nitroethane + Oxygen + H2O |

TABLE 10-continued

| KEGG REACTION ID | ENZYME NAME | EC NUMBER | REACTION |
|---|---|---|---|
| R01019 | acetaldehyde: pyrroloquinoline-quinone oxidoreductase | 1.2.99.3 | PQQ + Acetaldehyde + H2O <=> PQQH2 + Acetate |
| R01066 | 2-deoxy-D-ribose-5-phosphate acetaldehyde-lyase (D-glyceraldehyde-3-phosphate-forming) | 4.1.2.4 | 2-Deoxy-D-ribose 5-phosphate <=> D-Glyceraldehyde 3-phosphate + Acetaldehyde |
| R01410 | | | Hydrogen cyanide + Acetaldehyde + Ammonia <=> alpha-Aminopropiononitrile + H2O |
| R01841 | 17alpha-Hydroxyprogesterone acetaldehyde-lyase | 4.1.2.30 | 17alpha-Hydroxyprogesterone <=> Androstenedione + Acetaldehyde |
| R02345 | 3-Hydroxybutan-2-one: D-ribose-5-phosphate aldehydetransferase | 2.2.1.4 | Acetoin + D-Ribose 5-phosphate <=> Acetaldehyde + 1-Deoxy-D-altro-heptulose 7-phosphate |
| R03723 | 24R,24(1)R)-fucosterol-epoxide acetaldehyde-lyase (desmosterol-forming) | 4.1.2.33 | ((24R,24(1)R)-Fucosterol epoxide <=> Desmosterol + Acetaldehyde |
| R05198 | ethanol: cytochrome c oxidoreductase | 1.1.2.8 | Ethanol + 2 Ferricytochrome c <=> 2 Ferrocytochrome c + Acetaldehyde + 2H+ |
| R05380 | acetaldehyde hydro-lyase | 4.2.1.112 | Acetaldehyde <=> Acetylene + H2O |
| R05381 | diethanolamine ethanolamine-lyase (acetaldehyde-forming) | 4.3.3.- | Ethanolamine + Acetaldehyde <=> Diethanolamine |
| R05382 | triethanolamine diethanolamine-lyase (acetaldehyde-forming) | 4.3.3.- | Triethanolamine <=> Diethanolamine + Acetaldehyde |
| R05565 | | 1.14.15.- | 2 Atrazine + Oxygen <=> 2 Deethylatrazine + 2 Acetaldehyde |
| R05567 | | 1.14.15.- | 2 Deisopropylatrazine + Oxygen <=> 2 Deisopropyldeethylatrazine + 2 Acetaldehyde |
| R05811 | | 2.1.1.- | Cobalt-precorrin 5 + S-Adenosyl-L-methionine + H2O <=> Cobalt-precorrin 6 + S-Adenosyl-L-homocysteine + Acetaldehyde |
| R06171 | L-allo-threonine acetaldehyde-lyase (glycine-forming) | 4.1.2.5, 4.1.2.49 | L-Allothreonine <=> Glycine + Acetaldehyde |
| R06973 | | 4.1.1.- | 3-Oxopropanoate <=> Acetaldehyde + CO2 |
| R07247 | fluoroacetaldehyde: L-threonine aldehydetransferase | 2.2.1.8 | L-Threonine + Fluoroacetaldehyde <=> Acetaldehyde + 4-Fluoro-L-threonine |
| R07772 | cobalt-precorrin 5A acylhydrolase | 3.7.1.12 | Cobalt-precorrin 5A + H2O <=> Cobalt-precorrin 5B + Acetaldehyde |
| R08195 | D-threonine acetaldehyde-lyase (glycine-forming) | 4.1.2.42 | D-Threonine <=> Glycine + Acetaldehyde |
| R08196 | | | D-Allothreonine <=> Glycine + Acetaldehyde |
| R08516 | 17alpha-Hydroxypregnenolone acetaldehyde-lyase | 4.1.2.30 | 17alpha-Hydroxypregnenolone <=> Dehydroepiandrosterone + Acetaldehyde |
| R09127 | ethanol: cytochrome c oxidoreductase | 1.1.2.7 | Ethanol + 2 Ferricytochrome cL <=> Acetaldehyde + 2 Ferrocytochrome cL + 2H+ |
| R09156 | chloroethane, donor: oxygen oxidoreductase (dechlorinating, acetaldehyde-forming) | 1.13.12.-, 1.14.99.39 | Chloroethane + Oxygen + Reduced acceptor <=> Acetaldehyde + Hydrochloric acid + Acceptor + H2O |
| R09479 | ethanol: quinone oxidoreductase | 1.1.5.5 | Ethanol + Ubiquinone <=> Acetaldehyde + Ubiquinol |
| R09524 | acetyl-CoA: acetoin O-acetyltransferase | 2.3.1.190 | Acetoin + CoA + NAD+ <=> Acetaldehyde + Acetyl-CoA + NADH + H+ |
| R09552 | ethanol: N,N-dimethyl-4-nitrosoaniline oxidoreductase | 1.1.99.36 | Ethanol + N,N-Dimethyl-4-nitrosoaniline <=> Acetaldehyde + 4-(Hydroxylamino)-N,N-dimethylaniline |

TABLE 10-continued

| KEGG REACTION ID | ENZYME NAME | EC NUMBER | REACTION |
|---|---|---|---|
| R09959 | 7,8-dihydroneopterin 3'-triphosphate acetaldehyde-lyase (6-carboxy-5,6,7,8-tetrahydropterin and triphosphate-forming) | 4.1.2.50 | 7,8-Dihydroneopterin 3'-triphosphate + $H_2O$ <=> 6-Carboxy-5,6,7,8-tetrahydropterin + Acetaldehyde + Triphosphate |
| R10285 | choline trimethylamine-lyase (acetaldehyde-forming) | 4.3.99.4 | Choline <=> Trimethylamine + Acetaldehyde + $H^+$ |

In some embodiments, pyruvate is obtained by one or more of the reaction pathways identified in TABLE 11 below.

TABLE 11

| Kegg reaction ID | Enzyme Name | EC number | Reaction |
|---|---|---|---|
| R00006 | acetolactate synthase | 2.2.1.6 | 2-Acetolactate + $CO_2$ <=> 2 Pyruvate |
| R00008 | 4-hydroxy-4-methyl-2-oxoglutarate aldolase | 4.1.3.17 | Parapyruvate <=> 2 Pyruvate |
| R00014 | pyruvate dehydrogenase | 1.2.4.1 2.2.1.6 4.1.1.1 | Pyruvate + Thiamin diphosphate <=> 2-(alpha-Hydroxyethyl)thiamine diphosphate + $CO_2$ |
| R00195 | diaminopropionate ammonia-lyase | 4.3.1.15 | 2,3-Diaminopropanoate + $H_2O$ <=> Pyruvate + 2 Ammonia |
| R00196 | L-lactate dehydrogenase | 1.1.2.3 | (S)-Lactate + 2 Ferricytochrome c <=> Pyruvate + 2 Ferrocytochrome c + $2H^+$ |
| R00197 | D-lactate dehydrogenase | 1.1.2.4 | (R)-Lactate + 2 Ferricytochrome c <=> Pyruvate + 2 Ferrocytochrome c + $2H^+$ |
| R00198 | D-lactate dehydrogenase | 1.1.2.5 | (R)-Lactate + 2 Ferricytochrome c-553 <=> Pyruvate + 2 Ferrocytochrome c-553 + $2H^+$ |
| R00199 | pyruvate, water dikinase | 2.7.9.2 | ATP + Pyruvate + $H_2O$ <=> AMP + Phosphoenolpyruvate + Orthophosphate |
| R00200 | pyruvate kinase | 2.7.1.40 | ATP + Pyruvate <=> ADP + Phosphoenolpyruvate |
| R00203 | lactaldehyde dehydrogenase | 1.2.1.22 1.2.1.23 | Methylglyoxal + $NAD^+$ + $H_2O$ <=> Pyruvate + NADH + $H^+$ |
| R00205 | 2-oxoaldehyde dehydrogenase (NADP+) | 1.2.1.49 | Methylglyoxal + $NADP^+$ + $H_2O$ <=> Pyruvate + NADPH + $H^+$ |
| R00206 | pyruvate, phosphate dikinase | 2.7.9.1 | ATP + Pyruvate + Orthophosphate <=> AMP + Phosphoenolpyruvate + Diphosphate |
| R00207 | pyruvate oxidase | 1.2.3.3 | Pyruvate + Orthophosphate + Oxygen <=> Acetyl phosphate + Hydrogen peroxide + $CO_2$ |
| R00208 | phosphoenolpyruvate phosphatase | 3.1.3.60 | Phosphoenolpyruvate + $H_2O$ <=> Pyruvate + Orthophosphate |
| R00209 | pyruvate dehydrogenase (acetyl-transferring) | 1.2.4.1 1.8.1.4 2.3.1.12 | Pyruvate + CoA + $NAD^+$ <=> Acetyl-CoA + $CO_2$ + NADH + $H^+$ |
| R00210 | pyruvate dehydrogenase (NADP+) | 1.2.1.51 | Pyruvate + CoA + $NADP^+$ <=> Acetyl-CoA + $CO_2$ + NADPH + $H^+$ |
| R00211 | pyruvate oxidase (CoA-acetylating) | 1.2.3.6 | Pyruvate + CoA + Oxygen <=> Hydrogen peroxide + Acetyl-CoA $CO_2$ |
| R00212 | formate C-acetyltransferase | 2.3.1.54 | Acetyl-CoA + Formate <=> CoA + Pyruvate |
| R00213 | carbamoyl-serine ammonia-lyase | 4.3.1.13 | O-Carbamoyl-L-serine + $H_2O$ <=> Pyruvate + 2 Ammonia + $CO_2$ |
| R00214 | malate dehydrogenase (oxaloacetate-decarboxylating) | 1.1.1.38 1.1.1.39 | S)-Malate + $NAD^+$ <=> Pyruvate + $CO_2$ + NADH + $H^+$ |

TABLE 11-continued

| Kegg reaction ID | Enzyme Name | EC number | Reaction |
|---|---|---|---|
| R00215 | D-malate dehydrogenase (decarboxylating) | 1.1.1.83 | (R)-Malate + NAD+ <=> Pyruvate + CO2 + NADH + H+ |
| R00216 | malate dehydrogenase (oxaloacetate-decarboxylating) (NADP+) | 1.1.1.40 | (S)-Malate + NADP+ <=> Pyruvate + CO2 + NADPH + H+ |
| R00217 | malate dehydrogenase (oxaloacetate-decarboxylating) | 1.1.1.38 1.1.1.40 4.1.1.3 | Oxaloacetate <=> Pyruvate + CO2 |
| R00218 | acetylenedicarboxylate decarboxylase | 4.1.1.78 | Acetylenedicarboxylate + H2O <=> Pyruvate + CO2 |
| R00219 | | 4.1.1.- | 2-Hydroxyethylenedicarboxylate carboxy-lyase (pyruvate-forming |
| R00220 | L-serine ammonia-lyase | 4.3.1.17 4.3.1.19 | L-Serine <=> Pyruvate + Ammonia |
| R00221 | D-serine ammonia-lyase | 4.3.1.18 | D-Serine <=> Pyruvate + Ammonia |
| R00223 | diaminopropionate ammonia-lyase | 4.3.1.15 | Serine <=> Pyruvate + Ammonia |
| R00224 | pyruvate decarboxylase | 4.1.1.1 | Pyruvate <=> Acetaldehyde + CO2 |
| R00226 | acetolactate synthase | 2.2.1.6 | (S)-2-Acetolactate + CO2 <=> 2 Pyruvate |
| R00237 | (S)-citramalyl-CoA lyase | 4.1.3.25 | (3S)-Citramalyl-CoA <=> Acetyl-CoA + Pyruvate |
| R00258 | alanine transaminase | 2.6.1.2 | L-Alanine + 2-Oxoglutarate <=> Pyruvate + L-Glutamate |
| R00297 | D-lactate dehydrogenase (acceptor) | 1.1.99.6 | (R)-Lactate + Acceptor <=> Pyruvate + Reduced acceptor |
| R00324 | acetylpyruvate hydrolase | 3.7.1.6 | Acetylpyruvate + H2O <=> Acetate + Pyruvate |
| R00325 | citramalate lyase | 4.1.3.22 | (S)-2-Methylmalate <=> Acetate + Pyruvate |
| R00344 | pyruvate carboxylase | 6.4.1.1 | ATP + Pyruvate + HCO3− <=> ADP + Orthophosphate + Oxaloacetate |
| R00350 | 4-hydroxy-4-methyl-2-oxoglutarate aldolase | 4.1.3.17 | 4-Carboxy-4-hydroxy-2-oxoadipate <=> Oxaloacetate + Pyruvate |
| R00353 | methylmalonyl-CoA carboxytransferase | 2.1.3.1 | Malonyl-CoA + Pyruvate <=> Acetyl-CoA + Oxaloacetate |
| R00368 | strombine dehydrogenase | 1.5.1.22 | N-(Carboxymethyl)-D-alanine + NAD+ + H2O <=> Glycine + Pyruvate + NADH + H+ |
| R00369 | alanine-glyoxylate transaminase | 2.6.1.44 | L-Alanine + Glyoxylate <=> Pyruvate + Glycine |
| R00396 | alanine dehydrogenase | 1.4.1.1 | L-Alanine + NAD+ + H2O <=> Pyruvate + Ammonia + NADH + H+ |
| R00398 | alanopine dehydrogenase | 1.5.1.17 | Alanopine + NAD+ + H2O <=> L-Alanine + Pyruvate + NADH + H+ |
| R00400 | alanine-oxo-acid transaminase | 2.6.1.12 | L-Alanine + Oxaloacetate <=> Pyruvate + L-Aspartate |
| R00409 | methylisocitrate lyase | 4.1.3.30 | (2S,3R)-3-Hydroxybutane-1,2,3-tricarboxylate <=> Pyruvate + Succinate |
| R00430 | pyruvate kinase | 2.7.1.40 | GTP + Pyruvate <=> GDP + Phosphoenolpyruvate |
| R00452 | D-lysopine dehydrogenase | 1.5.1.16 | D-Lysopine + NADP+ + H2O <=> L-Lysine + Pyruvate + NADPH + H+ |
| R00453 | lysine-pyruvate 6-transaminase | 2.6.1.71 | L-Lysine + Pyruvate <=> L-2-Aminoadipate 6-semialdehyde + L-Alanine |
| R00470 | 4-hydroxy-2-oxoglutarate aldolase | 4.1.3.16 4.1.3.42 | 4-Hydroxy-2-oxoglutarate <=> Pyruvate + Glyoxylate |
| R00471 | 4.1.3.16 | 4.1.3.16 | (4R)-4-Hydroxy-2-oxoglutarate <=> Pyruvate + Glyoxylate |
| R00532 | serine-sulfate ammonia-lyase | 4.3.1.10 | L-Serine O-sulfate + H2O <=> Pyruvate + Ammonia + Sulfate |
| R00543 | acylpyruvate hydrolase | 3.7.1.5 | 3-Acylpyruvate + H2O <=> Carboxylate + Pyruvate |

TABLE 11-continued

| Kegg reaction ID | Enzyme Name | EC number | Reaction |
|---|---|---|---|
| R00562 | D-octopine dehydrogenase | 1.5.1.11 | D-Octopine + NAD+ + H2O <=> L-Arginine + Pyruvate + NADH + H+ |
| R00572 | pyruvate kinase | 2.7.1.40 | CTP + Pyruvate <=> CDP + Phosphoenolpyruvate |
| R00576 | glutamine-pyruvate transaminase | 2.6.1.15 | L-Glutamine + Pyruvate <=> 2-Oxoglutaramate + L-Alanine |
| R00585 | serine-pyruvate transaminase | 2.6.1.51 | L-Serine + Pyruvate <=> Hydroxypyruvate + L-Alanine |
| R00659 | pyruvate kinase | 2.7.1.40 | UTP + Pyruvate <=> UDP + Phosphoenolpyruvate |
| R00666 | N5-(carboxyethyl)ornithine synthase | 1.5.1.24 | N5-(L-1-Carboxyethyl)-L-ornithine + NADP+ + H2O <=> L-Ornithine + Pyruvate + NADPH + H+ |
| R00673 | Tryptophanase | 4.1.99.1 | L-Tryptophan + H2O <=> Indole + Pyruvate + Ammonia |
| R00692 | phenylalanine(histidine) transaminase | 2.6.1.58 | L-Phenylalanine + Pyruvate <=> Phenylpyruvate + L-Alanine |
| R00703 | L-lactate dehydrogenase | 1.1.1.27 | (S)-Lactate + NAD+ <=> Pyruvate + NADH + H+ |
| R00704 | D-lactate dehydrogenase | 1.1.1.28 | (R)-Lactate + NAD+ <=> Pyruvate + NADH + H+ |
| R00724 | pyruvate kinase | 2.7.1.40 | ITP + Pyruvate <=> IDP + Phosphoenolpyruvate |
| R00728 | tyrosine phenol-lyase | 4.1.99.2 | L-Tyrosine + H2O <=> Phenol + Pyruvate + Ammonia |
| R00750 | 4-hydroxy-2-oxovalerate aldolase | 4.1.3.39 | Acetaldehyde + Pyruvate <=> 4-Hydroxy-2-oxopentanoate |
| R00782 | cystathionine gamma-lyase | 4.4.1.1 4.4.1.8 4.4.1.28 | L-Cysteine +H2O <=> Hydrogen sulfide + Pyruvate + Ammonia |
| R00906 | beta-alanopine dehydrogenase | 1.5.1.26 | beta-Alanopine + NAD+ + H2O <=> beta-Alanine + Pyruvate + NADH + H+ |
| R00907 | beta-alanine-pyruvate transaminase | 2.6.1.18 | L-Alanine + 3-Oxopropanoate <=> Pyruvate + beta-Alanine |
| R00930 | methylmalonyl-CoA carboxytransferase | 2.1.3.1 | (S)-Methylmalonyl-CoA + Pyruvate <=> Propanoyl-CoA + Oxaloacetate |
| R00985 | anthranilate synthase | 4.1.3.27 | Chorismate + Ammonia <=> Anthranilate + Pyruvate + H2O |
| R00986 | anthranilate synthase | 4.1.3.27 | Chorismate + L-Glutamine <=> Anthranilate + Pyruvate + L-Glutamate |
| R01012 | phosphoenolpyruvate-glycerone phosphotransferase | 2.7.1.121 | Phosphoenolpyruvate + Glycerone <=> Pyruvate + Glycerone phosphate |
| R01031 | 3-chloro-D-alanine dehydrochlorinase | 4.5.1.2 | 3-Chloro-D-alanine + H2O <=> Pyruvate + Hydrochloric acid + Ammonia |
| R01032 | | unclear reaction | Cl− + Pyruvate + Ammonia <=> 3-Chloro-L-alanine + H2O |
| R01064 | 2-dehydro-3-deoxy-6-phosphogalactonate aldolase | 4.1.2.21 4.1.2.55 | 2-Dehydro-3-deoxy-6-phospho-D-galactonate <=> Pyruvate + D-Glyceraldehyde 3-phosphate |
| R01085 | acylpyruvate hydrolase | 3.7.1.5 3.7.1.20 | 3-Fumarylpyruvate + H2O <=> Fumarate + Pyruvate |
| R01138 | pyruvate kinase | 2.7.1.40 | dATP + Pyruvate <=> dADP + Phosphoenolpyruvate |
| R01147 | Pyridoxamine-5'-phosphate: 2-oxoglutarate aminotransferase | | Pyridoxamine phosphate + Pyruvate <=> Pyridoxal phosphate + D-Alanine |
| R01148 | D-amino-acid transaminase | 2.6.1.21 | D-Alanine + 2-Oxoglutarate <=> Pyruvate + D-Glutamate |
| R01196 | pyruvate synthase | 1.2.7.1 1.2.7.11 | 2 Reduced ferredoxin + Acetyl-CoA + CO2 + 2H+ <=> 2 Oxidized ferredoxin + Pyruvate + CoA |
| R01215 | valine-pyruvate transaminase | 2.6.1.66 | L-Valine + Pyruvate <=> 3-Methyl-2-oxobutanoic acid + L-Alanine |
| R01261 | alanine-oxo-acid transaminase | 2.6.1.12 | L-Alanine + 2-Oxo acid <=> Pyruvate + L-Amino acid |

TABLE 11-continued

| Kegg reaction ID | Enzyme Name | EC number | Reaction |
|---|---|---|---|
| R01286 | cystathionine beta-lyase | 4.4.1.8 | L-Cystathionine + H2O <=> L-Homocysteine + Ammonia + Pyruvate |
| R01302 | chorismate lyase | 4.1.3.40 | 4-Hydroxybenzoate + Pyruvate <=> Chorismate |
| R01335 | | 3.7.1.- | Glycolate + Pyruvate <=> 5-Hydroxy-2,4-dioxopentanoate + H2O |
| R01344 | D-amino-acid transaminase | 2.6.1.21 | D-Amino acid + Pyruvate <=> 2-Oxo acid + D-Alanine |
| R01355 | 2,3-dimethylmalate lyase | 4.1.3.32 | (2R,3S)-2,3-Dimethylmalate <=> Propanoate + Pyruvate |
| R01447 | lactate-malate transhydrogenase | 1.1.99.7 | (S)-Lactate + Oxaloacetate <=> (S)-Malate + Pyruvate |
| R01576 | 3-deoxy-D-manno-octulosonate aldolase | 4.1.2.23 | 3-Deoxy-D-manno-octulosonate <=> Pyruvate + D-Arabinose |
| R01584 | N-methylalanine dehydrogenase | 1.4.1.17 | N-Methyl-L-alanine + H2O + NADP+ <=> Pyruvate + Methylamine + NADPH + H+ |
| R01645 | 4-hydroxy-2-oxoheptanedioate aldolase | 4.1.2.52 | 4-Hydroxy-2-oxo-heptanedioate <=> Succinate semialdehyde + Pyruvate |
| R01647 | 4-hydroxy-2-oxoheptanedioate aldolase | 4.1.2.52 | Succinate semialdehyde + Pyruvate <=> 2,4-Dihydroxyhept-2-enedioate |
| R01683 | tauropine dehydrogenase | 1.5.1.23 | Tauropine + NAD+ + H2O <=> Taurine + Pyruvate + NADH + H+ |
| R01699 | pyruvate dehydrogenase (acetyl-transferring) | 1.2.4.1 | Pyruvate + Enzyme N6-(lipoyl)lysine <=> [Dihydrolipoyllysine-residue acetyltransferase] S-acetyldihydrolipoyllysine + CO2 |
| R01712 | pyridoxamine-pyruvate transaminase | 2.6.1.30 | Pyridoxamine + Pyruvate <=> Pyridoxal + L-Alanine |
| R01782 | 2-dehydro-3-deoxy-D-pentonate aldolase | 4.1.2.28 | 2-Dehydro-3-deoxy-D-xylonate <=> Pyruvate + Glycolaldehyde |
| R01784 | 2-dehydro-3-deoxy-L-pentonate aldolase | 4.1.2.18 | 2-Dehydro-3-deoxy-L-arabinonate <=> Pyruvate + Glycolaldehyde |
| R01811 | N-acetylneuraminate lyase | 4.1.3.3 | N-Acetylneuraminate <=> N-Acetyl-D-mannosamine + Pyruvate |
| R01858 | pyruvate kinase | 2.7.1.40 | dGTP + Pyruvate <=> dGDP + Phosphoenolpyruvate |
| R01874 | D-cysteine desulfhydrase | 4.4.1.15 | D-Cysteine + H2O <=> Hydrogen sulfide + Ammonia + Pyruvate |
| R02050 | (R)-3-amino-2-methylpropionate-pyruvate transaminase | 2.6.1.40 | (R)-3-Amino-2-methylpropanoate + Pyruvate <=> 2-Methyl-3-oxopropanoate + L-Alanine |
| R02261 | 2-keto-3-deoxy-L-rhamnonate aldolase | 4.1.2.53 | 2-Dehydro-3-deoxy-L-rhamnonate <=> (S)-Lactaldehyde + Pyruvate |
| R02271 | aminolevulinate transaminase | 2.6.1.43 | 5-Aminolevulinate + Pyruvate <=> 4,5-Dioxopentanoate + L-Alanine |
| R02293 | diaminobutyrate-pyruvate transaminase | 2.6.1.46 | L-2,4-Diaminobutanoate + Pyruvate <=> L-Aspartate 4-semialdehyde + L-Alanine |
| R02320 | pyruvate kinase | 2.7.1.40 | Nucleoside triphosphate + Pyruvate <=> NDP + Phosphoenolpyruvate |
| R02408 | cystathionine gamma-lyase | 4.4.1.1 4.4.1.8 | L-Cystine + H2O <=> Pyruvate + Ammonia + Thiocysteine |
| R02628 | phosphoenolpyruvate-protein phosphotransferase | 2.7.3.9 | Phosphoenolpyruvate + Protein histidine <=> Pyruvate + Protein N(pi)-phospho-L-histidine |
| R02721 | | unclear reaction | D-Glyceraldehyde 3-phosphate + Pyruvate <=> 5-(2-Hydroxyethyl)-4-methylthiazole |
| R02754 | 2-dehydro-3-deoxyglucarate aldolase | 4.1.2.20 | 5-Dehydro-4-deoxy-D-glucarate <=> Pyruvate + 2-Hydroxy-3-oxopropanoate |
| R02953 | S-alkylcysteine lyase | 4.4.1.6 | S-Alkyl-L-cysteine + H2O <=> Alkyl thiol + Ammonia + Pyruvate |
| R02970 | alanine-oxomalonate transaminase | 2.6.1.47 | Pyruvate + Aminomalonate <=> L-Alanine + Oxomalonate |

TABLE 11-continued

| Kegg reaction ID | Enzyme Name | EC number | Reaction |
|---|---|---|---|
| R03001 | D-methionine-pyruvate transaminase | 2.6.1.41 | D-Methionine + Pyruvate <=> 4-Methylthio-2-oxobutanoic acid + L-Alanine |
| R03037 | Isochorismatase | 3.3.2.1 | Isochorismate + H2O <=> (2S,3S)-2,3-Dihydro-2,3-dihydroxybenzoate + Pyruvate |
| R03050 | acetolactate synthase | 2.2.1.6 | 2-Acetolactate + Thiamin diphosphate <=> 2-(alpha-Hydroxyethyl)thiamine diphosphate + Pyruvate |
| R03081 | 2-dehydro-3-deoxy-L-pentonate aldolase | 4.1.2.18 | 2-Dehydro-3-deoxy-D-fuconate <=> Pyruvate + (R)-Lactaldehyde |
| R03105 | 3-mercaptopyruvate sulfurtransferase | 2.8.1.2 | Mercaptopyruvate + Sulfite <=> Thiosulfate + Pyruvate |
| R03106 | 3-mercaptopyruvate sulfurtransferase | 2.8.1.2 | Hydrogen cyanide + Mercaptopyruvate <=> Thiocyanate + Pyruvate |
| R03145 | pyruvate dehydrogenase (quinone) | 1.2.5.1 | Pyruvate + Ubiquinone + H2O <=> Acetate + Ubiquinol + CO2 |
| R03277 | 2-dehydro-3-deoxyglucarate aldolase | 4.1.2.20 | 2-Hydroxy-3-oxopropanoate + Pyruvate <=> 2-Dehydro-3-deoxy-D-glucarate |
| R03465 | 4-(2-carboxyphenyl)-2-oxobut-3-enoate aldolase | 4.1.2.34 | (3E)-4-(2-Carboxyphenyl)-2-oxobut-3-enoate + H2O <=> 2-Carboxybenzaldehyde + Pyruvate |
| R03502 | 1D-1-guanidino-3-amino-1,3-dideoxy-scyllo-inositol transaminase | 2.6.1.56 | 1D-1-Guanidino-3-amino-1,3-dideoxy-scyllo-inositol + Pyruvate <=> 1D-1-Guanidino-1-deoxy-3-dehydro-scyllo-inositol + L-Alanine |
| R03528 | cysteine-S-conjugate beta-lyase | 4.4.1.13 | L-Cysteine-S-conjugate + H2O <=> Aryl thiol + Ammonia + Pyruvate |
| R03732 | opine dehydrogenase | 1.5.1.28 | (2S)-2-{[1-(R)-Carboxyethyl]amino}pentanoate + NAD+ + H2O <=> L-Norvaline + Pyruvate + NADH + H+ |
| R03796 | oximinotransferase | 2.6.3.1 | Pyruvate oxime + Acetone <=> Pyruvate + Acetone oxime |
| R03854 | 2,2-dialkylglycine decarboxylase (pyruvate) | 4.1.1.64 | 2,2-Dialkylglycine + Pyruvate <=> Dialkyl ketone + CO2 + L-Alanine |
| R04152 | 2-aminoethylphosphonate-pyruvate transaminase | 2.6.1.37 | 2-Aminoethylphosphonate + Pyruvate <=> Phosphonoacetaldehyde + L-Alanine |
| R04187 | beta-alanine-pyruvate transaminase | 2.6.1.18 | L-Alanine + (S)-Methylmalonate semialdehyde <=> Pyruvate + L-3-Aminoisobutanoate |
| R04672 | acetolactate synthase | 2.2.1.6 | (S)-2-Acetolactate + Thiamin diphosphate <=> 2-(alpha-Hydroxyethyl)thiamine diphosphate + Pyruvate |
| R04861 | | non-enzymatic | 3-Sulfinylpyruvate + H2O <=> Sulfite + Pyruvate |
| R04941 | cystathionine beta-lyase | 4.4.1.8 | L-Selenocystathionine + H2O <=> Selenohomocysteine + Ammonia + Pyruvate |
| R05136 | trans-o-hydroxybenzylidene pyruvate hydratase-aldolase | 4.1.2.45 | Salicylaldehyde + Pyruvate <=> trans-o-Hydroxybenzylidenepyruvate + H2O |
| R05298 | 4-hydroxy-2-oxohexanoate aldolase | 4.1.3.43 | Propanal + Pyruvate <=> 4-Hydroxy-2-oxohexanoic acid |
| R05538 | | aldorase reaction | 2-Hydroxy-4-(1-oxo-1,3-dihydro-2H-inden-2-ylidene)-but-2-enoic acid + H2O <=> 2-Formyl-1-indanone + Pyruvate |
| R05544 | | | 2-Hydroxy-4-(2-oxo-1,3-dihydro-2H-inden-1-ylidene)but-2-enoic acid + H2O <=> 1-Formyl-2-indanone + Pyruvate |
| R05553 | aminodeoxychorismate lyase | 4.1.3.38 | 4-Amino-4-deoxychorismate <=> 4-Aminobenzoate + Pyruvate |

TABLE 11-continued

| Kegg reaction ID | Enzyme Name | EC number | Reaction |
|---|---|---|---|
| R05605 | 2-dehydro-3-deoxy-phosphogluconate aldolase | 4.1.2.14 4.1.2.55 | 2-Dehydro-3-deoxy-6-phospho-D-gluconate <=> D-Glyceraldehyde 3-phosphate + Pyruvate |
| R05636 | 1-deoxy-D-xylulose-5-phosphate synthase | 2.2.1.7 | Pyruvate + D-Glyceraldehyde 3-phosphate <=> 1-Deoxy-D-xylulose 5-phosphate + $CO_2$ |
| R05648 | | 4.1.2.- | cis-4-(1'-Hydroxynaphth-2'-yl)-2-oxobut-3-enoate + $H_2O$ <=> 1-Hydroxy-2-naphthaldehyde + Pyruvate |
| R05652 | taurine-pyruvate aminotransferase | 2.6.1.77 | Taurine + Pyruvate <=> Sulfoacetaldehyde + L-Alanine |
| R05861 | D-amino-acid oxidase | 1.4.3.3 1.4.3.19 | D-Alanine + $H_2O$ + Oxygen <=> Pyruvate + Ammonia + Hydrogen peroxide |
| R06602 | isochorismate lyase | 4.2.99.21 | Isochorismate <=> Salicylate + Pyruvate |
| R06603 | | | Chorismate <=> Salicylate + Pyruvate |
| R06913 | | 4.2.1.- | 2-Hydroxy-3-methylbenzalpyruvate + $H_2O$ <=> 3-Methylsalicylaldehyde + Pyruvate |
| R06923 | | 4.2.1.- | 2-Hydroxy-3-carboxybenzalpyruvate + $H_2O$ <=> 3-Formylsalicylic acid + Pyruvate |
| R06934 | | 4.2.1.- | 2-Hydroxy-4-hydroxymethylbenzalpyruvate + $H_2O$ <=> 4-Hydroxymethylsalicylaldehyde + Pyruvate |
| R07399 | (R)-citramalate synthase | 2.3.1.182 | Acetyl-CoA + Pyruvate + $H_2O$ <=> (R)-2-Methylmalate + CoA |
| R07633 | (2R)-sulfolactate sulfo-lyase | 4.4.1.24 | 3-Sulfolactate <=> Pyruvate + $HSO_3-$ |
| R07634 | L-cysteate sulfo-lyase | 4.4.1.25 | L-Cysteate + $H_2O$ <=> Pyruvate + $HSO_3-$ + Ammonia |
| R07685 | | | (Z)-4-(2-Hydroxy-5-sulfonatophenyl)-2-oxo-3-butenoate + $2H_2O$ <=> 5-Sulfosalicylate + Pyruvate |
| R07692 | | | 4-(3-Hydroxy-2-naphthyl)-2-oxobut-3-enoic acid + $2H_2O$ <=> 3-Hydroxy-2-naphthoate + Pyruvate |
| R07713 | 4-(2-carboxyphenyl)-2-oxobut-3-enoate aldolase | 4.1.2.34 | (3Z)-4-(2-Carboxyphenyl)-2-oxobut-3-enoate + $H_2O$ <=> 2-Carboxybenzaldehyde + Pyruvate |
| R08166 | 2-succinyl-6-hydroxy-2,4-cyclohexadiene-1-carboxylate synthase | 4.2.99.20 | 2-Succinyl-5-enolpyruvyl-6-hydroxy-3-cyclohexene-1-carboxylate <=> (1R,6R)-6-Hydroxy-2-succinylcyclohexa-2,4-diene-1-carboxylate + Pyruvate |
| R08170 | | 4.4.1.- | S-(Indolylmethylthiohydroximoyl)-L-cysteine + $H_2O$ <=> Indolylmethylthiohydroximate + Pyruvate + Ammonia |
| R08197 | arginine-pyruvate transaminase | 2.6.1.84 | L-Arginine + Pyruvate <=> 5-Guanidino-2-oxopentanoate + L-Alanine |
| R08200 | phosphonopyruvate hydrolase | 3.11.1.3 | 3-Phosphonopyruvate + $H_2O$ <=> Pyruvate + Orthophosphate |
| R08253 | | unclear reaction | Isoniazid + Pyruvate <=> Isoniazid pyruvate + $H_2O$ |
| R08570 | 2-dehydro-3-deoxy-D-gluconate aldolase | 4.1.2.51 4.1.2.55 | 2-Dehydro-3-deoxy-D-gluconate <=> D-Glyceraldehyde + Pyruvate |
| R08648 | acetolactate synthase | 2.2.1.6 | Pyruvate + 2-Oxobutanoate <=> (S)-2-Aceto-2-hydroxybutanoate + $CO_2$ |
| R08654 | | 4.4.1.- | S-(Phenylacetothiohydroximoyl)-L-cysteine + $H_2O$ <=> Phenylacetothiohydroximate + Pyruvate + Ammonia |

TABLE 11-continued

| Kegg reaction ID | Enzyme Name | EC number | Reaction |
|---|---|---|---|
| R08660 | | 4.4.1.- | S-(Hydroxyphenylacetothiohydroximoyl)-L-cysteine + H2O <=> p-Hydroxyphenylacetothiohydroximate + Pyruvate + Ammonia |
| R08667 | | 4.4.1.- | S-(4-Methylthiobutylthiohydroximoyl)-L-cysteine + H2O <=> 4-Methylthiobutylthiohydroximate + Pyruvate + Ammonia |
| R08686 | | 4.4.1.- | S-Alkyl-thiohydroximate + H2O <=> Thiohydroximic acid + Pyruvate + Ammonia |
| R08698 | | spontaneous | Dehydroalanine + H2O <=> Pyruvate + Ammonia |
| R08714 | | 2.6.1.- | Putrescine + Pyruvate <=> 4-Aminobutyraldehyde + L-Alanine |
| R09048 | | | 3 Cadaverine + 4 Pyruvate <=> 17-Oxosparteine + 4 L-Alanine + 3 H2O |
| R09088 | | | Benzoate + Pyruvate <=> Pyruvophenone + CO2 |
| R09238 | | 3.7.1.- | cis,cis-2,4-Dihydroxy-5-methyl-6-oxo-2,4-hexadienoate + H2O <=> (S)-Methylmalonate semialdehyde + Pyruvate |
| R09254 | phenylalanine(histidine) transaminase | 2.6.1.58 | L-Tyrosine + Pyruvate <=> 3-(4-Hydroxyphenyl)pyruvate + L-Alanine |
| R09366 | cystathionine gamma-lyase | 4.4.1.1 4.4.1.13 | Se-Methyl-L-selenocysteine + H2O <=> Pyruvate + Ammonia + Methaneselenol |
| R10147 | 4-hydroxy-tetrahydrodipicolinate synthase | 4.3.3.7 | L-Aspartate 4-semialdehyde + Pyruvate <=> (2S,4S)-4-Hydroxy-2,3,4,5-tetrahydrodipicolinate + H2O |
| R10178 | 4-aminobutyrate-pyruvate transaminase | 2.6.1.96 | 4-Aminobutanoate + Pyruvate <=> Succinate semialdehyde + L-Alanine |
| R10180 | L-tryptophan-pyruvate aminotransferase | 2.6.1.99 | L-Tryptophan + Pyruvate <=> Indolepyruvate + L-Alanine |
| R10283 | 4-hydroxy-2-oxoglutarate aldolase | 4.1.3.16 4.1.3.42 | (4S)-4-Hydroxy-2-oxoglutarate <=> Pyruvate + Glyoxylate |
| R10487 | (S)-dichlorprop dioxygenase (2-oxoglutarate) | 1.14.11.43 | (S)-(2,4-Dichlorophenoxy)propanoate + 2-Oxoglutarate + Oxygen <=> 2,4-Dichlorophenol + Pyruvate + Succinate + CO2 |
| R10527 | (S)-dichlorprop dioxygenase (2-oxoglutarate) | 1.14.11.43 | (S)-2-(4-Chloro-2-methylphenoxy)propanoate + 2-Oxoglutarate + Oxygen <=> 4-Chloro-2-methylphenol + Pyruvate + Succinate + CO2 |
| R10539 | (R)-dichlorprop dioxygenase (2-oxoglutarate) | 1.14.11.44 | Mecoprop-P + 2-Oxoglutarate + Oxygen <=> 4-Chloro-2-methylphenol + Pyruvate + Succinate + CO2 |
| R10542 | (R)-dichlorprop dioxygenase (2-oxoglutarate) | 1.14.11.44 | (R)-(2,4-Dichlorophenoxy)propanoate + 2-Oxoglutarate + Oxygen <=> 2,4-Dichlorophenol + Pyruvate + Succinate + CO2 |
| R10550 | L-threo-3-deoxy-hexylosonate aldolase | 4.1.2.54 | 2-Dehydro-3-deoxy-L-galactonate <=> Pyruvate + L-Glyceraldehyde |
| R10552 | tRNA 4-demethylwyosine synthase (AdoMet-dependent | 4.1.3.44 | N1-Methylguanine in tRNA(Phe) + Pyruvate + S-Adenosyl-L-methionine <=> 4-Demethylwyosine in tRNA(Phe) + L-Methionine + 5'-Deoxyadenosine + CO2 + H2O |
| R10583 | Chorismatase | 3.3.2.13 | Chorismate + H2O <=> (4R,5R)-4,5-Dihydroxycyclohexa-1(6),2-diene-1-carboxylate + Pyruvate |

TABLE 11-continued

| Kegg reaction ID | Enzyme Name | EC number | Reaction |
|---|---|---|---|
| R10597 | 3-hydroxybenzoate synthase | 4.1.3.45 | Chorismate <=> 3-Hydroxybenzoate + Pyruvate |
| R10616 | 2-dehydro-3-deoxy-D-gluconate aldolase | 4.1.2.51 4.1.2.55 | 2-Dehydro-3-deoxy-D-galactonate <=> Pyruvate + D-Glyceraldehyde |
| R10674 | (R)-citramalyl-CoA lyase | 4.1.3.46 | (3R)-Citramalyl-CoA <=> Acetyl-CoA + Pyruvate |
| R10691 | | 3.7.1.- | 2,4-Diketo-3-deoxy-L-fuconate + H2O <=> (S)-Lactate + Pyruvate |
| R10866 | | 1.2.7.- | Pyruvate + CoA + Oxidized flavodoxin <=> Acetyl-CoA + CO2 + Reduced flavodoxin |
| R10992 | alanine-glyoxylate transaminase | 2.6.1.44 | L-Alanine + 2-Oxobutanoate <=> Pyruvate + (S)-2-Aminobutanoate |
| R11023 | | 4.4.1.- | S-(Hercyn-2-yl)-L-cysteine S-oxide <=> Ergothioneine + Pyruvate + Ammonia |
| R11038 | (5-formylfuran-3-yl)methyl phosphate transaminase | 2.6.1.108 | (5-Formylfuran-3-yl)methyl phosphate + L-Alanine <=> [5-(Aminomethyl)furan-3-yl]methyl phosphate + Pyruvate |
| R11099 | | | 2-Iminopropanoate + H2O <=> Pyruvate + Ammonia |
| R11141 | 3-acetyloctanal synthase | 2.2.1.12 | Pyruvate + trans-2-Octenal <=> (S)-3-Acetyloctanal + CO2 |
| R11213 | 2-dehydro-3,6-dideoxy-6-sulfogluconate aldolase | 4.1.2.58 | 2-Dehydro-3,6-dideoxy-6-sulfo-D-gluconate <=> (2S)-3-Sulfolactaldehyde + Pyruvate |
| R11257 | maleylpyruvate hydrolase | 3.7.1.23 | Maleylpyruvate + H2O <=> Maleic acid + Pyruvate |

Microorganisms expressing enzyme(s) as described herein may be provided in various forms, including live forms e.g. in an aqueous solution or in culture medium or in "resting" forms such as in a freeze dried or tablet form.

In some embodiments, the method is carried out in culture, with one or more host microorganisms, producing the pathway enzyme(s).

In some embodiments, there is provided a microorganism which is genetically modified so as to contain a nucleic acid molecule encoding an aldolase as described herein capable of condensing two aldehyde molecules.

In some embodiments, there is provided a trans-2-unsaturated aldehyde pathway comprising a condensation step and a dehydration step. In some embodiments, the condensation step comprises the condensation of two aldehyde molecules to a 3-hydroxy aldehyde by using an aldolase. In some embodiments, the dehydration step comprises dehydration of the 3-hydroxy aldehyde to a trans-2-unsaturated aldehyde. In some embodiments, the dehydration step is via spontaneous dehydration. In some embodiments, the dehydration step comprises a dehydratase. In some embodiments, dehydration is aided by dehydratase.

In some embodiments, there is provided a non-naturally occurring microorganism having a trans-2-unsaturated aldehyde pathway, wherein the microorganism comprises at least one of the following trans-2-unsaturated aldehyde pathway enzymes: an aldolase that catalyzes condensation of two aldehydes to produce 3-hydroxy aldehyde; and a dehydratase that dehydrates the 3-hydroxy aldehyde to trans-2-unsaturated aldehyde (the dehydration step). In some embodiments, the dehydration step is via spontaneous dehydration. In some embodiments, the non-naturally occurring microorganism comprises an increased enzymatic activity of at least one enzyme in the trans-2-unsaturated aldehyde pathway in comparison with the enzymatic activity of the same enzyme in a corresponding unmodified, or naturally-occurring microorganism, or wild-type microorganism. In some embodiments, the trans-2-unsaturated aldehyde is converted to trans-2-unsaturated alcohol or trans-2-unsaturated carboxylic acids by using aldoketoreductases, oxidoreductases, aldehyde reductases or alcohol dehydrogenases. In some embodiments, the microorganism includes at least one exogenous nucleic acid encoding an enzyme from the trans-2-unsaturated aldehyde pathway. In some embodiments, the microorganism further includes a PDC for decarboxylation of pyruvate to yield acetaldehyde and carbon dioxide. In some embodiments, the microorganism expresses an enzyme identified in TABLE 9 and/or TABLE 10 or an active fragment or homologue thereof for producing acetaldehyde. In some embodiments, at least one or all the nucleic acids are exogenous to the host microorganism. In some embodiments, the aldolase is DERA. In some embodiments, the aldolase enzyme is a modified aldolase enzyme comprising an increased enzymatic activity in comparison with a corresponding unmodified or wild-type aldolase enzyme. In some embodiments, the non-naturally occurring microorganism expresses a modified aldolase. In some embodiments, the modified aldolase is a modified DERA. In some embodiments, the microorganism expressing a modified aldolase comprises an increased enzymatic activity of at least one enzyme in the trans-2-unsaturated aldehyde pathway, in comparison with the enzymatic activity of the same enzyme in the wild-type or naturally occurring, or unmodified microorganism. In some embodiments, the non-naturally occurring microorganism is derived from a wild-type or unmodified microorganism and the non-naturally occurring microorganism comprises an increased enzymatic activity of at least one enzyme in the trans-2-unsaturated aldehyde pathway, in comparison with the enzymatic activity of the same enzyme in the wild-type microorganism.

In some embodiments, trans-2-unsaturated aldehyde is produced by direct feeding of precursor aldehydes to cells expressing only aldolase (e.g., DERA or a similar aldolase). In some embodiments, trans-2-unsaturated aldehyde is produced from glucose. In some embodiments, precursor aldehydes are produced by the cell (e.g., via engineered pathways). In some embodiments, the engineered pathways require modification (e.g., expression or overexpression) of at least one gene. In some embodiments, strains (e.g., 2 different strains) are optimized to include at least one gene deletion(s). In some embodiments, acetaldehyde is produced in a cell (e.g., from glucose). In some embodiments, precursor aldehyde molecules (e.g., two precursor aldehydes) are produced from glucose. In some embodiments, precursor aldehyde molecules (e.g., two precursor aldehydes) are fed to the cell. In some embodiments, at least one precursor aldehyde is produced from glucose and at least one precursor aldehyde is fed to the cell. In some embodiments, at least one precursor aldehyde is fed to a cell following production of acetaldehyde from glucose.

In some embodiments, the trans-2-unsaturated aldehyde is produced by feeding precursor aldehydes to a microbial culture.

In some embodiments, the aldehyde precursors used for the formation of trans-2-unsaturated aldehyde are produced from glucose by an aldehyde producing pathway.

In some embodiments, there is provided a pathway for the production of acetaldehyde from glucose. In some embodiments, production of acetaldehyde from glucose is via decarboxylation of pyruvate by pyruvate decarboxylase.

In some embodiments, there is provided a non-naturally occurring microorganism having a trans-2-unsaturated aldehyde pathway and/or having the ability to produce precursor aldehydes (e.g., aldehydes, acetaldehydes, and butyraldehydes) leading to the production of trans-2-unsaturated aldehyde(s) (e.g., trans-2-hexenal). In some embodiments, the non-naturally occurring microorganism comprises: (a) at least one of the following trans-2-unsaturated aldehyde pathway enzymes: a pyruvate decarboxylase that catalyzes decarboxylation of pyruvate to acetealdehyde, an aspartokinase that catalyzes phosphorylation of L-asparate, a homoserine kinase that catalyzes phosphorylation of L-homoserine to O-phospho-Lhomoserine, a threonine synthase that catalyzes the hydration of O-phospho-Lhomoserine to L-threonine, a threonine desaminase that catalyzes the desamination of L-threonine into 2-ketobutyrate, an isopropylmalate synthase that catalyzes the acetylation of 2-keto butyrate into 2-ethyl malate, an acetohydroxy acid isomeroreductase that catalyzes the formation of 3-ethyl malate from 2-ethylmalate via a 2-ethyl maleate intermediate, an isopropylmalate dehydrogenase that catalyzes the oxidation of 3-ethyl malate into 2-ethyl-3-oxo succinate, and an alpha-ketoisovalerate decarboxylase that catalyzes the decarboxylation of 2-keto acid (e.g., 2-keto-valerate) into an aldehyde (e.g., butyraldehyde); and (b) at least one of the following enzymes: an aldolase that catalyzes condensation of acetaldehyde and aldehyde (e.g., butyraldehyde) to produce 3-hydroxy aldehyde (e.g., 3-hydroxy hexanal), and a dehydratase that dehydrates the 3-hydroxy aldehyde (e.g., 3-hydroxy hexanal) to trans-2-unsaturated aldehyde (e.g., trans-2-hexenal). In some embodiments, the microorganism comprises an aldolase that is specific for condensation of acetaldehyde and aldehyde to produce 3-hydroxy aldehyde. In some embodiments, the microorganism comprises at least one exogenous nucleic acid encoding an enzyme from said trans-2-unsaturated aldehyde pathway. In some embodiments, the non-naturally occurring microorganism comprises an increased enzymatic activity of at least one enzyme in the trans-2-unsaturated pathway in comparison with the enzymatic activity of the same enzyme in a corresponding unmodified or wild-type microorganism.

In some embodiments, there is provided a pathway for the production of butyraldehyde from glucose. This can be achieved by over production of L-threonin by overexpression of aspartokinase (thrA), overexpression of homoserine kinase (thrB), and/or overexpression of threonin synthase (thrC). Subsequently threonin can be transformed into butyraldehyde using threonin desaminase (ilvA), isoproylmalate synthase (leuA), isopropylmalate dehydrogenase (leuB), acetohydroxy acid isomeroreductase (leuC, leuD) and alpha-ketoisovalerate decarboxylase (kivD). [Atsumi et al. "Non-fermentative pathways for synthesis of branched-chain higher alcohols as biofuels" NATURE Vol 451 (2008).]

In some embodiments, the microorganism further includes a pathway for producing butyraldehyde, wherein the microorganism comprises at least one of the following butyraldehyde pathway enzymes: an aspartokinase that catalyzes phosphorylation of L-asparate, a homoserine kinase that catalyzes phosphorylation of L-homoserine to O-phospho-Lhomoserine, a threonine synthase that catalyzes the hydration of O-phospho-Lhomoserine to L-threonine, a threonine desaminase that catalyzes the desamination of L-threonine into 2-ketobutyrate, an isopropylmalate synthase that catalyzes the acetylation of 2-keto butyrate into 2-ethyl malate, an acetohydroxy acid isomeroreductase that catalyzes the formation of 3-ethyl malate from 2-ethylmalate via a 2-ethyl maleate intermediate, an isopropylmalate dehydrogenase that catalyzes the oxidation of 3-ethyl malate into 2-ethyl-3-oxo succinate, and an alphaketoisovalerate decarboxylase that catalyzes the decarboxylation of 2-keto-valerate into butyraldehyde. In some embodiments, the microorganism expresses an enzyme identified in TABLE 7 or an active fragment or homologue thereof for producing butyraldehyde.

In some embodiments, the non-naturally occurring microorganism includes at least one modification (e.g., deletion) to an endogenous nucleic acid encoding an enzyme from the trans-2-unsaturated pathway or at least one modification that affects the expression of an enzyme from the trans-2-unsaturated pathway.

In some embodiments, the non-naturally occurring microorganism includes at least one modification (e.g., deletion) to an endogenous nucleic acid encoding an enzyme effecting production of the trans-2-unsaturated aldehyde or any pathway intermediate.

In some embodiments, the trans-2-unsaturated aldehyde is converted to trans-2-unsaturated alcohol or trans-2-unsaturated carboxylic acids by using aldoketoreductase, oxidoreductase, aldehyde reductase, or alcohol dehydrogenase, wherein the microorganism includes at least one exogenous nucleic acid encoding an enzyme from said trans-2-unsaturated aldehyde pathway.

In some embodiments, the microoganism is genetically modified to contain a nucleic acid encoding an alcohol dehydrogenase capable of reducing trans-2-unsaturated aldehydes to trans-2-unsaturated alcohols. In some embodiments, the microoganism is genetically modified to contain a nucleic acid encoding an oxidoreductase capable of oxidizing trans-2-unsaturated aldehydes to trans-2-unsaturated carboxylic acids.

In some embodiments, a delta lactone pathway is disclosed that comprises: 1) condensation of two aldehyde molecules to a 3-hydroxy aldehyde intermediate using an aldolase enzyme; 2) condensation of the 3-hydroxy aldehyde intermediate and an aldehyde (e.g. acetaldehyde) to a 5,3-dihydroxy aldehyde intermediate using an aldolase enzyme 3) cyclization of 5,3-dihydroxy aldehyde to form a tetrahydro-2H-pyran-2,4-diol (compound of formula IV(b)); 4) oxidation of tetrahydro-2H-pyran-2,4-diol to a tetrahydro-4-hydroxy-2H-pyran-2-one (compound of formula V): 5) dehydration of the tetrahydro-4-hydroxy-2H-pyran-2-one (compound of formula V) to a 5,6-dihydro-2H-pyran-2-one (compound of formula VI); and 6) reduction of the 5,6-dihydro-2H-pyran-2-one (compound of formula VI) to a delta-lactone (compound of formula VII) using reductase.

In some embodiments, there is provided a non-naturally occurring microorganism having a delta lactone pathway. The microorganism includes at least one of the following delta lactone pathway enzymes: an aldolase that catalyzes the condensation of two aldehyde molecules to produce 3-hydroxy aldehyde (i.e., step 1): an aldolase that catalyzes condensation of the 3-hydroxy aldehyde intermediate and an aldehyde (e.g. acetaldehyde) to a 5,3-dihydroxy aldehyde intermediate (i.e., step 2); a lactonization enzyme that transforms a 5,3-dihydroxy aldehyde intermediate into a tetrahydro-4-hydroxy-2H-pyran-2-one: a dehydratase that dehydrates the tetrahydro-4-hydroxy-2H-pyran-2-one to a 5,6-dihydro-2H-pyran-2-one; and a reductase that reduces the 5,6-dihydro-2H-pyran-2-one to a delta-lactone. In some embodiments, the microorganism has at least one exogenous nucleic acid encoding an enzyme from said delta-lactone pathway. In some embodiments, the non-naturally occurring microorganism comprises an increased enzymatic activity of at least one enzyme in the delta lactone pathway in comparison with the enzymatic activity of the same enzyme in a corresponding unmodified, or a naturally occurring microorganism, or wild-type microorganism. In some embodiments, the microorganism further includes a PDC for decarboxylation of pyruvate to yield acetaldehyde and carbon dioxide. In some embodiments, the microorganism expresses an enzyme identified in TABLE 9 and/or TABLE 10, or an active fragment or homologue thereof for producing acetaldehyde. In some embodiments, at least one or all the nucleic acids are exogenous to the host microorganism. In some embodiments, the aldolase is DERA.

In some embodiments, there is provided a non-naturally occurring microorganism having a delta-lactone pathway. The microorganism includes at least one of the following delta-lactone pathway enzymes: an aldolase that catalyzes condensation of an acetaldehyde and an aldehyde to 3-hydroxy aldehyde (i.e., step 1); an aldolase that catalyzes condensation of the 3-hydroxy aldehyde and an acetaldehyde to 5,3-dihydroxy aldehyde, which undergoes cyclization to form tetrahydro-2H-pyran-2,4-diol (i.e., step 2); an oxidase enzyme that transforms the tetrahydro-2H-pyran-2,4-diol to a tetrahydro-4-hydroxy-2H-pyran-2-one: a dehydratase enzyme that dehydrates the tetrahydro-4-hydroxy-2H-pyran-2-one to a 5,6-dihydro-2H-pyran-2-one. In some embodiments, the microorganism has at least one exogenous nucleic acid encoding an enzyme from said delta-lactone pathway. In some embodiments, the non-naturally occurring microorganism comprises an increased enzymatic activity of at least one enzyme in the delta lactone pathway in comparison with the enzymatic activity of the same enzyme in a corresponding unmodified, or a naturally occurring microorganism, or wild-type microorganism. In some embodiments, the 5,6-dihydro-2H-pyran-2-one is massoia lactone (e.g., (R)-5,6-Dihydro-6-pentyl-2H-pyran-2-one). In some embodiments the massoia lactone is C-10 massoia lactone. In some embodiments, the massoia lactone is C-12 massoia lactone. In some embodiments, the massoia lactone is C-14 massoia lactone. In some embodiments, the microorganism further includes a PDC for decarboxylation of pyruvate to yield acetaldehyde and carbon dioxide. In some embodiments, the microorganism expresses an enzyme identified in table 3 or an active fragment or homologue thereof for producing acetaldehyde. In some embodiments, at least one or all the nucleic acids are exogenous to the host microorganism. In some embodiments, the aldolase is DERA.

In some embodiments, the aldolase in step 1 is different from the aldolase in step 2. In some embodiments, the aldolase that catalyzes the condensation of two aldehyde molecules to produce 3-hydroxy aldehyde is different from the aldolase that catalyzes condensation of a 3-hydroxy aldehyde intermediate and an aldehyde (e.g. acetaldehyde) to a 5,3-dihydroxy aldehyde intermediate. In some embodiments, the aldolase in step 1 is the same as the aldolase in step 2. In some embodiments, the aldolase in step 1 and the aldolase in step 2 are both DERA.

In some embodiments, the delta-lactone is produced by feeding the aldehyde molecules (i.e., precursor aldehydes) to a microbial culture. In some embodiments, the delta-lactone is produced by feeding both aldehyde molecules (i.e., precursor aldehydes) to a microbial culture. In some embodiments, the delta-lactone is produced by feeding at least one aldehyde molecules (i.e., precursor aldehydes) to a microbial culture. In some embodiments, the delta-lactone is produced by feeding one aldehyde molecule (i.e., precursor aldehydes) to a microbial culture.

In some embodiments, the aldehyde precursors for the formation of delta-lactone are produced from glucose, for example by aldehyde producing pathways. In some embodiments, both aldehyde precursors for the formation of delta-lactone are produced from glucose. In some embodiments, at least one aldehyde precursor for the formation of delta-lactone is produced from glucose. In some embodiments, one aldehyde precursor for the formation of delta-lactone is produced from glucose.

In some embodiments, there is provided a pathway for the production of acetaldehyde from glucose. In some embodiments, this is achieved by decarboxylation of pyruvate by pyruvate decarboxylase.

In some embodiments, two aldehyde precursors are fed to the cells (e.g., microbial culture). In some embodiments, two aldehyde precursors are produced from glucose. In some embodiments, at least one aldehyde precursor is produced from glucose and at least one aldehyde precursor is fed to the cell. In some embodiments, one aldehyde precursor is produced from glucose and one aldehyde precursor is fed to the cell.

In some embodiments, a delta-lactone is produced by feeding precursor aldehydes (e.g., two precursor aldehydes) to cells. In some embodiments, a delta-lactone is produced by feeding precursor aldehydes to cells expressing two engineered aldolases. In some embodiments, the two engineered aldolases are different aldolases. In some embodiments, an aldolase is specific for the first condensation reaction. In some embodiments, the first condensation reaction includes the condensation of two aldehydes. In some embodiments, an aldolase is specific for the condensation of 3-hydroxyaldehyde and aldehyde (i.e., second condensation reaction). In some embodiments, the aldolase specific for the first condensation reaction is different from the aldolase specific for the second condensation reaction. In some embodiments, the aldolases are DERA or derived from DERA. In some embodiments, delta-lactone is produced from glucose. In some embodiments, delta-lactone is produced by producing acetaldehyde in a cell (e.g., from glucose) and feeding at least one aldehyde. In some embodiments, precursor aldehydes are produced by the cell via engineered pathways. In some embodiments, the engineered pathways require modification (e.g., expression or overexpression) of at least one gene. In some embodiments, strains (e.g., 2 different strains) are optimized to include at least one gene deletion(s). In some embodiments, acetaldehyde is produced in a cell (e.g., from glucose). In some embodiments, precursor aldehyde molecules (e.g., two precursor aldehydes) are produced from glucose. In some embodiments, precursor aldehyde molecules (e.g., two precursor aldehydes) are fed to the cell. In some embodiments, at least one precursor aldehyde is produced from glucose and at least one precursor aldehyde is fed to the cell. In some embodiments, at least one precursor aldehyde is fed to a cell following production of acetaldehyde from glucose.

In some embodiments, the microorganism further includes a pathway for producing hexanal, wherein the microorganism comprises at least one of the hexanal pathway enzymes: an aspartokinase that catalyzes phosphorylation of L-asparate, a homoserine kinase that catalyzes phosphorylation of L-homoserine to O-phospho-Lhomoserine, a threonine synthase that catalyzes the hydration of O-phospho-Lhomoserine to L-threonine, a threonine desaminase that catalyzes the desamination of L-threonine into 2-ketobutyrate, an isopropylmalate synthase that catalyzes the acetylation of 2-keto butyrate into 2-ethyl malate, an acetohydroxy acid isomeroreductase that catalyzes the formation of 3-ethyl malate from 2-ethylmalate via a 2-ethyl maleate intermediate, an isopropylmalate dehydrogenase that catalyzes the oxidation of 3-ethyl malate into 2-ethyl-3-oxo succinate, and a ketoisovalerate decarboxylase that catalyzes decarboxylation of 2-keto-heptanoic acid into hexanal. Decarboxylation of 2-ethyl-3-oxo succinate to 2-ketovalerate may occur spontaneously. In some embodiments, 2-ketovalerate is converted into 2-keto-caproic acid and further into 2-keto-heptanoic acid by the same enzymes (e.g., a hexanal pathway enzyme).

In some embodiments, there is provided a non-naturally occurring microorganism having a delta-lactone pathway. The microorganism includes at least one of the following delta-lactone pathway enzymes: an aldolase that catalyzes condensation of an acetaldehyde and a hexanal to 3-hydroxy-octanal; an aldolase that catalyzes condensation of the 3-hydroxy-octanal and an acetaldehyde to 5,3-dihydroxy-decanal: a lactonization enzyme and/or a dehydratase enzyme to transform 5,3-dihydroxy-decanal to massoia lactone. In some embodiments, the microorganism has at least one exogenous nucleic acid encoding an enzyme from said delta-lactone pathway. In some embodiments, the microorganism further includes a PDC for decarboxylation of pyruvate to yield acetaldehyde and carbon dioxide. In some embodiments, the microorganism expresses an enzyme identified in TABLE 9 and/or TABLE 10, or an active fragment or homologue thereof for producing acetaldehyde. In some embodiments, at least one or all the nucleic acids are exogenous to the host microorganism. In some embodiments, the aldolase is DERA.

In some embodiments, the delta-lactone pathway comprises a dehydration step that is spontaneous dehydration. In some embodiments, the dehydration step comprises a dehydratase. In some embodiments, dehydration is a chemically catalyzed dehydration reaction. In some embodiments, dehydration is aided by dehydratase. In some embodiments, the lactonization is spontaneous. In some embodiments, the lactonization is enzymatic. In some embodiments, the lactonization is a non-enzymatic lactonization reaction. In some embodiments, the lactonization is a chemical lactonization reaction.

In some embodiments, there is provided a pathway for the production of hexanal from glucose. In some embodiments, production of hexanal from glucose can be by at least one of the following: over production of L-threonin, overexpression of aspartokinase (thrA), overexpression of homoserine kinase (thrB), and/or overexpression of threonin synthase (thrC). In some embodiments, threonin can be transformated into hexanal. In some embodiments, threonine is transformed into hexanal using at least one of threonin desaminase (ilvA), isoproylmalate synthase (leuA), isopropylmalate dehydrogenase (leuB), acetohydroxy acid isomeroreductase (leuC, leuD), and alpha-ketoisovalerate decarboxylase (kivD_VLV).

In some embodiments, there is provided a non-naturally occurring microorganism capable of producing delta-lactone by producing acetaldehyde and other aldehydes from glucose. In some embodiments, the non-naturally occurring microorganism converts the acetaldehyde and aldehyde molecules to delta-lactone using a delta-lactone pathway. In some embodiments, there is provided a non-naturally occurring microorganism capable of producing delta-lactone (e.g., delta-decalactone) by producing acetaldehyde and aldehyde (e.g., hexanal) from glucose and/or converting the acetaldehyde and aldehyde (e.g., hexanal) to delta-lactone (delta-decalactone) using a delta-lactone pathway. The microorganism includes at least one of the following delta-lactone pathway enzymes: a pyruvate decarboxylase that catalyzes decarboxylation of pyruvate to acetealdehyde, an aspartokinase that catalyzes phosphorylation of L-asparate, a homoserine kinase that catalyzes phosphorylation of L-homoserine to O-phospho-Lhomoserine, a threonine synthase that catalyzes the hydration of O-phospho-Lhomoserine to L-threonine, a threonine desaminase that catalyzes the desamination of L-threonine to 2-ketobutyrate, an isopropylmalate synthase that catalyzes the acetylation of 2-keto butyrate to 2-ethyl malate, an acetohydroxy acid isomeroreductase that catalyzes the formation of 3-ethyl malate from 2-ethylmalate via a 2-ethyl maleate intermediate, and an isopropylmalate dehydrogenase that catalyzes the oxidation of 3-ethyl malate to 2-ethyl-3-oxo succinate, and a ketoisovalerate decarboxylase (e.g., engineered enzyme) that catalyzes decarboxylation of 2-keto-acid to aldehyde (e.g., 2-keto-heptanoic acid to hexanal); and (b) at least one of the following enzymes: an aldolase that catalyzes condensation of acetaldehyde and an aldehyde (e.g., hexanal) to produce 3-hydroxy aldehyde (e.g., 3-hydroxyoctanal), an aldolase that catalyzes condensation of the 3-hydroxy aldehyde (e.g., 3-hydroxyoctanal) and acetaldehyde to a 5,3-dihydroxy aldehyde (e.g., a 5,3-dihydroxy decanal intermediate), which undergoes a spontaneous cyclization to form tetrahydro-2H-pyran-2,4-diol (e.g., 6-pentyltetrahydro-2H-pyran-2,4-diol), an oxidase that oxidizes tetrahydro-2H-pyran-2,4-diol (e.g., 6-pentyltetrahydro-2H-pyran-2,4-diol) into tetrahydro-4-hydroxy-2H-pyran-2-one (e.g., 4-hydroxy-6-pentyltetrahydro-2H-pyran-2-one), a dehydratase that dehydrates the tetrahydro-4-hydroxy-2H-pyran-2-one (e.g., 4-hydroxy-6-pentyltetrahydro-2H-pyran-2-one) to 5,6-dihydro-2H-pyran-2-one (e.g., 6-pentyl-5,6-dihydro-2H-pyran-2-one), and a reductase that reduces the 5,6-dihydro-2H-pyran-2-one (e.g., 6-pentyl-5,6-dihydro-2H-pyran-2-one) to a delta-lactone (e.g., delta-decalactone). In some embodiments, decarboxylation of 2-ethyl-3-oxo succinate to 2-ketovalerate occurs spontaneously. In some embodiments, 2-ketovalerate is converted to 2-keto-caproic acid and further to 2-keto-heptanoic acid. In some embodiments, the microorganism has at least one exogenous nucleic acid encoding an enzyme from said delta-lactone pathway.

In some embodiments, the pathway for aldehyde production is the same, thus involves the same pathway enzymes. For longer aldehydes the product for a first reaction cycle undergoes a second reaction cycle and so forth. Every cycle adds on to the chain length. In some embodiments, the resulting aldehyde is controlled by the co-expressed ketoaldehyde decarboxylase (e.g., GEO175).

In some embodiments, the non-naturally occurring microorganism includes at least one modification to an endogenous nucleic acid encoding an enzyme from the delta-lactone pathway or affecting the expression of an enzyme from this delta-lactone pathway.

In some embodiments, the non-naturally occurring microorganism includes at least one modification (e.g., deletion) to an endogenous nucleic acid encoding an enzyme effecting production of the delta lactone or any pathway intermediate.

In some embodiments, a microorganism is a microorganism which is genetically modified so as to contain a nucleic acid molecule encoding an aldolase capable of condensing an aldehyde molecule and a 3-hydroxy-aldehyde molecule to a 5,3-dihydroxyaldehyde.

In some embodiments, a gamma lactone pathway is disclosed that comprises: 1) condensation of an aldehyde molecule and a pyruvic acid to a 4-hydroxy-2-oxo carboxylic acid using aldolase (e.g, pyruvate-dependent aldolase): 2) reduction of the 4-hydroxy-2-oxo carboxylic acid to 2,4-dihydroxy carboxylic acid using dehydrogenase or keto-reductase; 3) lactonization of the 2,4-dihydroxy carboxylic acid to a 3-hydroxydihydro-2-(3H)-furanone: 4) dehydration of the 3-hydroxydihydro-2-(3H)-furanone to 2(5H)-furanone (compound of formula XI); and 5) reduction of 2(5H)-furanone (compound of formula XI) to a gamma-lactone (compound of formula XII) using reductase.

In some embodiments, there is provided a non-naturally occurring microorganism having a gamma-lactone pathway. The microorganism includes at least one of the following gamma-lactone pathway enzymes: an aldolase (e.g, pyruvate-dependent aldolase) that catalyzes condensation of an aldehyde molecule and a pyruvic acid (or pyruvate) to a 4-hydroxy-2-oxo carboxylic acid; a dehydrogenase or a keto-reductase that reduces the 4-hydroxy-2-oxo carboxylic acid to 2,4-dihydroxy carboxylic acid; a lactonization enzyme that transforms the 2,4-dihydroxy carboxylic acid to a 3-hydroxydihydro-2-(3H)-furanone; a dehydratase that dehydrates the 3-hydroxydihydro-2-(3H)-furanone to 2(5H)-furanone; and a reductase that reduces the 2(5H)-furanone to a gamma-lactone.

In some embodiments, there is provided a non-naturally occurring microorganism having a gamma-lactone pathway, wherein the microorganism comprises at least one of the following gamma-lactone pathway enzymes: an aldolase that catalyzes condensation of an aldehyde molecule and a pyruvic acid (or a pyruvate) to a 4-hydroxy-2-oxo carboxylic acid; a dehydrogenase or a keto-reductase that reduces the 4-hydroxy-2-oxo carboxylic acid to 2,4-dihydroxy acid; dehydration (e.g., a dehydration enzyme) of the 2,4-dihydroxy acid to 4-hydroxy-2-ene-acid: a lactonization enzyme that transforms the 4-hydroxy-2-ene acid to 2(5H)-furanone; and a reductase that reduces the 2(5H)-furanone to a gamma-lactone.

Figure 10:
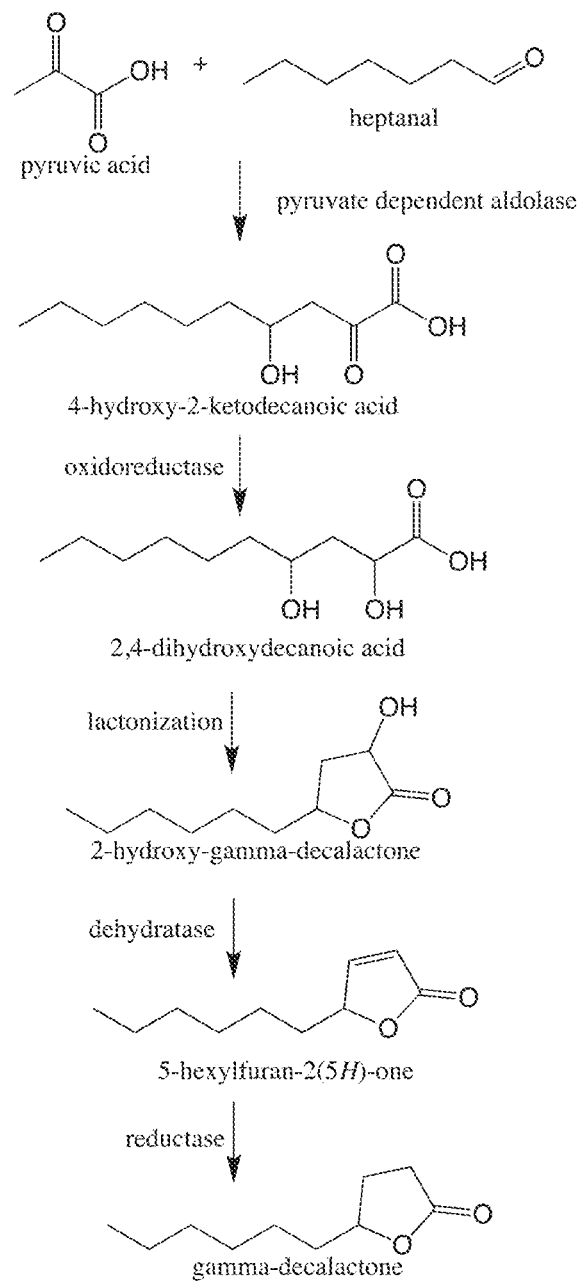
FIG. 10 exemplifies the pathway for producing gamma-lactone.

In some embodiments, there is provided a non-naturally occurring microorganism having a gamma-lactone pathway, wherein the microorganism comprises at least one of the following gamma-lactone pathway enzymes: an aldolase (e.g., pyruvate dependent aldolase) that catalyzes condensation of an aldehyde molecule and a pyruvic acid (or pyruvate) to a 4-hydroxy-2-oxo acid: an oxidoreductase that transforms the 4-hydroxy-2-oxo acid to a 2,4-dihydroxy acid; a lactonization enzyme that transforms the 2,4-dihydroxy acid to a 2-hydroxy-gamma-lactone; a dehydratase that dehydrates the 2-hydroxy-gamma-lactone to 5-furan-2 (5H)-one; and a reductase that reduces the 5-furan-2(5H)-one to a gamma-lactone (FIG. 10).

In some embodiments, the reductase is enoate reductase. In some embodiments, the microorganism comprises at least one exogenous nucleic acid encoding an enzyme from said gamma-lactone pathway. In some embodiments, the non-naturally occurring microorganism comprises an increased enzymatic activity of at least one enzyme in the gamma lactone pathway in comparison with the enzymatic activity of the same enzyme in a corresponding unmodified, or a naturally occurring microorganism, or wild-type microorganism.

In some embodiments, the microorganism further comprises modification to overproduce pyruvic acid. In some embodiments, the microorganism further includes a pathway for producing heptanal, wherein the microorganism comprises at least one of the following heptanal pathway enzymes: an aspartokinase that catalyzes phosphorylation of L-asparate, a homoserine kinase that catalyzes phosphorylation of L-homoserine to O-phospho-Lhomoserine, a threonine synthase that catalyzes the hydration of O-phospho-Lhomoserine to L-threonine, a threonine desaminase that catalyzes the desamination of L-threonine into 2-ketobutyrate, an isopropylmalate synthase that catalyzes the acetylation of 2-keto butyrate into 2-ethyl malate, an acetohydroxy acid isomeroreductase that catalyzes the formation of 3-ethyl malate from 2-ethylmalate via a 2-ethyl maleate intermediate, and an isopropylmalate dehydrogenase that catalyzes the oxidation of 3-ethyl malate into 2-ethyl-3-oxo succinate. Decarboxylation of 2-ethyl-3-oxo succinate to 2-ketovalerate may occur spontaneously, 2-ketovalerate is converted into 2-keto-caproic acid, into 2-keto-heptanoic acid, and further into 2-keto-octanoic acid by the same enzymes (e.g., a heptanal pathway enzyme), and an engineered ketoisovalerate decarboxylase that catalyzes decarboxylation of 2-keto-octanoic acid into heptanal.

In some embodiments, a microorganism used in a method according to the present disclosure is a microorganism which is genetically modified so as to contain a nucleic acid molecule encoding an aldolase (e.g, pyruvate-dependent aldolase) capable of condensing an aldehyde molecule and a pyruvic acid (or pyruvate) to 4-hydroxy-2-oxo carboxylic acid.

In some embodiments, the gamma-lactone pathway comprises a dehydration step that is spontaneous dehydration. In some embodiments, the dehydration step comprises a dehydratase. In some embodiments, dehydration is a chemically catalyzed dehydration reaction. In some embodiments, the lactonization is spontaneous. In some embodiments, the lactonization is enzymatic. In some embodiments, the lactonization is a non-enzymatic lactonization reaction. In some embodiments, the lactonization is a chemically catalyzed lactonization reaction.

In some embodiments, the gamma-lactone is produced by feeding the aldehyde molecule (i.e., precursor aldehyde) to a microbial culture (e.g., fed to the cells). In some embodiments, the precursor aldehyde is produced from glucose. In some embodiments, the precursor aldehyde is fed to the cell. In some embodiments, the pyruvate and/or pyruvic acid is produced from glucose. In some embodiments, the pyruvate and/or pyruvic acid is fed to the cell. In some embodiments, both the aldehyde molecule and the pyruvate and/or pyruvic acid is produced from glucose. In some embodiments, both the aldehyde molecule and the pyruvate and/or pyruvic acid is fed to the cell. In some embodiments, at least one of the aldehyde molecule and/or at least one of the pyruvate or pyruvic acid is fed to the cell. In some embodiments, at least one of the aldehyde molecule and/or at least one of the pyruvate or pyruvic acid is produced from glucose.

In some embodiments, the aldehyde molecule (i.e., aldehyde precursor) for the formation of the gamma-lactone are produced from glucose by aldehyde producing pathways. In some embodiments, there is provided a pathway for the production of heptanal from glucose. In some embodiments, production of heptanal from glucose comprises at least one of over production of L-threonin, overexpression of aspartokinase (thrA), overexpression of homoserine kinase (thrB), and overexpression of threonin synthase (thrC). In some embodiments, threonin is transformed into hexanal by at least one of threonin desaminase (ilvA), isoproylmalate synthase (leuA), isopropylmalate dehydrogenase (leuB), acetohydroxy acid isomeroreductase (leuC, leuD), and alpha-ketoisovalerate decarboxylase (geo175).

In some embodiments, there is provided a non-naturally occurring microorganism capable of producing pyruvate and aldehyde in a cell. In some embodiments, the non-naturally occurring microorganism produces pyruvate and aldehyde and has a gamma-lactone pathway.

In some embodiments, a microorganism strain is capable of producing pyruvate and aldehyde precursor in a cell (e.g., from glucose). In some embodiments, there is provided a non-naturally occurring microorganism capable of producing pyruvate and aldehyde (e.g., heptanal and/or having a gamma-lactone pathway for production of gamma-lactone (e.g., gamma-decalactone). The microorganism comprises at least one of the following gamma-lactone pathway enzymes: a) enzymes for production of aldehyde (e.g., heptanal), an aspartokinase that catalyzes phosphorylation of L-asparate, a homoserine kinase that catalyzes phosphorylation of L-homoserine to O-phospho-Lhomoserine, a threonine synthase that catalyzes the hydration of O-phospho-L-homoserine to L-threonine, a threonine desaminase that catalyzes the desamination of L-threonine into 2-ketobutyrate, an isopropylmalate synthase that catalyzes the acetylation of 2-keto butyrate into 2-ethyl malate, an acetohydroxy acid isomeroreductase that catalyzes the formation of 3-ethyl malate from 2-ethylmalate via a 2-ethyl maleate intermediate, an isopropylmalate dehydrogenase that catalyzes the oxidation of 3-ethyl malate into 2-ethyl-3-oxo succinate, and a ketoisovalerate decarboxylase (e.g., engineered enzyme) that catalyzes decarboxylation of 2-keto-acid to aldehyde (e.g., 2-keto-octanoic acid to heptanal); and (b) at least one of the following enzymes: b) enzymes for production of gamma-lactone (e.g., gamma-decalactone); an aldolase (e.g, pyruvate-dependent aldolase) that catalyzes condensation of an aldehyde molecule (e.g., heptanal) and pyruvic acid to a 4-hydroxy-2-oxo carboxylic acid (e.g., 4-hydroxy-2-oxo decanoic acid): a dehydrogenase or a keto-reductase that reduces the 4-hydroxy-2-oxo carboxylic acid to 2,4-dihydroxy carboxylic acid (e.g., 4-hydroxy-2-oxo decanoic acid to 2,4-dihydroxy decanoic acid): a lactonization enzyme that transforms the 2,4-dihydroxy carboxylic acid (e.g., 2,4-dihydroxy decanoic acid) to a 3-hydroxydihydro-2-(3H)-furanone (e.g., 5-hexyl-3-hydroxydihydrofuran-2(3H)-one): a dehydratase that dehydrates the 3-hydroxydihydro-2-(3H)-furanone to 2(5H)-furanone (e.g., 5-hexy-3-hydroxydihydrofuran-2(3H)-one to 5-hexylfuran-2(5H)-one); and a reductase that reduces the 2(5H)-furanone to a gamma-lactone (e.g., gamma-decalactone). In some embodiments, the microorganism has at least one exogenous nucleic acid encoding an enzyme from said gamma-lactone pathway. In some embodiments, decarboxylation of 2-ethyl-3-oxo succinate to 2-ketovalerate happens spontaneously. In some embodiments, 2-ketovalerate is converted into 2-keto-caproic acid, 2-keto acid (e.g., 2-keto-heptanoic acid and further into 2-keto-octanoic acid) by the same enzymes. In some embodiments, an engineered ketoisovalerate decarboxylase catalyzes decarboxylation of 2-keto acid to aldehyde (e.g., 2-keto-octanoic acid into heptanal).

In some embodiments, the non-naturally occurring microorganism includes at least one modification to an endogenous nucleic acid encoding an enzyme from the gamma-lactone pathway or affecting the expression of an enzyme from this gamma-lactone pathway.

In some embodiments, the non-naturally occurring microorganism includes at least one modification/deletion to an endogenous nucleic acid encoding an enzyme that has an effect on production of the gamma lactone or any pathway intermediate.

Also provided herein is a method of producing enantiopure (R)-configuration of the delta-lactone, the gamma-lactone, and/or the compound of formula II comprising culturing a non-naturally occurring microorganism as described herein or performing the biosynthetic process as described herein.

In some embodiments, a microorganism used in a method according to the present disclosure is a microorganism which is genetically modified so as to contain a nucleic acid molecule encoding an aldolase capable of condensing two aldehyde molecules to 3-hydroxy aldehyde. In some embodiments, a microorganism used in a method according to the present disclosure is a microorganism which is genetically modified so as to contain a nucleic acid molecule encoding an aldolase capable of condensing two acetaldehyde molecules to 3-hydroxybutanal. In some embodiments, a microorganism used in a method according to the present disclosure is a microorganism which is genetically modified so as to contain a nucleic acid molecule encoding an aldolase capable of condensing an acetaldehyde and formaldehyde to 3-hydroxy-propanal. In some embodiments, a microorganism used in a method according to the present disclosure is a microorganism which is genetically modified so as to contain a nucleic acid molecule encoding an aldolase capable of condensing an acetaldehyde and a propionaldehyde to 3-hydroxy-pentanal. In some embodiments, a microorganism used in a method according to the present disclosure is a microorganism which is genetically modified so as to contain a nucleic acid molecule encoding an aldolase capable of condensing an acetaldehyde and a butyraldehyde to 3-hydroxy-hexanal. In some embodiments, a microorganism used in a method according to the present disclosure is a microorganism which is genetically modified so as to contain a nucleic acid molecule encoding an aldolase capable of condensing an acetaldehyde and a pentaldehyde to 3-hydroxy-heptanal. In some embodiments, a microorganism used in a method according to the present disclosure is a microorganism which is genetically modified so as to contain a nucleic acid molecule encoding an aldolase capable of condensing an acetaldehyde and a hexaldehyde to 3-hydroxy-octanal. In some embodiments, a microorganism used in a method according to the present disclosure is a microorganism which is genetically modified so as to contain a nucleic acid molecule encoding an aldolase capable of condensing an acetaldehyde and a heptaldehyde to 3-hydroxy-nonanal. In some embodiments, a microorganism used in a method according to the present disclosure is a microorganism which is genetically modified so as to contain a nucleic acid molecule encoding an aldolase capable of condensing an acetaldehyde and a octaldehyde to 3-hydroxy-decanal. In some embodiments, a microorganism used in a method according to the present disclosure is a microorganism which is genetically modified so as to contain a nucleic acid molecule encoding an aldolase capable of condensing an acetaldehyde and a nonaldehyde to 3-hydroxy-undecanal. In some embodiments, a microorganism used in a method according to the present disclosure is a microorganism which is genetically modified so as to contain a nucleic acid molecule encoding an aldolase capable of condensing an acetaldehyde and a decaldehyde to 3-hydroxy-dodecanal. In some embodiments, a microorganism used in a method according to the present disclosure is a microorganism which is genetically modified so as to contain a nucleic acid molecule encoding an aldolase capable of condensing an acetaldehyde and a undecaldehyde to 3-hydroxy-tridecanal.

In some embodiments, a microorganism used in a method according to the present disclosure is a microorganism which is genetically modified so as to contain a nucleic acid molecule encoding an aldolase capable of condensing an aldehyde molecule and a 3-hydroxy aldehyde molecule to 5,3-dihydroxy aldehyde. In some embodiments, a microorganism used in a method according to the present disclosure is a microorganism which is genetically modified so as to contain a nucleic acid molecule encoding an aldolase capable of condensing an acetaldehyde molecule and a 3-hydroxybutanal molecule to 5,3-dihydroxyhexanal. In some embodiments, a microorganism used in a method according to the present disclosure is a microorganism which is genetically modified so as to contain a nucleic acid molecule encoding an aldolase capable of condensing an acetaldehyde and a 3-hydroxy-propanal molecule to 5,3-dihydroxypentanal. In some embodiments, a microorganism used in a method according to the present disclosure is a microorganism which is genetically modified so as to contain a nucleic acid molecule encoding an aldolase capable of condensing an acetaldehyde and a 3-hydroxypentanal molecule to 5,3-dihydroxyheptanal. In some embodiments, a microorganism used in a method according to the present disclosure is a microorganism which is genetically modified so as to contain a nucleic acid molecule encoding an aldolase capable of condensing an acetaldehyde and a 3-hydroxyhexanal to 5,3-dihydroxy-octanal. In some embodiments, a microorganism used in a method according to the present disclosure is a microorganism which is genetically modified so as to contain a nucleic acid molecule encoding an aldolase capable of condensing an acetaldehyde and a 3-hydroxyheptanal molecule to 5,3-dihydroxynonanal. In some embodiments, a microorganism used in a method according to the present disclosure is a microorganism which is genetically modified so as to contain a nucleic acid molecule encoding an aldolase capable of condensing an acetaldehyde and a 3-hydroxy-octanal molecule to 5,3-dihydroxydecanal. In some embodiments, a microorganism used in a method according to the present disclosure is a microorganism which is genetically modified so as to contain a nucleic acid molecule encoding an aldolase capable of condensing an acetaldehyde and a 3-hydroxynonanal molecule to 5,3-dihydroxyundecanal. In some embodiments, a microorganism used in a method according to the present disclosure is a microorganism which is genetically modified so as to contain a nucleic acid molecule encoding an aldolase capable of condensing an acetaldehyde and a 3-hydroxydecanal molecule to 5,3-dihydroxydodecanal. In some embodiments, a microorganism used in a method according to the present disclosure is a microorganism which is genetically modified so as to contain a nucleic acid molecule encoding an aldolase capable of condensing an acetaldehyde and a 3-hydroxy-undecanal molecule to 5,3-dihydroxytridecanal. In some embodiments, a microorganism used in a method according to the present disclosure is a microorganism which is genetically modified so as to contain a nucleic acid molecule encoding an aldolase capable of condensing an acetaldehyde and a 3-hydroxydodecanal molecule to 5,3-dihydroxytetradecanal. In some embodiments, a microorganism used in a method according to the present disclosure is a microorganism which is genetically modified so as to contain a nucleic acid molecule encoding an aldolase capable of condensing an acetaldehyde and a 3-hydroxytridecanal molecule to 5,3-dihydroxypentadecanal.

In some embodiments, the microoganism is genetically modified to contain a nucleic acid encoding an alcohol dehydrogenase capable of reducing trans-2-unsaturated aldehydes to trans-2-unsaturated alcohols. In some embodiments, the microoganism is genetically modified to contain a nucleic acid encoding an oxidoreductase capable of oxidizing trans-2-unsaturated aldehydes to trans-2-unsaturated carboxylic acids (e.g., gene ydcW, GI: 1742352; aldB, GI: 85676455). (Gruez et al. "Crystal structure and kinetics identify Escherichia coli YdcW gene product as a medium-chain aldehyde dehydrogenase" J Mol Biol. 2004, Oct. 8; 343(1):29-41]. In some embodiments, the microorganism is genetically modified to contain a nucleic acid encoding a PDC capable of decarboxylating pyruvate to yield acetaldehyde and carbon dioxide. See, TABLE 9.

When reference is made to at least one exogenous nucleic acid being included in a microorganism, it is to be understood that this refers to the referenced encoding nucleic acids or biochemical activities and not the number of separate nucleic acids introduced into the host organism. Such exogenous nucleic acids may be introduced into the host organism on separate nucleic acid molecules, on polycistronic nucleic acid molecules, or a combination thereof. For example, where two or more exogenous nucleic acids encoding different enzymatic activities are introduced into a host organism, the two or more exogenous nucleic acids maybe introduced as a single nucleic acid, for example, on a single plasmid, on separate plasmids, maybe integrated into the host chromosome at a single site or multiple sites, and still be considered as two or more exogenous nucleic acids.

Depending on the host microorganism selected, nucleic acids for some or all of the trans-2-unsaturated aldehyde pathway enzymes or the delta-lactone pathway enzymes or the gamma-lactone pathway enzymes described herein may be introduced into the host organism. If the host microorganism endogenously expresses one or more of the pathway genes then it may not be necessary to introduce these genes, but only those nucleic acids encoding enzyme(s) in the pathway for which the microorganism is deficient. Where a host microorganism is selected that expresses one or more of the pathway genes, the microorganism may be engineered such that the gene encoding the enzyme is overexpressed and/or genes encoding enzymes or proteins of competing pathways may be deleted.

The host microorganism may be engineered to increase co-factor pools of NADH and/or NADPH to improve metabolic flux. In some embodiments, if E. coli is to be used as the host organism, glucosephosphate isomerase (pgi) gene may be deleted to divert flux towards the pentose phosphate pathway to increase NADPH pools. Other strategies may involve switching the endogenous NADH-dependent glyceraldehyde-3-phosphate dehydrogenase (GAPDH) to the host *E. coli* strain with an exogenous NADPH-dependent glyceraldehyde-3-phosphate dehydrogenase derived from *Clostridium acetobutylicum*. In another method, an NADH kinase (Pos5P) maybe introduced from *S. cerevisiae* into the host *E. coli* strain. The latter was successfully used to increase several products that are produced through NADPH-dependent pathways [Lee, W.-H., Kim. M.-D., Jin. Y.-S., & Seo, J.-H. (2013). Engineering of NADPH regenerators in *Escherichia coli* for enhanced biotransformation. Applied Microbiology and Biotechnology, 97(7):2761-72].

If *E. coli* is chosen as the host organism. NADH pools may be increased by limiting competing pathways though the deletion of genes encoding NADH-dependent enzymes, including but not limited to: alcohol dehydrogenases (adhE; eutG; adhP; yjgB; yqhD), lactate dehydrogenase (idhA), and pyruvate-formate lyase (pflB).

Host microorganisms may be selected from, and the non-naturally occurring microorganisms generated in, for example, bacteria, yeast, fungus or any of a variety of other microorganisms may be used as a host organism.

In some embodiments, bacterial species may include: *Escherichia coli, Bacillus subtilis, Bacillus licheniformis, Bacillus cereus, Bacillus megaterium, Bacillus brevis, Bacillus pumilus, Corynebacterium glutamicum, Zymomonas mobilis. Clostridium acetobutylicum. Clostridium butylicum, Clostridium kluyveri, Clostridium autoethanogenum, Moorella thermoacetica, Clostridium aceticum, Clostridium beijerinckii, Clostridium saccharoperhulacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale. Clostridium sticklandii. Ralstonia eutropha, Mycobacterium bovis, Mycobacterium tuberculosis, Porphyromonas gingivalis, Pseudomonas fluorescens, Pseudomonas putida, Pseudomonas aeruginosa, Pseudomonas carboxidovorans (Oligotropha carboxidovorans), Pseudomonas stutzeri, Klebsiella pneumonia. Kebsiella oxytoca, Anaerobiospirillum succiniciproducens, Actinohacillus succinogenes, Mannheimia succiniciproducens, Rhizobium etli, Gluconobacter oxydans, Lactococcus lactis, Lactobacillus plantarum, Streptomyces coelicolor, Citrobacter freundii, Citrobacter amalonaticus, Acinetobacter calcoaceticus, Acinetobacter baylyi, Thermotoga maritima. Halobacterium salinarum, Serratia marcescens, Rhodospirillum rubrum, Ideonella* sp., *Rhodobacter capsulatus, Methyococcus capsulatus, Methylosinus trichosporium, Methylubacterium extorquens, Methylocystis* GB2.5, *Methylotrophus capsulatus, Methylomonas* sp. 16a, and *Pyrococcus furiosus*.

In some embodiments, yeasts or fungi may include; *Saccharomyces cerevisvae, Schizosaccharomyces pombe, Saccharomycopsis crataegensis, Kluyeromyces lactis, Kluyveromyces marxianus, Aspergillus terreus, Aspergillus niger, Pichia stipitis, Pichia pastoris, Rhizopus arrhizus, Rhizopus oryzae, Yarrowia lipoiytica, Issatchenkia orientalis, Issatchenkia occidentalis, Candida lambica, Candida sorboxylosa, Candida zempinina, Candida geochares, Pichia membranifaciens, Zygosaccharomyces kombuchaensis, Candida sorbosivorans, Candida vanderwaltii, Candida sorbophila, Zygosaccharomyces bisporus, Zygosaccharomyces lentus, Saccharomyces bayanus, Saccharomyces bulderi, Debaryomyces castellii, Candida boidinii Candida etchellsii, Pichia jadini, Pichia anomala*, and *Penicillium chrysogenun*.

In some embodiments, cyanobacteria may include: *Acaryochloris marina* MBIC11017, *Anabaena* sp. PCC 7120. *Anabaena variabilis* ATCC 29413. *Agmenellum quadruplicatum, Chlorobion tepidum* TLS, *Cyanothece* sp. ATCC 51142, *Gloeobacter violaceus* PCC 7421, *Microcystis aeruginosa* NIES-843, *Nostuc punctiforme* ATCC 29133, *Prochlorococcus marinus* MED4, *Prochlorococcus marinus* MiT9313, *Prochlorococcus marinus* SS120, *Prochlorococcus marinus* str. AS601, *Prochlorococcus marinus* str. MIT 9211. *Prochlorococcus marinus* str. MIT 9215, *Prochlorococcus marinus* sir. MIT 9301, *Prochlorococcus marinus* str. MIT 9303, *Prochlorococcus marinus* str. MIT 9312, *Prochlorococcus marinus* str. MIT 9515, *Prochlorococcus marinus* str. NATL1A, *Prochlorococcus marinus* str. NATL2A, *Rhodopseudomonas palustris* CGA009, *Synechococcus elongatus* PCC 6301, *Synechococcus elongatus* PCC 7942, *Synechococcus* sp. CC9311, *Synechococcus* sp. CC9605, *Synechococcus* sp. CC9902, *Synechococcus* sp. JA-2-3B, *Synechococcus* sp. JA-3-3Ab. *Synechococcus* sp. PCC 7002, *Synechococcus* sp. RCC307, *Synechococcus* sp. WH 7803, *Synechococcus* sp. WH8102, *Synechocystis* sp. PCC 6803. *Thermosynechococcus elongatus* BP-1, and *Trichodesmium erythraeum* IMS101.

In some embodiments, algae may include: *Botryococcus braunii, Chlamydomonas reinhardii, Chlorella* sp., *Crypthecodinium cohnii, Cylindrotheca* sp., *Dunaliella primolecta, Isochrvsis* sp., *Monallanthus salina, Nannochloris* sp., *Nannochloropsis* sp., *Neochloris oleoabundans, Nitzschia* sp., *Phaeodactylum tricornutum, Schizochytrium* sp., and *Tetraselmis sueica*.

In some embodiments, the host microorganism is not particularly restricted and the enzymatic activity or activities may be incorporated into any suitable host organism using methods, for example, as described herein. In some embodiments, the host is selected from bacteria, yeast, algae, cyanobacteria, fungi, or a plant cell, or any combination thereof. In some embodiments, the non-naturally occurring microorganism of the present disclosure or the process according to the present disclosure comprises a host microorganism. In some embodiments, the host microorganism is selected from a bacteria, yeast, algae, cyanobacteria, fungi, or a plant cell, or any combination thereof.

*E. coli* and *S. cerevisiae* are particularly useful host organisms since they are well characterized microorganisms suitable for genetic engineering. Further, acetaldehyde is a natural metabolite of both *E. coli* and *S. cerevisiae* present in the central carbon metabolism of both species.

A nucleic acid molecule encoding enzymes as described herein may be used alone or as part of a vector. The nucleic acid molecules may include expression control sequences operably linked to the polynucleotide comprised in the nucleic acid molecule. These expression control sequences may be suited to ensure transcription and synthesis of a translatable RNA in bacteria or fungi. Expression refers to the transcription of the heterologous DNA sequence, preferably into a translatable mRNA. Regulatory elements ensuring expression in fungi and bacteria encompass promoters, enhancers, termination signals, targeting signals and the like. Promoters for use in connection with the nucleic acid molecule may be homologous or heterologous with regard to its origin and/or with regard to the gene to be expressed. Suitable promoters are for instance promoters which lend themselves to constitutive expression. Promoters which are only activated at a point in time determined by external influences may also be used. Artificial and/or chemically inducible promoters may be used. Chemically inducible promoters may include but is not limited to: IPTG-inducible promoters such as T7 or Ptrc, or tetracycline-inducible promoters such as $P_{LtetO-1}$.

An overview of different expression systems is for instance contained in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene may be used as the promoter sequence, if it is active in the selected host organism. However, this sequence may also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms, including *E. coli* and *S. cerevisiae*, are described in the literature. Promoters permitting a particularly high expression of a downstream sequence are for instance the T7 promoter [Studier et al., Methods in Enzymology 185 (1990), 60-89], lacUV5, trp, trp-lacUV5 IDeBoer et al., in Rodriguez and Chamberlin (Eds). Promoters. Structure and Function: Praeger. New York, (1982), 462-481; DeBoer et al., Proc. Natl. Acad. Sci. USA (1983), 21-25], Ipi, rac [Boros et al., Gene 42 (1986), 97-100]. Termination signals for transcription are also described in the literature.

Inducible promoters which may provide higher polypeptide yields than constitutive promoters may be used. Suitably, in certain embodiments, a two-stage process may be used: the host cells are first cultured under optimum conditions up to a relatively high cell density; and transcription is then induced.

When two or more exogenous encoding nucleic acids are to be co-expressed, both nucleic acids may be inserted, for example, into one expression vector or into separate expression vectors. For single vector expression, the encoding nucleic acids may be operationally linked to a common expression control sequence or linked to different expression control sequences, such as one inducible promoter and one constitutive promoter.

In some embodiments, the present disclosure is directed to a gene encoding at least one aldolase (e.g., DERA) or at least one enzyme of the present disclosure, a recombinant vector containing the gene, and/or a recombinant microorganism containing said gene or recombinant vector.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably because most vector is a type of plasmid which is replicated independently.

It is to be understood that in some embodiments, a non-naturally occurring microorganism that produces a pathway intermediate or product, may be used in combination with another organism (or other organisms) expressing downstream or upstream pathway enzyme(s) to produce a desired product. For example, a wild-type or engineered organism may be used to produce and accumulate pyruvate, aldehydes, and/or 3-hydroxyaldehydes. These intermediates may then be used as a substrate for another engineered organism expressing one or more of the trans-2-unsaturated aldehyde pathway genes and/or the delta-lactone pathway genes and/or the gamma-lactone pathway genes.

In some embodiments, a microorganism as provided herein may optionally be engineered to delete one or more byproduct or alternative pathways. In some embodiments, the non-naturally occurring microorganism may be engineered to delete one or more genes encoding an enzyme that utilizes pyruvate. In some embodiments, the non-naturally occurring microorganism comprises deletion of one or more genes encoding an enzyme that utilizes pyruvate. In some embodiments, the non-naturally occurring microorganism comprises deletion of one or more genes encoding an enzyme capable of reacting with an acetaldehyde molecule, a pyruvate, or an aldehyde precursor. In some embodiments, the non-naturally occurring microorganism comprises deletion of one or more genes encoding an alcohol dehydrogenase, a lactate dehydrogenase, or a pyruvate formate lyase.

In some embodiments, one or more genes encoding an alcohol dehydrogenase, dihydroxy acid dehydratase, threonine transporter, aldehyde dehydrogenase, a lactate dehydrogenase or a pyruvate formate lyase are deleted from a host microorganism. In some embodiments, a deleted gene may be an alcohol dehydrogenase gene, a lactate dehydrogenase gene, and/or a pyruvate formate lyase gene. In some embodiments, the host microorganism is E col and one or more genes that are deleted is selected from aldB, poxB, yahK, deoC, paoA, paoB, paoC, ilvD, rhtA, dkgA pflB, ldhA, adhE, yqhD, eutG, adhP, and yjgB. Other genes native to *E. coli* and homologous to one or more of aldB, poxB, yahK, deoC, paoA, paoB, paoC, ilvD, rhtA, dkgA, pflB, ldhA, adhE, yqhD, eutG, adhP, and yjgB may also be deleted. In some embodiments, the host microorganism is *E. coli* and the one or more genes that is deleted is selected from pflB, ldhA, adhE, yqhD, eutG, adhP, and yjgB. In some embodiments, the host microorganism is *E. coli* and the one or more genes that is deleted is selected from aldB, poxB, ybbO, yahK, deoC, paoA/B/C (yagT/S/R), adhE, yqhD, eutG adhP, and yjgB. In some embodiments the microorganism comprising one or more gene deletions selected from aldB, poxB, ybbO, yahK, deoC, paoAJB/C (yagT/S/R), adhE, yqhD, eutG adhP, and yjgB can be used for producing trans-2-unsaturated aldehydes by feeding precursors (e.g., trans-2-hexenal production by feeding acetaldehyde and butyraldehyde). In some embodiments, the host microorganism is *E. coli* and the one or more genes that is deleted is selected from ilvD, rhtA, aldB, poxB, ybbO, yahK, deoC, paoA/B/C (yagT/S/R), pflB, ldhA, adhE, vqhD, eutG, adhP, and vjgB. In some embodiments the microorganism comprising one or more gene deletions selected from ilvD, rhtA, aldB, poxB, ybbO, yahK, deoC, paoA/B/C (yagT/S/R), pflB, ldhA, adhE, yqhD, eutG, adhP, and yjgB can be used for producing trans-2-unsaturated aldehydes from glucose (e.g., trans-2-hexenal production from glucose (i.e., internal production of the precursors)).

In some embodiments, the host microorganism is *E. coli* and the one or more genes that is deleted is selected from dkgA, aldB, poxB, ybbO, yahK, deoC, paoA/B/C (yagT/S/R,) adhE, yqhD, eutG, adhP, and yjgB. In some embodiments the microorganism comprising one or more gene deletions selected from dkgA, aldB, poxB, ybbO, yahK, deoC, paoA/B/C (yagT/S/R), adhE, yqhD, eutG, adhP, and yjgB, can be used for producing delta-lactone by feeding aldehyde precursors (e.g., delta-decalatone production by feeding acetaldehyde and hexanal). In some embodiments, the host microorganism is Eco/i and the one or more genes that is deleted is selected from ilvD, rhtA, dkgA, aldB, poxB, ybbO, ya, deoC, paoA/B/C (yagT/S/R), pflB, ldhA, adhE, yqhD, eutG, adhP, and yjgB. In some embodiments the microorganism comprising one or more gene deletions selected from ilvD, rhtA, dkgA, aldB, poxB, ybbO, yahK, deoC, paoA/B/C (yagT/S/R), pflB, IdhA, adhE, yqhD, eutG, adhP, and yjgB can be used for producing delta-lactones from glucose (e.g., delta-decalactone production from glucose (i.e., internal production of the precursors)).

In some embodiments, the host microorganism is *E. coli* and the one or more genes that is deleted is selected from dkgA, aldB, vbbO, yahK, deoC, paoA/B/C (yagT/S/R), adhE, yqhD, eutG, adhP, and, yjgB. In some embodiments the microorganism comprising one or more gene deletions selected from dkgA, aldB, ybbO, yahK, deoC, paoA/B/C (yagT/S/R), adhE, yqhD, eutG, adhP, and, yjgB can be used for producing gamma-lactone by feeding precursor(s) (e.g., gamma-decalatone production by feeding heptanal (pyruvate can be produced by the cells and/or be additionally fed)). In some embodiments, the host microorganism is *E. coli* and the one or more genes that is deleted is selected from ilvD, rhtA, dkgA, aldB, ybbO, yahK, deoC, paoA/B/C (yagT/S/R), pflB IdhA, adhE, yqhD, eutG, adhP, and yjgB. In some embodiments the microorganism comprising one or more gene deletions selected from ilvD, rhtA, dkgA, aldB, ybbO, yahK, deoC, paoA/BC (yagT/S/R), pflB IdhA, adhE, yqhD, eutG, adhP, and yjgB can be used for producing gamma-lactones from glucose (e.g., gamma-decalactone production from glucose (i.e., internal production of the precursors). In some embodiments, the host microorganism is *E. coli* and the one or more genes that is deleted is selected from pflB, ldhA, adhE. In some embodiments the microorganism comprising one or more gene deletions selected from pflB, ldhA, adhE can be used for producing gamma-lactones by feeding only the precursor alkyl aldehyde (e.g., heptanal) and internal production of pyruvate from glucose.

Multiple sequence alignment algorithms (such as ClustalW) may be used to identify aldehyde reductases and alcohol dehydrogenase that share similar function to adhE which catalyzes reduction of acetaldehyde to ethanol. Aldehyde reductases or alcohol dehydrogenases that are native to *E. coli* that show activity on aldehydes include but are not limited to sequence data found in the TABLE 12 below.

TABLE 12

| Gene name | GenBank Accession | GI | Organism |
| --- | --- | --- | --- |
| yahK | P75691.1 | 2492774 | *Escherichia coli* |
| yqhD | Q46856.1 | 3025295 | *Escherichia coli* |
| yjgB | AAA97166.1 | 537111 | *Escherichia coli* |
| gldA | BAE77365.1 | 85676115 | *Escherichia coli* |

TABLE 12-continued

| Gene name | GenBank Accession | GI | Organism |
| --- | --- | --- | --- |
| ybbO | BAE76272.1 | 85674632 | *Escherichia coil* |
| yghA | BAE77062.1 | 85675809 | *Escherichia coli* |
| adhP | BAA15126.1 | 1742410 | *Escherichia coli* |
| fucO | BAE76871.1 | 85675618 | *Escherichia coil* |
| eutG | BAA16331.1 | 1799879 | *Escherichia coli* |
| yiaY | YP_026233.1 | 49176377 | *Escherichia coli* |
| eutE | NP_416950.1 | 16130380 | *Escherichia coil* |
| betA | NP_414845.1 | 16128296 | *Escherichia coli* |

The activity of the aldehyde reductases and alcohol dehydrogenases described herein on the trans-2-unsaturated aldehydes may be determined. In some embodiments, one or more of the aldehyde reductases and alcohol dehydrogenases described herein that show substrate preference and activity towards trans-2-unsaturated aldehydes may be overexpressed in the host organism to improve production of trans-2-unsaturated alcohols. Sequence similarity search to identify homologues derived from other organisms to the native aldehyde reductases and alcohol dehydrogenases in *E. coli* that show activity on trans-2-unsaturated aldehydes may be performed.

In some embodiments, pyruvate used according to embodiments of the present disclosure is produced from renewable feedstock (such as glucose). In some embodiments, the host organism is provided with a feedstock of sugars. Such sources include, for example, sugars such as glucose, xylose, arabinose, glycerol, galactose, mannose, fructose, starch, and any combination thereof. Glucose may be obtained from various carbohydrate-containing sources including conventional bio-renewable sources such as corn (maize), wheat, potato, cassava and rice as well as alternative sources such as energy crops, plant biomass, agricultural wastes, forestry residues, sugar processing residues and plant-derived household wastes. Sources of carbohydrate include renewable feedstocks and biomass, e.g. cellulosic biomass, hemicellulosic biomass, and lignin feedstocks.

In some embodiments, the trans-2-unsaturated aldehyde process, or the delta-lactone process, or the gamma-lactone process comprises a fermentation process. In some embodiments, the fermentation process comprises a sugar-based fermentation process. In some embodiments, the sugar-based fermentation process comprises feeding sugar, feeding precursors, feeding sugar and precursors, feeding at least one aldehyde molecule (i.e., aldehyde precursor), feeding sugar and an aldehyde precursor, feeding only aldehyde precursors, feeding pyruvate and/or pyruvic acid, or any combination thereof. In some embodiments, the fermentation is partially anaerobic, substantially, or fully anaerobic.

In some embodiments, the fermentation is carried out in a single vessel. In some embodiments, the fermentation is a two-phase process. In some embodiments, the two-phase process comprises a strain growth phase and/or a production phase.

Bio-renewable feedstock sources that may be used in accordance with the present disclosure include any renewable organic matter that includes a source of carbohydrates. These include, for example, grasses, trees (hardwood and softwood), vegetation and crop residues. Other sources may include, for example, waste materials (e.g., spent paper, green waste, municipal waste, etc.). Suitable carbohydrates, including glucose, may be isolated from biorenewable materials. See, for example. Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006; Shang-Tian Yang, *Bioprocessing for Value-Added Products from Renewable Resources New Technologies and Applications*, Elsevier B. V. 2007; Furia, *Starch in the Food Industry*. Chapter 8, *CRC Handbook of Food Additives* 2nd Edition CRC Press, 1973. See also chapters devoted to Starch, Sugar and Syrups within *Kirk-Othmer Encyclopedia of Chemical Technology*, 5th Edition. John Wiley and Sons 2001. Processes to convert starch to glucose have been reported. See, for example, Schenck, *Glucose and Glucose containing Syrups* in *Ullmann's Encyclopedia of Industrial Chemistry*, Wiley-VCH 2009. Furthermore, methods to convert cellulose to glucose have been described. See, for example, Centi and van Santen, *Catalysis for Renewables*, Wiley-VCH, Weinheim 2007; Kamm, Gruber and Kamm, *Biorefineries-Industrial Processes and Products*, Wiley-VCH, Weinheim 2006: Shang-Tian Yang, *Bioprocessing for Value-Added Products from Renewable Resources New Technologies and Applications*, Elsevier B. V. 2007.

Alternative carbon sources may be crude glycerol obtained from biodiesel production plants, lactic acid obtained from degradation of waste poly-lactic acid, lactose or cheese whey permeate obtained from dairy industry, glucosamine obtained from chitin rich waste. The carbon sources may also be fatty acids and their esters (e.g., monoglycerides, diglycerides and triglycerides) obtained from plants or plant products such as canola oil, coconut oil, corn oil, olive oil, palm oil, safflower oil, peanut oil, soybean oil, sesame oil, sunflower oil and any combination thereof.

In some embodiments, the processes as provided may be carried out in a fermenter.

The engineered organism may be cultivated in a variety of reactor systems, and the process may be carried out in different modes of operations. The most commonly used bioreactor is a stirred tank bioreactor or aerated fermenter. The fermenter is equipped with sterile air supply, the mixing of bubble dispersion is achieved by mechanical agitation, and the temperature may be maintained using a jacket or coil that circulates steam or cooling water. For aerated vessels, high height/diameter ratio (>3) may be chosen to increase the contact time between the bubbles and liquid phase. Other variations of bioreactors are airlift bioreactor where mixing is achieved without mechanical agitation, and packed bed or fluidized bed bioreactors which are used when the biocatalyst is immobilized.

The fermentation may be carried out in three different modes: batch, fed-batch and continuous mode. A standard batch bioreactor is considered a "closed" system. In batch mode, all the media components are added to bioreactor while ensuring the sterility. Once the medium has been prepared, the bioreactor is inoculated with an appropriate inoculum and the fermentation is allowed to proceed until the end without any changes to the medium, i.e., without feeding of any additional components. Components such as acid and/or base can, however, be added to maintain the pH, and air/oxygen may be added to maintain the dissolved oxygen levels. In batch fermentation biomass and product concentration change over time until the fermentation is complete. The cells undergo classical lag-phase, exponential growth-phase, stationary phase growth, followed by death phase.

A variation of the batch mode is fed-batch mode where the nutrients including the carbon source is added to the fermenter as the process progresses.

In addition to batch or fed-batch mode, continuous mode of fermentation may also be used. A continuous system is considered to be "open" system in contrast to the batch mode. In continuous mode, defined production medium is added continuously to the bioreactor and equal amount of bioreactor contents are removed at the same rate. Continuous operation may be carried out in a chemostat where the vessel contents, including the cells are removed, or in a bioreactor that uses perfusion culture, which allows recycling of the viable cells back to the bioreactor, allowing high cell densities to be achieved.

The commonly used fermenter designs and different operation modes are very well-established in the literature [Biochemical Engineering Fundamentals, 2nd Ed. J. E. Bailey and D. F. Ollis, McGraw Hill, New York, 1986: Development of Sustainable Bioprocesses: Modeling and Assessment, E. Heinzle, A. P. Biwer and C. L. Cooney. John Wiley & Sons, Ltd., 2006; Bioprocess Engineering. Basic Concepts, 2nd Ed., M. L. Shuler and F. Kargi, Prentice Hall, 20011. Batch, fed-batch or continuous fermentation procedures may be employed.

In some embodiments, processes as provided herein are carried out in substantially anaerobic conditions. "Substantially anaerobic" when used in reference to a culture or growth condition means that, in some embodiments, the amount of oxygen is less than about 10% of saturation for dissolved oxygen in liquid media. In some embodiments, the term includes sealed chambers of liquid or solid medium maintained with an atmosphere less than about 1% oxygen. In some embodiments, the processes are conducted under substantially aerobic conditions. As used herein the term "substantially aerobic" when used in reference to a culture or growth condition means that, in some embodiments, that the amount of oxygen is equal to or greater than about 10% of saturation for dissolved oxygen in liquid media. In some embodiments, the term includes sealed chambers of liquid or solid medium maintained with an atmosphere greater than about 1% oxygen.

Various components may be added to the culture medium to support growth of the microorganism and/or the metabolic processes described herein, including, for example, nutrients, pH modifiers, osmoprotectants.

The organisms may be grown in any suitable medium for growth such as Luria-Bertani broth, Terrific broth or yeast extract-peptone-dextrose (YPD) medium. For production, depending up on the choice of the host, synthetic minimal media such as M9 minimal medium, yeast synthetic minimal medium, yeast nitrogen base, BG-11, or variations thereof may be used. A suitable minimal medium must contain at least one carbon source, at least one nitrogen source, salts, cofactors, buffers, and other components required to grow and maintain the recombinant microorganism. The carbon source may be one or more of the carbon sources described previously, the nitrogen source may be an ammonium salt or nitrate salt including but not limited to $(NH_4)_2SO_4$, $NH_4Cl$, $(NH_4)_2HPO_4$, $NH_4OH$, $KNO_3$, $NaNO_3$. The medium may be supplemented with complex or organic nitrogen sources such as urea, yeast extract, casamino acids, peptone, tryptone, soy flour, corn steep liquor, or casein hydrolysate. The minimal medium may be supplied with trace metals including but not limited to $H_3BO_3$, $MnCl_2$, $ZnSO_4$, $Na_2MoO_4$, $CuSO_4$, $Co(NO_3)_2$, $CuCl_2$, $ZnCl_2$, $CoCl_2$, $FeCl_3$, KI. The minimal medium may be supplemented with vitamins and/or non-vitamin compounds including but not limited to biotin, pantothanate, folic acid, inositol, nicotinic acid, p-aminobenzoic acid, pyridoxine, ribolavin, thiamine, cyanocobalamin, citric acid, ethylenediamine tetraacetic acid (EDTA), ferric ammonium citrate. The medium may be supplied by carbon dioxide either by direct sparging or in the form of NaHCO$_3$, or Na$_2$CO$_3$.

Depending upon the host organism used the minimal medium may suitably have a pH range between about pH 2.0 to about pH 10.0, between about pH 4.0 to about pH 10.0, between about pH 2.0 to about pH 8.0, between about pH 4.0 to about pH 8.0, between about pH 5.0 to about pH 8.0, between about pH 5.0 to about pH 7.0. Depending upon the host organism used the minimal medium may suitably have a pH of about 2.0, a pH of about 2.5, a pH of about 3.0, a pH of about 3.5, a pH of about 4.0, a pH of about 4.5, a pH of about 5.0, a pH of about 5.5, a pH of about 6.0, a pH of about 6.5, a pH of about 7.0, a pH of about 7.5, a pH of about 8.0, a pH of about 8.5, a pH of about 9.0, a pH of about 9.5, or a pH of about 10.0.

The fermentation may be carried out in temperature ranging from about 25° C., to about 42° C. The fermentation may be carried out in temperature ranging from about 30° C., to about 40° C. from about 33° C., to about 38° C., from about 35° C., to about 38° C., from about 35° C., to about 37° C., from about 36° C., to about 38° C., from about 36° C., to about 37° C., from about 35° C., to about 42° C., from about 25° C., to about 38° C., from about 27° C., to about 38° C., from about 29° C. to about 38° C. In some embodiments, the fermentation may be carried out at about 37° C. In some embodiments, the fermentation may be carried out at about 38° C. In some embodiments, the fermentation may be carried out at about 36° C. In some embodiments, the fermentation may be carried out at about 25° C., at about 28° C., at about 30° C., at about 32° C., at about 34° C., at about 35° C., at about 39° C., at about 40° C., at about 41° C., at about 42° C. Higher temperatures may be used if the host organism chosen is thermophilic where the cultivation temperature may be as high as about 80° C. In some embodiments, the fermentation may be carried out at least about 42° C. In some embodiments, the fermentation may be carried out in temperature ranging from about 42° C., to about 80° C.

The fermentation may be carried out under aerobic, microaerobic, or anaerobic conditions. It may also be carried out under two different phases involving aerobic growth-phase and a microaerobic or anaerobic production phase. In some embodiments, the fermentation is carried out under partially anaerobic conditions. In some embodiments, the fermentation is carried out under fully anaerobic conditions. Sterile air or oxygen may be introduced to maintain the desired dissolved oxygen levels in the medium.

Product, intermediate and byproduct formation may be analyzed by methods such as HPLC (High Performance Liquid Chromatography) equipped with a refractive index and/or photodiode array detector(s), GC-MS (Gas Chromatography-Mass Spectroscopy), GC-FID (Gas Chromatography-Flame Ionization Detector) and LC-MS (Liquid Chromatography-Mass Spectroscopy). Individual enzymatic activities from the exogenous DNA sequences may also be assayed.

The amount of product in the medium may be determined by using, for example, High Performance Liquid Chromatography (HPLC), Gas Chromatography (GC), Liquid Chromatography-Mass Spectrometry (LC-MS), and Gas Chromatography-Mass Spectrometry (GC-MS).

In some embodiments, processes as disclosed herein further include purifying the product of the processes. Such methods of purification may include, for example, liquid extraction, filtration, distillation or evaporation. Isolation of compound from the fermentation broth depends on the final purity of the compound required. The separation techniques may include: centrifugation, microfiltration, ultrafiltration, nano-filtration, evaporation, crystallization, distillation, and ion-exchange. Typical downstream processing operation may include a series of processes including separation of cells using centrifugation or microfiltration, removal of additional solids in the broth using ultrafiltration, removal of salts from the broth using nanofiltration, ion-exchange, or evaporative crystallization, and purification using distillation.

Microorganisms as described herein may be produced to secrete the resulting product, whether by choosing a host organism with a secretory signal corresponding to the product or by engineering the host organism to provide for the same. For example, membrane-bound transporter proteins may be overexpressed in the host organism to improve the secretion of the products to the fermentation broth, including but not limited to yhjX gene encoding a pyruvate-inducible inner membrane protein and putative transporter which belongs to the major facilitator superfamily of proteins, or phoE, phoF and phoC genes encoding porin E, porin F and porin C, respectively, which are responsible for membrane transport of aldehydes. The product may be recovered from the culture medium. In some embodiments, the product may be extracted from the microorganism. In some embodiments, the microorganisms may be ruptured and the culture medium or lysate may be centrifuged to remove particulate cell debris, and the membrane and soluble protein fractions may be separated if necessary.

Figure 4:
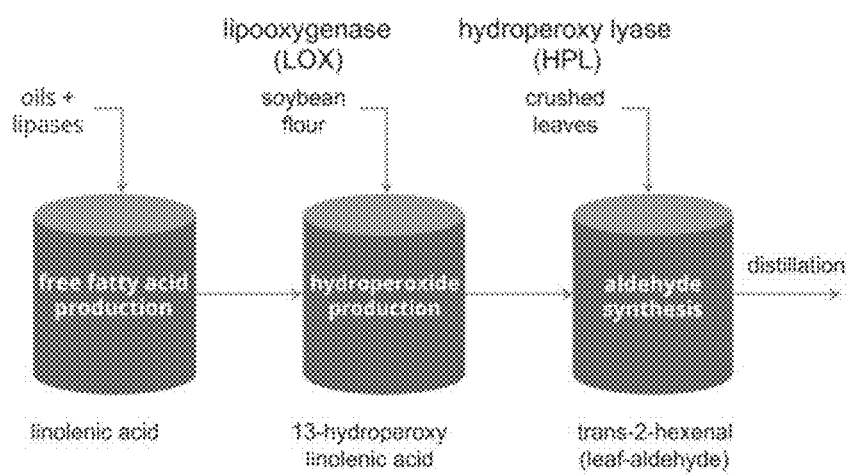
FIG. 4 exemplifies the current industrial process for making trans-2-hexenal and cis-3-hexenol.
Figure 5:
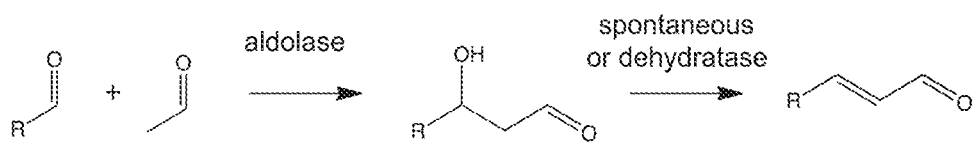
FIG. 5 exemplifies the general pathway for producing trans-2-unsaturated aldehydes using aldolase for aldehyde condensation.

In some embodiments, the present disclosure provides a pathway for producing trans-2-unsaturated aldehydes using aldehyde as a precursor. A general pathway is shown in FIG. 5. Trans-2-unsaturated aldehydes, such as hexenal, are currently produced using a fatty acid based pathway. A fatty acid based pathway is shown in FIG. 1. A fatty acid based pathway is a multistep enzymatic process that may use soybean flour and crushed leaves as the source of the enzymes 13-lipoxygenase and 13-hydroperoxide lyase [Gigot et al., "The lipoxygenase metabolic pathway in plants: potential for industrial production of natural green leaf volatiles," Biotechnol Agron soc Environ., 2010, 14(3), 451-460]. In contrast to multistep pathways for the production of trans-2-unsaturated aldehydes, such as for trans-2-hexenal (FIG. 4 shows multistep industrial process for making trans-2-hexenal), the pathway of the present disclosure is a shorter, single fermentation process. The pathways described herein, are based on sugars, giving a higher yield than fatty acid based pathways. The pathways disclosed herein, are based on microbial enzymes that are easily expressed in industrial hosts such as in *E. coli* and *S. cerevisiae*. In some embodiments, the pathways disclosed herein uses carbon-carbon bond forming aldolase enzymes. Aldolases may have broad substrate specificity, so the same pathway may be extended to make many products by changing chain length of the precursor molecules.

Figure 6:
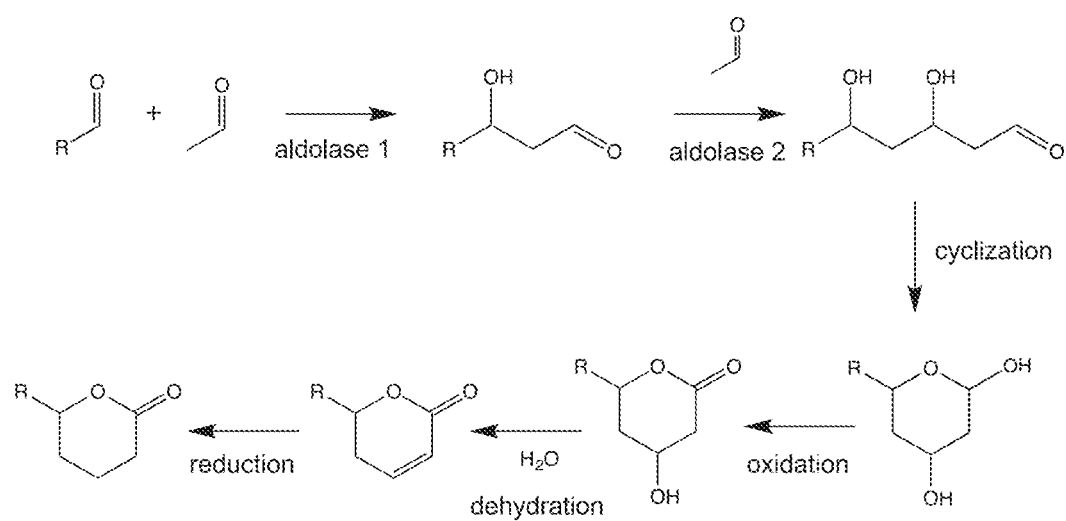
FIG. 6 exemplifies the general pathway for producing delta-lactones using aldolase for aldehyde condensation.

In some embodiments, the present disclosure provides a pathway for producing delta-lactones using aldehydes as a precursor. A general pathway is shown in FIG. 6.

Figure 7:
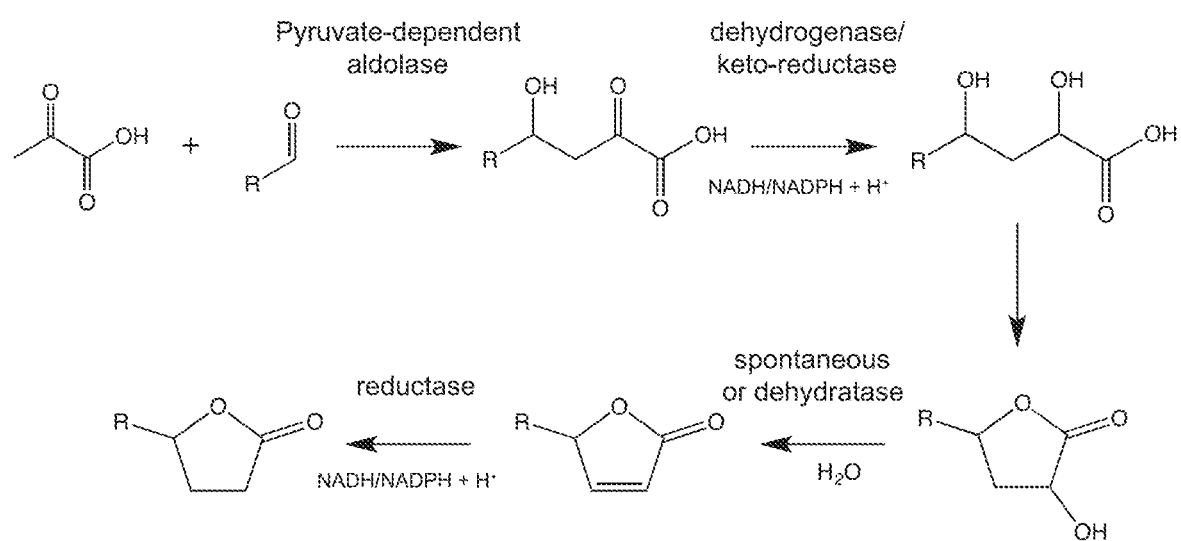
FIG. 7 exemplifies the general pathway for producing gamma-lactones using pyruvate dependent aldolase.
Figure 8:
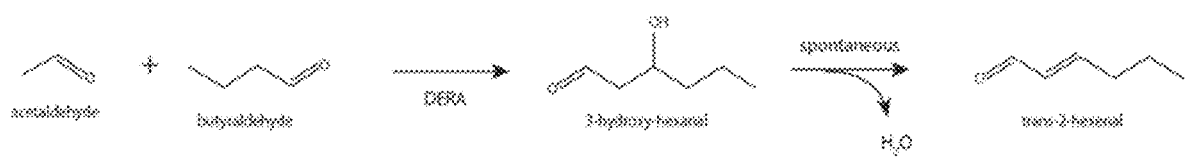
FIG. 8 exemplifies the pathway for producing trans-2-hexenal.

In some embodiments, the present disclosure provides a pathway for producing gamma-lactones using aldehyde and pyruvate as precursors. A general pathway is shown in FIG. 7.

In some embodiments, the aldehyde is selected from formaldehyde, acetaldehyde, propionaldehyde, n-butyraldehyde, iso-butyraldehyde, hexanal, n-pentanal (valeraldehyde), caproaldehyde, crotonaldehyde, n-heptaldhyde, n-octanal, n-nonylaldehyde, phenylacetaldehyde, benzaldehyde, p-tolualdehyde, salicylaldehyde, vanillin, piperonal, 2-ethyl-2-hex-enal, 2-ethylhexaldehyde, dodecyl aldehyde, undecaldehyde, decaldehyde, nonaldehyde, octaldehyde, heptaldehyde, hexaldehyde, pentaldehyde, butyraldehyde, or any combination thereof.

In some embodiments, the aldehyde used in the methods described herein is a compound represented by formula I:

wherein, R is hydrogen or $C_nH_{2n+1}$, and each n is independently 1, 2, 3, 4, 5, 6, 7, 8, 9, or 10.

In some embodiments, the present disclosure relates to any one of the compounds disclosed herein, wherein n is an integer. In some embodiments, the present disclosure relates to any one of the compounds disclosed herein, wherein n is 1. In some embodiments, the present disclosure relates to any one of compounds disclosed herein, wherein n is 2. In some embodiments, the present disclosure relates to any one of the compounds disclosed herein, wherein n is 3. In some embodiments, the present disclosure relates to any one of the compounds disclosed herein, wherein n is 4. In some embodiments, the present disclosure relates to any one of the compounds disclosed herein, wherein n is 5. In some embodiments, the present disclosure relates to any one of the compounds disclosed herein, wherein n is 6. In some embodiments, the present disclosure relates to any one of the compounds disclosed herein, wherein n is 7. In some embodiments, the present disclosure relates to any one of the compounds disclosed herein, wherein n is 8. In some embodiments, the present disclosure relates to any one of the compounds disclosed herein, wherein n is 9. In some embodiments, the present disclosure relates to any one of the compounds disclosed herein, wherein n is 10.

In some embodiments, the intermediate in the trans-2-unsaturated aldehyde pathway or the lactones pathways is a 3-hydroxy aldehyde compound represented by formula II:

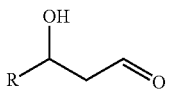

wherein R is hydrogen or $C_nH_{2n+1}$, and each 'n' is independently 1, 2, 3, 4, 5, 6, 7, 8, 9, or 10.

In some embodiments, there is provided a process comprising reacting acetaldehyde and an aldehyde of formula R—CHO, wherein R is hydrogen or $C_nH_{2n+1}$, and each 'n' is independently 1, 2, 3, 4, 5, 6, 7, 8, 9, or 10, in the presence of an aldolase enzyme, to form the 3-hydroxy aldehyde compound of formula II, wherein R is hydrogen or $C_nH_{2n+1}$, and each 'n' is independently 1, 2, 3, 4, 5, 6, 7, 8, 9, or 10. In some embodiments, the aldolase enzyme is specific for the condensation of an acetaldehyde and an aldehyde molecule. In some embodiments, the aldolase enzyme is a modified aldolase enzyme comprising an increased enzymatic activity in comparison with a corresponding unmodified or wild-type aldolase enzyme.

In some embodiments, the 3-hydroxy aldehyde is 3-hydroxy-propanal, 3-hydroxy-butanal, 3-hydroxy-pentanal, 3-hydroxy-hexanal, 3-hydroxy-heptanal, 3-hydroxy-octanal, 3-hydroxy-nonanal, 3-hydroxy-decanal, 3-hydroxy-undecanal, 3-hydroxy-dodecanal, 3-hydroxy-tridecanal, or any combination thereof.

In some embodiments, the 3-hydroxy aldehyde comprises 3-hydroxy-propanal, 3-hydroxy-butanal, 3-hydroxy-pentanal, 3-hydroxy-hexanal, 3-hydroxy-heptanal, 3-hydroxy-octanal, 3-hydroxy-nonanal, 3-hydroxy-decanal, 3-hydroxy-undecanal, 3-hydroxy-dodecanal, 3-hydroxy-tridecanal, and any combination thereof.

In some embodiments, the 3-hydroxy aldehyde compound of formula II is in enantiomeric excess. In some embodiments, the enantiomer of 3-hydroxy aldehyde produced in excess is (R)-3-hydroxy aldehyde. In some embodiments, the enantiomer of 3-hydroxy aldehyde produced in excess is (S)-3-hydroxy aldehyde. In some embodiments, the 3-hydroxy aldehyde compound of formula II comprises (R)-3-hydroxy-propanal, (R)-3-hydroxy-butanal, (R)-3-hydroxy-pentanal, (R)-3-hydroxy-hexanal, (R)-3-hydroxy-heptanal, (R)-3-hydroxy-octanal, (R)-3-hydroxy-nonanal, (R)-3-hydroxy-decanal, (R)-3-hydroxy-undecanal, (R)-3-hydroxy-dodecanal, (R)-3-hydroxy-tridecanal, and any combination thereof.

In some embodiments, the 3-hydroxy aldehyde compound of formula II contains at least about 50% of a compound of formula II in the (R)-configuration. In some embodiments, the product of the method of the present disclosure contains at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula II in the (R)-configuration. For example, the product is free of undesired byproduct or starting material. For example, the impurities (e.g., undesired byproduct, starting material, or the (S)-configuration of compound of formula II) present in the (R)-configuration of the compound of formula II is less than about 50%, less than about 45%, less than about 40%, less than about 35%, less than about 30%, less than about 25%, or less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, a trans-2-unsaturated aldehyde pathway is disclosed herein that comprises condensation of two aldehyde molecules to a 3-hydroxy aldehyde intermediate using an enzyme from class aldolases, and spontaneous dehydration of the 3-hydroxy aldehyde intermediate to alpha-beta unsaturated aldehyde. FIG. 5 shows the schematic of this pathway. In some embodiments, a pathway is disclosed that comprises condensation of two aldehyde molecules to a 3-hydroxy aldehyde intermediate using an enzyme from class aldolase, and dehydration of the 3-hydroxy aldehyde intermediate to alpha-beta unsaturated aldehyde by using dehydratase. In some embodiments, the alpha-beta unsaturated aldehydes comprise trans-2-unsaturated aldehydes. In some embodiments, the alpha-beta unsaturated aldehyde is a trans-2-unsaturated aldehyde. In some embodiments, a pathway is disclosed that comprises condensation of two aldehyde molecules to a beta-hydroxy aldehyde intermediate using the aldolase enzyme deoxyribosephosphate (DERA), and dehydration of the beta-hydroxy aldehyde intermediate to alpha-beta unsaturated aldehyde. In some embodiments, the dehydration is spontaneous. In some embodiments the dehydration is via a dehydratase. In some embodiments the aldolase comprises DERA. In some embodiments, the aldolase enzyme is DERA.

In some embodiments, the present disclosure provides a process comprising a dehydration step to dehydrate the compound of formula II to form a trans-2-unsaturated aldehyde compound.

In some embodiments, the trans-2-unsaturated aldehyde described herein is a compound represented by formula III:

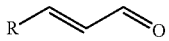

wherein R is hydrogen or $C_nH_{2n+1}$, and each 'n' is independently 1, 2, 3, 4, 5, 6, 7, 8, 9, or 10.

In some embodiments, the trans-2-unsaturated aldehyde is selected from trans-prop-2-enal, trans-2-butenal, trans-2-pentenal, trans-2-hexenal, trans-2-heptenal, trans-2-octenal, trans-2-nonenal, trans-2-decenal, trans-2-undecenal, trans-2-dodecenal, trans-2-tridecenal, and any combination thereof.

In some embodiments, the trans-2-unsaturated aldehyde comprises trans-prop-2-enal, trans-2-butenal, trans-2-pentenal, trans-2-hexenal, trans-2-heptenal, trans-2-octenal, trans-2-nonenal, trans-2-decenal, trans-2-undecenal, trans-2-dodecenal, trans-2-tridecenal, and any combination thereof.

In some embodiments, the trans-2-unsaturated aldehyde compound of formula III is 2-propenal, wherein R is hydrogen. In some embodiments, the trans-2-unsaturated aldehyde compound of formula III is trans-2-butenal, wherein n is 1. In some embodiments, the trans-2-unsaturated aldehyde compound of formula III is trans-2-pentenal, wherein n is 2. In some embodiments, the trans-2-unsaturated aldehyde compound of formula III is trans-2-hexenal, wherein n is 3. In some embodiments, the trans-2-unsaturated aldehyde compound of formula III is trans-2-heptenal, wherein n is 4. In some embodiments, the trans-2-unsaturated aldehyde compound of formula III is trans-2-octenal, wherein n is 5. In some embodiments, the trans-2-unsaturated aldehyde compound of formula III is trans-2-nonenal, wherein n is 6. In some embodiments, the trans-2-unsaturated aldehyde compound of formula III is trans-2-decenal, wherein n is 7. In some embodiments, the trans-2-unsaturated aldehyde compound of formula III is trans-2-undecenal, wherein n is 8. In some embodiments, the trans-2-unsaturated aldehyde compound of formula III is trans-2-dodecenal, wherein n is 9. In some embodiments, the trans-2-unsaturated aldehyde compound of formula III is trans-2-tridecenal, wherein n is 10.

In some embodiments, the trans-2-unsaturated aldehydes may be converted to trans-2-unsaturated alcohols. In some embodiments, the trans-2-unsaturated aldehydes may be converted to trans-2-unsaturated alcohols by using alcohol dehydrogenase or an enzyme having alcohol dehydrogenase activity. In some embodiments, trans-prop-2-enal is converted to trans-prop-2-enol. In some embodiments, trans-2-butenal is converted to trans-2-butenol. In some embodiments, trans-2-pentenal is converted to trans-2-pentenol. In some embodiments, trans-2-hexenal is converted to trans-2-hexenol. In some embodiments, trans-2-heptenal is converted to trans-2-heptenol. In some embodiments, trans-2-octenal is converted to trans-2-octenol. In some embodiments, trans-2-nonenal is converted to trans-2-nonenol. In some embodiments, trans-2-decenal is converted to trans-2-decenol. In some embodiments, trans-2-undecenal is converted to trans-2-undecenol. In some embodiments, trans-2-dodecenal is converted to trans-2-dodecenol. In some embodiments, trans-2-tridecenal is converted to trans-2-tridecenol.

Alcohol dehydrogenase (ADH) is an enzyme that catalyzes reduction of aldehydes and/or ketones into alcohols. Alcohol dehydrogenase is also known as aldehyde reductase, ADH, NAD-dependent alcohol dehydrogenase, NADH-alcohol dehydrogenase, primary alcohol dehydrogenase, aldehyde reductase (NADPH), NADP-alcohol dehydrogenase. NADP-aldehyde reductase, NADP-dependent aldehyde reductase, NADPH-aldehyde reductase. NADPH-dependent aldehyde reductase, and alcohol dehydrogenase (NADP).

In some embodiments, the trans-2-unsaturated aldehydes may be converted to trans-2-unsaturated carboxylic acids. In some embodiments, the trans-2-unsaturated aldehydes may be converted to trans-2-unsaturated carboxylic acids by using oxidoreductase. In some embodiments, trans-prop-2-enal is converted to trans-prop-2-enoic acid. In some embodiments, trans-2-butenal is converted to trans-2-butenoic acid. In some embodiments, trans-2-pentenal is converted to trans-2-pentenoic acid. In some embodiments, trans-2-hexenal is converted to trans-2-hexenoic acid. In some embodiments, trans-2-heptenal is converted to trans-2-heptenoic acid. In some embodiments, trans-2-octenal is converted to trans-2-octenoic acid. In some embodiments, trans-2-nonenal is converted to trans-2-nonenoic acid. In some embodiments, trans-2-decenal is converted to trans-2-decenoic acid. In some embodiments, trans-2-undecenal is converted to trans-2-undecenoic acid. In some embodiments, trans-2-dodecenal is converted to trans-2-dodecenoic acid. In some embodiments, trans-2-tridecenal is converted to trans-2-tridecenoic acid.

The reduction of trans-2-unsaturated aldehydes to trans-2-unsaturated alcohols or trans-2-unsaturated carboxylic acids may be carried out by using appropriate alcohol dehydrogenase (ADH), aldo-ketoreductases, oxidoreductase, or aldehyde reductase using a reducing equivalent as cofactor, which, in some embodiments, may be NADH or NADPH. In some embodiments, the ADH, AKR, oxidoreductase, or aldehyde reductase is substantially specific towards the trans-2-unsaturated aldehydes and does not act on acetaldehyde, thereby substantially avoiding or eliminating the production of ethanol as a side product.

In some embodiments, an acetaldehyde and a butyraldehyde undergo condensation to a 3-hydroxy-hexanal intermediate in the presence of an enzyme aldolase. In some embodiments, the 3-hydroxy-hexanal intermediate is dehydrated to trans-2-hexenal. In some embodiments, an acetaldehyde and a formaldehyde undergo condensation to a 3-hydroxy-propanal intermediate in the presence of an enzyme aldolase. In some embodiments, the 3-hydroxy-propanal intermediate is dehydrated to trans-prop-2-enal. In some embodiments, two acetaldehyde molecules undergo condensation to a 3-hydroxy-butanal intermediate in the presence of an enzyme aldolase. In some embodiments, the 3-hydroxy-butanal intermediate is dehydrated to trans-2-butenal. In some embodiments, an acetaldehyde and a propionaldehyde undergo condensation to a 3-hydroxy-pentanal intermediate in the presence of an enzyme aldolase. In some embodiments, the 3-hydroxy-pentanal intermediate is dehydrated to trans-2-pentenal. In some embodiments, an acetaldehyde and a pentaldehyde undergo condensation to a 3-hydroxy-heptanal intermediate in the presence of an enzyme aldolase. In some embodiments, the 3-hydroxy-heptanal intermediate is dehydrated to trans-2-heptenal. In some embodiments, an acetaldehyde and a hexaldehyde undergo condensation to a 3-hydroxy-octanal intermediate in the presence of an enzyme aldolase. In some embodiments, the 3-hydroxy-octanal intermediate is dehydrated to trans-2-octenal. In some embodiments, an acetaldehyde and a heptaldehyde undergo condensation to a 3-hydroxy-nonanal intermediate in the presence of an enzyme aldolase. In some embodiments, the 3-hydroxy-nonanal intermediate is dehydrated to trans-2-nonenal. In some embodiments, an acetaldehyde and an octaldehyde undergo condensation to a 3-hydroxy-decanal intermediate in the presence of an enzyme aldolase. In some embodiments, the 3-hydroxy-decanal intermediate is dehydrated to trans-2-decenal. In some embodiments, an acetaldehyde and a nonaldehyde undergo condensation to a 3-hydroxy-undecanal intermediate in the presence of an enzyme aldolase. In some embodiments, the 3-hydroxy-undecanal intermediate is dehydrated to trans-2-undecenal. In some embodiments, an acetaldehyde and a decaldehyde undergo condensation to a 3-hydroxy-dodecanal intermediate in the presence of an enzyme aldolase. In some embodiments, the 3-hydroxy-dodecanal intermediate is dehydrated to trans-2-dodecenal. In some embodiments, an acetaldehyde and an undecaldehyde undergo condensation to a 3-hydroxy-tridecanal intermediate in the presence of an enzyme aldolase. In some embodiments, the 3-hydroxy-tridecanal intermediate is dehydrated to trans-2-tridecenal.

In some embodiments, any of the pathways disclosed herein may further comprise addition of alcohol dehydrogenase to the alpha-beta unsaturated aldehyde to generate alpha-beta unsaturated alcohols. In some embodiments, any of the aforementioned pathways may further comprise addition of oxidoreductase to the alpha-beta unsaturated aldehyde to generate alpha-beta unsaturated carboxylic acid. In some embodiments, the aldolase is DERA In some embodiments, the intermediate 3-hydroxy aldehyde produced by any one of the pathway disclosed herein is in enantiomeric excess. In some embodiments, the enantiomer of 3-hydroxy aldehyde produced in excess is (R)-3-hydroxy aldehyde. In some embodiments, the enantiomer of 3-hydroxy aldehyde produced in excess is (S)-3-hydroxy aldehyde.

In some embodiments, the present disclosure relates to the production of delta-lactones by using aldolases, as illustrated in FIG. 6. Delta-lactones may be produced via chemical synthesis as described in Ramachandran et al. (Tetrahedron Letters 41 (2000), 583-586) and in Nobuhara (Agr. Biol. Chem., (1968) vol. 32, no. 8, p 1016-1020). Delta-lactones may also be isolated from natural sources, such as from extracts of roots (Ricardo et al., ARKIVOC (2004) (vi), 127-136). WO2007068498 discloses production of delta-lactones by reacting acetaldehyde and a substituted acetaldehyde. WO2007068498 discloses the production of delta-lactones by sequential reactions of the same aldolase. Many of these processes have disadvantages. Disadvantages include the number of required steps, low yield, expensive reagents, hazardous reagents, scarcity of natural sources, and cost. In addition, sequential reactions are known to be poor.

In some embodiments, it is the object of the present disclosure to provide with improved processes that provide higher specificity and higher activity. The present disclosure differs from WO2007068498 at least in that two different aldolases are used to produce delta-lactones. Advantages of the present disclosure include, but it is not limited to, the use of renewable resources, clean production, less pollution and less energy intensive processes in biological systems. In some embodiments, enzyme screening or protein engineering may be used to identify DERA or DERA like enzymes that are highly specific, for example for hexenal and acetaldehyde condensation to produce 3-hydroxy octanal (See, FIG. 6 (DERA 1 or aldolase 1)). In some embodiments, another or a second aldolase may be DERA or a DERA like enzyme which is specific for a reaction of, for example 3-hydroxy-octanal with acetaldehyde (See, FIG. 6 (DERA2 or aldolase 2)). In some embodiments, the second enzyme (e.g., DERA 2) may be identified through screening or protein engineering. In some embodiments, both enzymes may be derived from the same enzyme but may differ in specific mutations to improve efficiency for a desired reaction.

In some embodiments, a delta lactone pathway is disclosed that comprises: 1) condensation of two aldehyde molecules to a 3-hydroxy aldehyde intermediate using an aldolase enzyme; 2) condensation of the 3-hydroxy aldehyde intermediate and an aldehyde (e.g. acetaldehyde) to a 5,3-dihydroxy aldehyde intermediate using an aldolase enzyme; 3) cyclization of 5,3-dihydroxy aldehyde to form a tetrahydro-2H-pyran-2,4-diol (compound of formula IV(b)); 4) oxidation of tetrahydro-2H-pyran-2,4-diol to a tetrahydro-4-hydroxy-2H-pyran-2-one (compound of formula V); 5) dehydration of the tetrahydro-4-hydroxy-2H-pyran-2-one (compound of formula V) to a 5,6-dihydro-2H-pyran-2-one (compound of formula VI); and 6) reduction of the 5,6-dihydro-2H-pyran-2-one (compound of formula VI) to a delta-lactone (compound of formula VII) using reductase. FIG. 6 shows the schematic of this pathway.

In some embodiments, the dehydration step is spontaneous. In some embodiments, the dehydration step is by using dehydratase. In some embodiments, the lactonization is spontaneous. In some embodiments, the lactonization is enzymatic. In some embodiments, the lactonization is a non-enzymatic lactonization reaction. In some embodiments, the lactonization is a chemical lactonization reaction. In some embodiments, the reduction step comprises NADH or NADPH. In some embodiments, the aldolase enzyme is deoxyribosephosphate (DERA). In some embodiments, the aldolase in step 1 is different from the aldolase in step 2 (FIG. 6). In some embodiments, the aldolase in step 1 is the same as the aldolase in step 2. In some embodiments, step 1-5 is in sequential order. In some embodiments, the pathway comprises steps 1-4.

In some embodiments, the present disclosure provides a process of making a 5, 3-dihydroxy aldehyde compound by condensing a 3-hydroxy aldehyde compound of formula II and an acetaldehyde in the presence of an aldolase.

In some embodiments, the intermediate 5,3-dihydroxy aldehyde compound is represented by formula IV:

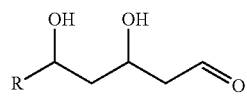

wherein R is hydrogen or $C_nH_{2n+1}$, and each 'n' is independently 1, 2, 3, 4, 5, 6, 7, 8, 9, or 10.

In some embodiments, the aldolase enzyme is specific for the condensation of the compound of formula II and an acetaldehyde molecule to form a compound of formula IV. In some embodiments, the aldolase enzyme that is specific for the condensation of the compound of formula II and an acetaldehyde molecule to form a compound of formula IV is different from the aldolase enzyme that is specific for the condensation of an acetaldehyde and an aldehyde molecule. In some embodiments, the aldolase enzyme that is specific for the condensation of the compound of formula II and an acetaldehyde molecule to form a compound of formula IV is the same as the aldolase enzyme that is specific for the condensation of an acetaldehyde and an aldehyde molecule. In some embodiments, the aldolase enzyme that is specific for the condensation of the compound of formula II and an acetaldehyde molecule to form a compound of formula IV is a modified aldolase enzyme comprising an increased enzymatic activity in comparison with a corresponding unmodified or naturally occurring or wild-type aldolase enzyme.

In some embodiments, the 5,3-dihydroxy aldehyde is 5,3-dihydroxypentanal, 5,3-dihydroxyhexanal, 5,3-dihydroxyheptanal, 5,3-dihydroxyoctanal, 5,3-dihydroxynonanal, 5,3-dihydroxydecanal, 5,3-dihydroxyundecanal, 5,3-dihydroxydodecanal, 5,3-dihydroxytridecanal, 5,3-dihydroxytetradecanal, 5,3-dihydroxypentadecanal, or any combination thereof.

In some embodiments, the 5,3-dihydroxy aldehyde comprises 5,3-dihydroxypentanal, 5,3-dihydroxyhexanal, 5,3-dihydroxyheptanal, 5,3-dihydroxyoctanal, 5,3-dihydroxynonanal, 5,3-dihydroxydecanal, 5,3-dihydroxyundecanal, 5,3-dihydroxydodecanal, 5,3-dihydroxytridecanal, 5,3-dihydroxytetradecanal, 5,3-dihydroxypentadecanal, and any combination thereof.

In some embodiments, the 5,3-dihydroxy aldehyde compound of formula IV is 5,3-dihydroxypentanal, wherein R is hydrogen. In some embodiments, the 5,3-dihydroxy aldehyde compound of formula IV is 5,3-dihydroxyhexanal, wherein n is 1. In some embodiments, the 5,3-dihydroxy aldehyde compound of formula IV is 5,3-dihydroxyheptanal, wherein n is 2. In some embodiments, the trans-2-unsaturated aldehyde compound of formula IV is 5,3-dihydroxyoctanal, wherein n is 3. In some embodiments, the 5,3-dihydroxy aldehyde compound of formula IV is 5,3-dihydroxynonanal, wherein n is 4. In some embodiments, the 5,3-dihydroxy aldehyde compound of formula IV is 5,3-dihydroxydecanal, wherein n is 5. In some embodiments, the 5,3-dihydroxy aldehyde compound of formula IV is 5,3-dihydroxyundecanal, wherein n is 6. In some embodiments, the 53-dihydroxy aldehyde compound of formula IV is 5,3-dihydroxydodecanal, wherein n is 7. In some embodiments, the 5,3-dihydroxy aldehyde compound of formula IV is 5,3-dihydroxytridecanal, wherein n is 8. In some embodiments, the 5,3-dihydroxy aldehyde compound of formula IV is 5,3-dihydroxytetradecanal, wherein n is 9. In some embodiments, the 5,3-dihydroxy aldehyde compound of formula IV is 5,3-dihydroxypentadecanal, wherein n is 10.

In some embodiments, the compound of formula IV (i.e., 5,3-dihydroxy aldehyde) undergoes cyclization to a tetrahydro-2H-pyran-2,4-diol compound of formula IV(b). In some embodiments, the hemi-acetal intermediate, tetrahydro-2H-pyran-2,4-diol, is a compound represented by formula IV(b),

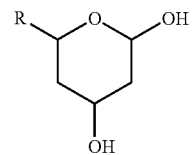

wherein R is hydrogen or $C_nH_{2n+1}$, and each 'n' is independently 1, 2, 3, 4.5, 6, 7, 8, 9, or 10.

In some embodiments, the compound of formula IV(b) undergoes oxidation to a tetrahydro-4-hydroxy-2H-pyran-2-one. In some embodiments, the oxidation comprises an enzymatic oxidation. In some embodiments, the oxidation is an enzymatic oxidation. In some embodiments, the delta lactone intermediate, tetrahydro-4-hydroxy-2H-pyran-2-one, is a compound represented by formula V:

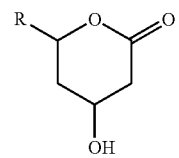

wherein R is hydrogen or $C_nH_{2n+1}$, and each 'n' is independently 1, 2, 3, 4, 5, 6, 7, 8, 9, or 10.

In some embodiments, the compound of formula V undergoes dehydration to form a compound of formula VI. In some embodiments, the dehydration comprises dehydratase. In some embodiments, the delta lactone is a compound represented by formula VI:

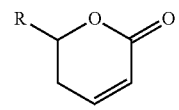

wherein R is hydrogen or $C_nH_{2n+1}$, and each 'n' is independently 1, 2, 3, 4, 5, 6, 7, 8, 9, or 10.

In some embodiments, the delta lactone disclosed herein is in enantiomeric excess. In some embodiments, the enantiomer of delta lactone produced in excess is (R)-delta lactone. In some embodiments, the enantiomer of delta lactone produced in excess is (S)-delta lactone. In some embodiments, the compound of formula VI is in enantiomeric excess.

In some embodiments, the delta-lactone of formula VI is massoia lactone, C-10 massoia lactone (5,6-dihydro-6-pentyl-2H-pyran-2-one), C-12 massoia lactone (5,6-dihydro-6-heptyl-2H-pyran-2-one), C-14 massoia lactone (5,6-dihydro-6-nonyl-2H-pyran-2-one), 5,6-dihydro-2H-pyran-2-one, 5,6-dihydro-6-methyl-2H-pyran-2-one, 5,6-dihydro-6-hexyl-2H-pyran-2-one, 5,6-dihydro-6-ethyl-2H-pyran-2-one, 5,6-dihydro-6-propyl-2H-pyran-2-one, 5,6-dihydro-6-butyl-2H-pyran-2-one, 5,6-dihydro-6-decyl-2H-pyran-2-one, 5,6-dihydro-6-octyl-2H-pyran-2-one, or any combination thereof.

In some embodiments, the delta-lactone of formula VI comprises massoia lactone, C-10 massoia lactone (5,6-dihydro-6-pentyl-2H-pyran-2-one), C-12 massoia lactone (5,6-dihydro-6-heptyl-2H-pyran-2-one), C-14 massoia lactone (5,6-dihydro-6-nonyl-2H-pyran-2-one), 5,6-dihydro-2H-pyran-2-one, 5,6-dihydro-6-methyl-2H-pyran-2-one, 5,6-dihydro-6-hexyl-2H-pyran-2-one, 5,6-dihydro-6-ethyl-2H-pyran-2-one, 5,6-dihydro-6-propyl-2H-pyran-2-one, 5,6-dihydro-6-butyl-2H-pyran-2-one, 5,6-dihydro-6-decyl-2H-pyran-2-one, 5,6-dihydro-6-octyl-2H-pyran-2-one, and any combination thereof.

In some embodiments, the delta-lactone of formula VI is (R)-5,6-dihydro-2H-pyran-2-one, (R)-massoia lactone, (R)-massoia lactone, (R)-5,6-dihydro-6-pentyl-2H-pyran-2-one, (R)-5,6-dihydro-6-heptyl-2H-pyran-2-one, (R)-5,6-dihydro-6-nonyl-2H-pyran-2-one, (R)-5,6-dihydro-2H-pyran-2-one, (R)-5,6-dihydro-6-methyl-2H-pyran-2-one, (R)-5,6-dihydro-6-hexyl-2H-pyran-2-one, (R)-5,6-dihydro-6-ethyl-2H-pyran-2-one, (R)-5,6-dihydro-6-propyl-2H-pyran-2-one, (R)-5,6-dihydro-6-butyl-2H-pyran-2-one, (R)-5,6-dihydro-6-decyl-2H-pyran-2-one, (R)-5,6-dihydro-6-octyl-2H-pyran-2-one, or any combination thereof.

In some embodiments, the delta-lactone of formula VI comprises (R)-5,6-dihydro-2H-pyran-2-one, (R)-massoia lactone, (R)-massoia lactone, (R)-5,6-dihydro-6-pentyl-2H-pyran-2-one, (R)-5,6-dihydro-6-heptyl-2H-pyran-2-one, (R)-5,6-dihydro-6-nonyl-2H-pyran-2-one, (R)-5,6-dihydro-2H-pyran-2-one, (R)-5,6-dihydro-6-methyl-2H-pyran-2-one, (R)-5,6-dihydro-6-hexyl-2H-pyran-2-one, (R)-5,6-dihydro-6-ethyl-2H-pyran-2-one, (R)-5,6-dihydro-6-propyl-2H-pyran-2-one, (R)-5,6-dihydro-6-butyl-2H-pyran-2-one, (R)-5,6-dihydro-6-decyl-2H-pyran-2-one, (R)-5,6-dihydro-6-octyl-2H-pyran-2-one, and any combination thereof.

Massoia lactones are 10, 12 and 14 carbon chain compounds, also referred to as the C-10, C-12 and C-14 massoia lactones, respectively, that possess characteristic α,β-unsaturated δ-lactone moieties. Massoia lactones may have substitution at the C6 position of the α,β-unsaturated δ-lactone structures with chains of variable length containing five, seven or nine carbons.

In some embodiments, the 5,6-dihydro-2H-pyran-2-one, compound of formula VI undergoes reduction to a compound of formula VII. In some embodiments, the reduction comprises a reductase. In some embodiments, the reduction is by using a reductase. In some embodiments, the delta-lactone is a compound represented by formula VII:

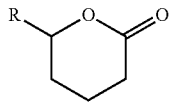

wherein R is hydrogen or $C_nH_{2n+1}$, and each 'n' is independently 1, 2, 3, 4, 5, 6, 7, 8, 9, or 10.

In some embodiments, the delta-lactone compound of formula VII is delta-valerolactone, wherein R is hydrogen. In some embodiments, delta-lactone compound of formula VII is delta-hexalactone, wherein n is 1. In some embodiments, the delta-lactone compound of formula VII is delta-heptalactone, wherein n is 2. In some embodiments, the delta-lactone compound of formula VII is delta-octalactone, wherein n is 3. In some embodiments, the delta-lactone compound of formula VII is delta-nonalactone, wherein n is 4. In some embodiments, the delta-lactone compound of formula VII is delta-decalactone, wherein n is 5. In some embodiments, the delta-lactone compound of formula VII is delta-undecalactone, wherein n is 6. In some embodiments, the delta-lactone compound of formula VII is delta-dodecalactone, wherein n is 7. In some embodiments, the delta-lactone compound of formula VII is delta-tridecalactone, wherein n is 8. In some embodiments, the delta-lactone compound of formula VII is delta-tetradecalactone, wherein n is 9. In some embodiments, the delta-lactone compound of formula VII is delta-pentadecalactone, wherein n is 10.

In some embodiments, the delta-lactone of formula VII is delta-valerolactone, delta-hexalactone, delta-heptalactone, delta-octalactone, delta-nonalactone, delta-decalactone, delta-undecalactone, delta-dodecalactone, delta-tridecalactone, delta-tetradecalactone, delta-pentadecalactone, or any combination thereof.

In some embodiments, the delta-lactone of formula VII comprises delta-valerolactone, delta-hexalactone, delta-heptalactone, delta-octalactone, delta-nonalactone, delta-decalactone, delta-undecalactone, delta-dodecalactone, delta-tridecalactone, delta-tetradecalactone, delta-pentadecalactone, and any combination thereof.

In some embodiments, the delta lactone disclosed herein is in enantiomeric excess. In some embodiments, the enantiomer of delta lactone produced in excess is (R)-delta lactone. In some embodiments, the enantiomer of delta lactone produced in excess is (S)-delta lactone. In some embodiments, the compound of formula VII is in enantiomeric excess.

In some embodiments, the delta-lactone of formula VII is (R)-delta-hexalactone, (R)-delta-heptalactone, (R)-delta-octalactone, (R)-delta-nonalactone, (R)-delta-decalactone, (R)-delta-undecalactone, (R)-delta-dodecalactone, (R)-delta-tridecalactone, (R)-delta-tetradecalactone, (R)-delta-pentadecalactone, or any combination thereof.

In some embodiments, the delta-lactone of formula VII comprises (R)-delta-hexalactone, (R)-delta-heptalactone, (R)-delta-octalactone, (R)-delta-nonalactone, (R)-delta-decalactone, (R)-delta-undecalactone, (R)-delta-dodecalactone, (R)-delta-tridecalactone, (R)-delta-tetradecalactone, (R)-delta-pentadecalactone, and any combination thereof.

In some embodiments, the delta-lactone of formula VII comprises (S)-delta-hexalactone, (S)-delta-heptalactone, (S)-delta-octalactone, (S)-delta-nonalactone, (S)-delta-decalactone, (S)-delta-undecalactone, (S)-delta-dodecalactone, (S)-delta-tridecalactone. (S)-delta-tetradecalactone. (S)-delta-pentadecalactone, and any combination thereof.

Figure 9:
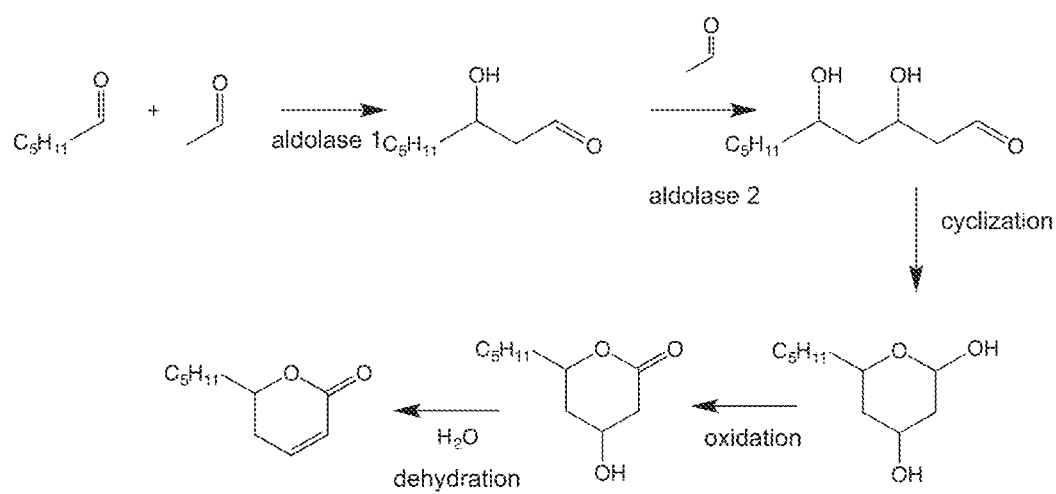
FIG. 9 exemplifies the pathway for producing massoia lactone.

In some embodiments, a massoia lactone pathway comprises: condensation of an acetaldehyde and a hexanal to 3-hydroxy-octanal by using aldolase DERA; condensation of the 3-hydroxy-octanal and an acetaldehyde to 5,3-dihydroxy-decanal by using aldolase DERA; and cyclization of 5,3-dihydroxy-decanal followed by oxidation and dehydration to form massoia lactone. In some embodiments, the massoia lactone is (R)-massoia lactone. In some embodiments the dehydration is spontaneous. In some embodiments, the dehydration is via a dehydratase. In some embodiments, the oxidation is spontaneous. In some embodiments, the oxidation is via an enzymatic oxidation. FIG. 9 shows the schematic of this pathway.

In some embodiments, a gamma lactone pathway is disclosed that comprises: 1) condensation of an aldehyde molecule and a pyruvic acid to a 4-hydroxy-2-oxo carboxylic acid (compound of formula VIII) using aldolase (e.g. pyruvate-dependent aldolase); 2) reduction of the 4-hydroxy-2-oxo carboxylic acid to 2,4-dihydroxy carboxylic acid (compound of formula IX) using dehydrogenase or keto-reductase; 3) lactonization of the 2,4-dihydroxy carboxylic acid to a 3-hydroxydihydro-2(3H)-furanone (compound of formula X); 4) dehydration (e.g. spontaneous dehydration or dehydratase) of the 3-hydroxydihydro-2(3H)-furanone (compound of formula X) to 2(5H)-furanone (compound of formula XI); and 5) reduction of 2(5H)-furanone (compound of formula XI) to a gamma-lactone (compound of formula XII) using reductase. FIG. 7 shows the schematic of this pathway.

In some embodiments, the present disclosure discloses a process of producing gamma-lactone. In some embodiments, condensation of an aldehyde molecule and a pyruvic acid in the presence of an aldolase enzyme results in a 4-hydroxy-2-oxo carboxylic acid compound. In some embodiments, the aldolase enzyme is specific for the condensation of the pyruvic acid and an aldehyde molecule. In some embodiments, the aldolase enzyme (e.g., DERA) is a modified aldolase enzyme. In some embodiments, the modified aldolase enzyme comprises an increased enzymatic activity in comparison with a corresponding unmodified, naturally occurring, or wild-type aldolase enzyme. In some embodiments, a gamma-lactone intermediate, 4-hydroxy-2-oxo carboxylic acid, is a compound represented by formula VIII:

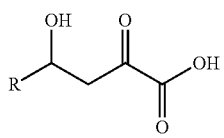

wherein R is hydrogen or $C_nH_{2n+1}$, and each 'n' is independently 1, 2, 3, 4, 5, 6, 7, 8, 9, or 10.

In some embodiments, the compound of formula VIII is reduced to 2,4-dihydroxy carboxylic acid. In some embodiments, the compound of formula VIII is reduced to 2,4-dihydroxy carboxylic acid in the presence of dehydrogenase and/or a keto-reductase. In some embodiments, a gamma-lactone intermediate, 2,4-dihydroxy carboxylic acid, is a compound represented by formula IX:

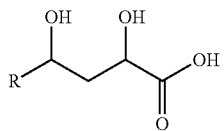

wherein R is hydrogen or $C_nH_{2n+1}$, and each 'n' is independently 1, 2, 3, 4, 5, 6, 7, 8, 9, or 10.

In some embodiments, the 2,4-dihydroxy carboxylic acid compound of formula IX undergoes lactonization to form a 3-hydroxydihydro-2(3H)-furanone (e.g., a compound of formula X). In some embodiments, a gamma-lactone intermediate, 3-hydroxydihydro-2(3H)-furanone, is a compound represented by formula X:

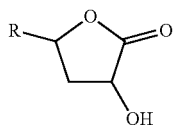

wherein R is hydrogen or $C_nH_{2n+1}$, and each 'n' is independently 1, 2, 3, 4, 5, 6, 7, 8, 9, or 10.

In some embodiments, the 3-hydroxydihydro-2(3H)-furanone compound of formula X undergoes dehydration to form 2(5H)-furanone (e.g., compound of formula XI). In some embodiments, a gamma-lactone intermediate, 2(5H)-furanone, is a compound represented by formula XI:

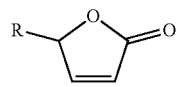

wherein R is hydrogen or $C_nH_{2n+1}$, and each 'n' is independently 1, 2, 3, 4, 5, 6, 7, 8, 9, or 10. In some embodiments, dehydration occurs spontaneously. In some embodiments, dehydration comprises dehydratase.

In some embodiments, 2(5H)-furanone compound of formula XI is reduced to a gamma-lactone. In some embodiments, the reduction of 2(5H)-furanone compound of formula XI to gamma-lactone is in the presence of a reductase. In some embodiments, the gamma-lactone is a compound represented by formula XII:

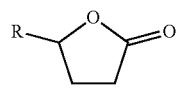

wherein R is hydrogen or $C_nH_{2n+1}$, and each 'n' is independently 1, 2, 3, 4, 5, 6, 7, 8, 9, or 10.

In some embodiments, the gamma-lactone compound of formula XII is gamma-butyrolactone, wherein R is hydrogen. In some embodiments, the gamma-lactone compound of formula XII is gamma-valerolactone, wherein n is 1. In some embodiments, gamma-lactone compound of formula XII is gamma-hexalactone, wherein n is 2. In some embodiments, the gamma-lactone compound of formula XII is gamma-heptalactone, wherein n is 3. In some embodiments, the gamma-lactone compound of formula XII is gamma-octalactone, wherein n is 4. In some embodiments, the gamma-lactone compound of formula XII is gamma-nonalactone, wherein n is 5. In some embodiments, the gamma-lactone compound of formula XII is gamma-decalactone, wherein n is 6. In some embodiments, the gamma-lactone compound of formula XII is gamma-undecalactone, wherein n is 7. In some embodiments, the gamma-lactone compound of formula XII is gamma-dodecalactone, wherein n is 8. In some embodiments, the gamma-lactone compound of formula XII is gamma-tridecalactone, wherein n is 9. In some embodiments, the gamma-lactone compound of formula XII is gamma-tetradecalactone, wherein n is 10.

In some embodiments, the gamma lactone disclosed herein is in enantiomeric excess. In some embodiments, the enantiomer of gamma lactone produced in excess is (R)-gamma lactone. In some embodiments, the enantiomer of gamma lactone produced in excess is (S)-gamma lactone. In some embodiments, the compound of formula XII is in enantiomeric excess.

In some embodiments, the gamma-lactone of formula XII is (R)-gamma-hexalactone, (R)-gamma-heptalactone, (R)-gamma-octalactone, (R)-gamma-nonalactone, (R)-gamma-decalactone, (R)-gamma-undecalactone, (R)-gamma-dodecalactone, (R)-gamma-tridecalactone, (R)-gamma-tetradecalactone, (R)-gamma-valerolactone, (R)-gamma-butyrolactone, or any combination thereof.

In some embodiments, the gamma-lactone of formula XII comprises (R)-gamma-hexalactone, (R)-gamma-heptalactone, (R)-gamma-octalactone, (R)-gamma-nonalactone, (R)-gamma-decalactone, (R)-gamma-undecalactone, (R)-gamma-dodecalactone, (R)-gamma-tridecalactone, (R)-gamma-tetradecalactone, (R)-gamma-butyrolactone, (R)-gamma-valerolactone, and any combination thereof.

In some embodiments, a gamma lactone pathway is disclosed that comprises, but not necessarily in this order: condensation of an aldehyde molecule and a pyruvate to a 2-keto-4-hydroxy acid using aldolase (e.g. pyruvate class II aldolase, BphI, HpaI); reduction of the 2-keto-4-hydroxy acid to 2,4-dihydroxy acid using dehydrogenase or keto-reductase; dehydration of the 2,4-dihydroxy acid to 4-hydroxy-2-ene-acid; lactonization of the 4-hydroxy-2-ene acid to 2(5H)-furanone (compound of formula XI); and reduction of 2(5H)-furanone (compound of formula XI) to a gamma-lactone (compound of formula XII) using reductase. FIG. 10 shows the schematic of this pathway.

In some embodiments, a gamma lactone pathway is disclosed that comprises: 1) condensation of a heptanal molecule and a pyruvate (or pyruvic acid) to a 2-keto-4-hydroxydecanoic acid using pyruvate dependent aldolase (e.g., BphI/HpaI aldolase); 2) reduction of the 2-keto-4-hydroxydecanoic acid to 2,4-dihydroxy-decanoic acid using keto-reductase and NADH/NADPH; 3) dehydration of the 2,4-dihydroxy-decanoic acid to 4-hydroxy-2-decenoic acid 4) lactonization of the 4-hydroxy-2-decenoic acid to 5-hexyl-furanone; and 5) reduction of 5-hexyl-furanone to a gamma-decalactone using enoate reductase.

In some embodiments, the lactonization may be spontaneous, chemical, enzymatic, non-enzymatic, or any combination thereof.

In some embodiments, the dehydration step is spontaneous. In some embodiments, the dehydration step is In some embodiments, the dehydration step is by using dehydratase. In some embodiments, the lactonization is spontaneous. In some embodiments, the lactonization is enzymatic. In some embodiments, the lactonization is a non-enzymatic lactonization reaction. In some embodiments, the lactonization is a chemical lactonization reaction. In some embodiments, the reduction step comprises NADH or NADPH. In some embodiments, the aldolase enzyme is deoxyribosephosphate (DERA).

In some embodiments, the gamma lactone disclosed herein is in enantiomeric excess. In some embodiments, the enantiomer of gamma lactone produced in excess is (R)-gamma lactone. In some embodiments, the enantiomer of gamma lactone produced in excess is (S)-gamma lactone.

An example of a reductase enzyme is an enoate-reductase capable of hydrogenating the alpha, beta carbon-carbon double bond at the alpha, beta position next to a carboxylic acid group into a carbon-carbon single bond. Example of enzymes having alpha, beta enoate reductase activity may be found in US applications 20070117191 and 20070254341. In some embodiments, the enoate reductase is a 2-enoate reductase, a NADH-dependent fumarate reductase, a succinate dehydrogenase, a coumarate reductase, a beta-nitroacrylate reductase, a methylacetate reductase, a NADPH 2-enoyl CoA reductase, enoyl-[acyl-carrier protein] reductase, N-ethylmaleimide reductase, crotonobetaine reductase, or a gamma-butyrobetaine reductase.

Enzymes belonging to the ketoreductase (KRED) or carbonyl reductase class (EC1.1.1.184) are useful for the synthesis of optically active alcohols from the corresponding prostereoisomeric ketone substrates and by stereospecific reduction of corresponding racemic aldehyde and ketone substrates. KREDs typically convert a ketone or aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED may require a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state).

KRED enzymes may be found in a wide range of bacteria and yeasts (for reviews: Kraus and Waldman. Enzyme catalysis in organic synthesis Vols. 1&2.VCH Weinheim 1995; Faber, K., Biotransformations in organic chemistry, 4th Ed. Springer, Berlin Heidelberg New York. 200 Hummel and Kula Eur. J. Biochem. 1989 184:1-13). Several KRED gene and enzyme sequences have been reported, e.g., *Candida magnoliae* (Genbank Acc. No. JC7338; GI: 11360538) *Candida parapsilosis* (Genbank Acc. No. BAA24528.1; GI: 2815409), *Sporobolomyces salmonicolor* (Genbank Acc. No. AF160799: GI: 6539734).

The reduction of 2-keto-4-hydroxy aldehyde to 2,4-dihydroxy aldehyde may be carried out by using appropriate alcohol dehydrogenase (ADH), aldo-ketoreductases, oxidoreductase, or aldehyde reductase using a reducing equivalent as cofactor, which in some embodiments, may be NADH or NADPH. In some embodiments, the ADH AKR, oxidoreductase, or aldehyde reductase, however, is substantially specific towards 2-keto-4-hydroxy aldehyde and does not act on acetaldehyde, thereby substantially avoiding or eliminating the production of ethanol as a side product.

In some embodiments, the present disclosure relates to a method of producing trans-2-unsaturated aldehyde from aldehydes and aldolases comprising at least one of the following trans-2-unsaturated aldehyde pathway enzymes: an aldolase enzyme that catalyzes condensation of two aldehyde molecules to produce 3-hydroxy aldehyde; and a dehydratase that dehydrates the 3-hydroxy aldehyde to trans-2-unsaturated aldehyde. In some embodiments, the at least one of the trans-2-unsaturated aldehyde pathway enzymes is partially purified, is purified, is a modified enzyme, or any combinations thereof.

In some embodiments, the present disclosure relates to a method of producing trans-2-unsaturated aldehyde from aldehydes and aldolases comprising an aldolase enzyme that catalyzes condensation of two aldehyde molecules to produce 3-hydroxy aldehyde. In some embodiments the method of producing trans-2-unsaturated aldehyde comprises a dehydratase that dehydrates the 3-hydroxy aldehyde to trans-2-unsaturated aldehyde. In some embodiments, the aldolase enzyme is partially purified, is purified, is a modified enzyme, or any combinations thereof.

In some embodiments, the present disclosure relates to a method of producing delta-lactones from aldehydes and aldolases comprising at least one of the following delta-lactone pathway enzymes: an aldolase enzyme that catalyzes condensation of two aldehyde molecules to produce a 3-hydroxy aldehyde (i.e., step 1): an aldolase enzyme that catalyzes condensation of the 3-hydroxy aldehyde and an aldehyde molecule to a 5,3-dihydroxy aldehyde (i.e., step 2); an oxidase that oxidizes of tetrahydro-2H-pyran-2,4-diol to a tetrahydro-4-hydroxy-2H-pyran-2-one a dehydratase that dehydrates the tetrahydro-4-hydroxy-2H-pyran-2-one to a 5,6-dihydro-2H-pyran-2-one; and a reductase that reduces the 5,6-dihydro-2H-pyran-2-one to a delta-lactone. In some embodiments, the aldolase in step 1 is different from the aldolase in step 2. In some embodiments, the at least one of the delta-lactone pathway enzymes is partially purified, is purified, is a modified enzyme, or any combinations thereof.

In some embodiments, the present disclosure relates to a method of producing delta-lactones from aldehydes and aldolases comprising the following delta-lactone pathway enzymes: an aldolase enzyme that catalyzes condensation of two aldehyde molecules to produce a 3-hydroxy aldehyde (i.e., step 1); and, an aldolase enzyme that catalyzes condensation of the 3-hydroxy aldehyde and an aldehyde molecule to a 5,3-dihydroxy aldehyde (i.e., step 2). In some embodiments, the aldolase in step 1 is different from the aldolase in step 2. In some embodiments, the method further comprises at least one of the following delta-lactone pathway enzymes: an oxidase that oxidizes tetrahydro-2H-pyran-2,4-diol to a tetrahydro-4-hydroxy-2H-pyran-2-one; a dehydratase that dehydrates the tetrahydro-4-hydroxy-2H-pyran-2-one to a 5,6-dihydro-2H-pyran-2-one; and a reductase that reduces the 5,6-dihydro-2H-pyran-2-one to a delta-lactone. In some embodiments, the at least one of the delta-lactone pathway enzymes of any one of the above-mentioned steps is partially purified, is purified, is a modified enzyme, or any combinations thereof.

In some embodiments, the present disclosure relates to a method of producing gamma-lactones from an aldehyde molecule, a carboxylic acid, and aldolase comprising at least one of the following gamma-lactone pathway enzymes: an aldolase enzyme that catalyzes condensation of an aldehyde molecule and a pyruvic acid to a 4-hydroxy-2-oxo carboxylic acid; a dehydrogenase or a keto-reductase that reduces the 4-hydroxy-2-oxo carboxylic acid to 2,4-dihydroxy carboxylic acid; a lactonization enzyme that transforms the 2,4-dihydroxy carboxylic acid to a 3-hydroxydihydro-2-(3H)-furanone; a dehydratase that dehydrates the 3-hydroxydihydro-2-(3H)-furanone to 2(5H)-furanone; and a reductase that reduces the 2(5H)-furanone to a gamma-lactone. In some embodiments, the at least one of the gamma-lactone pathway enzymes is partially purified, is purified, is a modified enzyme, or any combinations thereof.

In some embodiments, the present disclosure relates to a method of producing gamma-lactones from an aldehyde molecule, a carboxylic acid, and aldolase comprising an aldolase enzyme that catalyzes condensation of an aldehyde molecule and a pyruvic acid to a 4-hydroxy-2-oxo carboxylic acid. In some embodiments, the method further comprises at least one of the following gamma-lactone pathway enzymes: a dehydrogenase or a keto-reductase that reduces the 4-hydroxy-2-oxo carboxylic acid to 2,4-dihydroxy carboxylic acid; a lactonization enzyme that transforms the 2,4-dihydroxy carboxylic acid to a 3-hydroxydihydro-2-(3H)-furanone: a dehydratase that dehydrates the 3-hydroxydihydro-2-(3H)-furanone to 2(5H)-furanone; and a reductase that reduces the 2(5H)-furanone to a gamma-lactone. In some embodiments, the at least one of the enzymes is partially purified, is purified, is a modified enzyme, or any combinations thereof.

In some embodiments, the present disclosure relates to a method of producing gamma-lactones from an aldehyde, a pyruvate, and aldolase comprising at least one of the following gamma-lactone pathway enzymes: an aldolase that catalyzes condensation of an aldehyde molecule and a pyruvate to a 4-hydroxy-2-oxo carboxylic acid; a dehydrogenase or a keto-reductase that reduces the 4-hydroxy-2-oxo carboxylic acid to 2,4-dihydroxy carboxylic acid; a dehydratase that dehydrates 2,4-dihydroxy carboxylic acid to 4-hydroxy-2-ene acid; a lactonization enzyme that transforms the 4-hydroxy-2-ene acid to 2(5H)-furanone; and a reductase that reduces the 2(5H)-furanone to a gamma-lactone. In some embodiments, the at least one of the gamma-lactone pathway enzymes is partially purified, is purified, is a modified enzyme, or any combinations thereof.

In some embodiments, the present disclosure relates to a method of producing gamma-lactones from an aldehyde, a pyruvate, and an aldolase comprising an aldolase that catalyzes condensation of an aldehyde molecule and a pyruvate to a 4-hydroxy-2-oxo carboxylic acid. In some embodiments, the method further comprises at least one of the following gamma-lactone pathway enzymes: a dehydrogenase or a keto-reductase that reduces the 4-hydroxy-2-oxo carboxylic acid to 2,4-dihydroxy carboxylic acid; a dehydratase that dehydrates 2,4-dihydroxy carboxylic acid to 4-hydroxy-2-ene acid; a lactonization enzyme that transforms the 4-hydroxy-2-ene acid to 2(5H)-furanone; and a reductase that reduces the 2(5H)-furanone to a gamma-lactone. In some embodiments, the at least one of the enzymes is partially purified, is purified, is a modified enzyme, or any combinations thereof.

In some embodiments, the aldolase is a deoxyribose-5-phosphate aldolase DERA enzyme. In some embodiments, the DERA enzyme is modified. In some embodiments, the aldolase comprises an amino acid sequence of SEQ ID NO: 11, 12, 13, 14, 15, 16, 17, 18, 19, or 20, or an active fragment, or a homologue thereof. In some embodiments, the aldolase comprises at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% amino acid sequence identity to any one of SEQ ID NOs: 11, 12, 13, 14, 15, 16, 17, 18, 19, or 20.

In some embodiments, an exogenous nucleic acid encoding the aldolase comprises a nucleotide sequence of SEQ ID NO: 1, 2, 3, 4, 5, 6, 7, 8, 9, or 10. In some embodiments, the exogenous nucleic acid encoding the aldolase comprises a nucleotide sequence that is at least about 50%, at least about 55%, at least about 60%, at least about 65%, at least about 70%, at least about 75%, at least about 80%, at least about 85%, at least about 90%, at least about 95%, or at least about 99% nucleotide sequence identity to any one of SEQ ID NOs: 1, 2, 3, 4, 5, 6, 7, 8, 9, or 10.

In some embodiments, the modified DERA enzyme comprises at least one mutation, wherein the at least one mutation corresponds to or is at an amino acid position selected from R190, T12, and S238 of SEQ ID NO: 18. In some embodiments, the DERA enzyme comprises at least one mutation selected from R190K, R190I, R190F, R190A, R190L, R190M, T12A, and S238A of SEQ ID NO: 18. In some embodiments, the modified DERA enzyme comprises mutations corresponding to each or at each amino acid position selected from R190, T12, and S238 of SEQ ID NO: 18. In some embodiments, the modified DERA enzyme comprises mutations at each amino acid position corresponding to or selected from R190, T12, and S238 of SEQ ID NO: 18

In some embodiments, the method or the process of the present disclosure is performed in a culture. In some embodiments, the culture is a microbial culture. In some embodiments, the aldehyde molecules according to the method or the process of the present disclosure are fed to the culture. In some embodiments, the aldehyde molecules according to the method or the process of the present disclosure are produced from glucose. In some embodiments, at least one aldehyde molecule is produced from glucose and the other aldehyde molecule is fed to the culture.

In some embodiments, the method or the process of the present disclosure comprises expressing at least one of the enzymes in a host cell. In some embodiments, the host cell is a microbial cell. In some embodiments, the host cell is a fungal or bacterial cell. In some embodiments, the microbial host cell is a transformed microbial host cell selected from the group consisting of *Comamonas* sp., *Corynebacterium* sp., *Brevibacterium* sp. *Rhodococcus* sp., *Azotobacter* sp., *Citrobacter* sp., *Enterobacter* sp., *Clostridium* sp., *Klebsiella* sp., *Salmonella* sp., *Lactobacillus* sp., *Aspergillus* sp., *Saccharomyces* sp., *Yarrowia* sp., *Zygosaccharomyces* sp., *Pichia* sp., *Kluyveromyces* sp., *Candida* sp., *Hansenula* sp., *Dunaliella Debaryomyces* sp., *Mucor* sp., *Torulopsis* sp., *Methylobacteria* sp., *Bacillus* sp., *Escherichia* sp., *Pseudomonas* sp., *Rhizobium* sp., and *Streptomyces* sp. In some embodiments, the microbial host cell is *Escherichia coli*. In some embodiments, the microbial cell is a viable cell. In some embodiments, the microbial cell produces a crude cell lysate. In some embodiments, crude cell lysate is purified. In some embodiments, the microbial cell comprises one or more gene deletions to increase the availability of aldehyde and/or pyruvate. In some embodiments, the microbial cell comprises one or more gene deletions encoding an alcohol dehydrogenase, a lactate dehydrogenase, or a pyruvate formate lyase.

In some embodiments, the present disclosure relates to a method of producing delta-lactone comprising a non-naturally occurring microorganism for producing delta-lactone from precursor aldehyde molecules in the presence of aldolases. In some embodiments, the non-naturally occurring microorganism comprises an increased enzymatic activity of at least one enzyme in the delta-lactone pathway in comparison with the enzymatic activity of the same enzyme in a corresponding unmodified, naturally occurring, or wild-type microorganism. In some embodiments, the aldolases are two aldolases. In some embodiments, one aldolase is specific for the condensation of an acetaldehyde and an aldehyde molecule and the other aldolase is specific for the condensation of 3-hydroxy aldehyde and an acetaldehyde molecule. In some embodiments, the two aldolases are two different aldolases. In some embodiments, the two aldolases are the same aldolase. In some embodiments, the two aldolases are DERA, or a variant, or homologue thereof.

In some embodiments, the present disclosure relates to a method of producing gamma-lactone comprising a non-naturally occurring microorganism for producing gamma-lactone from a precursor aldehyde molecule in the presence of aldolases. In some embodiments, the non-naturally occurring microorganism comprises an increased enzymatic activity of at least one enzyme in the gamma-lactone pathway in comparison with the enzymatic activity of the same enzyme in a corresponding unmodified, naturally occurring, or wild-type microorganism.

In some embodiments, the present disclosure relates to a method of producing trans-2-unsaturated aldehyde comprising a non-naturally occurring microorganism for producing trans-2-unsaturated aldehyde from precursor aldehyde molecules in the presence of aldolases. In some embodiments, the non-naturally occurring microorganism comprises an increased enzymatic activity of at least one enzyme in the trans-2-unsaturated aldehyde pathway in comparison with the enzymatic activity of the same enzyme in a corresponding unmodified or wild-type microorganism.

In some embodiments, the precursor aldehyde molecules are two aldehyde molecules. In some embodiments, the precursor aldehyde molecule is one aldehyde molecule. In some embodiments, the two aldehyde molecules are fed to a microbial culture. In some embodiments, the one aldehyde molecule is fed to a microbial culture. In some embodiments, at least one of the aldehyde molecule, the pyruvate, or pyruvic acid is fed to a microbial culture. In some embodiments, the aldehyde molecule is produced from glucose via an aldehyde producing pathway. In some embodiments, at least one of the two aldehyde molecules is produced from glucose and at least one of the two aldehyde molecules is fed to a microbial culture. In some embodiments, at least one of the two aldehyde molecules is acetaldehyde. In some embodiments, the acetaldehyde is produced from glucose via decarboxylation of pyruvate by pyruvate decarboxylase.

In some embodiments, the method or the process of the present disclosure comprises a non-naturally occurring enzyme. In some embodiments, the non-naturally occurring enzyme comprises at least one modified aldolase enzyme. In some embodiments, the modified aldolase enzyme comprises an increased activity towards an aldehyde condensation reaction in comparison to an unmodified aldolase enzyme. In some embodiments, the modified aldolase enzyme is a modified deoxyribose-5-phosphate aldolase (DERA) enzyme.

In some embodiments, the present disclosure relates to a non-naturally occurring microorganism capable of synthesizing delta-lactone from aldehydes and aldolases. In some embodiments, the non-naturally occurring microorganism is derived from a wild-type or unmodified microorganism and the non-naturally occurring microorganism comprises an increased enzymatic activity of at least one enzyme in the delta-lactone pathway, in comparison with the enzymatic activity of the same enzyme in the wild-type microorganism.

In some embodiments, the present disclosure relates to a non-naturally occurring microorganism capable of synthesizing gamma-lactone from an aldehyde, a pyruvate, and aldolases. In some embodiments, the non-naturally occurring microorganism is derived from a wild-type or unmodified microorganism and the non-naturally occurring microorganism comprises an increased enzymatic activity of at least one enzyme in the gamma-lactone pathway, in comparison with the enzymatic activity of the same enzyme in the wild-type microorganism.

In some embodiments, the present disclosure relates to a non-naturally occurring microorganism capable of synthesizing trans-2-unsaturated aldehyde from aldehydes and aldolases. In some embodiments, the non-naturally occurring microorganism is derived from a wild-type or unmodified microorganism and the non-naturally occurring microorganism comprises an increased enzymatic activity of at least one enzyme in the trans-2-unsaturated aldehyde pathway, in comparison with the enzymatic activity of the same enzyme in the wild-type microorganism.

In some embodiments, the non-naturally occurring microorganism comprises one or more gene deletions encoding enzymes that consume aldehyde and/or pyruvate. In some embodiments, the one or more gene deletions is selected from an alcohol dehydrogenase, a lactate dehydrogenase, or a pyruvate formate lyase.

In some embodiments, the one or more genes that is deleted corresponds to one or more genes selected from pflB, ldhA, adhE, yqhD, eutG, adhP, and yjgB in *E. coli*. In some embodiments, the one or more genes that is deleted corresponds to one or more genes selected from aldB, poxB, ybbO, yahK, deoC, paoA/B/C (yagT/S/R), adhE, yqhD, eutG adhP, and yjgB in *E. coli*. In some embodiments, the one or more genes that is deleted corresponds to one or more genes selected from ilvD, rhtA, aldB, poxB, ybbO, yahK, deoC, paoA/B/C (yagT/S/R), pflB, ldhA, adhE, yqhD, eutG, adhP, and yjgB in *E. coli*. In some embodiments, the one or more genes that is deleted corresponds to one or more genes selected from dkgA aldB poxB ybbO yahK deoC paoAB/C (yagT/S/R) adhE yqhD eutG adhP and yjgB in *E. coli*. In some embodiments, the one or more genes that is deleted corresponds to one or more genes selected from ilvD, rhtA, dkgA, aldB, poxB, ybbO, yahK, deoC, paoA/B/C (yagT/S/R), pflB, ldhA, adhE, yqhD, eutG, adhP, and yjgB in *E. coli*. In some embodiments, the one or more genes that is deleted corresponds to one or more genes selected from dkgA, aldB, ybbO, yahK, deoC, paoA/B/C (yagT/S/R), adhE, yqhD, eutG, adhP, and, yjgB in *E. coli*. In some embodiments, the one or more genes that is deleted corresponds to one or more genes selected from ilvD, rhtA, dkgA, aldB, ybbO, yahK, deoC, paoAB/C (yagT/S/R), pflB ldhA, adhE, yqhD, eutG, adhP and yjgB in *E. coli*. In some embodiments, the one or more genes that is deleted corresponds to one or more genes selected from pflB, ldhA, adhE in *E. coli*.

In some embodiments, the present disclosure relates to a recombinant vector comprising a gene encoding DERA enzyme, and/or encoding KDC, and/or encoding BFD, and/or encoding decarboxylase. In some embodiments, the present disclosure relates to an expression vector comprising a nucleic acid sequence corresponding to any SEQ ID NO disclosed in the present disclosure or corresponding to any enzyme disclosed in the present disclosure. In some embodiments, a host cell comprises the expression vector. In some embodiments, the host cell is a microbial cell.

In some embodiments, the present disclosure relates to an isolated non-naturally occurring microorganism comprising a gene encoding a DERA enzyme, and/or an aldolase, and/or any enzyme disclosed in the present disclosure, and/or encoding a KDC, and/or encoding a BFD, and/or encoding a decarboxylase.

In some embodiments, a non-naturally occurring microorganism is obtained by introducing a recombinant vector into a host microorganism.

In some embodiments, the present disclosure relates to a method of preparing a modified enzyme, comprising: (a) subjecting a deoxyribonucleic acid (DNA) sequence encoding the enzyme to random or site directed mutagenesis; (b) expressing the modified DNA sequence obtained in (a) in a host cell; and (c) screening for host cells expressing the modified enzyme. In some embodiments, the enzyme has improved aldehyde condensation activity. In some embodiments, the enzyme is an aldolase. In some embodiments, the aldolase is DERA. In some embodiments, DERA comprises SEQ ID NO: 1, 2, 3, 4, 5, 6, 7, 8, 9, or 10. In some embodiments, the modified DNA sequence is expressed by transforming a suitable host cell with the modified DNA sequence and culturing the host cell obtained in (b) under suitable conditions for expressing the modified DNA sequence. In some embodiments, host cells screened in (c) may be subjected to a second mutagenesis treatment, and/or to rescreening, and/or to reisolation, and/or to recloning.

In some embodiments, the present disclosure relates to any one of the compounds disclosed herein, wherein R is hydrogen.

In some embodiments, the present disclosure relates to any one of the compounds disclosed herein, wherein R is $C_nH_{2n+1}$, and each 'n' is independently 1, 2, 3, 4, 5, 6, 7, 8, 9, or 10.

In some embodiments, the trans-2-unsaturated aldehyde of the methods of the present disclosure has a percent of theoretical yield of not less than about 3%, not less than about 4%, not less than about 5%, not less than about 6%, not less than about 7%, not less than about 8%, not less than about 9%, not less than about 10%, not less than about 11%, not less than about 12%, not less than about 13%, not less than about 14%, not less than about 15%, not less than about 16%, not less than about 17%, not less than about 18%, not less than about 19%, not less than about 20%, not less than about 22%, not less than about 25%, not less than about 27%, not less than about 30%, not less than about 32%, not less than about 35%, not less than about 37%, not less than about 40%, not less than about 42%, not less than about 45%, not less than about 47%, not less than about 50%, not less than about 52%, not less than about 55%, not less than about 57%, not less than about 60%, not less than about 65%, not less than about 70%, not less than about 75%, not less than about 80%, not less than about 85%, not less than about 90%, or not less than about 95%.

In some embodiments, the delta-lactone of the methods of the present disclosure has a percent of theoretical yield of not less than about 1.5%, not less than about 2%, not less than about 2.5%, not less than about 3%, not less than about 4%, not less than about 5%, not less than about 6%, not less than about 7%, not less than about 8%, not less than about 9%, not less than about 10%, not less than about 11%, not less than about 12%, not less than about 13%, not less than about 14%, not less than about 15%, not less than about 16%, not less than about 17%, not less than about 18%, not less than about 19%, not less than about 20%, not less than about 22%, not less than about 25%, not less than about 27%, not less than about 30%, not less than about 32%, not less than about 35%, not less than about 37%, not less than about 40%, not less than about 42%, not less than about 45%, not less than about 47%, not less than about 50%, not less than about 52%, not less than about 55%, not less than about 57%, not less than about 60%, not less than about 65%, not less than about 70%, not less than about 75%, not less than about 80%, not less than about 85%, not less than about 90%, or not less than about 95%.

In some embodiments, the gamma-lactone of the methods of the present disclosure has a percent of theoretical yield of not less than about 1.5%, not less than about 2%, not less than about 2.5%, not less than about 3%, not less than about 4%, not less than about 5%, not less than about 6%, not less than about 7%, not less than about 8%, not less than about 9%, not less than about 10%, not less than about 11%, not less than about 12%, not less than about 13%, not less than about 14%, not less than about 15%, not less than about 16%, not less than about 17%, not less than about 18%, not less than about 19%, not less than about 20%, not less than about 22%, not less than about 25%, not less than about 27%, not less than about 30%, not less than about 32%, not less than about 35%, not less than about 37%, not less than about 40%, not less than about 42%, not less than about 45%, not less than about 47%, not less than about 50%, not less than about 52%, not less than about 55%, not less than about 57%, not less than about 60%, not less than about 65%, not less than about 70%, not less than about 75%, not less than about 80%, not less than about 85%, not less than about 90%, or not less than about 95%.

In some embodiments, the trans-2-unsaturated aldehyde from the methods of the present disclosure is at least about 45%, at least about 47%, at least about 50%, at least about 52%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% pure, 1H NMR and gas chromatography may be used to characterize the desired trans-2-unsaturated aldehyde product. For example, the trans-2-unsaturated aldehyde is free of undesired byproduct or starting material. For example, the impurities (e.g., byproduct and starting material) in the trans-2-unsaturated aldehyde product is less than about 25% (e.g., less than about 20%, less than about 18%, less than about 15%, less than about 13%, less than about 10%, less than about 8%, less than about 5%, less than about 3%, less than about 2%, less than about 1.5%, or less than about 1%).

In some embodiments, the delta-lactone from the method of the present disclosure is at least about 45%, at least about 47%, at least about 50%, at least about 52%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% pure, 1H NMR and gas chromatography may be used to characterize the desired delta-lactone product. For example, the delta-lactone is free of undesired byproduct or starting material. For example, the impurities (e.g., byproduct and starting material) in the delta-lactone product is less than about 25% (e.g., less than about 20%, less than about 18%, less than about 15%, less than about 13%, less than about 10%, less than about 8%, less than about 5%, less than about 3%, less than about 2%, less than about 1.5%, or less than about 1%).

In some embodiments, the gamma-lactone from the methods of the present disclosure is at least about 45%, at least about 47%, at least about 50%, at least about 52%, at least about 55%, at least about 60% at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% pure, 1H NMR and gas chromatography may be used to characterize the desired delta-lactone product. For example, the gamma-lactone is free of undesired byproduct or starting material. For example, the impurities (e.g., byproduct and starting material) in the gamma-lactone product is less than about 25% (e.g., less than about 20%, less than about 18%, less than about 15%, less than about 13%, less than about 10%, less than about 8%, less than about 5%, less than about 3%, less than about 2%, less than about 1.5%, or less than about 1%).

In some embodiments, the compound of formula III of the present disclosure is at least about 45%, at least about 47%, at least about 50%, at least about 52%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% pure.

In some embodiments, the compound of formula VI of the present disclosure is at least about 45%, at least about 47%, at least about 50%, at least about 52%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about %%, at least about 97%, at least about 98%, at least about 98.5%, at least about 99%, or at least about 99.5% pure.

In some embodiments, the compound of formula VII of the present disclosure is at least about 45%, at least about 47%, at least about 50%, at least about 52%, at least about 55%, at least about 60%, at least about 65%, at least about 70%, at least about 75%, at least about 76%, at least about 77%, at least about 78%, at least about 79%, at least about 80%, at least about 81%, at least about 82% at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% pure.

In some embodiments, the compound of formula XII of the present disclosure is at least about 45%, at least about 47%, at least about 50%, at least about 52%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about %%, at least about 97%, at least about 98%, at least about 98.5%, at least about 99%, or at least about 99.5% pure.

In some embodiments, the trans-2-unsaturated aldehyde product of the method of the present disclosure contains at least about 80% of a compound of formula Ill. In some embodiments, the product of the methods of the present disclosure contains at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula III. For example, the product is free of undesired byproduct or starting material. For example, the impurities in the trans-2-unsaturated aldehyde compound of formula III is less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, the delta-lactone product of the method of the present disclosure contains at least about 80% of a compound of formula VI. In some embodiments, the product of the method of the present disclosure contains at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula VI. For example, the product is free of undesired byproduct or starting material. For example, the impurities in the delta-lactone compound of formula VI is less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, the delta-lactone product of the method of the present disclosure contains at least about 80% of a compound of formula VII. In some embodiments, the product of the method of the present disclosure contains at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula VII. For example, the product is free of undesired byproduct or starting material. For example, the impurities in the delta-lactone compound of formula VII is less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, the gamma-lactone product of the method of the present disclosure contains at least about 80% of a compound of formula XII. In some embodiments, the product of the method of the present disclosure contains at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula XII. For example, the product is free of undesired byproduct or starting material. For example, the impurities in the gamma-lactone compound of formula XII is less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, the delta-lactone product of the method of the present disclosure contains at least about 50% of a compound of formula VI in the (R)-configuration. In some embodiments, the product of the method of the present disclosure contains at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula VI in the (R)-configuration. For example, the product is free of undesired byproduct or starting material. For example, the impurities (e.g., undesired byproduct, starting material, or the (S)-configuration of compound of formula VI) in the delta-lactone compound of formula VI in the (R)-configuration is less than about 50%, less than about 45%, less than about 40%, less than about 35%, less than about 30%, less than about 25%, or less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, the delta-lactone product of the method of the present disclosure contains at least about 50% of a compound of formula VII in the (R)-configuration. In some embodiments, the product of the method of the present disclosure contains at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula VII in the (R)-configuration. For example, the product is free of undesired byproduct or starting material. For example, the impurities (e.g., undesired byproduct, starting material, or the (S)-configuration of compound of formula VII) in the delta-lactone compound of formula VII in the (R)-configuration is less than about 50%, less than about 45%, less than about 40%, less than about 35%, less than about 30%, less than about 25%, or less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

In some embodiments, the gamma-lactone product of the method of the present disclosure contains at least about 50% of a compound of formula XII in the (R)-configuration. In some embodiments, the product of the method of the present disclosure contains at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 98.5%, at least about 99%, or at least about 99.5% of a compound of formula X in the (R)-configuration. For example, the product is free of undesired byproduct or starting material. For example, the impurities (e.g., undesired byproduct, starting material, or the (S)-configuration of compound of formula XII) in the gamma-lactone compound of formula XII in the (R)-configuration is less than about 50%, less than about 45%, less than about 40%, less than about 35%, less than about 30%, less than about 25%, or less than about 20% (e.g., less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1.5%, less than about 1%, or less than about 0.5%).

It will be appreciated that the methods disclosed herein are suitable for both large-scale and small-scale preparations of the desired compounds. In some embodiments of the methods described herein, compounds of formula III, or compounds of formula VI, or compounds of formula VII, or compounds of formula XII may be prepared on a large scale, for example on an industrial production scale rather than on an experimental/laboratory scale. For example, the methods described herein allow for the preparation of batches of at least about 1 g, or at least about 5 g, or at least about 10 g, or at least about 100 g, or at least about 1 kg, or at least about 10 kg, or at least about 100 kg, or at least about 500 kg, or at least about 700 kg, or at least about 1000 kg, or at least about 2000 kg, or at least about 2500 kg, or at least about 5000 kg, or at least about 10000 kg of product.

In some embodiments, the overall yield of the compounds produced by the pathway of the present disclosure is equal to or higher than the overall yield of the compounds produced via a fatty acid oxidation pathway. For example, in some embodiments, the overall yield of a trans-2-unsaturated aldehyde produced via the pathway of the present disclosure is equal to or higher than the overall yield of the trans-2-unsaturated aldehyde produced via a fatty acid oxidation pathway. In some embodiments, the sugar based fermentation process provides a higher yield of the trans-2-aldehyde than a fatty acid based process.

In some embodiments, the overall yield of a trans-2-unsaturated aldehyde compound of formula III according to the method of the present disclosure is equal to or higher than the overall yield of the trans-2-unsaturated aldehyde compound of formula III produced via a fatty acid oxidation pathway. In some embodiments, the overall yield of the trans-2-unsaturated aldehyde according to the present disclosure is about or at least about 1.1 times, about or at least about 1.2 times, about or at least about 1.3 times, about or at least about 1.4 times, about or at least about 1.5 times, about or at least about 1.6 times, about or at least about 1.7 times, about or at least about 1.8 times, about or at least about 1.9 times, about or at least about 2 times, about or at least about 2.1 times, about or at least about 3 times, about or at least about 4 times, about or at least about 5 times the overall yield of the trans-2-unsaturated aldehyde produced via a fatty acid oxidation pathway. In some embodiments, the overall yield of the trans-2-unsaturated aldehyde according to the present disclosure is between about 1.1 and about 2 times, between about 1.5 and about 2.5 times, between about 1.2 to about 2.1 times, between about 1.8 to about 2.2 times, between about 1.1 and about 2.5 times, or between about 1.1 and about 3 times the overall yield of the trans-2-unsaturated aldehyde produced via a fatty acid oxidation pathway.

In some embodiments, the theoretical yield of a trans-2-unsaturated aldehyde compound of formula III according to the method of the present disclosure is equal to or at least about 0.045 moles, equal to or at least about 0.050 moles, equal to or at least about 0.055 moles, equal to or at least about 0.056 moles, equal to or at least about 0.057 moles, equal to or at least about 0.058 moles, equal to or at least about 0.059 moles, equal to or at least about 0.060 moles, equal to or at least about 0.065 moles, equal to or at least about 0.070 moles, equal to or at least about 0.075 moles, equal to or at least about 0.080 moles, equal to or at least about 0.085 moles, equal to or at least about 0.090 moles, equal to or at least about 0.095 moles, equal to or at least about 0.096 moles, equal to or at least about 0.097 moles, equal to or at least about 0.098 moles, equal to or at least about 0.099 moles, equal to or at least about 0.1 moles, equal to or at least about 0.11 moles, equal to or at least about 0.12 moles, or equal to or at least about 0.13 moles of trans-2-unsaturated aldehyde per mole of carbon. In some embodiments, the theoretical yield of a trans-2-unsaturated aldehyde compound of formula III according to the method of the present disclosure is between about 0.055 and about 0.12 moles, between about 0.056 and about 0.11 moles, between about 0.060 and about 0.11 moles, between about 0.070 and about 0.12 moles, or between about 0.075 and about 0.11 moles of trans-2-unsaturated aldehyde per mole of carbon.

In some embodiments, the overall yield of a delta-lactone compound of formula VI and/or of formula VII according to the methods of the present disclosure is equal to or at least about 0.25 times, equal to or at least about 0.28 times, equal to or at least about 0.30 times, equal to or at least about 0.35 times, equal to or at least about 0.40 times, equal to or at least about 0.45 times, equal to or at least about 0.50 times, equal to or at least about 0.55 times, equal to or at least about 0.60 times, equal to or at least about 0.65 times, equal to or at least about 0.70 times, equal to or at least about 0.75 times, equal to or at least about 0.80 times, equal to or at least about 0.81 times, equal to or at least about 0.82 times, equal to or at least about 0.83 times, equal to or at least about 0.84 times, equal to or at least about 0.85 times, equal to or at least about 0.86 times, equal to or at least about 0.87 times, equal to or at least about 0.88 times, equal to or at least about 0.90 times, equal to or at least about 1 time, or equal to or at least about two times the overall yield of the delta-lactone produced via a fatty acid oxidation pathway.

In some embodiments, the theoretical yield of a delta-lactone compound of formula VI and/or of formula VII according to the methods of the present disclosure is equal to or at least about 0.030 moles, equal or at least about 0.035 moles, equal to or at least about 0.040 moles, equal to or at least about 0.041 moles, equal to or at least about 0.042 moles, equal to or at least about 0.043 moles, equal to or at least about 0.044 moles, equal to or at least about 0.045 moles, equal to or at least about 0.046 moles, equal to or at least about 0.047 moles, equal to or at least about 0.048 moles, equal to or at least about 0.049 moles, equal to or at least about 0.050 moles, equal to or at least about 0.055 moles, equal to or at least about 0.060 moles, equal to or at least about 0.065 moles, equal to or at least about 0.070 moles, equal to or at least about 0.080 moles, equal to or at least about 0.090 moles, or equal to or at least about 0.1 moles of delta-lactone per mole of carbon. In some embodiments, the theoretical yield of a delta-lactone compound of formula VI and/or of formula VII according to the methods of the present disclosure is between about 0.035 and about 0.048 moles, between about 0.030 and about 0.050 moles, between about 0.040 and about 0.048 moles, between about 0.045 and about 0.055 moles, or between about 0.020 and about 0.060 moles of delta-lactone per mole of carbon.

In some embodiments, the overall yield of a gamma-lactone compound of formula XII according to the methods of the present disclosure is equal to or at least about 0.25 times, equal to or at least about 0.28 times, equal to or at least about 0.30 times, equal to or at least about 0.35 times, equal to or at least about 0.40 times, equal to or at least about 0.45 times, equal to or at least about 0.50 times, equal to or at least about 0.55 times, equal to or at least about 0.60 times, equal to or at least about 0.65 times, equal to or at least about 0.70 times, equal to or at least about 0.75 times, equal to or at least about 0.80 times, equal to or at least about 0.81 times, equal to or at least about 0.82 times, equal to or at least about 0.83 times, equal to or at least about 0.84 times, equal to or at least about 0.85 times, equal to or at least about 0.86 times, equal to or at least about 0.87 times, equal to or at least about 0.88 times, equal to or at least about 0.90 times, equal to or at least about 1 time, or equal to or at least about two times the gamma-lactone produced via a fatty acid oxidation pathway.

In some embodiments, the theoretical yield of a gamma-lactone compound of formula XII according to the methods of the present disclosure is equal to or at least about 0.030 moles, equal or at least about 0.035 moles, equal to or at least about 0.040 moles, equal to or at least about 0.041 moles, equal to or at least about 0.042 moles, equal to or at least about 0.043 moles, equal to or at least about 0.044 moles, equal to or at least about 0.045 moles, equal to or at least about 0.046 moles, equal to or at least about 0.047 moles, equal to or at least about 0.048 moles, equal to or at least about 0.049 moles, equal to or at least about 0.050 moles, equal to or at least about 0.055 moles, equal to or at least about 0.060 moles, equal to or at least about 0.065 moles, equal to or at least about 0.070 moles, equal to or at least about 0.080 moles, equal to or at least about 0.090 moles, or equal to or at least about 0.1 moles of delta-lactone per mole of carbon. In some embodiments, the theoretical yield of a gamma-lactone compound of formula XII according to the methods of the present disclosure is between about 0.035 and about 0.048 moles, between about 0.030 and about 0.050 moles, between about 0.040 and about 0.048 moles, between about 0.045 and about 0.055 moles, or between about 0.020 and about 0.060 moles of gamma-lactone per mole of carbon.

In some embodiments, the trans-2-unsaturated aldehyde process, or the delta-lactone process, or the gamma-lactone process is cell-free. In some embodiments, the trans-2-unsaturated aldehyde process, or the delta-lactone process, or the gamma-lactone process is a biotransformation process.

Genetic Engineering Technologies

The technologies for deriving the genetically engineered (e.g., non-naturally occurring) microorganism from a wild-type microorganism may be used to genetically modify any enzymes in the wild-type microorganism that may be involved in the trans-2-unsaturated aldehyde pathway, the delta-lactone pathway, and/or the gamma-lactone pathway, and thereby derive the genetically engineered microorganism therefrom.

Increase or decrease an enzymatic activity: the target gene, which is an enzyme that directly or indirectly affects the yield and/or selectivity of the trans-2-unsaturated aldehyde pathway, the delta-lactone pathway, and/or the gamma-lactone pathway, may have its enzymatic activity increased or decreased. When the target encodes an enzyme that contributes to the biosynthesis of the trans-2-unsaturated aldehyde, the delta-lactone, and/or the gamma-lactone, the present disclosure uses genetic engineering technologies to increase the enzymatic activity of the enzyme. The increase of an enzymatic activity of a target gene (encoding the enzyme) in a genetically engineered microorganism may be achieved in one of three ways: by either replacing the native enzyme with an exogenous enzyme which is more active than the native enzyme encoded by the target gene, by enhancing the expression level of the target gene, or both. The exogenous enzyme may be an ortholog, a homolog, or an up-mutant of the target gene. When the target gene is overexpressed in the genetically engineered microorganism, the enzyme encoded by the target gene may be produced in a larger quantity. Thus the genetically engineered microorganism can have an increased enzymatic activity of the target gene. The up-mutant can have point mutations, deletions or insertions.

Expression

In some embodiments of the present disclosure, a DNA sequence encoding an enzyme of the present disclosure, or a mutated DNA sequence encoding a variant or modified enzyme (e.g., aldolase. DERA) prepared by methods described herein, or any alternative methods known in the art, can be expressed, in enzyme form, using an expression vector which typically includes control sequences encoding a promoter, operator, ribosome binding site, translation initiation signal, and, optionally, a repressor gene or various activator genes.

In some embodiments, the recombinant expression vector carrying the DNA sequence encoding an enzyme of the present disclosure may be any vector which may conveniently be subjected to recombinant DNA procedures, and the choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In some embodiments, in the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

The expression vector of the present disclosure may also comprise a suitable transcription terminator and, in eukaryotes, polyadenylation sequences operably connected to the DNA sequence encoding a variant of the present disclosure. Termination and polyadenylation sequences may suitably be derived from the same sources as the promoter.

The vector may further comprise a DNA sequence enabling the vector to replicate in a host cell. Examples of such sequences are the origins of replication of plasmids pUC19, pACYC177, pUBI10, pE194, pAMB1 and pIJ702.

The vector may also comprise a selectable marker, e.g., a gene the product of which complements a defect in the host cell, such as the dal genes from *B. subtilis* or *B. licheniformis*, or one which confers antibiotic resistance such as ampicillin, kanamycin, chloramphenicol or tetracyclin resistance.

In some embodiments, intracellular expression may be advantageous in some respects, e.g., when using certain bacteria as host cells. In some embodiments, the expression is extracellular. The parent enzyme (e.g., aldolase, DERA) may in itself comprise a preregion permitting secretion of the expressed enzyme into the culture medium. In some embodiments, this preregion may be replaced by a different preregion or signal sequence, convenient accomplished by substitution of the DNA sequences encoding the respective preregions.

The procedures used to ligate the DNA construct of the present disclosure encoding an enzyme of the present disclosure, the promoter, terminator and other elements, respectively, and to insert them into suitable vectors containing the information necessary for replication, are well known to persons skilled in the art (Sambrook et al. (1989)).

A cell of the present disclosure either comprising a DNA construct or an expression vector of the disclosure as defined herein is advantageously used as a host cell in the production of an enzyme of the present disclosure. The cell may be transformed with the DNA construct of the present disclosure encoding a variant, or a wild-type, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination.

Alternatively, the cell may be transformed with an expression vector as described herein in connection with the different types of host cells.

The cell of the present disclosure may be a cell of a higher organism such as a mammal or an insect. In some embodiments the cell is a microbial cell. e.g., a bacterial or a fungal (including yeast) cell.

Examples of suitable bacteria are gram-positive bacteria such as *Bacillus subtilis. Bacillus licheniformis, Bacillus lentus, Bacillus brevis. Bacillus stearothermophilus, Bacillus alkalophilus, Bacillus amyloliquefaciens, Bacillus coagulans, Bacillus circulars, Bacillus lautus, Bacillus megaterium, Bacillus thuringaensis*, or *Streptomyces lividans*, or *Streptomyces murinus*, or gram-negative bacteria such as *E. coli*. The transformation of the bacteria may for instance be effected by protoplast transformation or by using competent cells in a manner known in the art.

The yeast organism may be selected from a species of *Saccharomyces* or *Schizosaccharomyces*, e.g., *Saccharomyces cerevisiae*. The filamentous fungus may belong to a species of *Aspergillus*, e.g., *Aspergillus oryzae, Aspergillus niger* or *Aspergillus nidulans*. Fungal cells may be transformed by a process involving protoplast formation and transformation of the protoplasts followed by regeneration of the cell wall in a manner known in the art.

In some embodiments, the present disclosure relates to a method of producing an enzyme of the present disclosure, or a variant thereof, which method comprises cultivating a host cell as described above under conditions conducive to the production of the variant and recovering the variant from the cells and/or culture medium.

The medium used to cultivate the cells may be any conventional medium suitable for growing a host cell and obtaining expression of the enzyme of the disclosure or a variant thereof. Suitable media are available from commercial suppliers or may be prepared according to published recipes (e.g., in catalogues of the American Type Culture Collection).

The enzyme of the present disclosure, or a variant thereof secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

Methods

Growth of *E. Coli* according to the methods of the present disclosure may include at least two phases: seed growth and fermentation. The seed growth phase, as described further below, may proceed in one or more seed culture stages (e.g., two stages or three stages).

A seed culture is first grown by inoculating seed medium with a sample from a stock culture (e.g., a working cell bank (WCB)). A sample of this seed culture is used either to inoculate a second seed culture or to inoculate a relatively large fermentation culture. Such seed cultures are typically carried out to allow the quantity of the microorganism from a stored culture (e.g., WCB) to be exponentially increased (scaled-up). Seed cultures may also be used to rejuvenate relatively dormant microbes in stored cultures. As is well understood in the art, at least one seed culture (e.g., two or three cultures or stages) may be used to scale-up the quantity of bacteria (e.g., *E. coli*) for inoculation into the fermentation medium.

The number of seed cultures (or stages) used depends on, for example, the size and volume of the fermentation step. For example, the culture process may involve two seed cultures: a first seed culture is grown from an inoculation of a stock (stage one seed culture), a sample of this seed culture is used to inoculate a second seed culture (stage two seed culture), and a sample from this second culture is used to inoculate a fermentation culture (fermentation stage). In some embodiments, the first and/or second seed cultures are grown in M9 media. In some embodiments, the cultures are cultured under pH controlled conditions. In some embodiments, a pH 7 is maintained with 5% ammonium hydroxide. In some embodiments, the cultures are cultured under uncontrolled pH conditions.

In stage one, a culture of E Cob is suspended in seed medium and is incubated at a temperature between about 30-40° C., preferably at 37±1 deg. C. In stage two, a sample of the stage one seed medium is used to inoculate a stage two seed medium for further growth. After inoculation, the stage two medium is incubated at a temperature between about 30-40° C., preferably at 37±1° C. Preferably, growth in seed media at any stage does not result in cell lysis before inoculation of fermentation media. Additional growth in a third (fourth, etc.) stage seed culture may also be carried out.

All references cited within this disclosure are hereby incorporated by reference in their entirety. It should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference. Certain embodiments are further described in the following examples. These embodiments are provided as examples only and are not intended to limit the scope of the claims in any way.

It will be understood that numerous modifications thereto will appear to those skilled in the art. Accordingly, the above description and accompanying drawings should be taken as illustrative of the present disclosure and not in a limiting sense. It will further be understood that it is intended to cover any variations, uses, or adaptations of the present disclosure following, in general, the principles of the present disclosure and including such departures from the present disclosure as come within known or customary practice within the art to which the present disclosure pertains and as may be applied to the essential features herein before set forth, and as follows in the scope of the appended claims.

The following examples are provided to further illustrate the advantages and features of the present disclosure, but are not intended to limit the scope of the disclosure. While they are typical of those that may be used, other procedures, methodologies, or techniques may alternatively be used.

EXAMPLES

The following specific examples are illustrative and non-limiting. The examples described herein reference and provide non-limiting support to the various embodiments described in the preceding sections.

The strains and plasmids constructed and used in the examples herein include those listed in TABLE 13.

TABLE 13

| Strain designation | Genotype |
| --- | --- |
| Wild type (K-12 MG1655) | E. coli MG1655 |
| Ardra008 | E. coli MG1655 ΔadhE, ΔldhA, ΔpflB ΔyqhD, ΔeutG, ΔadhP ΔyjgB:: cmR + pArdra002 |

| DNA parts and plasmids | Description |
| --- | --- |
| Empty vector | pBluescript II KS(+) |
| pArdra002 | pBluescript II KS(+) expressing PDC, BH1352, PA1127 each under own promoter |

Gene deletions were preformed using the lamda-red protocol and deletion primers provided within the publication (Baba, T., et al., Construction of *Escherichia coli* K-12 in-frame single-gene knockout mutants: the Keio collection. Mol Syst Biol, 2006, 2: p. 2006 0008).

The gene an dprotein sequences of BH1352(DERA *Bacillus halodurans*). PA127 (Akr *Pseudomonas aeruginosa* PAO1), PDC from *Zymomonas mobilis*, pyruate dependent aldolase (Eda *Escherichia coli* K-12MG1655), 4-hydroxy-2-oxovalerate aldolase (MphE *Escherichia coli* K-12 MGg1655), 4-hydroxy-2-oxovalerate aldolase (*Paraburkholderia xenovorans* LB4g), 4-hydroxy-2-oxoheptanedioate aldolase (HpcH/HpaI *Escherichia coli* ATCC8739). L-Threonine dehydratase ilvA (*Escherichia coli* K-12 MG1655), alpha-ketoisovalerate decarboxylase (kivD *Lactococcus lactis lactis* KF147), 2-isopropylmalate synthase (leuA *Escherichia coli* K-13 MG1655), 3-isopropylmalate dehydrogenase (leuB *Escherichia coli* K-12 MG1655), Isopropylmalate dehydratase (leuC *Escherichia coli* K-12Mg655), Isopropylmalate dehydratase (leuD *Escherichia coli* K-12 Mg1655), aspartate kinase homoserine dehydrogenase (thra *Escherichia coli* MG1655), homoserine kinase (thrB *Escherichia coli* MG1655), threonine synthase (thrC *Escherichia coli* MG1655). Themi-acetal oxidase (zwf *Escherichia coli*), the DERA sequences, the BFD and KDC sequences are shown in TABLE 14.

TABLE 14

| Name | Gene sequence | SEQ ID NO |
| --- | --- | --- |
| PA1127 (Akr Pseudomonas aeruginosa PAO1) | atgagcgttgaaagcattcgcatcgagggtatcgacacgccggtctcgcg catcggcctcggcacctgggccatcggcggctggatgtggggcggcgctg acgacgcgacgtcggtggaaaccatccggcgtgcggtggaatccgggatc aacctgatcgacaccgcgccggtctatggcttcggccattccgaagaggt cgtcggcaaggccttgcagggcctgcgcgacaaggcggtgatcgccacca aggcggcgctggagtggagcgacgcgggcatccaccgcaacgcctccgcc gcacgcatccgccgggaggtcgaggactcgctgcggcggctgaagaccga | 34 |

TABLE 14-continued

| Name | Sequence | SEQ ID NO |
|---|---|---|
| | tcgtatcgacctgtaccagattcactggccggacccgctggtggcgcacg<br>aggaaaccgccggcgaactggagcgcctgcgccgcgacggcaagatcctc<br>gccatcggcgtgagcaactattcgccggaacagatggacggggttccgcca<br>gttcgctccgctggccagcgtgcagccaccctacaacctgttcgagcgcg<br>ccatcgacgccgacgtgctgccctacgccgagcgtaacggcatcgtcgtg<br>ctggcctacggagcgctgtgccgcgcctgctttccggacggatgaacgc<br>cgagacccgcttcgatggcgacgacctgcgcaagtccgacccgaagttcc<br>agcagcccgcttcgcccagtacctggcagcggtcgcgcaactggaggaa<br>ctggctcgcgagcgctatggcaagtcggtgctggccctggccatccgctg<br>gattctcgatcgcgggccctacggtggcgctgtgggggcgcgcaagccgg<br>agcagttgaacggcatcgccgacgccttcggctggcgcctggacgacgag<br>gccatggcccgcatcgagcggatcctcgccgagaccatccaggatccggt<br>cggtcccgagttcatggcgccgcccagccgcaacgcctaa | |
| PDC<br>Z. mobilis<br>ZM4 =<br>ATCC 31821 | atgagttatactgtcggtacctatttagcggagcggcttgtccagattgg<br>tctcaagcatcacttcgcagtcgcgggcgactacaacctcgtccttcttg<br>acaacctgcttttgaacaaaaacatggagcaggtttattgctgtaacgaa<br>ctgaactgcggtttcagtgcagaaggttatgctcgtgccaaaggcgcagc<br>agcagccgtcgttacctacagcgtcggtgcgctttccgcatttgatgcta<br>tcggtggcgcctatgcagaaaaccttccggttatcctgatctccggtgct<br>ccgaacaacaatgatcacgctgctggtcacgtgttgcatcacgctcttgg<br>caaaaccgactatcactatcagttggaaatggccaagaacatcacggccg<br>ccgctgaagcgatttacacccccggaagaagctccggctaaaatcgatcac<br>gtgattaaaactgctcttcgtgagaagaagccggtttatctcgaaatcgc<br>ttgcaacattgcttccatgccctgcgccgctcctggaccggcaagcgcat<br>tgttcaatgacgaagccagcgacgaagcttctttgaatgcagcggttgaa<br>gaaaccctgaaattcatcgccaaccgcgacaaagttgccgtcctcgtcgg<br>cagcaagctgcgcgcagctggtgctgaagaagctgctgtcaaatttgctg<br>atgctctcggtggcgcagttgctaccatggctgctgcaaaaagcttcttc<br>ccagaagaaacccgcattacatcggcacctcatggggtgaagtcagcta<br>tccgggcgttgaaaagacgatgaaagaagccgatgcggttatcgctctgg<br>ctcctgtcttcaacgactactccaccactggttggacggatattcctgat<br>cctaagaaactggttctcgctgaaccgcgttctgtcgtcgttaacggcat<br>tcgcttccccagcgtccatctgaaagactatctgacccgtttggctcaga<br>agtttccaagaaaaccggtgcattggacttcttcaaatccctcaatgca<br>ggtgaactgaagaaagccgctccggctgatccgagtgctccgttggtcaa<br>cgcagaaatcgcccgtcaggtcgaagctcttctgaccccgaacacgacgg<br>ttattgctgaaaccggtgactcttggttcaatgctcagcgcatgaagctc<br>ccgaacggtgctcgcgttgaatatgaaatgcagtggggtcacattggttg<br>gtccgttcctgccgcccttcggttatgccgtcggtgctccggaacgtcgca<br>acatcctcatggttggtgatggttccttccagctgacggctcaggaagtc<br>gctcagatggttcgcctgaaactgccggttatcatcttcttgatcaataa<br>ctatggttacaccatcgaagttatgatccatgatggtccgtacaacaaca<br>tcaagaactgggattatgccggtctgatggaagtgttcaacggtaacggt<br>ggttatgacagcggtgctggtaaaggcctgaaggctaaaaccggtggcga<br>actggcagaagctatcaaggttgctctggcaaacaccgacggcccaaccc<br>tgatcgaatgcttcatcggtcgtgaagactgcactgaagaattggtcaaa<br>tggggtaagcgcgttgctgccgccaacagccgtaagcctgttaacaagct<br>cctctag | 75 |
| Pyruvate<br>dependent<br>aldolase<br>(Eda<br>Escherichia<br>coli K-12<br>MG1655) | atgaaaaactggaaaacaagtgcagaatcaatcctgaccaccggcccggt<br>tgtaccggttatcgtggtaaaaaaactggaacacgcggtgccgatggcaa<br>aagcgttggttgctggtggggtgcgcgttctggaagtgactctgcgtacc<br>gagtgtgcagttgacgctatccgtgctatcgccaaagaagtgcctgaagc<br>gattgtgggtgccggtacggtgctgaatccacagcagctggcagaagtca<br>ctgaagcgggtgcacagttcgcaattagcccgggtctgaccgaagcgctg<br>ctgaaagctgctaccgaagggactattcctctgattccggggatcagcac<br>tgtttccgaactgatgctgggtatggactacggtttgaaagagttcaaat<br>tcttcccggctgaagctaacggcggcgtgaaagccctgcaggcgatcgcg<br>ggtccgttctcccaggtccgtttctgcccgacgggtggtatttctccggc<br>taactaccgtgactacctggcgctgaaaagcgtgctgtgcatcggtcggt<br>cctggctggttccggcagatgcgctggaagcgggcgattacgaccgcatt<br>actaagctggcgcgtgaagctgtagaaggcgctaagctgtaa | 28 |
| 4-hydroxy-<br>2-oxovalerate<br>aldolase<br>(MphE<br>Escherichia<br>coli K-12<br>MG1655) | atgaacggtaaaaaactttatatctcggacgtcacattgcgtgacggtat<br>gcacgccattcgtcatcagtattcgctgaaaaacgttcgccagattgcca<br>aagcactggacgatgcccgcgtggattcgattgaagtggcccacggcgac<br>ggtttgcaaggttccagcttaactatggtttcggcgcacatagcgacct<br>tgaatggattgaagcggcggcggatgtggtgaagcacgccaaaatcgcga<br>cgttgttgctgccaggaatcggcactattcacgatctgaaaaatgcctgg<br>caggctggcgcgcgggtggttcgtgtggcaacgcactgtaccgaagctga<br>tgtttccgcccagcatattcagtatgcccgcgagctcggaatggacaccg<br>ttggttttctgatgatgagccatatgaccacgccggagaatctcgccaag<br>caggcaaagctgatggaaggctacggtgcgacctgtatttatgtggtgga<br>ttctggcggtgcgatgaacatgagcgatatccgtgaccgtttccgcgccc<br>tgaaagcagagctgaaaccagaaacgcaaactggcatgcacgctcaccat<br>aacctgagtcttggcgtggcgaactctatcgcggcggtggaagagggctg | 29 |

TABLE 14-continued

| Name | | SEQ ID NO |
|---|---|---|
| | cgaccgaatcgacgccagcctcgcgggaatgggcgcgggcgcaggtaacg<br>caccgctggaagtgtttattgccgccgcggataaactgggctggcagcat<br>gggaccgatctctatgcgttaatggatgccgccgacgacctggtgcgtcc<br>gttgcaggatcgaccggtacgagtcgatcgcgaaacgctggcgctgggat<br>acgctggtgtttactcgagcttcctgcgtcactgtgaaacggcggcggcg<br>cgttatggcttaagtgcggtggatattctcgttgagctgggcaaacgccg<br>gatggttggcggccaggaggatatgatcgttgacgtggcgctggatctgc<br>gcaacaacaaataa | |
| 4-hydroxy-<br>2-oxovalerate<br>aldolase<br>(*Paraburkholderia*<br>*xenovorans*<br>LB400) | atgaagctagaaggcaaaaaagtcaccgtccacgacatgacgctgcgcga<br>cggcatgcaccccaagcgccaccagatgacgctggagcaaatgaaatcca<br>tcgcctgcggcctggatgccgcgggcatcccgctgatcgaagtcacccac<br>ggcgacggcctgggcggctcctccgtcaactacggctttccggcgcacag<br>cgacgaggaatacctgggcgccgttgattccgttgatgaagcaggccaagg<br>tcagtgccctgctcttgcccggcatcggcaccgtcgaacacctgaagatg<br>gccaaggacctgggcgtgaacaccatccgcgtggccaccactgcaccga<br>agccgatgtgtcggagcagcacatcacccaatcgcgcaagctgggtctgg<br>acaccgtgggcttttttgatgatggcgcacatggccagcccagaaaagctg<br>gtcagccaggcactcttgatgcaaggctacggcgccaactgcatctacgt<br>caccgactcggccggctacatgctgcctgacgacgtgaaagcgcgcctga<br>gtgccgtgcgtgccgcgctcaaacccgaaaccgagttgggctttcacggc<br>catcacaacctggccatgggcgtcgccaactcgatcgccgcgatcgaggc<br>cggggccaccccgcatcgatgccgctgccgctggcctgggtgccggcgcc<br>gcaacacgccgatggaggtgttcatcgccgtatgcgcgcgcatgggatc<br>gaaaccggagtcgatgtgttcaagatccaggacgtggccgaagacctggt<br>ggtgccgatcatggaccatgtcatccgcatcgaccgcgactc | 80 |
| 4-hydroxy-<br>2-oxoheptane<br>dioate<br>aldolase<br>(HpcH/HpaI<br>*Escherichia*<br>*coli*<br>ATCC8739) | atggaaaacagttttaaagcggcgctgaaagcaggccgcccgcagatcgg<br>attatggctggggctgagtagcagttacagcgcagagttactggcggag<br>caggattcgactggttgttgatcgacggtgaacacgcgccgaataacgtg<br>caaaccgtgctcacccagctacaggcgattgcgccctaccccagtcagcc<br>agtggtacgcccatcgtgaacgatccggtgcaaatcaaacaactgctgg<br>acgtcggcacacaaaccttgctggtgccgatggtacaaaacgctgacgaa<br>gcccgtgaagcggtacgcgccacccgttatcccccgccggtattcgcgg<br>tgtgggcagtgcgctggccgcgcctcgcgctggaatcgtattcctgatt<br>acctgcaaaaagccaacgatcaaatgcgtgcgtgctggtgcagatcgaaacg<br>cgtgaggcaatgaagaacttaccgcagattctgacgtggaaggcgtcga<br>cggcgtgtttatcggcccggcggatctgagcgccgatatgggttatgccg<br>gtaatccgcagcacccggaagtacaggccgccattgagcaggcgatcgtg<br>cagatccgtgaatcgggcaaagcgccggggatcctgatcgccaatgagca<br>actggcaaaacgctatctggaactgggcgcgctgtttgtcgccgtcggcg<br>ttgacaccaccctgctcgcccgcgccgctgaagcgctggcagcacggttt<br>ggtgcgcaggccaccgccgtgaagcccggcgtgtattaa | 81 |
| Threonine<br>dehydratase<br>ilvA<br>(*Escherichia*<br>*coli* K-12<br>MG1655) | atggctgactcgcaacccctgtccggtgctccggaaggtgccgaatattt<br>aagagcagtgctgcgcgcgccggtttacgaggcggcgcaggttacgccgc<br>tacaaaaaatggaaaaactgtcgtcgcgtcttgataacgtcattctggtg<br>aagcgcgaagatcgccagccagtgcacagctttaagctgcgcggcgcata<br>cgccatgatggcgggcctgaaagaacaagaaaagcgcaccggcgtgatca<br>ctgcttctgcgggtaaccacgcgcagggcgtcgcgttttcttctgcgcgg<br>ttaggcgtgaaggccctgatcgttatgccaaccgccaccgccgacatcaa<br>agtcgacgcggtgcgcggcttcggcggcgaagtgctgctccacggcgcga<br>actttgatgaagcgaaagccaaagcgatcgaactgtcacagcagcagggg<br>ttcacctgggtgccgccgttcgaccatccgatggtgattgccgggcaagg<br>cacgctggcgctggaactgctccagcaggacgcccatctcgaccgcgtat<br>ttgtgccagtcggcggcggcgtctggctgctggcgtggcggtgctgatc<br>aaacaactgatgccgcaaatcaaagtgatcgccgtagaagcggaagactc<br>cgcctgcctgaaagcagcgctggatgcgggtcatccggttgatctgccgc<br>gcgtagggctatttgctgaaggcgtagcggtaaaacgcatcggtgacgaa<br>accttccgttatgccaggagtatctcgacgacatcatcaccgtcgatag<br>cgatgcgatctgtgcggcgatgaaggatttattcgaagatgtgcgcgcgg<br>tggcggaaccctctggcgcgctggcgctggcgcggaatgaaaaaatatatc<br>gccctgcacaacattcgcggcgaacggctggcgcatattctttccggtgc<br>caacgtgaacttccacggcctgcgctacgtctcagaacgctgcgaactgg<br>gcgaacagcgtgaagcgttgttggcggtgaccattccggaagaaaaaggc<br>agcttcctcaaattctgccaactgcttggcgggcgttcggtcaccgagtt<br>caactaccgttttgccgatgccaaaaacgcctgcatctttgtcggtgtgc<br>gcctgagccgcggcctcgaagagcgcaaagaaattttgcagatgctcaac<br>gacggcggctacacgcgtggttgatctctccgacgacgaaatggcgaagct<br>acacgtgcgctatatggtcggcggaacgtccatcgcgcgttgcaggaac<br>gcctctacagcttcgaattcccggaatcaccgggcgcgctgctgcgcttc<br>ctcaacacgctgggtacgtactggaacatttctttgttccactatcgcag<br>ccatggcaccgactacggcgcgtactggcggcgttcgaacttggcgacc<br>atgaaccggatttcgaaacccggctgaatgagctgggctacgattgccac<br>gacgaaaccaataaccccggcgttcaggttctttttggcgggttag | 50 |

TABLE 14-continued

| Name | | SEQ ID NO |
|---|---|---|
| Alpha-ketoisovalerate decarboxylase (kivD Lactococcus lactis lactis KF147) | atgtatacagtaggagattacctattagaccgattacacgagttaggaat tgaagaaattttggagtccctggagactataacttacaattttagatc aaattatttcccgcaaggatatgaaatgggtcggaaatgctaatgaatta aatgcttcttatatggctgatggctatgctcgtactaaaaaagctgccgc atttcttacaacctttggagtaggtgaattgagtgcagttaatggattag caggaagttacgccgaaaatttaccagtagtagaaatagtgggatcacct acatcaaaagtccaaaatgaaggaaaatttgttcatcatacgctggctga cggtgattttaaacactttatgaaatgcacgaacctgttacagcagctc gaactttactgacagcagaaaatgcaaccgttgaaattgaccgagtactt tctgcactactaaaagaaagaaaacctgtctatatcaacttaccagttga tgttgctgctgcaaaagcagagaaaccctcactccctttgaaaaaagaaa atccaacttcaaatacaagtgaccaagagattttgaataaaattcaagaa agcttgaaaaatgccaaaaaaccaatcgtgattacaggacgtgaaataat tagctttggcttagaaaatacagtcactcaatttatttcaaagacaaaac tccctattacgacattaaactttggaaaaagttcagttgatgaaactctc ccttcattttaggaatctataatggtaaactctcagagcctaatcttaa agaattcgtggaatcagccgacttcatcctgatgcttggagttaaactca cagactcttcaacaggagcatttacccatcatttaaatgaaaataaaatg atttcactgaacatagacgaaggaaaaatatttaacgaaagcatccaaaa ttttgattttgaatccctcatctcctctctcttagacctaagcggaatag aatacaaaggaaaatatatcgataaaaagcaagaagactttgttccatca aatgcgcttttatcacaagaccgcctatggcaagcagttgaaaacctaac tcaaagcaatgaaacaatcgttgctgaacaagggacatcattctttggcg cttcatcaatttcttaaaaccaaagagtcattttattggtcaacccttat gggggatcaattggatatacattcccagcagcattaggaagccaaattgc agataaagaaagcagacaccttttattattggtgatggttcacttcaac ttacagtgcaagaattaggattagcaatcagagaaaaaattaatccaatt tgctttattatcaataatgatggttatacagtcgaaagagaaattcatgg accaaatcaaagctacaatgatattccaatgtgaattactcaaaattac cagaatcattggaacaacagaagaacgagtagtctcgaaaatcgttaga actgaaaatgaatttgtgtctgtcatgaaagaagctcaagcagatccaaa tagaatgtactggattgagttagtttttggcaaaagaagatgcaccaaaag tactgaaaaaaatgggtaaactatttgctgaacaaaataaatcataa | 69 |
| 2-isopropylmalate synthase (leuA Escherichia coli K-12 MG1655) | atgagccagcaagtcattattttcgataccacattgcgcgacggtgaaca ggcgttacaggcaagcttgagtgtgaaagaaaaactgcaaattgcgctgg cccttgagcgtatgggtgttgacgtgatggaagtcggtttccccgtctct tcgccgggcgattttgaatcggtgcaaaccatcgcccgccaggttaaaaa cagccgcgtatgtgcgttagctcgctgcgtggaaaaagatatcgacgtgg cggccgaatccctgaaagtcgccgaagccttccgtattcatacctttatt gccacttcgccaatgcacatcgccaccaagctgcgcagcacgctggacga ggtgatcgaacgcgctatctatatggtgaaacgcgcccgtaattacaccg atgatgttgaattttcttgcgaagatgccgggcgtacacccattgccgat ctggcgcgagtggtcgaagcggcgattaatgccggtgccaccaccatcaa cattccggacaccgtgggctacaccatgccgtttgagttcgccggaatca tcagcggcctgtatgaacgcgtgcctaacatcgacaaagccattatctcc gtacatacccacgacgatttgggcctggcggtcggaaactcactggcggc ggtacatgccggtgcacgccaggtggaaggcgcaatgaacgggatcggcg agcgtgccggaaactgttccctggaagaagtcatcatggcgatcaaagtt cgtaaggatattctcaacgtccacaccgccattaatcaccaggagatatg gcgcaccagccagttagttagccagatttgtaatatgccgatccccggcaa acaaagccattgttggcagcggcgcattcgcacactcctccggtatacac caggatggcgtgctgaaaaaccgcgaaaactacgaaatcatgacaccaga atctattggtctgaaccaaatccagctgaatctgacctctcgttcggggc gtgcggcggtgaaacatcgcatggatgagatgggtataaagaaagtgaa tataatttagacaaatttgtacgatgctttcctgaagctggcggacaaaa aggtcaggtgtttgattacgatctggaggcgctggccttcatcggtaagc agcaagaagagccggagcatttccgtctggattacttcagcgtgcagtct ggctctaacgatatcgccaccgccgccgtcaaactggcctgtggcgagaa agtcaaagcagaagccgccaacggtaacggtccggtcgatgccgtctatc aggcaattaaccgcatcactgaatataacgtcgaactggtgaaatacagc ctgaccgccaaaggccacggtaaagatgcgctgggtcaggtggatatcgt cgctaactacaacggtcgccgcttccacggcgtcggcctggctaccgata ttgtcgagtcatctgccaaagccatggtgcacgttctgaacaatatctgg cgtgccgcagaagtcgaaaaagagttgcaacgcaaagctcaacacaacga aacaacaaggaaaccgtgtga | 63 |
| 3-isopropylmalate dehydrogenase (leuB Escherichia coli K-12 MG1655) | Atgtcgaagaattaccatattgccgtattgccggggacggtattggtcc ggaagtgatgacccaggcgctgaaagtgctggatgccgtgcgcaaccgct ttgcgatgcgcatcaccaccagccattacgatgtaggcggcgcagccatt gataaccacgggcaaccactgccgcctgcgacggttgaaggttgtgagca agccgatgccgtgctgtttggctcggtaggcggcccgaagtgggaacatt taccaccagaccagcaaccagaacgcggcgcgctgctgcctctgcgtaag cacttcaaattattcagcaacctgcgcccggcaaaactgtatcagggggct ggaagcattctgtccgctgcgtgcagacattgccgcaaacggcttcgaca tcctgtgtgtgcgcgaactgaccggcggcatctatttcggtcagccaaaa | 64 |

TABLE 14-continued

| Name | | SEQ ID NO |
|---|---|---|
| | ggccgcgaaggtagcggacaatatgaaaaagcctttgataccgaggtgta tcaccgttttgagatcgaacgtatcgcccgcatcgcgtttgaatctgctc gcaagcgtcgccacaaagtgacgtcgatcgataaagccaacgtgctgcaa tcctctatttatggcgggagatcgttaacgagatcgccacggaataccc ggatgtcgaactggcgcatatgtacatcgacaacgccaccatgcagctga ttaaagatccatcacagtttgacgttctgctgtgctccaacctgcttggc gacattctgtctgacgagtgcgcaatgatcactggctcgatggggatgtt gccttccgccagcctgaacgagcaaggttttggactgtatgaaccggcgg gcggctcggcaccagatatcgcaggcaaaaacatcgccaacccgattgca caaatcctttcgctggcactgctgctgcgttacagcctggatgccgatga tgcggcttgcgccattgaacgcgccattaaccgcgcattagaagaaggca ttcgcaccggggatttagcccgtggcgctgccgccgttagtaccgatgaa atgggcgatatcattgcccgctatgtagcagaagggggtgtaa | |
| Isopropylmalate dehydratase (leuC Escherichia coli K-12 Mg1655) | atggctaagacgttatacgaaaaattgttcgacgctcacgttgtgtacga agccgaaaacgaaaccccactgttatatatcgaccgccacctggtgcatg aagtgacctcaccgcaggcgttcgatggtctgcgcgcccacggtcgcccg gtacgtcagccgggcaaaaccttcgctaccatggatcacaacgtctctac ccagaccaaagacattaatgcctgcggtgaaatggcgcgtatccagatgc aggaactgatcaaaaactgcaaagaatttggcgtcgaactgtatgacctg aatcacccgtatcaggggatcgtccacgtaatgggccggaacagggcgt caccttgccggggatgaccattgtctgcggcgactcgcataccgccaccc acggcgcgtttggcgcactggcctttggtatcggcacttccgaagttgaa cacgtactggcaacgcaaaccctgaaacagggccgcgcaaaaaccatgaa aattgaagtccagggcaaagccgcgccgggcattaccgcaaaagatatcg tgctggcaattatcggtaaaaccggtagcgcaggcggcaccgggcatgtg gtggagttttgcggcgaagcaatccgtgatttaagcatggaaggtcgtat gaccctgtgcaatatggcaatcgaaatgggcgcaaaagccggtctggttg caccggacgaaaccaccttttaactatgtcaaaggccgtctgcatgcgccg aaaggcaaagatttcgacgacgccgttgcctactggaaaaaccctgcaaac cgacgaaggcgcaactttcgataccgttgtcactctgcaagcagaagaaa tttcaccgcaggtcacctggggcaccaatcccggccaggtgatttccgtg aacgacaatattcccgatccggcttcgtttgccgatccggttgaacgcgc gtcggcagaaaaagcgctggcctatatggggctgaaaccgggtattccgc tgaccgaagtggctatcgacaaagtgttatcggttcctgtaccaactcg cgcattgaagatttacgcgcggcagcggagatcgccaaagggcgaaaagt cgcgccaggcgtgcaggcactggtggttcccggctctggcccggtaaaag cccaggcggaagcggaaggtctgataaaatctttattgaagccggttt gaatggcgcttgcctggctgctcaatgtgtctggcgatgaacaacgaccg tctgaatccgggcgaacgttgtgcctccaccagcaaccgtaactttgaag gccgccaggggcgcggcgggcgcacgcatctggtcagcccggcaatggct gccgctgctgctgtgaccggacatttcgccgacattcgcaacattaaata a | 65 |
| Isopropylmalate dehydratase (leuD Escherichia coli K-12 Mg1655) | Atggcagagaaatttatcaaacacacaggcctggtggttccgctggatgc cgccaatgtcgataccgatgcaatcatcccgaaacagtttttgcagaaag tgacccgtacgggttttggcgcgcatctgtttaacgactggcgttttctg gatgaaaaaggccaacagccaaaccccggacttcgtgctgaacttccccgca gtatcagggcgcttccatttttgctggcacgagaaaacttcggctgtggct cttcgcgtgagcacgcgccctgggcattgaccgactacggttttaaagtg gtgattgcgccgagttttgctgacatcttctacggcaatagctttaacaa ccagctgctgccggtgaaattaagcgatgcagaagtggacgaactgtttg cgctggtgaaagctaatccggggatccatttcgacgtggatctggaagcg caagaggtgaaagcgggagagaaaacctatcgctttaccatcgatgcctt ccgccgccactgcatgatgaacggtctggacagtattgggcttaccttgc agcacgacgacgccattgccgcttatgaagcaaaacaacctgcgtttatg aattaa | 82 |
| aspartate kinase/ homoserine dehydrogenase (thrA Eschrichia coli MG1655) | atgcgagtgttgaagttcggcggtacatcagtggcaaatgcagaacgttt tctgcgtgttgccgatattctggaaaacaatgccaggcaggggcaggtgg ccaccgtcctctctgccccgccaaaatcaccaaccacctggtggcgatg attgaaaaaccattagcggccaggatgctttacccaatatcagcgatgc cgaacgtatttttgccgaactttgacgggactcgccgccgcccagccgg ggtcccgctggcgcaattgaaaacttcgtcgatcaggaatttgcccaa ataaaacatgtcctgcatggcattagtttgttggggcagtgcccggatag catcaacgctgcgctgatttgccgtggcgagaaaatgtcgatcgccatta tggccggcgtattagaagcgcgcggtcacaacgttactgttatcgatccg gtcgaaaaactgctggcagtggggcattacctcgaatctaccgtcgatat tgctgagtccacccgccgtattgcggcaagccgcattccggctgatcaca tggtgctgatggcaggtttcaccgccggtaatgaaaaaggcgaactggtg gtgcttggacgcaacggttccgactactctgctgcggtgctggctgcctg tttacgcgccgattgttgcgagatttggacggacgttgacggggtctata cctgcgacccgcgtcaggtgcccgatgcgaggttgttgaagtcgatgtcc taccaggaagcgatggagctttcctacttcggcgctaaagttcttcaccc cgcaccattaccccatcgcccagttccagatccctttgcctgattaaaa ataccgaaatcctcaagcaccaggtacgctcattggtgccagccgtgat gaagacgaattaccggtcaagggcatttccaatctgaataacatggcaat | 44 |

TABLE 14-continued

| Name | | SEQ ID NO |
|---|---|---|
| | gttcagcgtttctggtccggggatgaaagggatggtcggcatggcggcgc gcgtctttgcagcgatgtcacgcgcccgtatttccgtggtgctgattacg caatcatcttccgaatacagcatcagtttctgcgttccacaaagcgactg tgtgcgagctgaacgggcaatgcaggaagagttctacctggaactgaaag aaggcttactggagccgctggcagtgacggaacggctggccattatctcg gtggtaggtgatggtatgcgcaccttgcgtgggatctcggcgaaattctt tgccgcactggcccgcgccaatatcaacattgtcgccattgctcagggat cttctgaacgctcaatctctgtcgtggtaaataacgatgatgcgaccact ggcgtgcgcgttactcatcagatgctgttcaataccgatcaggttatcga agtgtttgtgattggcgtcggtggcgttggcggtgcgctgctggagcaac tgaagcgtcagcaaagctggctgaagaataaacatatcgacttacgtgtc tgccggtgttgccaactcgaaggctctgctcaccaatgtacatggcctta atctggaaaactggcaggaagaactggcgcaagccaaagagccgtttaat ctcgggcgcttaattcgcctcgtgaaagaatatcatctgctgaacccggtc attgttgactgcacttccagccaggcagtggcggatcaatatgccgactt cctgcgcgaaggtttccacgttgtcacgccgaacaaaaaggccaacacct cgtcgatggattactaccatcagttgcgttatgcggcggaaaaatcgcgg cgtaaattcctctatgacaccaacgttggggctggattaccggttattga gaacctgcaaaatctgctcaatgcaggtgatgaattgatgaagttctccg gcattctttctggttcgctttcttatatcttcggcaagttagacgaaggc atgagtttctccgaggcgaccacgctggcgcgggaaatgggttataccga accggaccgcgagatgatctttctggtatggatgtggcgcgtaaactat tgattctcgctcgtgaaacgggacgtgaactggagctggcggatattgaa attgaacctgtgctgccccgcagagtttaacgccgagggtgatgttgccgc ttttatggcgaatctgtcacaactcgacgatctctttgccgcgcgcgtgg cgaaggcccgtgatgaaggaaaagtttttgcgctatgttggcaatattgat gaagatggcgtctgccgcgtgaagattgccgaagtggatggtaatgatcc gctgttcaaagtgaaaaatggcgaaaacgccctggccttctatagccact attatcagccgctgccgttggtactgcgcggatatggtgcgggcaatgac gttacagctgccggtgtctttgctgatctgctacgtaccctctcatggaa gttaggagtctga | |
| homoserine kinase (thrB Escherichia coli MG1655) | atggttaaagtttatgccccggcttccagtgccaatatgagcgtcgggtt tgatgtgctcggggcggcggtgacacctgttgatggtgcattgctcggag atgtagtcacggttgaggcggcagagacattcagtctcaacaacctcgga cgctttgccgataagctgccgtcagaaccacgggaaaatatcgtttatca gtgctgggagcgttttgccaggaactgggtaagcaaattccagtggcga tgacctggaaaagaatatgccgatcggttcgggcttaggctccagtgcc tgttcggtggtcgcggcgctgatggcgatgaataacactgcggcaagcc gcttaatgacactcgtttgctggctttgatgggcgagctggaaggccgta tctccggcagcattcattacgacaacgtggcaccgtgttttctcggtggt atgcagttgatgatcgaagaaaacgacatcatcagccagcaagtgccagg gtttgatgagtggctgtgggtgctggcgtatccggggattaaagtctga cggcagaagcccagggctattttaccggcgcagtatcgccgccaggattgc attgcgcacggggcgacatctggcaggcttcattcacgcctgctattccg tcagcctgagcttgccgcgaagctgatgaaagatgttatcgctgaaccct accgtgaacggttactgccaggcttccggcaggcgcggcaggcggtcgtg gaaatcggcgcggtagcgagcggtatctccggctccggccgacttgtt cgctctgtgtgacaagccggaaaccgcccagcgcgttgccgactggttgg gtaagaactacctgcaaaatcaggaaggttttgttcatatttgccggctg gatacggcgggcgcacgagtactggaaaactaa | 45 |
| threonine synthase (thrC Escherichia coli MG1655) | atgaaactctacaatctgaaagatcacaacgagcaggtcagctttgcgca agccgtaacccaggggtggcaaaaatcaggggctgttttttccgcacg acctgccggaattcagcctgactgaaattgatgagatgctgaagctggat tttgtcacccgcagtgcgaagatcctctcggcgtttattgatgatgaaat cccacaggaaatcctggaagagcgcgtgcgcgcggcgtttgccttcccgg ctccggtcgccaatgttgaaagcgatgtcggttgtctggaattgttccac gggccaacgctggcatttaaagatttcggcggtcgctttatggcacaaat gctgacccatattgcgggtgataagccagtgaccattctgaccgcgacct ccggtgataccggagcggcagtggctggctcatgctttctacggtttaccgaat gtgaaagtggttatcctctatccacgaggcaaaatcagtccactgcaaga aaaactgttctgtacattgggcggcaatatcgaaactgttgccatcgacg gcgatttcgatgcctgtcaggcgctggtgaagcaggcgtttgatgatgaa gaactgaaagtggcgctagggttaaactcggctaactcgattaacatcag ccgtttgctggcgcagatttgctactactttgaagctgttgcgcagctgc cgcaggagacgcgcaaccagctggttgtctcggtgccaagcggaaacttc ggcgatttgacggcgggtctgctggcgaagtcactcggtctgccggtgaa acgttttattgctgcgaccaacgtgaacgataccgtgccacgtttcctgc acgacggtcagtggtcaccccaaagcgactcaggcgacgttatccaacgcg atggacgtgagtcagccgaacaactggccgtgtggaagttgttccg ccgcaaaatctggcaactgaaagagctgggttatgcagccgtggatgatg aaaccacgcaacagacaatgcgtgagttaaaagaactgggctacacttcg gagccgcacgctgccgtagccttatcgtgcgctgcgtgatcagttgaatcc aggcgaatatggcttgttcctcggcaccgcgcatccggcgaatttaaag agagcgtggaagcgattctcggtgaaacgttggatctgccaaaagagctg | 46 |

TABLE 14-continued

| Name | | SEQ ID NO |
|---|---|---|
| | gcagaacgtgctgatttacccttgctttcacataatctgcccgccgattt tgctgcgttgcgtaaattgatgatgaatcatcagtaa | |
| glucose-6-phosphate 1-dehydrogenase (zwf Escherichia coli K-12 MG1655) | atggcggtaacgcaaacagcccaggcctgtgacctggtcattttcggcgc gaaaggcgaccttgcgcgtcgtaaattgctgccttccctgtatcaactgg aaaaagccggtcagctcaacccggacacccggattatcggcgtagggcgt gctgactgggataaagcggcatataccaaagttgtccgcgaggcgctcga aactttcatgaaagaaaccattgatgaaggtttatgggacacccctgagtg cacgtctggattttgtaatctcgatgtcaatgacactgctgcattcagc cgtctcggcgcgatgctggatcaaaaaaatcgtatcaccattaactactt tgccatgccgcccagcacttttggcgcaatttgcaaagggcttggcgagg caaaactgaatgctaaaccggcacgcgtagtcatggagaaaccgctgggg acgtcgctggcgacctcgcaggaaatcaatgatcaggttggcgaatactt cgaggagtgccaggtttaccgtatcgaccactatcttggtaaagaaacgg tgctgaacctgttggcgctgcgttttgctaactccctgtttgtgaataac tgggacaatcgcaccattgatcatgttgagattaccgtggcagaagaagt ggggatcgaagggcgctggggctattttgataaagccggtcagatgcgcg acatgatccagaaccacctgctgcaaattctttgcatgattgcgatgtct ccgccgtctgacctgagcgcagacagcatccgcgatgaaaaagtgaaagt actgaagtctctgcgccgcatcgaccgctccaacgtacgcgaaaaaaccg tacgcgggcaatatactgcgggcttcgcccagggcaaaaaagtgccggga tatctggaagaaga gggcgcgaacaagagcagcaatacagaaactttcgt ggcgatccgcgtcgacattgataactggcgctgggccggtgtgccattct acctgcgtactggtaaacgtctgccgaccaaatgttctgaagtcgtggtc tatttcaaaacacctgaactgaatctgtttaaagaatcgtggcaggatct gccgcagaataaactgactatccgtctgcaacctgatgaaggcgtggata tccaggtactgaataaagttcctggccttgaccacaaacataacctgcaa atcaccaagctggatctgagctattcagaaaccttta atcagacgcatct ggcggatgcctatgaacgtttgctgctggaaaccatgcgtggtattcagg cactgtttgtacgtcgcgacgaagtggaagaagcctggaaatgggtagac tccattactgaggcgtgggcgatggacaatgatgcgccgaaaccgtatca ggccggaacctggggacccgttgcctcggtggcgatgattacccgtgatg gtcgttcctggaatgagtttgagtaa | 24 |
| DERA (Bacillus cereus ATCC 10987; AE017194.1) | atgaacattgcaaagttaattgaccatacaattttaaaagctaatactac taaagaagatgttatgaaagtaatcgaagaagcaaaggaatataaattcg cttctgtttgtattaatcctacatgggtaaagctagctgctgaggaatta gctggacatgatgtagatgtttgtactgtaatcggtttcccattaggcgc aagtactactgaaacaaaagcttttgaaacaaaaagatgctatcgcaaaag gtgcaactgaagttgacatggtaatcaacgtaggcgctttaaaagatggc gacgacgaacttgttgaaaaagacatttatgaagtagtacaagcagcaaa aggaaaagctcttgtaaaagtaatcattgaaacttgcctattaacagatg aagagaaagtacgcgcttgtgaattatcagtaaaagctggggctgatttc gtaaaaaacttcaactggattctcaactggcggagcaactgctgaagatat cgcattaatgcgtaaaacagttggaccaaacgttggtgtaaaagcatctg gtggcgttcgtacacgtgaagatgcagaaaaaatggtagctgctggagct tctcgcgttggagcaagtgctagtgttgcaatcgtattaaatgatgcaaa aggtgctacagataactactaa | 1 |
| DERA (Escherichia coli K12; CP009685) | atgactgatctgaaagcaagcagcctgcgtgcactgaaattgatggacct gaccacccctgaatgacgacgacgacgacgagaaagtgatcgccctgtgtc atcaggccaaaactccggtcggcaataccgccgtatctgtatctatcct cgctttatcccgattgctcgcaaaactctgaaagagcagggcacccccgga aatccgtatcgctacggtaaccaacttcccacacggtaacgacgacatcg acatcgcgctggcagaaacccgtgcggcaatcgcctacggtgctgatgaa gttgacgttgtgttcccgtaccgcgcgctgatggcgggtaacgagcaggt tggttttgacctggtgaaagcctgtaaagaggcttgcgcggcagcgaatg tactgctgaaagtgatcatcgaaaccggcgaactgaaagacgaagcgctg atccgtaaagcgtctgaaatctccatcaaagcgggtgcggacttcatcaa aacctctaccggtaaagtggctgtgaacgcgacgccggaaagcgcgcgca tcatgatggaagtgatccgtgatatgggcgtagaaaaaaccgttggtttc aaaccggcggcggcgtgcgtactgcggaagatgcgcagaaatatctcgc cattgcagatgaactgttcggtgctgactgggcagatgcgcgtcactacc gctttggcgcttccagcctgctggcaagcctgctgaaagcgctgggtcac ggcgacggtaagagcgccagcagctactaa | 2 |
| DERA (Bacillus halodurans C-125; BA000004) | atgtcacgttcgattgcacaaatgattgatcatacgctacttaaaccaaa tacaacagaagaccaaattgtaaagctctgtgaggaagcaaaggaatatt catttgcatctgtttgtgtgaatcctacttgggtcgctcttgctgcgcag ttgctaaaagatgcacctgatgtgaaagtatgtacagttatcggctttcc gttaggggcaacgactccggaagtgaaagcgtttgaaacgactaatgcca ttgaaaatggagcgacgaagtggacatggtcattaacattggaggttta aaagataaacaatacgagcttgttggacgcgacattcaagcggttgttaa agcagcagaagggaaagcattaacgaaagtaatcattgaaacatcgttat taacggaggaagagaagaaggctgcgtgtgagcttgccgtaaaagcagga gccgactttgtcaaaacgtcgactggattctctggcggaggtgctacggc tgaggatatcgcgctcatgcgaaaagtggtcggaccaaatttaggagtca | 3 |

TABLE 14-continued

| Name | | SEQ ID NO |
|---|---|---|
| | aagcttctggaggtgttagagatctgtccgacgcgaaagcgatgattgat gctggtgctactcggattggtgcgagtgctggggtggcgattgttaacgg ggagcgtagcgaagggagttattaa | |
| DERA (Bacillus subtilis subsp. subtilis str. 168; AL009126.3) | atgtcattagccaacataattgatcatacagctttgaaaccgcatacaca aaaagcggacattctaaaactaattgaagaagcgaaaacatacaaatttg cttcagtatgtgtcaatccgacatgggtggagcttgctgcaaaagagctt aagggaactggagtcgacgtttgtacggtcatcggcttcccgctcggtgc caatacaactgaaacaaaagcgttcgaaacaaaagacgccatttcaaaag cgccactgaagtggatatggtcattaatattgccgctttaaaagacaag gaagacgatgtggtggaagctgatatccgcggtgtagtggaagctgtagc cggaaaagcgcttgtcaaagtcattatcgaaacgtgccttctgactgatg aagaaaaagaacgtgcatgccgtttagcggtgtctgcgggagcggatttc gtaaaaacatcaacaggcttttctacaggcggcgcaacgaaggaagatat cgccttaatgcgcaaaacagtagggcctgatatcggcgtgaaagcatctg gcggcgtcagaacgaaagaagatgtagacacaatggtagaggccggagca agccgaattggcgccagcgcaggcgtttctatcgtaaaaggagaaaatgc atcaggcggagacaactattaa | 4 |
| DERA (Thermotoga maritima; CP011108) | atgatagagtacaggattgaggaggcagtagcgaagtacagagagttcta cgaattcaagcccgtcagagaaagcgcaggtattgaagatgtgaaaagtg ctatagagcacacgaatctgaaaccgtttgccacaccagacgatataaaa aaactctgtcttgaagcaagggaaaatcgtttccatggagtctgtgtgaa tccgtgttatgtgaaactggctcgtgaagaactcgaaggaaccgatgtga aagtcgtcaccgttgttggttttccactgggagcgaacgaaactcggacg aaagcccatgaggcgattttcgctgttgagagtggagccgatgagatcga tatggtcatcaacgttggcatgctcaaggcaaaggagtgggagtacgttt acgaggatataagaagtgttgtcgaatcggtgaaaggaaaagttgtgaag gtgatcatcgaaacgtgctatctggatacggaagagaagatagcggcgtg tgtcatttccaaacttgctggagctcatttcgtgaagacttccacgggat ttggaacaggaggggcgaccgcagaagacgttcatctcatgaaatggatc gtgggagatgagatgggtgtaaaagcttccggagggatcagaaccttcga ggacgctgttaaaatgatcatgtacggtgctgataagaataggaacgagtt cgggagttaagatcgttcagggggagaagagagatatggaggttaa | 5 |
| DERA (Methano- thermobacter thermau- trophicus; AP011952) | gtggttaaaatgaatgtggagacaagggaggaacttgcatcacttataga ccacaccaatgtgagggctgatgcaacgaaaatgatattgagaggctat gcagggaggcggtcagctacggcttcaggtgcgcggtggtcacaccccacc aatgtcaggctggcggctgaactcttgaggggaccgatgtgacggtctg ctcagttgttggtttcccggcaggcgtcagtacaccccgcgttaaggccc ttgaagcctctgaggccgttgagaacggggccggtgaggtggacatggtc atgaatatcggggccatgaagtcaggcaataggagctcgtatacaggga tatcagcggcgttgttgatgccgccggcgtccccgtcaaggttatacttg aaacagcctatctcacagacaaggagaaggttgaagcctgccttataagt aaagaggccggtgcggcatttgttaaaacatcaacagcctatggtggact agccggcgccacagttgaggatgtgatgctcatgcggaaaacggtgggtg atgagatgggagtcaaggcatctgggggaataagggatcttgaaacagcc cttgcgatgatagatgctggggcagacaggatcgggacatcaaccggtgt acagataatcgagggatggaggtaa | 6 |
| DERA (Deinococcus radiodurans; AE000513) | atgtcactcgcctcctacatcgaccacacgctgcttaaggccaccgccac gctcgccgacatccgcacgctgtgtgaggaagcccgcgagcactcgttct acgcggtgtgcatcaacccggtctttattccccacgcccgcgcctggctc gaaggcagcgacgtgaaggtcgccaccgtctgcggctttcccctcggcgc catcagctccgagcagaaagctctggaagcccgcctgagcgccgaaacgg gcgccgacgaaatcgatatggtcatccacatcggctcggcgcttgccggc gactgggacgcggtggaagccgacgtgcgggcagtgcgccgcgcggtgcc cgagcaggtgctcaaggtgattatcgaaacctgctacctgaccgacgagc aaaaagcgcttggcgactgaggtcgccgtacagggcggcgccgacttcgtg aagacgagcacaggcttcggcaccggcggcgccaccgtggacgacgtgcg cctgatggcggaagtgatcggggccgcgccggactcaaggcggcgggcg gcgtccgcactcctgccgacgcgcaagccatgatcgaggcgggcgcgacc cggctgggcacctcgggcggcgtgggtctggtgtcgggcggcgaaaacgg agccggctactaa | 7 |
| DERA (Staphylococcus aureus subsp. aureus Mu50; BA000017) | atgaatagtgcaaaattgattgatcacactttattgaagcctgagtcaac acgtacgcaaatcgatcaaatcatcgatgaagcgaaagcataccatttta aatctgtatgtgtgaatccaacgcatgtttaaatatgcagcagagcgacta gctgattcagaggtgttagtttgtacggtaataggattcccattaggtgc atcgacaactgcgacgaaagcatttgaaacagaagatgcgattcaaatg gtgcagatgaaattgacatggtcatcaacatcggcgcattaaaagatgga cgttttgatgatgtacaacaagacattgaagcagtggtgaaagctgcgaa aggtcacacagtaaaagtgattattgagacggtattgttggaccatgacg aaatcgtaaaagcgagtgaattaacaaaagtggctggtgcggacttcgtt aaaacttcaacaggttttgcaggtggcggtgcgactgcagaagacgttaa attaatgaaagatacagtaggtgctgatgtagaagtaaaagcatcaggtg gcgtacgtaatttagaagatttccaataaaatggttgaagcaggtgcgaca | 8 |

TABLE 14-continued

| Name | | SEQ ID NO |
|---|---|---|
| | cgtattggtgcgagcgcaggcgttcaaattatgcaaggtttagaagcaga ttcagattactaa | |
| DERA (*Listeria monocytogenes* EGD-e; HG421741) | atgacaattgctaaaatgatcgatcatactgctttaaaaccagacacaac gaaagaacaaattttaaccctaacaaaagaagcaagagaatacggctttg catccgtatgtgtgaacccaacttgggtaaaactatccgctgaacaactt gctggagcagaatccgtagtatgtactgttatcggtttcccactaggagc gaatacccctgaagtaaaagcatttgaagtgaaagatgccatccaaaacg gcgcgaaagaagtcgatatggttatcaatatcggtgcacttaaagacaag gacgacgaattagtagaacgcgatattcgcgctgttgtcgatgttgctaa aggcaaagcattagtaaaagtaattatcgaaacttgcctattaacagacg aagaaaaagtgcgcgcatgcgaaatcgctgtaaaagcaggaacagacttc gttaaaacatctacaggatttttcaacaggtggcgcaactgccgaagatat cgccttgatgcgtaaaacagttggaccgaacatcggtgtaaaagcatctg gtgggttcgtacgaaagaagacgtagaaaaaatgatcgaagcaggcgca actcgtatcggcgcaagtgcaggcgttgcaattgtttccggcgaaaaacc agctaaacctgataattactaa | 9 |
| DERA (*Streptococcus pneumoniae* TIGR4; AE005672) | atgaaattaaataaatatatagatcatacgcttttaaaacaagatgcaaa gaaaaaacaaattgatagtttgttgtctgaggctagagagtatgactttg ccagtgtttgcgttaatccgacctggggttgaacatgctaaaaaaggactt gaaggcacagatgttaaggtttgcacagtagtaggtttcccttttgggag caacaacttcagccgtgaaagcatttgagacaaaagaagctatccaaaatg gtgcagatgagattgatatggtgatcaatgttggagctctcaaatcaggt aatttagccttggttgagtcagatattcgcgcagtagtggaagcaagtgg tgataagttagtgaaagtcattattgaagcttgccttctgacagaccaag aaaaagttgttgtttgccaattggcccaaaaagctggggctgactttgtc aaaacatctactggcttttcaactggtggtgctacgatagcagatgttac attaatgcgtgaaacagttggatctgatatgggtgtcaaggccgccggtg gagctcgttcttatgcagatgctcttgccttttgtcgaagcaggtgcgacc cgtatcggaacgtcagctggggtagctattttaaaaggagaattggcaga tggcgactactaa | 10 |
| BFD (*Pseudomonas putida*; Ap013070.1) | atggcttcggtacacggcaccacatacgaactcttgcgacgtcaaggcat cgatacggtcttcggcaatcctggctcgaacgagctcccgttttgaagg actttccagaggactttcgatacatcctggctttgcaggaagcgtgtgtg gtgggcattgcagacggctatgcgcaagccagtcggaagccggctttcat taacctgcattctgctgctggtaccggcaatgctatgggtgcactcagta acgcctggaactcacattcccgctgatcgtcactgccggccagcagacc agggcgatgattggcgttgaagctctgctgaccaacgtcgatgccgccaa cctgccacgaccacttgtcaaatggagctacgagcccgcaagcgcagcag aagtccctcatgcgatgagcagggctatccatatggcaagcatggcgcca caaggccctgtctatctttcggtgccatatgacgattgggataaggatgc tgatcctcagtcccaccaccttttttgatcgccatgtcagttcatcagtac gcctgaacgaccaggatctcgatattctggtgaaagctctcaacagcgca tccaacccggcgatcgtcctgggcccggacgtcgacgcagcaaatgcgaa cgcagactgcgtcatgttggccgaacgcctcaaagctccggttttgggttg cgccatccgctccacgctgcccattccctacccgtcatccttgcttccgt ggattgatgccagctggcatcgcagcgatttctcagctgctcgaaggtca cgatgtggttttggtaatcggcgctccagtgttccgttaccaccaatacg acccaggtcaatatctcaaacctggcacgcgattgatttcggtgacctgc gaccegctcgaagctgcacgcgcgccaatgggcgatgcgatcgtggcaga cattggtgcgatggctagcgctcttgccaacttggttgaagagagcagcc gccagctcccaactgcagctccggaacccgcgaaggttgaccaagacgct ggccgacttcacccagagacagtgttcgacacactgaacgacatggcccc ggagaatgcgatttacctgaacgagtcgacttcaacgaccgcccaaatgt ggcagcgcctgaacatgcgcaaccctggtagctactactttctgtgcagct ggcggactgggcttcgccctgcctgcagcaattggcgttcaactcgcaga acccgagcgacaagtcatcgccgtcattggcgacggatcggcgaactaca gcattagtgcgttgtggactgcagctcagtacaacatccccactatcttc gtgatcatgaacaacggcacctacggtgcgttgcgatggtttgccggcgt tctcgaagcagaaaacgttcctgggctggatgtgccagggatcgacttcc gcgcactcgccaagggctatggtgtccaagcgctgaaagccgacaaccctt gagcagctcaagggttcgctacaagaagcgctttctgccaaaggcccggt acttatcgaagtaagcaccgtaagcccggtgaagtga | 78 |
| KDC (*Lactococcus lactis*; AY548760.1) | atgtatacagtaggagattacctgttagaccgattacacagagttgggaat tgaagaaatttttggagttcctggtgactataacttacaaattttagatc aaattatttcacgcgaagatatgaaatggattggaaatgctaatgaatta aatgcttcttatatggctgatggttatgctcgtactaaaaaagctgccgc atttctcaccacatttggagtcggcgaattgagtgcgatcaatggactgg caggaagttatgccgaaaatttaccagtagtagaaaattgttggttcacca acttcaaaagtacaaaatgacggaaaatttgtccatcatacactagcaga tggtgattttaaacactttatgaagatgcatgaacctgttacagcagcgc ggactttactgacagcagaaaatgccacatatgaaattgaccgagtactt tctcaattactaaaagaaagaaaaccagtctatattaacttaccagtcga tgttgctgcagcaaaagcagagaagcctgcattatcttagaaaaagaaa | 79 |

TABLE 14-continued

| Name | | SEQ ID NO |
|---|---|---|
| | gctctacaacaaatacaactgaacaagtgattttgagtaagattgaagaa<br>agtttgaaaaatgcccaaaaaccagtagtgattgcaggacacgaagtaat<br>tagttttggtttagaaaaaacggtaactcagtttgtttcagaaacaaaac<br>taccgattacgacactaaattttggtaaaagtgctgttgatgaatctttg<br>ccctcattttaggaatatataacgggaaactttcagaaatcagtcttaa<br>aattttgtggagtccgcagacttatcctaatgcttggagtgaagctta<br>cggactcctcaacaggtgcattcacacatcatttagatgaaaataaaatg<br>atttcactaaacatagatgaaggaataattttcaataaagtggtagaaga<br>ttttgattttagagcagtggtttcttcttcatcagaattaaaaggaatag<br>aatatgaaggacaatatattgataagcaatatgaagaatttattccatca<br>agtgctcccttatcacaagaccgtctatggcaggcagttgaaagtttgac<br>tcaaagcaatgaaacaatcgttgctgaacaaggaacctcatttttttggag<br>cttcaacaattttcttaaaatcaaatagtcgttttattggacaaccttta<br>tggggttctattggatatacttttccagcggctttaggaagccaaattgc<br>ggataaagagagcagacacctttatttattggtgatggttcacttcaac<br>ttaccgtacaagaattaggactatcaatcagagaaaaactcaatccaatt<br>tgttttatcataaataatgatggttatacagttgaaagagaaatccacgg<br>acctactcaaagttataacgacattccaatgtggaattactcgaaattac<br>cagaaacatttggagcaacagaagatcgtgtagtatcaaaaattgttaga<br>acagagaatgaatttgtgtctgtcatgaaagaagcccaagcagatgtcaa<br>tagaatgtattggatagaactagttttggaaaaagaagatgcgccaaat<br>tactgaaaaaaatgggtaaattatttgctgagcaaaataaatag | |
| KDC<br>(Mycobacterium<br>smegmatis<br>(strain<br>ATCC<br>700084/<br>mc(2)155);<br>A0R480) | atgaccgatgacggctacacagtcggtgactacctcctggaccggctcgc<br>cgaactcggcgtgaccgaggtcttcggcgtcccggcgactatcagctgg<br>agttcctcgaccacgtcgtggcgcaccccgcgcatcacgtgggtcggcggc<br>gcgaacgaactcaacgcgggctacgccgccgacggctacggccggctgcg<br>gggcatggcggcgttggtcaccacgttcggcgtcggtgagctctcggcgg<br>ccaacgccatcgcaggcagctacgccgagcacgtcccggtggtgcacatc<br>gtcggcgcgccgtcgaaggattcgcaggccgcgcggcgcatcgtgcacca<br>cacgctgggtgacggcgatttcgagcacttcctgcgcatgagccgcggga<br>tcacctgcgcgcaggccaatctggtgcccgccacggcgacccgcgagatc<br>gaccgcgtgctctcggaggtgcacgagcagaagcggcccggctatctgct<br>gatcgcgaccgacgtcgcccgcttccccaccgaaccaccgaccgccccgc<br>tgccgccgccacagcgggggcaccagcccacgggcgctgtcgctgttcacc<br>gaggccgcaacgcaactcatcggcgagcaccggttgaccgtgctggccga<br>tttcctggtgcaccgcatgggatgcgtcgaggcgctcaacaagctgctga<br>ccgccgacaccgtgccgcacgccacgctgatgtggggcaagagcctggtc<br>gacgagagttcgccgaacttcctgggcatctacgccggtgccgccagtga<br>gggctcggtgcgcgaggtgatcgaggacgcgcctgtgctggtgaccgcag<br>gtgtgctgttcaccgacatggtcagcgggttcttcagccagcgcatcgac<br>ccggcacgcacgatcgacatcggggtcaaccagagcgtcgtcgccgggca<br>ggtgttcgcgccgctggacatggctgccgcgctcgacgcgctcgcgtcga<br>tcctcgccgaacgcggcatcgagtcgcccgcactgccgccggccccgca<br>ccgcagcggcccgcagcgccgccgcgtgacgcggtgcttacacaggaagc<br>gttgtgggacaggctcgccgaggcgttgacgccgggcaacgtggtgctcg<br>ccgaccagggcacgtctttctacggcctggccggggcaccggctggcgtcg<br>ggcgtgacattcatcggtcagccgttgtgggcgtcgatcggctacacact<br>gcccgccgcgctcggcgcgggtctggccgaccgcgaccggcgcacggtgc<br>tgctgatcggcgacggcgcagcgcagttgacggtgcaggaactcggcgcg<br>ttcggccgcgaggggctcacgcccgtggtggtggtcgtcaacaacaacgg<br>ctacaccgtggagcgcgcgatccacggtgtcacggcccgctacaacgaca<br>tcacggcgtggcggtggaccgagttgccggccgcactcggtgtgcccgat<br>gcgctgacgttccgctgcgccacctacggcgaactcgacgacgcgctgac<br>cgtcgccgccgagacgcaggaccgcatggtgttcgtcgaggtgatgcttg<br>agcgcatggacattccgccgctgctgggcgagctcgcacagtcggcgtcg<br>gccgccaacgccaaatag | 70 |
| | Protein sequence | |
| PA1127<br>(Akr<br>Pseudomonas<br>aeruginosa<br>PAO1) | MSVESIRIEGIDTPVSRIGLGTWAIGGWMWGGADDAT<br>SVETIRRAVESGINLIDTAPVYGFGHSEEVVGKALQG<br>LRDKAVIATKAALEWSDAGIHRNASAARIRREVEDSL<br>RRLKTDRIDLYQIHWPDPLVAHEETAGELERLRRDGK<br>ILAIGVSNYSPEQMDGFRQFAPLASVQPPYNLFERAI<br>DADVLPYAERNGIVVLAYGALCRGLLSGRMNAETRFD<br>GDDLRKSDPKFQQPRFAQYLAAVAQLEELARERYGKS<br>VLALAIRWILDRGPTVALWGARKPEQLNGIADAFGWR<br>LDDEAMARIERILAETIQDPVGPEFMAPPSRNA | 31 |
| PDC Z.<br>mobilis<br>ZM4 =<br>ATCC 31821 | MSYTVGTYLAERLVQIGLKHHFAVAGDYNLVLLDNLL<br>LNKNMEQVYCCNELNCGFSAEGYARAKGAAAAVVTYS<br>VGALSAFDAIGGAYAENLPVILISGAPNNNDHAAGHV<br>LHHALGKTDYHYQLEMAKNITAAAEAIYTPEEAPAKI<br>DHVIKTALREKKPVYLEIACNIASMPCAAPGPASALF<br>NDEASDEASLNAAVEETLKFIANRDKVAVLVGSKLRA<br>AGAEEEAAVKFADALGGAVATMAAAKSFFPEENPHYIG | 71 |

TABLE 14-continued

| Name | | SEQ ID NO |
|---|---|---|
| | TSWGEVSYPGVEKTMKEADAVIALAPVFNDYSTTGWT DIPDPKKLVLAEPRSVVVNGIRFPSVHLKDYLTRLAQ KVSKKTGALDFFKSLNAGELKKAAPADPSAPLVNAEI ARQVEALLTPNTTVIAETGDSWFNAQRMKLPNGARVE YEMQWGHIGWSVPAAFGYAVGAPERRNILMVGDGSFQ LTAQEVAQMVRLKLPVIIFLINNYGYTIEVMIHDGPY NNIKNWDYAGLMEVFNGNGGYDSGAGKGLKAKTGGEL AEAIKVALANTDGPTLIECFIGREDCTEELVKWGKRV AAANSRKPVNKLL* | |
| Pyruvate dependent aldolase (Eda *Escherichia coli* K-12 MG1655) | MKNWKTSAESILTTGPVVPVIVVKKLEHAVPMAKALV AGGVRVLEVTLRTECAVDAIRAIAKEVPEAIVGAGTV LNPQQLAEVTEAGAQFAISPGLTEPLLKAATEGTIPL IPGISTVSELMLGMDYGLKEFKFFPAEANGGVKALQA IAGPFSQVRFCPTGGISPANYRDYLALKSVLCIGGSW LVPADALEAGDYDRITKLAREAVEGAKL | 25 |
| 4-hydroxy-2-oxovalerate aldolase (MphE *Escherichia coli* K-12 MG1655) | MNGKKLYISDVTLRDGMHAIRHQYSLENVRQIAKALD DARVDSIEVAHGDGLQGSSFNYGFGAHSDLEWIEAAA DVVKHAKIATLLLPGIGTIHDLKNAWQAGARVVRVAT HCTEADVSAQHIQYARELGMDTVGFLMMSHMTTPENL AKQAKLMEGYGATCIYVVDSGGAMNMSDIRDRFRALK AELKPETQTGMHAHHNLSLGVANSIAAVEEGCDRIDA SLAGMGAGAGNAPLEVFIAAADKLGWQHGTDLYALMD AADDLVRPLQDRPVRVDRETLALGYAGVYSSFLRHCE TAAARYGLSAVDILVELGKRRMVGGQEDMIVDVALDL RNNK | 26 |
| 4-hydroxy-2-oxovalerate aldolase (*Paraburkholderia xenovorans* LB400) | MKLEGKKVTVHDMTLRDGMHPKRHQMTLEQMKSIACG LDAAGIPLIEVTHGDGLGGSSVNYGFPAHSDEEYLGA VIPLMKQAKVSALLLPGIGTVEHLKMAKDLGVNTIRV ATHCTEADVSEQHITQSRKLGLDTVGFLMMAHMASPE KLVSQALLMQGYGANCIYVTDSAGYMLPDDVKARLSA VRAALKPETELGFHGHHNLAMGVANSIAAIEAGATRI DAAAAGLGAGAGNTPMEVFIAVCARMGIETGVDVFKI QDVAEDLVVPIMDHVIRIDRDSLTLGYAGVYSSFLLF AKRASAKYGVPARDILVELGRRGMVGGQEDMIEDTAM TMARERGLTLTAA | 27 |
| 4-hydroxy-2-oxoheptane dioate aldolase (HpcH/HpaI *Escherichia coli* ATCC8739) | MENSFKAALKAGRPQIGLWLGLSSSYSAELLAGAGFD WLLIDGEHAPNNVQTVLTQLQAIAPYPSQPVVRPSWN DPVQIKQLLDVGTQTLLVPMVQNADEAREAVRATRYP PAGIRGVGSALARASRWNRIPDYLQKANDQMCVLVQI ETREAMKNLPQILDVEGVDGVFIGPADLSADMGYAGN PQHPEVQAAIEQAIVQIRESGKAPGILIANEQLAKRY LELGALFVAVGVDTTLLARAAEALAARFGAQATAVKP GVY | 83 |
| Threonine dehydratase ilvA (*Escherichia coli* K-12 MG1655) | MADSQPLSGAPEGAEYLRAVLRAPVYEAAQVTPLQKM EKLSSRLDNVILVKREDRQPVHSFKLRGAYAMMAGLT EEQKAHGVITASAGNHAQGVAFSSARLGVKALIVMPT ATADIKVDAVRGFGGEVLLHGANFDEAKAKAIELSQQ QGFTWVPPFDHPMVIAGQGTLALELLQQDAHLDRVFV PVGGGGLAAGVAVLIKQLMPQIKVIAVEAEDSACLKA ALDAGHPVDLPRVGLFAEGVAVKRIGDETFRLCQEYL DDIITVDSDAICAAMKDLFEDVRAVAEPSGALALAGM KKYIALHNIRGERLAHILSGANVNFHGLRYVSERCEL GEQREALLAVTIPEEKGSFLKFCQLLGGRSVTEFNYR FADAKNACIFVGVRLSRGLEERKEILQMLNDGGYSVV DLSDDEMAKLHVRYMVGGRPSHPLQERLYSFEFPESP GALLRFLNTLGTYWNISLFHYRSHGTDYGRVLAAFEL GDHEPDFETRLNELGYDCHDETNNPAFRFFLAG | 47 |
| Alpha-ketoisovalerate decarboxlase kivD (*Lactococcus lactis lactis* KF147) | MYTVGDYLLDRLHELGIEEIFGVPGDYNLQFLDQIIS RKDMKWVGNANELNASYMADGYARTKKAAAFLTTFGV GELSAVNGLAGSYAENLPVVEIVGSPTSKVQNEGKFV HHTLADGDFKHFMKMHEPVTAARTLLTAENATVEIDR VLSALLKERKPVYINLPVDVAAAKAEKPSLPLKKENP TSNTSDQEILNKIQESLKNAKKPIVITGHEIISFGLE NTVTQFISKTKLPITTLNFGKSSVDETLPSFLGIYNG KLSEPNLKEFVESADFILMLGVKLTDSSTGAFTHHLN ENKMISLNIDEGKIFNESIQNFDFESLISSLLDLSGI EYKGKYIDKKQEDFVPSNALLSQDRLWQAVENLTQSN ETIVAEQGTSFFGASSIFLKPKSHFIGQPLWGSIGYT FPAALGSQIADKESRHLLFIGDGSLQLTVQELGLAIR EKINPICFIINNDGYTVEREIHGPNQSYNDIPMWNYS | 66 |

TABLE 14-continued

| Name | | SEQ ID NO |
|---|---|---|
| | KLPESFGATEERVVSKIVRTENEFVSVMKEAQADPNR MYWIELVLAKEDAPKVLKKMGKLFAEQNKS | |
| 2-isopropylmalate synthase (leuA *Escherichia coli* K-13 MG1655) | MSQQVIIFDTTLRDGEQALQASLSVKEKLQIALALER MGVDVMEVGFPVSSPGDFESVQTIARQVKNSRVCALA RCVEKDIDVAAESLKVAEAFRIHTFIATSPMHIATKL RSTLDEVIERAIYMVKRARNYTDDVEFSCEDAGRTPI ADLARVVEAAINAGATTINIPDTVGYTMPFEFAGIIS GLYERVPNIDKAIISVHTHDDLGLAVGNSLAAVHAGA RQVEGAMNGIGERAGNCSLEEVIMAIKVRKDILNVHT AINHQEIWRTSQLVSQICNMPIPANKAIVGSGAFAHS SGIHQDGVLKNRENYEIMTPESIGLNQIQLNLTSRSG RAAVKHRMDEMGYKESEYNLDNLYDAFLKLADKKGQV FDYDLEALAFIGKQQEEPEHFRLDYFSVQSGSNDIAT AAVKLACGEEVKAEAANGNGPVDAVYQAINRITEYNV ELVKYSLTAKGHGKDALGQVDIVANYNGRRFHGVGLA TDIVESSAKAMVHVLNNIWRAAEVEKELQRKAQHNEN NKETV | 51 |
| 3-isopropylmalate dehydrogenase (leuB *Escherichia coli* K-12 MG1655) | MSKNYHIAVLPGDGIGPEVMTQALKVLDAVRNRFAMR ITTSHYDVGGAAIDNHGQPLPPATVEGCEQADAVLFG SVGGPKWEHLPPDQQPERGALLPLRKHFKLFSNLRPA KLYQGLEAFCPLRADIAANGFDILCVRELTGGIYFGQ PKGREGSGQYEKAFDTEVYHRFEIERIARIAFESARK RRHKVTSIDKANVLQSSILWREIVNEIATEYPDVELA HMYIDNATMQLIKDPSQFDVLLCSNLFGDILSDECAM ITGSMGMLPSASLNEQGFGLYEPAGGSAPDIAGKNIA NPIAQILSLALLLRYSLDADDAACAIERAINRALEEG IRTGDLARGAAAVSTDEMGDIIARYVAEGV | 54 |
| Isopropylmalate dehydratase (leuC *Escherichia coli* K-12 Mg1655 | MAKTLYEKLFDAHVVYEAENETPLLYIDRHLVHEVTS PQAFDGLRAHGRPVRQPGKTFATMDHNVSTQTKDINA CGEMARIQMQELIKNCKEFGVELYDLNHPYQGIVHVM GPEQGVTLPGMTIVCGDSHTATHGAFGALAFGIGTSE VEHVLATQTLKQGRAKTMKIEVQGKAAPGITAKDIVL AIIGKTGSAGGTGHVVEFCGEAIRDLSMEGRMTLCNM AIEMGAKAGLVAPDETTFNYVKGRLHAPKGKDFDDAV AYWKTLQTDEGATFDTVVTLQAEEISPQVTWGTNPGQ VISVNDNIPDPASFADPVERASAEKALAYMGLKPGIP LTEVAIDKVFIGSCTNSRIEDLRAAAEIAKGRKVAPG VQALVVPGSGPVKAQAEAEGLDKIFIEAGFEWRLPGC SMCLAMNNDRLNPGERCASTSNRNFEGRQGRGGRTHL VSPAMAAAAAVTGHFADIRNIK | 57 |
| Isopropylmalate dehydratase (leuD *Escherichia coli* K-12 Mg1655) | MAEKFIKHTGLVVPLDAANVDTDAIIPKQFLQKVTRT GFGAHLFNDWRFLDEKGQQPNPDFVLNFPQYQGASIL LARENFGCGSSREHAPWALTDYGFKVVIAPSFADIFY GNSFNNQLLPVKLSDAEVDELFALVKANPGIHFDVDL EAQEVKAGEKTYRFTIDAFRRHCMMNGLDSIGLTLQH DDAIAAYEAKQPAFMN | 60 |
| aspartate kinase/ homoserine dehydrogenase (thra *Escherichia coli* MG1655) | MRVLKFGGTSVANAERFLRVADILESNARQGQVATVL SAPAKITNHLVAMIEKTISGQDALPNISDAERIFAEL LTGLAAAQPGFPLAQLKTFVDQEFAQIKHVLHGISLL GQCPDSINAALICRGEKMSIAIMAGVLEARGHNVTVI DPVEKLLAVGHYLESTVDIAESTRRIAASRIPADHMV LMAGFTAGNEKGELVVLGRNGSDYSAAVLAACLRADC CEIWTDVDGVYTCDPRQVPDARLLKSMSYQEAMELSY FGAKVLHPRTITPIAQFQIPCLIKNTGNPQAPGTLIG ASRDEDELPVKGISNLNNMAMFSVSGPGMKGMVGMAA RVFAAMSRARISVVLITQSSSEYSISFCVPQSDCVRA ERAMQEEFYLELKEGLLEPLAVTERLAIISVVGDGMR TLRGISAKFFAALARANINIVAIAQGSSERSISVVVN NDDATTGVRVTHQMLFNTDQVIEVFVIGVGGVGGALL EQLKRQQSWLKNKHIDLRVCGVANSKALLLTNVHGLNL ENWQEELAQAKEPFNLGRLIRLVKEYHLLNPVIVDCT SSQAVADQYADFLREGFHVVTPNKKANTSSMDYYHQL RYAAEKSRRKFLYDTNVGAGLPVIENLQNLLNAGDEL MKFSGILSGSLSYIFGKLDEGMSFSEATTLAREMGYT EPDPRDDLSGMDVARKLLILARETGRELELADIEIEP VLPAEFNAEGDVAAFMANLSQLDDLFAARVAKARDEG KVLRYVGNIDEDGVCRVKIAEVDGNDPLFKVKNGENA LAFYSHYYQPLPLVLRGYGAGNDVTAAGVFADLLRTL SWKLGV | 35 |
| homoserine kinase | MVKVYAPASSANMSVGFDVLGAAVTPVDGALLGDVVT VEAAETFSLNNLGRFADKLPSEPRENIVYQCWERFCQ | 38 |

TABLE 14-continued

| Name | | SEQ ID NO |
|---|---|---|
| (thrB Escherichia coli MG1655) | ELGKQIPVAMTLEKNMPIGSGLGSSACSVVAALMAMN EHCGKPLNDTRLLALMGELEGRISGSIHYDNVAPCFL GGMQLMIEENDIISQQVPGFDEWLWVLAYPGIKVSTA EARAILPAQYRRQDCIAHGRHLAGFIHACYSRQPELA AKLMKDVIAEPYRERLLPGFRQARQAVAEIGAVASGI SGSGPTLFALCDKPETAQRVADWLGKNYLQNQEGFVH ICRLDTAGARVLEN | |
| threonine synthase (thrC Escherichia coli MG1655) | MKLYNLKDHNEQVSFAQAVTQGLGKNQGLFFPHDLPE FSLTEIDEMLKLDFVTRSAKILSAFIGDEIPQEILEE RVRAAFAFPAPVANVESDVGCLELFHGPTLAFKDFGG RFMAQMLTHIAGDKPVTILTATSGDTGAAVAHAFYGL PNVKVVILYPRGKISPLQEKLFCTLGGNIETVAIDGD FDACQALVKQAFDDEELKVALGLNSANSINISRLLAQ ICYYFEAVAQLPQETRNQLVVSVPSGNFGDLTAGLLA KSLGLPVKRFIAATNVNDTVPRFLHDGQWSPKATQAT LSNAMDVSQPNNWPRVEELFRRKIWQLKELGYAAVDD ETTQQTMRELKELGYTSEPHAAVAYRALRDQLNPGEY GLFLGTAHPAKFKESVEAILGETLDLPKELAERADLP LLSHNLPADFAALRKLMMNHQ | 41 |
| glucose-6-phosphate 1-dehydrogenase (zwf Escherichia coli K-12 MG1655) | MAVTQTAQACDLVIFGAKGDLARRKLLPSLYQLEKAG QLNPDTRIIGVGRADWDKAAYTKVVREALETFMKETI DEGLWDTLSARLDFCNLDVNDTAAFSRLGAMLDQKNR ITINYFAMPPSTFGAICKGLGEAKLNAKPARVVMEKP LGTSLATSQEINDQVGEYFEECQVYRIDHYLGKETVL NLLALRFANSLFVNNWDNRTIDHVEITVAEEVGIEGR WGYFDKAGQMRDMIQNHLLQILCMIAMSPPSDLSADS IRDEKVKVLKSLRRIDRSNVREKTVRGQYTAGFAQGK KVPGYLEEEGANKSSNTETFVAIRVDIDNWRWAGVPF YLRTGKRLPTKCSEVVVYFKTPELNLFKESWQDLPQN KLTIRLQPDEGVDIQVLNKVPGLDHKHNLQITKLDLS YSETFNQTHLADAYERLLLETMRGIQALFVRRDEVEE AWKWVDSITEAWAMDNDAPKPYQAGTWGPVASVAMIT RDGRSWNEFE | 21 |
| DERA (Thermotoga maritima; AAD36625.1) | MIEYRIEEAVAKYREFYEFKPVRESAGIEDVKSAIEH TNLKPFATPDDIKKLCLEARENRFHGVCVNPCYVKLA REELEGTDVKVVTVVGFPLGANETRTKAHEAIFAVES GADEIDMVINVGMLKAKEWEYVYEDIRSVVESVKGKV VKVIIETCYLDTEEKIAACVISKLAGAHFVKTSTGFG TGGATAEDVHLMKWIVGDEMGVKASGGIRTFEDAVKM IMYGADRIGTSSGVKIVQGGEERYGG | 11 |
| DERA (Methanothermobacter thermautotrophicus; AAB85318.1) | MVKMNVETREELASLIDHTNVRADATENDIERLCREA VSYGFRCAVVTPTNVRLAAELLEGTDVTVCSVVGFPA GVSTPRVKALEASEAVENGAGEVDMVMNIGAMKSGNR ELVYRDISGVVDAAGVPVKVILETAYLTDKEKVEACL ISKEAGAAFVKTSTAYGGLAGATVEDVMLMRKTVGDE MGVKASGGIRDLETALAMIDAGADRIGTSTGVQIIEG WR | 12 |
| DERA (Deinococcus radiodurans; AAF10775.1) | MSLASYIDHTLLKATATLADIRTLCEEAREHSFYAVC INPVFIPHARAWLEDSDVKVATVCGFPLGAISSEQKA LEARLSAETGADEIDMVIHIGSALAGDWDAVEADVRA VRRAVPEQVLKVIIETCYLTDEQKRLATEVAVQGGAD FVKTSTGFGTGGATVDDVRLMAEVIGGRAGLKAAGGV RTPADAQAMIEAGATRLGTSGGVGLVSGGENGAGY | 13 |
| DERA (Staphylococcus aureus; strain Mu50; WP_001083318.1) | MNSAKLIDHTLLKPESTRTQIDQIIDEAKAYHFKSVC VNPTHVKYAAERLADSEVLVCTVIGFPLGASTTATKA FETEDAIQNGADEIDMVINIGALKDGRFDDVQQDIEA VVKAAKGHTVKVIIETVLLDHDEIVKASELTKVAGAD FVKTSTGFAGGGATAEDVKLMKDTVGADVEVKASGGV RNLEDFNKMVEAGATRIGASAGVQIMQGLEADSDY | 14 |
| DERA (Streptococcus pneumoniae serotype 4 (strain ATCC BAA-334/ TIGR4); WP_000773677.1) | MKLNKYIDHTLLKQDAKKKQIDSLLSEAREYDFASVC VNPTWVEHAKKGLEGTDVKVCTVVGFPLGATTSAVKA FETKEAIQNGADEIDMVINVGALKSGNLALVESDIRA VVEASGDKLVKVIIEACLLTDQEKVVVCQLAQKAGAD FVKTSTGFSTGGATIADVTLMRETVGSDMGVKAAGGA RSYADALAFVEAGATRIGTSAGVAILKGELADGDY | 15 |

TABLE 14-continued

| Name | Sequence | SEQ ID NO |
|---|---|---|
| DERA (Escherichia coli (strain K12); NP_418798.1) | MTDLKASSLRALKLMDLTTLNDDDTDEKVIALCHQAK TPVGNTAAICIYPRFIPIARKTLKEQGTPEIRIATVT NFPHGNDDIDIALAETRAAIAYGADEVDVVFPYRALM AGNEQVGFDLVKACKEACAAANVLLKVIIETGELKDE ALIRKASEISIKAGADFIKTSTGKVAVNATPESARIM MEVIRDMGVEKTVGFKPAGGVRTAEDAQKYLAIADEL FGADWADARHYRFGASSLLASLLKALGHGDGKSASSY | 16 |
| DERA (Listeria monocytogenes serovar 1/2a (strain ATCC BAA-679/ EGD-e); NP_465519.1) | MTIAKMIDHTALKPDTTKEQILTLTKEAREYGFASVC VNPTWVKLSAEQLAGAESVVCTVIGFPLGANTPEVKA FEVKDAIQNGAKEVDMVINIGALKDKDDELVERDIRA VVDVAKGKALVKVIIETCLLTDEEKVRACEIAVKAGT DFVKTSTGFSTGGATAEDIALMRKTVGPNIGVKASGG VRTKEDVEKMIEAGATRIGASAGVAIVSGEKPAKPDN Y | 17 |
| DERA (Bacillus halodurans (strain ATCC BAA-125/ DSM 18197/ FERM 7344/ JCM 9153/ C-125); WP_010897517.1) | MSRSIAQMIDHTLLKPNTTEDQIVKLCEEAKEYSFAS VCVNPTWVALAAQLLKDAPDVKVCTVIGFPLGATTPE VKAFETTNAIENGATEVDMVINIGALKDKQYELVGRD IQAVVKAAEGKALTKVIIETSLLTEEEKKAACELAVK AGADFVKTSTGFSGGGATAEDIALMRKVVGPNLGVKA SGGVRDLSDAKAMIDAGATRIGASAGVAIVNGERSEG SY | 18 |
| DERA (Bacillus cereus (strain ATCC10987/ NRS 248); WP_001017443.1) | MNIAKLIDHTILKANTTKEDVMKVIEEAKEYKFASVC INPTWVKLAAEELAGHDVDVCTVIGFPLGASTTETKA FETKDAIAKGATEVDMVINVGALKDGDDELVEKDIYE VVQAAKGKALVKVIIETCLLTDEEKVRACELSVKAGA DFVKTSTGFSTGGATAEDIALMRKTVGPNVGVKASGG VRTREDAEKMVAAGASRVGASASVAIVLNDAKGATDN Y | 19 |
| DERA (Bacillus subtilis (strain 168); CAB15978.2) | MSLANIIDHTALKPHTQKADILKLIEEAKTYKFASVC VNPTWVELAAKELKGTGVDVCTVIGFPLGANTTETKA FETKDAISKGATEVDMVINIAALKDKEDDVVEADIRG VVEAVAGKALVKVIIETCLLTDEEKERACRLAVSAGA DFVKTSTGFSTGGATKEDIALMRKTVGPDIGVKASGG VRTKEDVDTMVEAGASRIGASAGVSIVKGENASGGDN Y | 20 |
| BFD (Benzoylformate decarboxylase; Pseudomonas putida NBRC 14164; WP_016501746.1) | MASVHGTTYELLRRQGIDTVFGNPGSNELPFLKDFPE DFRYILALQEACVVGIADGYAQASRKPAFINLHSAAG TGNAMGALSNAWNSHSPLIVTAGQQTRAMIGVEALLT NVDAANLPRPLVKWSYEPASAAEVPHAMSRAIHMASM APQGPVYLSVPYDDWDKDADPQSHHLFDRHVSSSVRL NDQDLDILVKALNSASNPAIVLGPDVDAANANADCVM LAERLKAPVWVAPSAPRCPFPTRHPCFRGLMPAGIAA ISQLLEGHDVVLVIGAPVFRYHQYDPGQYLKPGTRLI SVTCDPLEAARAPMGDAIVADIGAMASALANLVEESS RQLPTAAPEPAKVDQDAGRLHPETVFDTLNDMAPENA IYLNESTSTTAQMWQRLNMRNPGSYYFCAAGGLGFAL PAAIGVQLAEPERQVIAVIGDGSANYSISALWTAAQY NIPTIFVIMNNGTYGALRWFAGVLEAENVPGLDVPGI DFRALAKGYGVQALKADNLEQLKGSLQEALSAKGPVL IEVSTVSPVK | 76 |
| KDC (indole-3-pyruvate decarboxylase; Lactococcus lactis WP_046124870.1) | MYTVGDYLLDRLHELGIEEIFGVPGDYNLQFLDQIIS REDMKWIGNANELNASYMADGYARTKKAAAFLTTFGV GELSAINGAGSYAENLPVVEIVGSPTSKVQNDGKFVH HTLADGDFKHFMKMHEPVTAARTLLTAENATYEIDRV LSQLLKERKPVYINLPVVAAAKAEKPALSLEKESSTT NTTEQVILSKIEESLKNAQKPVVIAGHEVISFGLEKT VTQFVSETKLPITTLNFGKSAVDESLPSFLGIYNGKL SEISLKNFVESADFILMLGVKLTDSSTGAFTHHLDEN KMISLNIDEGIIFNKVVEDFDFRAVVSSLSELKGIEY EGQYIKQYEEFIPSSAPLSQDRLWQAVESLTQSNETI VAEQGTSFFGASTIFLKSNSRFIGQPLWGSIGYTFPA ALGSQIADKESRHLLFIGDGSLQLTVQELGLSIREKL NPICFIINNDGYTVEREIHGPTQSYNDIPMWNYSKLP | 77 |

TABLE 14-continued

| Name | Sequence | SEQ ID NO |
|---|---|---|
| | ETFGATEDRVVSKIVRTENEFVSVMKEAQADVNRMYW IELVLEKEDAPKLLKKMGKLFAEQNK | |
| KDC (Mycobacterium smegmatis (strain ATCC 700084/ mc(2)155) WP_011730751.1) | MTDDGYTVGDYLLDRLAELGVTEVFGVPGDYQLEFLD HVVAHPRITWVGGANELNAGYAADGYGRLRGMAALVT TFGVGELSAANAIAGSYAEHVPVVHIVGAPSKDSQAA RRIVHHTLGDGDFEHFLRMSREITCAQANLVPATATR EIDRVLSEVHEQKRPGYLLIATDVARFPTEPPTAPLP RHSGGTSPRALSLFTEAATQLIGEHRLTVLADFLVHR MGCVEALNKLLTADTVPHATLMWGKSLVDESSPNFLG IYAGAASEGSVREVIEDAPVLVTAGVLFTDMVSGFFS QRIDPARTIDIGVNQSVVAGQVFAPLDMAAALDALAS ILAERGIESPALPPAPAPQRPAAPPRDAVLTQEALWD RLAEALTPGNVVLADQGTSFYGLAGHRLASGVTFIGQ PLWASIGYTLPAALGAGLADRDRRTVLLIGDGAAQLT VQELGAFGREGLTPVVVVVNNNGYTVERAIHGVTARY NDITAWRWTELPAALGVPDALTFRCATYGELDDALTV AAETQDRMVFVEVMLERMDIPPLLGELAQSASAANAK | 68 |

Example 1: Selection of Adolase Enzymes for the Trans-2-Unsaturated Aldehyde and Delta-Lactone Pathways The first operation in the trans-2-unsaturated aldehyde pathway and the delta-lactone pathway is the condensation of two aldehyde molecules by analdolase enzyme. To identify the aldolase enzymes that may catalyze the aldehyde condensation reaction, a list of various aldolase homologues or putative aldolases was identified based on sequence similarity to E. coli deoxyribose-5-phosphate aldolase (DERA). These various aldolases are listed in TABLE 15.

Example 2: Selection of Aldolase Enzymes for the Gamma-Lactone Pathway

The first step in the gamma-lactone pathway is the condensation of analdehyde and a pyruvate or pyruvic acid by analdolase enzyme. To identify the aldolase enzymes that may catalyze the condensation reaction, a list of various aldolase homologues or putative aldolases was identified based on sequence similarity to E. coli pyruvate dependent aldolase Eda (listed in TABLE 16), E. coli 4-hydroxy-2-oxoheptanedioate aldolase HpcH (listed in TABLE 17). E. coli 4-hydroxy-2-oxovalerate aldolase MphE (listed in

TABLE 15

| Name | Organism | PDB No. | GI | % Identity to BH1352 |
|---|---|---|---|---|
| Aldolase | Thermus thermophilus HB8 | 1J2W | | 45 |
| deoxyribose-5-phosphate aldolase | Escherichia coli (K201L mutant) | 1JCJ | 16974931 | 35 |
| deoxyribose-5-phosphate aldolase | Escherichia coli | 1KTN | 28372821 | 36 |
| Aldolase | Aquifex aeolicus | 1MZH | 29726561 | 43 |
| Aldolase | Aeropyrum pernix | 1N7K | 29726561 | 37 |
| deoxyribose-5-phosphate aldolase | Pyrobaculum aerophilum | 1VCV | 73535346 | 36 |
| deoxyribose-5-phosphate aldolase | Plasmodium yoelii | 2A4A | 75766024 | 35 |
| Hydrolase | Streptomyces griseus | 3I78 | 297342939 | 39 |
| deoxyribose-5-phosphate aldolase | Mycobacterium smegmatis | 3NDO | 30101668 | 44 |
| deoxyribose-5-phosphate aldolase | Mycobacterium avium 104 | 3NG3 | 299689368 | 46 |
| deoxyribose-5-phosphate aldolase | Entamoeba histolydca | 3NGJ | 301016075 | 69 |
| Putative deoxyribose-5-phosphate aldolase | Coccidioides immitis | 3OA3 | 303325189 | 51 |
| deoxyribose-5-phosphate aldolase | Thermotoga maritima | 3R12 | 329666268 | 55 |
| deoxyribose-5-phosphate aldolase | Lactobacilus brevis | 4XBK | 946926237 | 53 |
| deoxyribose-5-phosphate aldolase | Lactobacilus brevis (E78K mutant) | 4XBS | 946926241 | 53 |
| deoxyribose-5-phosphate aldolase | Colwelia psychereythraea | 5C2X | 985483947 | 37 |
| deoxyribose-5-phosphate aldolase | Shewanella halifaxensis | 5C6M | 985483957 | 34 |
| deoxyribose-5-phosphate aldolase | Streptococcus suis | 5DBT | 1018192340 | 69 |

TABLE 18), and *Paraburkholderia xenovorans* LB400 4-hydroxy-2-oxovalerate aldolase BphI (listed in TABLE 19).

TABLE 16

| Name | Organism | PDB No. | GI | % Ident to Eda |
|---|---|---|---|---|
| KDPG aldolase | *Escherichia coli* | 1FQ0 | 10835436 | 100 |
| KDPG aldolase | *E. coil* (K133Q/T161K mutant) | 1FWR | 10835451 | 99 |
| KDPG aldolase | *Pseudomonas putida* | 1MXS | 37926857 | 46 |
| Putatve KDPG aldolase | *Haemophilus influenza* | 1VHC | 40889919 | 37 |
| KDPG aldolase | *Thermotoga maritima* MSB8 | 1VLW | 52696233 | 33 |
| KDPG aldolase | *Thermotoga maritima* | 1WA3 | 60593837 | 33 |
| KDPG aldolase | *E. coli* | 2C0A | 75766436 | 99 |
| KDPG aldolase | *E. coli* (E45N mutant) | 1WAU | 88191724 | 99 |
| KDGgal | *E. coli* | 2V81 | 157836718 | 25 |
| Oxoglutarate Aldolase | *Thermus thermophilus* HB8 | 2YW3 | 159795598 | 40 |
| KDPG aldolasc | *Oleispira antarctica* | 3VCR | 372467175 | 50 |
| Keto-hydroxyglutarte-aldolase | *Vibrionales bacterium* SWAT-3 | 4E38 | 380765206 | 40 |
| KDPG Aldolase | *Zymomonas mobilis* | 4BK9 | 635576158 | 54 |
| Unknown protein | *E. coli* | 4QCC | 723586857 | 26 |

TABLE 17

| Name | Organism | PDB No. | GI | % Ident to HpcH |
|---|---|---|---|---|
| Apo Class II Aldolase Hpch | *Escherichia coli* C | pdb\|2V5J\|A | 158430996 | 100 |
| Pyruvate Aldolase (HpaI), Mutant D42a | *Escherichia coli* ATCC 8739 | pdb\|4B5X\|A | 402550309 | 99 |
| Pyruvate Aldolase R70a Mutant, HpaI | *Escherichia coli* ATCC 8739 | pdb\|4B5W\|A | 402550303 | 99 |
| Pyruvate Aldolase, HpaI, | *Escherichia coli* ATCC 8739 | pdb\|4B5S\|A | 402550295 | 10 |
| Class II Aldolase | *Escherichia coli* K-12 | pdb\|2VWS\|A | 198443128 | 56 |
| 2-Dehydro-3-Deoxy-Galactarate Aldolase | *Escherichia coli* | pdb\|1DXE\|A | 10120730 | 48 |
| Hpch/hpal Aldolase/citrate Lyase Family Protein | *Burkholderia cenocepacia* J2315 | pdb\|4MF4\|A | 538261383 | 42 |
| HpchHPAI ALDOLASE | *Desulfitobacterium hafniense* DCB-2 | pdb\|3QZ6\|A | 326328104 | 33 |
| Citrate Synthase Sbng | *Staphylococcus aureus* subsp. *aureus* str. Newman | pdb\|4TV5\|A | 700588452 | 28 |
| Citrate Synthase Variant Sbng E151q | *Staphylococcus aureus* subsp. *aureus* str. Newman | pdb\|4TV6\|A | 700588453 | 27 |
| Macrophomate Synthase | *Macrophoma commelinae* | pdb\|1IZC\|A | 29726304 | 25 |

TABLE 18

| Name | Organism | PDB No. | GI | % Ident to MphE |
|---|---|---|---|---|
| Bifunctional Aldolase-Dehydrogenase | *Pseudomonas* sp. CF600 | pdb\|1NVM\|A | 33357505 | 83 |
| Aldolase/aldehyde Dehydrogenas | *Thermomonospora curvata* DSM 43183 | pdb\|4LRS\|A | 538261320 | 53 |
| Aldolase-dehydrogenase | *Mycobacterium tuberculosis* | pdb\|4JN6\|A | 491668629 | 52 |
| Putative Aldolase (Bvu_2661) | *Bacteroides vulgatus* ATCC 8482 | pdb\|3DXI\|A | 197305157 | 25 |
| Truncated Alpha-isopropylmalate Synthase | *Neisseria meningitidis* serogroup B | pdb\|3RMJ\|A | 380258925 | 26 |
| 2-Isopropylmalate Synthase | *Cytophaga hutchinsonii* ATCC 33406 | pdb\|3EEG\|A | 203282565 | 23 |
| Isopropylmalate Synthase | *Leptospira biflexa serovar* Patoc strain 'Patoc 1 (Paris)' | pdb\|4OV4\|A | 673541345 | 22 |

TABLE 19

| Name | Organism | PDB No. | GI | % Ident to BphI |
|---|---|---|---|---|
| Bifunctional Aldolase-Dehydrogenase | *Pseudomonas* sp. CF600 | pdb\|1NVM\|A | 33357505 | 57 |
| Aldolase-dehydrogenase | *Mycobacterium tuberculosis* | pdb\|4JN6\|A | 491668629 | 51 |
| The Bifunctional Enzyme (aldolase/aldehyde Dehydrogenase) | *Thermomonospora curvata* DSM 43183 | pdb\|4LRS\|A | 538261320 | 52 |
| 2-Isopropylmalate Synthase | *Cytophaga hutchinsonii* ATCC 33406 | pdb\|3EEG\|A | 203282565 | 25 |
| Putative 2-Isopropylmalate Synthase | *Listeria monocytogenes* serotype 4b str. F2365 | pdb\|3EWB\|X | 218766747 | 27 |
| Putative Aldolase (Bvu_2661) | *Bacteroides vulgatus* ATCC 8482 | pdb\|3DXI\|A | 197305157 | 40 |
| Homocitrate Synthase | *Thermus thermophilus* HB27 | pdb\|2ZTJ\|A | 261278579 | 37 |
| Oxaloacetate Decarboxylase | *Vibrio cholerae* | pdb\|2NX9\|A | 122921155 | 24 |
| Isopropylmalate Synthase | *Leptospira biflexa* serovar Patoc strain 'Patoc 1 (Paris)' | pdb\|4OV4\|A | 673541345 | 29 |
| Carboxyl Transferase | *Rhizobium etli* CFN 42 | pdb\|4JX6\|A | 508123917 | 35 |
| Multifunctional Pyruvate Carboxylase | *Rhizobium etli* CFN 42 | pdb\|2QF7\|A | 158430175 | 35 |

Example 3: Strain for Producing Trans-2-Hexenal Using Aldolase-Based Pathway Strain *E. coli* MG1655 ΔpflB ΔldhA ΔadhE ΔyqhD ΔeutG ΔadhP ΔyjgB::cmR containing pArdra002 plasmid expressing pyruvate decarboxylase from *Zymomonas mobilis* (PDC), deoxyribose-5-phosphate aldolase from *Bacillus halodurans* (BH1352), and aldo-keto reductase from *Pseudomonas aeruginosa* (PA1127) was examined for the production of trans-2-hexenal. The strain was prepared by deleting seven genes, pflB, ldhA, adhE, yqhD, eutG, adhP, and yjgB using the lambda red recombinase method described in Datsenko and Wanner (Datsenko et al., PNAS USA 97: 6640-6645 (2000)).

Seed Preparation: Two seed cultures were prepared. The first seed culture was prepared by inoculating a glycerol stock in 5 mL medium and grown overnight. A second seed culture was prepared in 50 mL falcon tubes by inoculating 100 μL of the first seed culture in 10 mL media and grown overnight. The cultures were used to inoculate the fermenter to an optical density at 600 nm ($OD_{600}$) of approximately 0.2 (range from about 0.15 to about 0.25).

Growth Phase: Cells were grown in a 2 L fermenter with an agitation set to 1000 RPM and DO over 50% until an $OD_{600}$ of approximately 18 was reached. Protein expression was then induced with 0.1 M IPTG (1.5 mL of 1 M stock). Protein expression was carried out for about 7 hours. At about 7 hours or when the glucose from the medium was completely consumed, additional glucose was fed to the cells.

Production Phase: The production phase started after about 7 hours of protein expression by reducing the agitation to 500 RPM and by shutting down the air-flow. In addition to the 3.3 g/L glucose (10 mL of 50% glucose stock), 3 g/L of both acetaldehyde and butyraldehyde were added to the culture at the start and after 2 hours from the start of the production phase. Additional 3 g/L of both acetaldehyde and butyraldehyde were added to the culture after about 15 hours. The total production time was approximately 20 hours.

Sampling: 1 mL samples were taken throughout and especially before and after addition of glucose.

Figure 11:
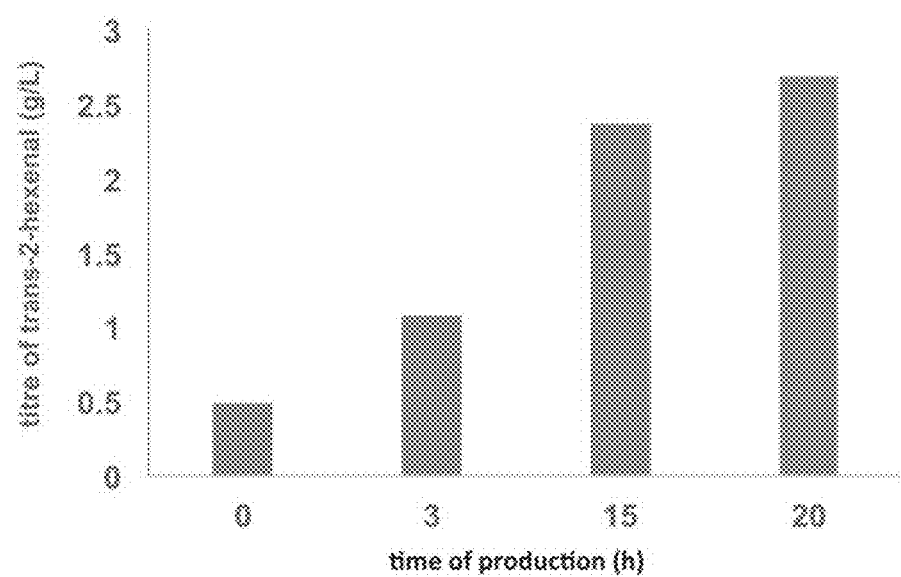
FIG. 11 exemplifies production of trans-2-hexenal by acetaldehyde and butyraldehyde.

Results: 2.5 g/L of trans-2-hexenal was produced in about 20 hours. The progression of the trans-2-hexenal production during the production phase is shown in FIG. 11.

Example 4: Theoretical Yield Calculation of Trans-2-Hexenal

FIG. 1 describes a fatty acid oxidation pathway used in the industry to produce natural trans-2-hexenal. As shown in FIG. 1, one mole of linolenic acid provides 1 mole of trans-2-hexenal. The theoretical yield of trans-2-hexenal per mole of carbon according to the pathway of FIG. 1 can be calculated as follows:

| Mole amount | Theoretical yield of trans-2-hexenal |
|---|---|
| 1 mole of linolenic acid | 1 mole of trans-2-hexenal |
| 18 moles of carbon | 1 mole of trans-2-hexenal |
| 1 mole of carbon | 0.055 mole of trans-2-hexenal |

The theoretical yield of trans-2-hexenal according to the present disclosure is about twice as much as the theoretical yield of natural trans-2-hexenal. According to the present disclosure:
(1) 0.5 mole of glucose=1 mole of acetaldehyde
(2) 1 mole of glucose=1 mole of butyraldehyde
(3) 1 mole of acetaldehyde+1 mole of butyraldehyde=1 mole of trans-2-hexenal Thus, the theoretical yield of trans-2-hexenal according to the present disclosure can be determined as follow:

| Mole amount | Theoretical yield of trans-2-hexenal |
|---|---|
| 1.5 moles of glucose | 1 mole of trans-2-hexenal |
| 9 moles of carbon | 1 mole of trans-2-hexenal |
| 1 mole of carbon | 0.11 mole of trans-2-hexenal |

Example 5: Theoretical Yield Calculation of Delta-Decalactone

The theoretical yield of delta decalactone according to the present disclosure:

(1) 1 mole of glucose=2 moles of acetaldehyde
(2) 2.5 moles of glucose=1 mole of hexanal
(3) 2 moles of acetaldehyde+1 mole of hexanal=1 mole of delta-decalactone Thus, the theoretical yield of delta-decalactone according to the present disclosure can be determined as follow:

| Mole amount | Theoretical yield of delta-decalactone |
|---|---|
| 3.5 moles of glucose | 1 mole of delta-decalactone |
| 21 moles of carbon | 1 mole of delta-decalactone |
| 1 mole of carbon | 0.048 mole of delta-decalactone |

Example 6: Theoretical Yield Calculation of Gamma-Decalactone

The theoretical yield of gamma-decalactone according to the present disclosure:
(1) 1 mole of glucose=2 moles of pyruvate
(2) 3 moles of glucose=1 mole of heptanal
(3) 1 mole of pyruvate+1 mole of heptanal=1 mole of gamma-decalactone Thus, the theoretical yield of gamma-decalactone according to the present disclosure can be determined as follow:

| Mole amount | Theoretical yield of gamma-decalactone |
|---|---|
| 3.5 moles of glucose | 1 mole of gamma-decalactone |
| 21 moles of carbon | 1 mole of gamma-decalactone |
| 1 mole of carbon | 0.048 mole of gamma-decalactone |

Example 7: Construction Of Pyruvate-Accumulating Strain

As pyruvate is the first metabolite in the trans-2-unsaturated aldehydes, delta-lactones, and gamma-lactones pathways, increasing production requires a host organism that can accumulate pyruvate. The latter represents a key metabolite in the central carbon metabolism of most common microorganisms. In *E. coli*, pyruvate is the main precursor to several native fermentative by-products. To produce high titres of pyruvate in *E. coli*, pathways draining pyruvate to fermentative products were deleted. Seven genes, adhE (encoding alcohol dehydrogenase), ldhA (encoding lactate dehydrogenase), pflB (encoding pyruvate formate lyase), yqhD (encoding NADP-dependent alcohol dehydrogenase), eutG (encoding alcohol dehydrogenase), adhP (encoding alcohol dehydrogenase), and yjgB (encoding ZN-dependent alcohol dehydrogenase) were deleted from *E. coli*. The gene deletions were sequentially transferred from the corresponding single gene deletion mutants from KEIO collection to the wild type strain using P1 transduction method. The gene deletions were confirmed using PCR using at least the primers provided in the sequences: F-adhE-check (ggtcaactaa tccttaactg atcg) and R-adhEcheck (aagcaaatca tcaccgcact gac), F-ldhA-check (caggcttagc gcaacaaacg) and R-ldhA-check (ggttgcgcct acactaagc), F-pflBcheck (tccacttaag aaggtaggtg ttac) and R-pflA-check (aaagttgccg ctttacgggg aaa). The resultant strain with seven gene deletions was designated as LMSE-40C.

What is claimed is:

1. A non-naturally occurring microorganism having a trans-2-unsaturated aldehyde pathway, wherein the non-naturally occurring microorganism is transformed with an exogenous nucleic acid encoding an aldolase comprising the amino acid sequence of SEQ ID NOs: 11, 12, 13, 14, 15, 16, 17, 18, 19, or 20, an exogenous nucleic acid encoding a decarboxylase comprising the amino acid sequence of SEQ ID NOs: 68, 71, 76, or 77 and an exogenous nucleic acid encoding an aldo-ketoreductase comprising the amino acid sequence of SEQ ID NOs: 30, 31, 32, or 33, wherein the non-naturally occurring microorganism produces a trans-2-unsaturated aldehyde.

2. The non-naturally occurring microorganism of claim 1, wherein the non-naturally occurring microorganism comprises an increased enzymatic activity of at least one enzyme in said trans-2-unsaturated aldehyde pathway in comparison with the enzymatic activity of the same enzyme in a corresponding unmodified or wild-type microorganism.

3. The non-naturally occurring microorganism of claim 1, wherein the non-naturally occurring microorganism further comprises an exogenous nucleic acid encoding a ketoreductase, oxidoreductase, aldehyde reductase, enoate reductase, dehydratase, lactonization enzyme, or alcohol dehydrogenase.

4. The non-naturally occurring microorganism of claim 1, wherein the decarboxylase comprises the amino acid sequence of SEQ ID NO: 71.

5. The non-naturally occurring microorganism of claim 1, wherein the decarboxylase comprises the amino acid sequence of SEQ ID NO: 76.

6. The non-naturally occurring microorganism of claim 1, wherein the decarboxylase comprises the amino acid sequence of SEQ ID NO: 68 or 77.

7. The non-naturally occurring microorganism of claim 1, wherein the non-naturally occurring microorganism further comprises an exogenous nucleic acid encoding an, ethylnitronate:oxygen 2-oxidoreductase (nitriteforming), pyruvate carboxy-lyase (acetaldehyde-forming), acetaldehyde:NAD+ oxidoreductase (CoA-acetylating), acetaldehyde:acceptor oxidoreductase, Acetaldehyde:NAD+ oxidoreductase, Acetaldehyde:NADP+ oxidoreductase, Ethanol:NADP+ oxidoreductase, 2-Phosphonoacetaldehyde phosphonohydrolase, ethanolamine-phosphate phosphate-lyase (deaminating; acetaldehyde-forming), ethanolamine ammonia-lyase (acetaldehyde-forming), 4-hydroxy-2-oxopentanoate pyruvate-lyase (acetaldehyde-forming), L-threonine acetaldehyde-lyase (glycine-forming), (S)-lactate acetaldehyde-lyase (formate-forming), ethanol:NAD+ oxidoreductase, Pyruvate decarboxylase, TPP dependent reaction, Nitroethane:oxygen oxidoreductase, acetaldehyde: pyrroloquinoline-quinone oxidoreductase, 2-deoxy-D-ribose-S-phosphate acetaldehyde-lyase (D-glyceraldehyde-3-phosphate-forming), 17alpha-Hydroxyprogesterone acetaldehyde-lyase, 3-Hydroxybutan-2-one:D-ribose-5-phosphate aldehydetransferase, 24R,24(1)R)-fucosterol-epoxide acetaldehyde-lyase (desmosterol-forming), ethanol: cytochrome c oxidoreductase, acetaldehyde hydro-lyase, diethanolamine ethanolamine-lyase (acetaldehyde-forming), triethanolamine diethanolamine-lyase (acetaldehyde-forming), L-allo-threonine acetaldehyde-lyase (glycine-forming), fluoroacetaldehyde:L-threonine aldehydetransferase, cobalt-precorrin 5A acylhydrolase, D-threonine acetaldehyde-lyase (glycine-forming), 17alpha-Hydroxypregnenolone acetaldehyde-lyase, ethanol:cytochrome c oxidoreductase, chloroethane, donor:oxygen oxidoreductase (dechlorinating, acetaldehydeforming), ethanol:quinone oxidoreductase, acetyl-CoA:acetoin O-acetyltransferase, ethanol:N,N-dimethyl-4-nitrosoaniline oxidoreductase, 7,8-dihydroneopterin 3'-triphosphate acetaldehyde-lyase (6-carboxy-5,6,7,8-tetrahydropterin and triphosphate-forming), or choline trimethylamine-lyase (acetaldehyde-forming).

8. The non-naturally occurring microorganism of claim 1, wherein one or more genes encoding an enzyme that utilizes pyruvate are deleted from the non-naturally occurring microorganism as compared to a wild-type microorganism.

9. The non-naturally occurring microorganism of claim 1, wherein one or more genes encoding an enzyme capable of catalyzing a reaction involving an acetaldehyde molecule, a pyruvate, or an aldehyde precursor are deleted from the non-naturally occurring microorganism as compared to a wild-type microorganism.

10. The non-naturally occurring microorganism of claim 8, wherein the trans-2-unsaturated aldehyde is trans-2-hexenal.

* * * * *

```
SEQUENCE LISTING

<160> NUMBER OF SEQ ID NOS: 89

<210> SEQ ID NO 1
<211> LENGTH: 672
<212> TYPE: DNA
<213> ORGANISM: Bacillus cereus

<400> SEQUENCE: 1
atgaacattg caaagttaat tgaccataca attttaaaag ctaatactac taagaagat      60 gttatgaaag taatcgaaga agcaaaggaa tataaattcg cttctgtttg tattaatcct     120
acatgggtaa agctagctgc tgaggaatta gctggacatg atgtagatgt ttgtactgta     180
atcggtttcc cattaggcgc aagtactact gaaacaaaag ctttcgaaac aaaagatgct     240
atcgcaaaag gtgcaactga agttgacatg gtaatcaacg taggcgcttt aaaagatggc     300
gacgacgaac ttgttgaaaa agacatttat gaagtagtac aagcagcaaa aggaaaagct     360
cttgtaaaag taatcattga aacttgccta ttaacagatg aagagaaagt acgcgcttgt     420
gaattatcag taaaagctgg ggctgatttc gtaaaaactt caactggatt ctcaactggc     480
ggagcaactg ctgaagatat cgcattaatg cgtaaaacag ttggaccaaa cgttggtgta     540
aaagcatctg gtggcgttcg tacacgtgaa gatgcagaaa aatggtagc  tgctggagct     600 tctcgcgttg gagcaagtgc tagtgttgca atcgtattaa atgatgcaaa aggtgctaca     660
gataactact aa                                                         672

<210> SEQ ID NO 2
<211> LENGTH: 780
```

```
<212> TYPE: DNA
<213> ORGANISM: Escherichia coli

<400> SEQUENCE: 2
atgactgatc tgaaagcaag cagcctgcgt gcactgaaat tgatggacct gaccaccctg    60
aatgacgacg acaccgacga aaagtgatc gccctgtgtc atcaggccaa aactccggtc    120
ggcaataccg ccgctatctg tatctatcct cgctttatcc cgattgctcg caaaactctg    180
aaagagcagg gcaccccgga atccgtatc gctacggtaa ccaacttccc acacggtaac    240
gacgacatcg acatcgcgct ggcagaaacc cgtgcggcaa tcgcctacgg tgctgatgaa    300
gttgacgttg tgttcccgta ccgcgcgctg atggcgggta acgagcaggt tggttttgac    360
ctggtgaaag cctgtaaaga ggcttgcgcg gcagcgaatg tactgctgaa agtgatcatc    420
gaaaccggcg aactgaaaga cgaagcgctg atccgtaaag cgtctgaaat ctccatcaaa    480
gcgggtgcgg acttcatcaa aacctctacc ggtaaagtgg ctgtgaacgc gacgccggaa    540
agcgcgcgca tcatgatgga agtgatccgt gatatgggcg tagaaaaaac cgttggtttc    600
aaaccggcgg gcggcgtgcg tactgcggaa gatgcgcaga aatatctcgc cattgcagat    660
gaactgttcg gtgctgactg ggcagatgcg cgtcactacc gctttggcgc ttccagcctg    720
ctggcaagcc tgctgaaagc gctgggtcac ggcgacggta agagcgccag cagctactaa    780

<210> SEQ ID NO 3
<211> LENGTH: 675
<212> TYPE: DNA
<213> ORGANISM: Bacillus halodurans

<400> SEQUENCE: 3
atgtcacgtt cgattgcaca atgattgat catacgctac ttaaaccaaa tacaacagaa    60
gaccaaattg taaagctctg tgaggaagca aggaatatt catttgcatc tgtttgtgtg   120
aatcctactt gggtcgctct tgctgcgcag ttgctaaaag atgcacctga tgtgaaagta   180
tgtacagtta tcggctttcc gttaggggca acgactccgg aagtgaaagc gtttgaaacg   240
actaatgcca ttgaaaatgg agcgacagaa gtggacatgg tcattaacat tggagcgtta   300
aaagataaac aatacgagct tgttggacgc gacattcaag cggttgttaa agcagcagaa   360
gggaaagcat taacgaaagt aatcattgaa acatcgttat taacggagga agagaagaag   420
gctgcgtgtg agcttgccgt aaaagcagga gccgactttg tcaaaacgtc gactggattc   480
tctggcggag gtgctacggc tgaggatatc gcgctcatgc gaaaagtggt cggaccaaat   540
ttaggagtca aagcttctgg aggtgttaga gatctgtccg acgcgaaagc gatgattgat   600
gctggtgcta ctcggattgg tgcgagtgct ggggtggcga ttgttaacgg ggagcgtagc   660
gaagggagtt attaa                                                   675

<210> SEQ ID NO 4
<211> LENGTH: 672
<212> TYPE: DNA
<213> ORGANISM: Bacillus subtilis

<400> SEQUENCE: 4
atgtcattag ccaacataat tgatcataca gctttgaaac cgcatacaca aaaagcggac    60
attctaaaac taattgaaga agcgaaaaca tacaaatttg cttcagtatg tgtcaatccg   120
acatgggtgg agcttgctgc aaaagagctt aagggaactg gagtcgacgt ttgtacggtc   180
atcggcttcc cgctcggtgc caatacaact gaaacaaaag cgttcgaaac aaaagacgcc   240
```

```
atttcaaaag gcgccactga agtggatatg gtcattaata ttgccgcttt aaaagacaag    300
gaagacgatg tggtggaagc tgatatccgc ggtgtagtgg aagctgtagc cggaaaagcg    360
cttgtcaaag tcattatcga acgtgccttt ctgactgatg aagaaaaaga acgtgcatgc    420
cgtttagcgg tgtctgcggg agcggatttc gtaaaaacat caacaggctt ttctacaggc    480
ggcgcaacga aggaagatat cgccttaatg cgcaaaacag tagggcctga tatcggcgtg    540
aaagcatctg gcggcgtcag aacgaaagaa gatgtagaca caatggtaga ggccggagca    600
agccgaattg gcgccagcgc aggcgtttct atcgtaaaag gagaaaatgc atcaggcgga    660
gacaactatt aa                                                       672
```

```
<210> SEQ ID NO 5
<211> LENGTH: 747
<212> TYPE: DNA
<213> ORGANISM: Thermotoga maritima

<400> SEQUENCE: 5
atgatagagt acaggattga ggaggcagta gcgaagtaca gagagttcta cgaattcaag     60
cccgtcagag aaagcgcagg tattgaagat gtgaaaagtg ctatagagca cgaatctg     120 aaaccgtttg ccacaccaga cgatataaaa aaactctgtc ttgaagcaag gaaaatcgt     180 ttccatggag tctgtgtgaa tccgtgttat gtgaaactgg ctcgtgaaga actcgaagga    240
accgatgtga aagtcgtcac cgttgttggt tttccactgg gagcgaacga aactcggacg    300
aaagcccatg aggcgatttt cgctgttgag agtggagccg atgagatcga tatggtcatc    360
aacgttggca tgctcaaggc aaaggagtgg gagtacgttt acgaggatat aagaagtgtt    420
gtcgaatcgg tgaaaggaaa agttgtgaag gtgatcatcg aaacgtgcta tctggatacg    480
gaagagaaga tagcggcgtg tgtcatttcc aaacttgctg gagctcattt cgtgaagact    540
tccacgggat ttggaacagg agggggcgacc gcagaagacg ttcatctcat gaaatggatc    600
gtgggagatg agatgggtgt aaaagcttcc ggagggatca gaaccttcga ggacgctgtt    660
aaaatgatca tgtacggtgc tgatagaata ggaacgagtt cgggagttaa gatcgttcag    720
gggggagaag agagatatgg aggttaa                                        747
```

```
<210> SEQ ID NO 6
<211> LENGTH: 675
<212> TYPE: DNA
<213> ORGANISM: Methanothermobacter thermautrophicus

<400> SEQUENCE: 6
gtggttaaaa tgaatgtgga gacaagggag gaacttgcat cacttataga ccacaccaat     60
gtgagggctg atgcaacaga aaatgatatt gagaggctat gcagggaggc ggtcagctac    120
ggcttcaggt gcgcggtggt cacacccacc aatgtcaggc tggcggctga actccttgag    180
gggaccgatg tgacggtctg ctcagttgtt ggtttcccgg caggcgtcag tacaccccgc    240
gttaaggccc ttgaagcctc tgaggccgtt gagaacgggg ccggtgaggt ggacatggtc    300
atgaatatcg gggccatgaa gtcaggcaat agggagctcg tatacaggga tatcagcggc    360
gttgttgatg ccgccggcgt ccccgtcaag gttatacttg aaacagccta tctcacagac    420
aaggagaagg ttgaagcctg ccttataagt aaagaggccg gtgcggcatt tgttaaaaca    480
tcaacagcct atggtggact agccggcgcc acagttgagg atgtgatgct catgcggaaa    540
acggtgggtg atgagatggg agtcaaggca tctgggggaa taaggggatct tgaaacagcc    600 cttgcgatga tagatgctgg ggcagacagg atcgggacat caaccggtgt acagataatc    660
```

```
gagggatgga ggtaa                                                        675

<210> SEQ ID NO 7
<211> LENGTH: 663
<212> TYPE: DNA
<213> ORGANISM: Deinococcus radiodurans

<400> SEQUENCE: 7
atgtcactcg cctcctacat cgaccacacg ctgcttaagg ccaccgccac gctcgccgac        60
atccgcacgc tgtgtgagga agcccgcgag cactcgttct acgcggtgtg catcaacccg       120
gtctttattc cccacgcccg cgcctggctc gaaggcagcg acgtgaaggt cgccaccgtc       180
tgcggctttc ccctcggcgc catcagctcc gagcagaaag ctctggaagc ccgcctgagc       240
gccgaaacgg cgccgacga atcgatatg gtcatccaca tcggctcggc gcttgccggc         300
gactgggacg cggtggaagc cgacgtgcgg gcagtgcgcc gcgcggtgcc cgagcaggtg       360
ctcaaggtga ttatcgaaac ctgctacctg accgacgagc aaaagcgctt ggcgactgag       420
gtcgccgtac agggcggcgc cgacttcgtg aagacgagca caggcttcgg caccggcggc       480
gccaccgtgg acgacgtgcg cctgatggcg gaagtgatcg gggccgcgc cggactcaag        540 gcggcgggcg gcgtccgcac tcctgccgac gcgaagcca tgatcgaggc gggcgcgacc       600
cggctgggca cctcgggcgg cgtgggtctg gtgtcgggcg gcgaaaacgg agccggctac       660
taa                                                                    663

<210> SEQ ID NO 8
<211> LENGTH: 663
<212> TYPE: DNA
<213> ORGANISM: Staphylococcus aureus

<400> SEQUENCE: 8
atgaatagtg caaaattgat tgatcacact ttattgaagc ctgagtcaac acgtacgcaa        60
atcgatcaaa tcatcgatga agcgaaagca taccatttta atctgtatg tgtgaatcca       120 acgcatgtta aatatgcagc agagcgacta gctgattcag aggtgttagt ttgtacggta       180
ataggattcc cattaggtgc atcgacaact gcgacgaaag catttgaaac agaagatgcg       240
attcaaaatg gtgcagatga aattgacatg gtcatcaaca tcggcgcatt aaaagatgga       300
cgttttgatg atgtacaaca agacattgaa gcagtggtga agctgcgaa aggtcacaca       360 gtaaaagtga ttattgagac ggtattgttg gaccatgacg aaatcgtaaa agcgagtgaa       420
ttaacaaaag tggctggtgc ggacttcgtt aaaacttcaa caggttttgc aggtggcggt       480
gcgactgcag aagacgttaa attaatgaaa gatacagtag gtgctgatgt agaagtaaaa       540
gcatcaggtg gcgtacgtaa tttagaagat ttcaataaaa tggttgaagc aggtgcgaca       600
cgtattggtg cgagcgcagg cgttcaaatt atgcaaggtt agaagcaga ttcagattac       660 taa                                                                    663

<210> SEQ ID NO 9
<211> LENGTH: 672
<212> TYPE: DNA
<213> ORGANISM: Listeria monocytogenes

<400> SEQUENCE: 9
atgacaattg ctaaaatgat cgatcatact gctttaaaac cagacacaac gaaagaacaa        60 atttttaaccc taacaaaaga agcaagagaa tacggctttg catccgtatg tgtgaaccca      120
```

```
acttgggtaa aactatccgc tgaacaactt gctggagcag aatccgtagt atgtactgtt      180
atcggtttcc cactaggagc gaatacccct gaagtaaaag catttgaagt gaaagatgcc      240
atccaaaacg gcgcgaaaga agtcgatatg gttatcaata tcggtgcact aaagacaag       300 gacgacgaat tagtagaacg cgatattcgc gctgttgtcg atgttgctaa aggcaaagca      360
ttagtaaaag taattatcga aacttgccta ttaacagacg aagaaaaagt gcgcgcatgc      420
gaaatcgctg taaagcagg aacagacttc gttaaaacat ctacaggatt ttcaacaggt       480
ggcgcaactg ccgaagatat cgccttgatg cgtaaaacag ttggaccgaa catcggtgta      540
aaagcatctg gtggggttcg tacgaaagaa gacgtagaaa aatgatcga agcaggcgca       600 actcgtatcg gcgcaagtgc aggcgttgca attgtttccg gcgaaaaacc agctaaacct      660
gataattact aa                                                         672
```

<210> SEQ ID NO 10
<211> LENGTH: 663
<212> TYPE: DNA
<213> ORGANISM: Streptococcus pneumoniae

<400> SEQUENCE: 10

```
atgaaattaa ataaatatat agatcatacg cttttaaaac aagatgcaaa gaaaaaacaa      60
attgatagtt tgttgtctga ggctagagag tatgactttg ccagtgtttg cgttaatccg     120
acctgggttg aacatgctaa aaaaggactt gaaggcacag atgttaaggt ttgcacagta     180
gtaggtttcc ctttgggagc aacaacttca gccgtgaaag catttgagac aaaagaagct     240
atccaaaatg gtgcagatga gattgatatg gtgatcaatg ttggagctct caaatcaggt     300
aatttagcct tggttgagtc agatattcgc gcagtagtgg aagcaagtgg tgataagtta     360
gtgaaagtca ttattgaagc ttgccttctg acagaccaag aaaagttgt tgtttgccaa      420 ttggcccaaa aagctggggc tgactttgtc aaaacatcta ctggcttttc aactggtggt     480
gctacgatag cagatgttac attaatgcgt gaaacagttg gatctgatat gggtgtcaag    540
gccgccggtg gagctcgttc ttatgcagat gctcttgcct tgtcgaagc aggtgcgacc     600 cgtatcggaa cgtcagctgg ggtagctatt ttaaaaggag aattggcaga tggcgactac     660
taa                                                                  663
```

<210> SEQ ID NO 11
<211> LENGTH: 248
<212> TYPE: PRT
<213> ORGANISM: Thermotoga maritima

<400> SEQUENCE: 11

```
Met Ile Glu Tyr Arg Ile Glu Glu Ala Val Ala Lys Tyr Arg Glu Phe
1               5                   10                  15

Tyr Glu Phe Lys Pro Val Arg Glu Ser Ala Gly Ile Glu Asp Val Lys
                20                  25                  30

Ser Ala Ile Glu His Thr Asn Leu Lys Pro Phe Ala Thr Pro Asp Asp
            35                  40                  45

Ile Lys Lys Leu Cys Leu Glu Ala Arg Glu Asn Arg Phe His Gly Val
        50                  55                  60

Cys Val Asn Pro Cys Tyr Val Lys Leu Ala Arg Glu Glu Leu Glu Gly
65                  70                  75                  80

Thr Asp Val Lys Val Val Thr Val Val Gly Phe Pro Leu Gly Ala Asn
                85                  90                  95

Glu Thr Arg Thr Lys Ala His Glu Ala Ile Phe Ala Val Glu Ser Gly
```

```
                100             105             110
Ala Asp Glu Ile Asp Met Val Ile Asn Val Gly Met Leu Lys Ala Lys
            115                 120             125

Glu Trp Glu Tyr Val Tyr Glu Asp Ile Arg Ser Val Glu Ser Val
        130                 135             140

Lys Gly Lys Val Val Lys Val Ile Ile Glu Thr Cys Tyr Leu Asp Thr
145                 150                 155                 160

Glu Glu Lys Ile Ala Ala Cys Val Ile Ser Lys Leu Ala Gly Ala His
                165                 170                 175

Phe Val Lys Thr Ser Thr Gly Phe Gly Thr Gly Ala Thr Ala Glu
            180                 185                 190

Asp Val His Leu Met Lys Trp Ile Val Gly Asp Glu Met Gly Val Lys
        195                 200                 205

Ala Ser Gly Gly Ile Arg Thr Phe Glu Asp Ala Val Lys Met Ile Met
            210                 215                 220

Tyr Gly Ala Asp Arg Ile Gly Thr Ser Ser Gly Val Lys Ile Val Gln
225                 230                 235                 240

Gly Gly Glu Glu Arg Tyr Gly Gly
            245
```

<210> SEQ ID NO 12
<211> LENGTH: 224
<212> TYPE: PRT
<213> ORGANISM: Methanothermobacter thermautotrophicus

<400> SEQUENCE: 12

```
Met Val Lys Met Asn Val Glu Thr Arg Glu Glu Leu Ala Ser Leu Ile
1               5                   10                  15

Asp His Thr Asn Val Arg Ala Asp Ala Thr Glu Asn Asp Ile Glu Arg
            20                  25                  30

Leu Cys Arg Glu Ala Val Ser Tyr Gly Phe Arg Cys Ala Val Val Thr
        35                  40                  45

Pro Thr Asn Val Arg Leu Ala Ala Glu Leu Leu Glu Gly Thr Asp Val
    50                  55                  60

Thr Val Cys Ser Val Val Gly Phe Pro Ala Gly Val Ser Thr Pro Arg
65                  70                  75                  80

Val Lys Ala Leu Glu Ala Ser Glu Ala Val Glu Asn Gly Ala Gly Glu
                85                  90                  95

Val Asp Met Val Met Asn Ile Gly Ala Met Lys Ser Gly Asn Arg Glu
            100                 105                 110

Leu Val Tyr Arg Asp Ile Ser Gly Val Val Asp Ala Ala Gly Val Pro
        115                 120                 125

Val Lys Val Ile Leu Glu Thr Ala Tyr Leu Thr Asp Lys Glu Lys Val
    130                 135                 140

Glu Ala Cys Leu Ile Ser Lys Glu Ala Gly Ala Ala Phe Val Lys Thr
145                 150                 155                 160

Ser Thr Ala Tyr Gly Gly Leu Ala Gly Ala Thr Val Glu Asp Val Met
                165                 170                 175

Leu Met Arg Lys Thr Val Gly Asp Glu Met Gly Val Lys Ala Ser Gly
            180                 185                 190

Gly Ile Arg Asp Leu Glu Thr Ala Leu Ala Met Ile Asp Ala Gly Ala
        195                 200                 205

Asp Arg Ile Gly Thr Ser Thr Gly Val Gln Ile Glu Gly Trp Arg
    210                 215                 220
```

<210> SEQ ID NO 13
<211> LENGTH: 220
<212> TYPE: PRT
<213> ORGANISM: Deinococcus radiodurans

<400> SEQUENCE: 13

Met Ser Leu Ala Ser Tyr Ile Asp His Thr Leu Leu Lys Ala Thr Ala
1               5                   10                  15

Thr Leu Ala Asp Ile Arg Thr Leu Cys Glu Glu Ala Arg Glu His Ser
            20                  25                  30

Phe Tyr Ala Val Cys Ile Asn Pro Val Phe Ile Pro His Ala Arg Ala
        35                  40                  45

Trp Leu Glu Gly Ser Asp Val Lys Val Ala Thr Val Cys Gly Phe Pro
    50                  55                  60

Leu Gly Ala Ile Ser Ser Glu Gln Lys Ala Leu Glu Ala Arg Leu Ser
65                  70                  75                  80

Ala Glu Thr Gly Ala Asp Glu Ile Asp Met Val Ile His Ile Gly Ser
                85                  90                  95

Ala Leu Ala Gly Asp Trp Asp Ala Val Glu Ala Asp Val Arg Ala Val
            100                 105                 110

Arg Arg Ala Val Pro Glu Gln Val Leu Lys Val Ile Glu Thr Cys
        115                 120                 125

Tyr Leu Thr Asp Glu Gln Lys Arg Leu Ala Thr Glu Val Ala Val Gln
    130                 135                 140

Gly Gly Ala Asp Phe Val Lys Thr Ser Thr Gly Phe Gly Thr Gly Gly
145                 150                 155                 160

Ala Thr Val Asp Asp Val Arg Leu Met Ala Glu Val Ile Gly Gly Arg
                165                 170                 175

Ala Gly Leu Lys Ala Ala Gly Gly Val Arg Thr Pro Ala Asp Ala Gln
            180                 185                 190

Ala Met Ile Glu Ala Gly Ala Thr Arg Leu Gly Thr Ser Gly Gly Val
        195                 200                 205

Gly Leu Val Ser Gly Gly Glu Asn Gly Ala Gly Tyr
    210                 215                 220

<210> SEQ ID NO 14
<211> LENGTH: 220
<212> TYPE: PRT
<213> ORGANISM: Staphylococcus aureus

<400> SEQUENCE: 14

Met Asn Ser Ala Lys Leu Ile Asp His Thr Leu Leu Lys Pro Glu Ser
1               5                   10                  15

Thr Arg Thr Gln Ile Asp Gln Ile Asp Glu Ala Lys Ala Tyr His
            20                  25                  30

Phe Lys Ser Val Cys Val Asn Pro Thr His Val Lys Tyr Ala Ala Glu
        35                  40                  45

Arg Leu Ala Asp Ser Glu Val Leu Val Cys Thr Val Ile Gly Phe Pro
    50                  55                  60

Leu Gly Ala Ser Thr Thr Ala Thr Lys Ala Phe Glu Thr Glu Asp Ala
65                  70                  75                  80

Ile Gln Asn Gly Ala Asp Glu Ile Asp Met Val Ile Asn Ile Gly Ala
                85                  90                  95

Leu Lys Asp Gly Arg Phe Asp Asp Val Gln Gln Asp Ile Glu Ala Val
            100                 105                 110

```
Val Lys Ala Ala Lys Gly His Thr Val Lys Val Ile Glu Thr Val
            115                 120                 125

Leu Leu Asp His Asp Glu Ile Val Lys Ala Ser Glu Leu Thr Lys Val
    130                 135                 140

Ala Gly Ala Asp Phe Val Lys Thr Ser Thr Gly Phe Ala Gly Gly Gly
145                 150                 155                 160

Ala Thr Ala Glu Asp Val Lys Leu Met Lys Asp Thr Val Gly Ala Asp
                165                 170                 175

Val Glu Val Lys Ala Ser Gly Gly Val Arg Asn Leu Glu Asp Phe Asn
            180                 185                 190

Lys Met Val Glu Ala Gly Ala Thr Arg Ile Gly Ala Ser Ala Gly Val
    195                 200                 205

Gln Ile Met Gln Gly Leu Glu Ala Asp Ser Asp Tyr
    210                 215                 220
```

<210> SEQ ID NO 15
<211> LENGTH: 220
<212> TYPE: PRT
<213> ORGANISM: Streptococcus pneumoniae

<400> SEQUENCE: 15

```
Met Lys Leu Asn Lys Tyr Ile Asp His Thr Leu Leu Lys Gln Asp Ala
1               5                   10                  15

Lys Lys Lys Gln Ile Asp Ser Leu Leu Ser Glu Ala Arg Glu Tyr Asp
            20                  25                  30

Phe Ala Ser Val Cys Val Asn Pro Thr Trp Val Glu His Ala Lys Lys
        35                  40                  45

Gly Leu Glu Gly Thr Asp Val Lys Val Cys Thr Val Gly Phe Pro
    50                  55                  60

Leu Gly Ala Thr Thr Ser Ala Val Lys Ala Phe Glu Thr Lys Glu Ala
65                  70                  75                  80

Ile Gln Asn Gly Ala Asp Glu Ile Asp Met Val Ile Asn Val Gly Ala
                85                  90                  95

Leu Lys Ser Gly Asn Leu Ala Leu Val Glu Ser Asp Ile Arg Ala Val
            100                 105                 110

Val Glu Ala Ser Gly Asp Lys Leu Val Lys Val Ile Glu Ala Cys
            115                 120                 125

Leu Leu Thr Asp Gln Glu Lys Val Val Val Cys Gln Leu Ala Gln Lys
    130                 135                 140

Ala Gly Ala Asp Phe Val Lys Thr Ser Thr Gly Phe Ser Thr Gly Gly
145                 150                 155                 160

Ala Thr Ile Ala Asp Val Thr Leu Met Arg Glu Thr Val Gly Ser Asp
                165                 170                 175

Met Gly Val Lys Ala Ala Gly Gly Ala Arg Ser Tyr Ala Asp Ala Leu
            180                 185                 190

Ala Phe Val Glu Ala Gly Ala Thr Arg Ile Gly Thr Ser Ala Gly Val
    195                 200                 205

Ala Ile Leu Lys Gly Glu Leu Ala Asp Gly Asp Tyr
    210                 215                 220
```

<210> SEQ ID NO 16
<211> LENGTH: 259
<212> TYPE: PRT
<213> ORGANISM: Escherichia coli

<400> SEQUENCE: 16

```
Met Thr Asp Leu Lys Ala Ser Ser Leu Arg Ala Leu Lys Leu Met Asp
1               5                   10                  15

Leu Thr Thr Leu Asn Asp Asp Thr Asp Glu Lys Val Ile Ala Leu
            20                  25                  30

Cys His Gln Ala Lys Thr Pro Val Gly Asn Thr Ala Ala Ile Cys Ile
            35                  40                  45

Tyr Pro Arg Phe Ile Pro Ile Ala Arg Lys Thr Leu Lys Glu Gln Gly
    50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
            100                 105                 110

Gly Asn Glu Gln Val Gly Phe Asp Leu Val Lys Ala Cys Lys Glu Ala
            115                 120                 125

Cys Ala Ala Ala Asn Val Leu Leu Lys Val Ile Glu Thr Gly Glu
            130                 135                 140

Leu Lys Asp Glu Ala Leu Ile Arg Lys Ala Ser Glu Ile Ser Ile Lys
145                 150                 155                 160

Ala Gly Ala Asp Phe Ile Lys Thr Ser Thr Gly Lys Val Ala Val Asn
                165                 170                 175

Ala Thr Pro Glu Ser Ala Arg Ile Met Met Glu Val Ile Arg Asp Met
            180                 185                 190

Gly Val Glu Lys Thr Val Gly Phe Lys Pro Ala Gly Gly Val Arg Thr
            195                 200                 205

Ala Glu Asp Ala Gln Lys Tyr Leu Ala Ile Ala Asp Glu Leu Phe Gly
    210                 215                 220

Ala Asp Trp Ala Asp Ala Arg His Tyr Arg Phe Gly Ala Ser Ser Leu
225                 230                 235                 240

Leu Ala Ser Leu Leu Lys Ala Leu Gly His Gly Asp Gly Lys Ser Ala
                245                 250                 255

Ser Ser Tyr

<210> SEQ ID NO 17
<211> LENGTH: 223
<212> TYPE: PRT
<213> ORGANISM: Listeria monocytogenes

<400> SEQUENCE: 17

Met Thr Ile Ala Lys Met Ile Asp His Thr Ala Leu Lys Pro Asp Thr
1               5                   10                  15

Thr Lys Glu Gln Ile Leu Thr Leu Thr Lys Glu Ala Arg Glu Tyr Gly
            20                  25                  30

Phe Ala Ser Val Cys Val Asn Pro Thr Trp Val Lys Leu Ser Ala Glu
            35                  40                  45

Gln Leu Ala Gly Ala Glu Ser Val Val Cys Thr Val Ile Gly Phe Pro
    50                  55                  60

Leu Gly Ala Asn Thr Pro Glu Val Lys Ala Phe Glu Val Lys Asp Ala
65                  70                  75                  80

Ile Gln Asn Gly Ala Lys Glu Val Asp Met Val Ile Asn Ile Gly Ala
                85                  90                  95

Leu Lys Asp Lys Asp Asp Glu Leu Val Glu Arg Asp Ile Arg Ala Val
            100                 105                 110
```

```
Val Asp Val Ala Lys Gly Lys Ala Leu Val Lys Val Ile Ile Glu Thr
    115                 120                 125
Cys Leu Leu Thr Asp Glu Glu Lys Val Arg Ala Cys Glu Ile Ala Val
    130                 135                 140
Lys Ala Gly Thr Asp Phe Val Lys Thr Ser Thr Gly Phe Ser Thr Gly
145                 150                 155                 160
Gly Ala Thr Ala Glu Asp Ile Ala Leu Met Arg Lys Thr Val Gly Pro
                165                 170                 175
Asn Ile Gly Val Lys Ala Ser Gly Gly Val Arg Thr Lys Glu Asp Val
            180                 185                 190
Glu Lys Met Ile Glu Ala Gly Ala Thr Arg Ile Gly Ala Ser Ala Gly
        195                 200                 205
Val Ala Ile Val Ser Gly Glu Lys Pro Ala Lys Pro Asp Asn Tyr
    210                 215                 220

<210> SEQ ID NO 18
<211> LENGTH: 224
<212> TYPE: PRT
<213> ORGANISM: Bacillus halodurans

<400> SEQUENCE: 18

Met Ser Arg Ser Ile Ala Gln Met Ile Asp His Thr Leu Leu Lys Pro
1               5                   10                  15
Asn Thr Thr Glu Asp Gln Ile Val Lys Leu Cys Glu Glu Ala Lys Glu
            20                  25                  30
Tyr Ser Phe Ala Ser Val Cys Val Asn Pro Thr Trp Val Ala Leu Ala
        35                  40                  45
Ala Gln Leu Leu Lys Asp Ala Pro Asp Val Lys Val Cys Thr Val Ile
    50                  55                  60
Gly Phe Pro Leu Gly Ala Thr Thr Pro Glu Val Lys Ala Phe Glu Thr
65                  70                  75                  80
Thr Asn Ala Ile Glu Asn Gly Ala Thr Glu Val Asp Met Val Ile Asn
                85                  90                  95
Ile Gly Ala Leu Lys Asp Lys Gln Tyr Glu Leu Val Gly Arg Asp Ile
            100                 105                 110
Gln Ala Val Val Lys Ala Ala Glu Gly Lys Ala Leu Thr Lys Val Ile
        115                 120                 125
Ile Glu Thr Ser Leu Leu Thr Glu Glu Lys Lys Ala Ala Cys Glu
    130                 135                 140
Leu Ala Val Lys Ala Gly Ala Asp Phe Val Lys Thr Ser Thr Gly Phe
145                 150                 155                 160
Ser Gly Gly Gly Ala Thr Ala Glu Asp Ile Ala Leu Met Arg Lys Val
                165                 170                 175
Val Gly Pro Asn Leu Gly Val Lys Ala Ser Gly Gly Val Arg Asp Leu
            180                 185                 190
Ser Asp Ala Lys Ala Met Ile Asp Ala Gly Ala Thr Arg Ile Gly Ala
        195                 200                 205
Ser Ala Gly Val Ala Ile Val Asn Gly Glu Arg Ser Glu Gly Ser Tyr
    210                 215                 220

<210> SEQ ID NO 19
<211> LENGTH: 223
<212> TYPE: PRT
<213> ORGANISM: Bacillus cereus

<400> SEQUENCE: 19
```

Met Asn Ile Ala Lys Leu Ile Asp His Thr Ile Leu Lys Ala Asn Thr
1               5                   10                  15

Thr Lys Glu Asp Val Met Lys Val Ile Glu Glu Ala Lys Glu Tyr Lys
            20                  25                  30

Phe Ala Ser Val Cys Ile Asn Pro Thr Trp Val Lys Leu Ala Ala Glu
        35                  40                  45

Glu Leu Ala Gly His Asp Val Asp Val Cys Thr Val Ile Gly Phe Pro
    50                  55                  60

Leu Gly Ala Ser Thr Thr Glu Thr Lys Ala Phe Glu Thr Lys Asp Ala
65                  70                  75                  80

Ile Ala Lys Gly Ala Thr Glu Val Asp Met Val Ile Asn Val Gly Ala
                85                  90                  95

Leu Lys Asp Gly Asp Asp Glu Leu Val Glu Lys Asp Ile Tyr Glu Val
            100                 105                 110

Val Gln Ala Ala Lys Gly Lys Ala Leu Val Lys Val Ile Glu Thr
        115                 120                 125

Cys Leu Leu Thr Asp Glu Glu Lys Val Arg Ala Cys Glu Leu Ser Val
    130                 135                 140

Lys Ala Gly Ala Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                165                 170                 175

Asn Val Gly Val Lys Ala Ser Gly Gly Val Arg Thr Arg Glu Asp Ala
            180                 185                 190

Glu Lys Met Val Ala Ala Gly Ala Ser Arg Val Gly Ala Ser Ala Ser
        195                 200                 205

Val Ala Ile Val Leu Asn Asp Ala Lys Gly Ala Thr Asp Asn Tyr
    210                 215                 220

<210> SEQ ID NO 20
<211> LENGTH: 223
<212> TYPE: PRT
<213> ORGANISM: Bacillus subtilis

<400> SEQUENCE: 20

Met Ser Leu Ala Asn Ile Ile Asp His Thr Ala Leu Lys Pro His Thr
1               5                   10                  15

Gln Lys Ala Asp Ile Leu Lys Leu Ile Glu Glu Ala Lys Thr Tyr Lys
            20                  25                  30

Phe Ala Ser Val Cys Val Asn Pro Thr Trp Val Glu Leu Ala Ala Lys
        35                  40                  45

Glu Leu Lys Gly Thr Gly Val Asp Val Cys Thr Val Ile Gly Phe Pro
    50                  55                  60

Leu Gly Ala Asn Thr Thr Glu Thr Lys Ala Phe Glu Thr Lys Asp Ala
65                  70                  75                  80

Ile Ser Lys Gly Ala Thr Glu Val Asp Met Val Ile Asn Ile Ala Ala
                85                  90                  95

Leu Lys Asp Lys Glu Asp Val Val Glu Ala Asp Ile Arg Gly Val
            100                 105                 110

Val Glu Ala Val Ala Gly Lys Ala Leu Val Lys Val Ile Ile Glu Thr
        115                 120                 125

Cys Leu Leu Thr Asp Glu Glu Lys Glu Arg Ala Cys Arg Leu Ala Val
    130                 135                 140

Ser Ala Gly Ala Asp Phe Val Lys Thr Ser Thr Gly Phe Ser Thr Gly
145                 150                 155                 160

```
Gly Ala Thr Lys Glu Asp Ile Ala Leu Met Arg Lys Thr Val Gly Pro
            165                 170                 175

Asp Ile Gly Val Lys Ala Ser Gly Gly Val Arg Thr Lys Glu Asp Val
            180                 185                 190

Asp Thr Met Val Glu Ala Gly Ala Ser Arg Ile Gly Ala Ser Ala Gly
            195                 200                 205

Val Ser Ile Val Lys Gly Glu Asn Ala Ser Gly Gly Asp Asn Tyr
            210                 215                 220

<210> SEQ ID NO 21
<211> LENGTH: 491
<212> TYPE: PRT
<213> ORGANISM: Escherichia coli

<400> SEQUENCE: 21

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
            165                 170                 175

His Tyr Leu Gly Lys Glu Thr Val Leu Asn Leu Ala Leu Arg Phe
        180                 185                 190

Ala Asn Ser Leu Phe Val Asn Asn Trp Asp Asn Arg Thr Ile Asp His
    195                 200                 205

Val Glu Ile Thr Val Ala Glu Glu Val Gly Ile Glu Gly Arg Trp Gly
210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
            260                 265                 270

Arg Ile Asp Arg Ser Asn Val Arg Glu Lys Thr Val Arg Gly Gln Tyr
        275                 280                 285

Thr Ala Gly Phe Ala Gln Gly Lys Lys Val Pro Gly Tyr Leu Glu Glu
    290                 295                 300

Glu Gly Ala Asn Lys Ser Ser Asn Thr Glu Thr Phe Val Ala Ile Arg
```

```
                305                 310                 315                 320
Val Asp Ile Asp Asn Trp Arg Trp Ala Gly Val Pro Phe Tyr Leu Arg
                    325                 330                 335

Thr Gly Lys Arg Leu Pro Thr Lys Cys Ser Glu Val Val Tyr Phe
                340                 345                 350

Lys Thr Pro Glu Leu Asn Leu Phe Lys Glu Ser Trp Gln Asp Leu Pro
                355                 360                 365

Gln Asn Lys Leu Thr Ile Arg Leu Gln Pro Asp Glu Gly Val Asp Ile
                370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                    405                 410                 415

Leu Ala Asp Ala Tyr Glu Arg Leu Leu Leu Glu Thr Met Arg Gly Ile
                420                 425                 430

Gln Ala Leu Phe Val Arg Arg Asp Glu Val Glu Glu Ala Trp Lys Trp
                435                 440                 445

Val Asp Ser Ile Thr Glu Ala Trp Ala Met Asp Asn Asp Ala Pro Lys
450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                    485                 490

<210> SEQ ID NO 22
<211> LENGTH: 491
<212> TYPE: PRT
<213> ORGANISM: Dickeya dadantii

<400> SEQUENCE: 22

Met Ala Val Thr Ser Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
                20                  25                  30

Leu Glu Lys Ala Gly His Ile His Pro Glu Thr Arg Ile Ile Gly Val
            35                  40                  45

Gly Arg Ala Glu Trp Asp Arg Asp Ala Tyr Ile Lys Val Val Arg Glu
        50                  55                  60

Ala Leu Glu Thr Phe Leu Lys Glu Pro Leu Asp Pro Ala Leu Trp Thr
65                  70                  75                  80

Thr Leu Ser Asn Arg Leu Asp Phe Cys Asn Leu Asp Val Glu Asp Thr
                85                  90                  95

Glu Gly Phe Lys Arg Leu Gly Thr Met Leu Asp Gln Gln Asn Arg Thr
            100                 105                 110

Thr Ile Asn Tyr Phe Ala Met Pro Pro Ser Thr Phe Gly Ala Ile Cys
        115                 120                 125

Arg Gly Leu Gly Gln Ala Gly Leu Asn Lys Glu Pro Ala Arg Val Val
130                 135                 140

Met Glu Lys Pro Leu Gly Thr Asn Leu Ala Ser Ser Arg Val Ile Asn
145                 150                 155                 160

Asn Gln Val Ala Glu Phe Phe Asn Glu Cys Gln Val Tyr Arg Ile Asp
                165                 170                 175

His Tyr Leu Gly Lys Glu Thr Val Leu Asn Leu Leu Ala Leu Arg Phe
            180                 185                 190
```

```
Ala Asn Ser Leu Phe Ala Asn Asn Trp Asp Asn Arg Thr Ile Asp His
            195                 200                 205

Val Gln Ile Thr Val Ala Glu Glu Val Gly Ile Glu Gly Arg Trp Gly
210                 215                 220

Tyr Phe Asp Gln Ala Gly Gln Met Arg Asp Met Ile Gln Asn His Leu
225                 230                 235                 240

Leu Gln Ile Leu Thr Met Ile Ala Met Ser Pro Pro Ala Asp Leu Ser
            245                 250                 255

Thr Asp Arg Ile Arg Asp Glu Lys Lys Val Leu Arg Ser Leu Arg
                260                 265                 270

Arg Ile Asp Arg Ser Asn Val His Glu Val Thr Val Arg Gly Gln Tyr
                275                 280                 285

Thr Ser Gly Phe Val Gln Gly Lys Lys Val Pro Gly Tyr Leu Glu Glu
290                 295                 300

Glu Gly Ala Asn Lys Thr Ser Asn Thr Glu Thr Phe Val Ala Ile Arg
305                 310                 315                 320

Val Asp Ile Asp Asp Trp Arg Trp Ser Gly Val Pro Phe Tyr Leu Arg
                325                 330                 335

Thr Gly Lys Arg Leu Pro Ser Lys Cys Ser Glu Val Val Val Tyr Phe
            340                 345                 350

Lys Asn Pro Ala Leu Asn Leu Phe His Asp Ser Tyr Gln Gln Leu Pro
            355                 360                 365

Gln Asn Lys Leu Ile Ile Arg Leu Gln Pro Asp Gly Val Glu Ile
370                 375                 380

Gln Ile Leu Asn Lys Ile Pro Gly Leu Asp His Lys His Arg Leu Gln
385                 390                 395                 400

Thr Thr Lys Leu Asp Leu Ser Phe Ser Glu Thr Phe Asn Gln Gln His
            405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Ala Trp Lys Trp
435                 440                 445

Val Asp Ser Ile Met Asp Ala Trp Ala Met Asp Asn Asp Ser Pro Lys
450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Val Glu
                485                 490

<210> SEQ ID NO 23
<211> LENGTH: 512
<212> TYPE: PRT
<213> ORGANISM: Chlamydia pneumoniae

<400> SEQUENCE: 23

Met Thr Asn Val Val Gln Glu Thr Ile Gly Gly Leu Asn Ser Pro Arg
1               5                   10                  15

Thr Cys Pro Pro Cys Ile Leu Val Ile Phe Gly Ala Thr Gly Asp Leu
            20                  25                  30

Thr Ala Arg Lys Leu Leu Pro Ala Leu Tyr His Leu Thr Lys Glu Gly
            35                  40                  45

Arg Leu Ser Asp Gln Phe Val Cys Val Gly Phe Ala Arg Arg Glu Lys
    50                  55                  60

Ser Asn Glu Leu Phe Arg Gln Glu Met Lys Gln Ala Val Ile Gln Phe
65                  70                  75                  80
```

```
Ser Pro Ser Glu Leu Asp Ile Lys Val Trp Glu Asp Phe Gln Gln Arg
                85                  90                  95

Leu Phe Tyr His Arg Ser Glu Phe Asp Asn Asn Met Gly Tyr Thr Ser
            100                 105                 110

Leu Lys Asp Ser Leu Glu Asp Leu Asp Lys Thr Tyr Gly Thr Arg Gly
            115                 120                 125

Asn Arg Leu Phe Tyr Leu Ser Thr Pro Gln Tyr Phe Ser Arg Ile
        130                 135                 140

Ile Glu Asn Leu Asn Lys His Lys Leu Phe Tyr Lys Asn Gln Asp Gln
145                 150                 155                 160

Gly Lys Pro Trp Ser Arg Val Ile Ile Glu Lys Pro Phe Gly Arg Asp
                165                 170                 175

Leu Asp Ser Ala Lys Gln Leu Gln Gln Cys Ile Asn Glu Asn Leu Asn
            180                 185                 190

Glu Asn Ser Val Tyr His Ile Asp His Tyr Leu Gly Lys Glu Thr Val
            195                 200                 205

Gln Asn Ile Leu Thr Thr Arg Phe Ala Asn Thr Ile Phe Glu Ser Cys
    210                 215                 220

Trp Asn Ser Gln Tyr Ile Asp His Val Gln Ile Ser Leu Ser Glu Thr
225                 230                 235                 240

Ile Gly Ile Gly Ser Arg Gly Asn Phe Phe Glu Lys Ser Gly Met Leu
                245                 250                 255

Arg Asp Met Val Gln Asn His Met Met Gln Leu Leu Cys Leu Leu Thr
            260                 265                 270

Met Glu Pro Pro Thr Thr Phe Asp Ala Asp Glu Ile Arg Lys Glu Lys
            275                 280                 285

Ile Lys Ile Leu Gln Arg Ile Ser Pro Phe Ser Glu Gly Ser Ser Ile
    290                 295                 300

Val Arg Gly Gln Tyr Gly Pro Gly Thr Val Gln Gly Val Ser Val Leu
305                 310                 315                 320

Gly Tyr Arg Glu Glu Glu Asn Val Asp Lys Asp Ser Arg Val Glu Thr
                325                 330                 335

Tyr Val Ala Leu Lys Thr Val Ile Asn Asn Pro Arg Trp Leu Gly Val
            340                 345                 350

Pro Phe Tyr Leu Arg Ala Gly Lys Arg Leu Ala Lys Lys Ser Thr Asp
            355                 360                 365

Ile Ser Ile Ile Phe Lys Lys Ser Pro Tyr Asn Leu Phe Ala Ala Glu
    370                 375                 380

Glu Cys Ser Arg Cys Pro Ile Glu Asn Asp Leu Leu Ile Ile Arg Ile
385                 390                 395                 400

Gln Pro Asp Glu Gly Val Ala Leu Lys Phe Asn Cys Lys Val Pro Gly
                405                 410                 415

Thr Asn Asn Ile Val Arg Pro Val Lys Met Asp Phe Arg Tyr Asp Ser
            420                 425                 430

Tyr Phe Gln Thr Thr Pro Glu Ala Tyr Glu Arg Leu Leu Cys Asp
        435                 440                 445

Cys Ile Ile Gly Asp Arg Thr Leu Phe Thr Gly Gly Asp Glu Val Met
    450                 455                 460

Ala Ser Trp Lys Leu Phe Thr Pro Val Leu Glu Glu Trp Asp Gln Asp
465                 470                 475                 480

Ser Ser Pro Ser Phe Pro Asn Tyr Pro Ala Gly Ser Ser Gly Pro Lys
                485                 490                 495
```

Glu Ala Asp Ala Leu Ile Glu Arg Asp Gly Arg Ser Trp Arg Pro Leu
            500                 505                 510

<210> SEQ ID NO 24
<211> LENGTH: 1476
<212> TYPE: DNA
<213> ORGANISM: Escherichia coli

<400> SEQUENCE: 24

| | | | | | |
|---|---|---|---|---|---|
| atggcggtaa | cgcaaacagc | ccaggcctgt | gacctggtca | ttttcggcgc | gaaaggcgac | 60 |
| cttgcgcgtc | gtaaattgct | gccttccctg | tatcaactgg | aaaaagccgg | tcagctcaac | 120 |
| ccggacaccc | ggattatcgg | cgtagggcgt | gctgactggg | ataaagcggc | ataccaaa | 180 |
| gttgtccgcg | aggcgctcga | aactttcatg | aaagaaacca | ttgatgaagg | tttatgggac | 240 |
| accctgagtg | cacgtctgga | ttttgtaat | ctcgatgtca | atgacactgc | tgcattcagc | 300 |
| cgtctcggcg | cgatgctgga | tcaaaaaaat | cgtatcacca | ttaactactt | tgccatgccg | 360 |
| cccagcactt | ttggcgcaat | ttgcaaaggg | cttggcgagg | caaaactgaa | tgctaaaccg | 420 |
| gcacgcgtag | tcatggagaa | accgctgggg | acgtcgctgg | cgacctcgca | ggaaatcaat | 480 |
| gatcaggttg | gcgaatactt | cgaggagtgc | caggtttacc | gtatcgacca | ctatcttggt | 540 |
| aaagaaacgg | tgctgaacct | gttggcgctg | cgttttgcta | actccctgtt | tgtgaataac | 600 |
| tgggacaatc | gcaccattga | tcatgttgag | attaccgtgg | cagaagaagt | ggggatcgaa | 660 |
| gggcgctggg | gctattttga | taaagccggt | cagatgcgcg | acatgatcca | gaaccacctg | 720 |
| ctgcaaattc | tttgcatgat | tgcgatgtct | ccgccgtctg | acctgagcgc | agacagcatc | 780 |
| cgcgatgaaa | aagtgaaagt | actgaagtct | ctgcgccgca | tcgaccgctc | caacgtacgc | 840 |
| gaaaaaaccg | tacgcgggca | atatactgcg | ggcttcgccc | agggcaaaaa | agtgccggga | 900 |
| tatctggaag | aagagggcgc | gaacaagagc | agcaatacag | aaactttcgt | ggcgatccgc | 960 |
| gtcgacattg | ataactggcg | ctgggccggt | gtgccattct | acctgcgtac | tggtaaacgt | 1020 |
| ctgccgacca | aatgttctga | agtcgtggtc | tatttcaaaa | cacctgaact | gaatctgttt | 1080 |
| aaagaatcgt | ggcaggatct | gccgcagaat | aaactgacta | tccgtctgca | acctgatgaa | 1140 |
| ggcgtggata | tccaggtact | gaataaagtt | cctggccttg | accacaaaca | taacctgcaa | 1200 |
| atcaccaagc | tggatctgag | ctattcagaa | acctttaatc | agacgcatct | ggcggatgcc | 1260 |
| tatgaacgtt | tgctgctgga | aaccatgcgt | ggtattcagg | cactgtttgt | acgtcgcgac | 1320 |
| gaagtggaag | aagcctggaa | atgggtagac | tccattactg | aggcgtgggc | gatggacaat | 1380 |
| gatgcgccga | aaccgtatca | ggccggaacc | tggggacccg | ttgcctcggt | ggcgatgatt | 1440 |
| acccgtgatg | gtcgttcctg | gaatgagttt | gagtaa | | | 1476 |

<210> SEQ ID NO 25
<211> LENGTH: 213
<212> TYPE: PRT
<213> ORGANISM: Escherichia coli

<400> SEQUENCE: 25

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val

```
             50                  55                  60
Pro Glu Ala Ile Val Gly Ala Gly Thr Val Leu Asn Pro Gln Gln Leu
 65                  70                  75                  80

Ala Glu Val Thr Glu Ala Gly Ala Gln Phe Ala Ile Ser Pro Gly Leu
                 85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
            115                 120                 125

Leu Lys Glu Phe Lys Phe Phe Pro Ala Glu Ala Asn Gly Gly Val Lys
        130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
            195                 200                 205

Glu Gly Ala Lys Leu
        210

<210> SEQ ID NO 26
<211> LENGTH: 337
<212> TYPE: PRT
<213> ORGANISM: Escherichia coli

<400> SEQUENCE: 26

Met Asn Gly Lys Lys Leu Tyr Ile Ser Asp Val Thr Leu Arg Asp Gly
  1               5                  10                  15

Met His Ala Ile Arg His Gln Tyr Ser Leu Glu Asn Val Arg Gln Ile
                 20                  25                  30

Ala Lys Ala Leu Asp Asp Ala Arg Val Asp Ser Ile Glu Val Ala His
             35                  40                  45

Gly Asp Gly Leu Gln Gly Ser Ser Phe Asn Tyr Gly Phe Gly Ala His
         50                  55                  60

Ser Asp Leu Glu Trp Ile Glu Ala Ala Ala Asp Val Val Lys His Ala
 65                  70                  75                  80

Lys Ile Ala Thr Leu Leu Leu Pro Gly Ile Gly Thr Ile His Asp Leu
                 85                  90                  95

Lys Asn Ala Trp Gln Ala Gly Ala Arg Val Val Arg Val Ala Thr His
            100                 105                 110

Cys Thr Glu Ala Asp Val Ser Ala Gln His Ile Gln Tyr Ala Arg Glu
            115                 120                 125

Leu Gly Met Asp Thr Val Gly Phe Leu Met Met Ser His Met Thr Thr
        130                 135                 140

Pro Glu Asn Leu Ala Lys Gln Ala Lys Leu Met Glu Gly Tyr Gly Ala
145                 150                 155                 160

Thr Cys Ile Tyr Val Val Asp Ser Gly Gly Ala Met Asn Met Ser Asp
                165                 170                 175

Ile Arg Asp Arg Phe Arg Ala Leu Lys Ala Glu Leu Lys Pro Glu Thr
            180                 185                 190

Gln Thr Gly Met His Ala His His Asn Leu Ser Leu Gly Val Ala Asn
            195                 200                 205
```

```
Ser Ile Ala Ala Val Glu Glu Gly Cys Asp Arg Ile Asp Ala Ser Leu
210                 215                 220

Ala Gly Met Gly Ala Gly Ala Gly Asn Ala Pro Leu Glu Val Phe Ile
225                 230                 235                 240

Ala Ala Ala Asp Lys Leu Gly Trp Gln His Gly Thr Asp Leu Tyr Ala
                245                 250                 255

Leu Met Asp Ala Ala Asp Asp Leu Val Arg Pro Leu Gln Asp Arg Pro
                260                 265                 270

Val Arg Val Asp Arg Glu Thr Leu Ala Leu Gly Tyr Ala Gly Val Tyr
                275                 280                 285

Ser Ser Phe Leu Arg His Cys Glu Thr Ala Ala Ala Arg Tyr Gly Leu
290                 295                 300

Ser Ala Val Asp Ile Leu Val Glu Leu Gly Lys Arg Arg Met Val Gly
305                 310                 315                 320

Gly Gln Glu Asp Met Ile Val Asp Val Ala Leu Asp Leu Arg Asn Asn
                325                 330                 335

Lys

<210> SEQ ID NO 27
<211> LENGTH: 346
<212> TYPE: PRT
<213> ORGANISM: Paraburkholderia xenovorans

<400> SEQUENCE: 27

Met Lys Leu Glu Gly Lys Lys Val Thr Val His Asp Met Thr Leu Arg
1               5                   10                  15

Asp Gly Met His Pro Lys Arg His Gln Met Thr Leu Glu Gln Met Lys
                20                  25                  30

Ser Ile Ala Cys Gly Leu Asp Ala Ala Gly Ile Pro Leu Ile Glu Val
            35                  40                  45

Thr His Gly Asp Gly Leu Gly Gly Ser Ser Val Asn Tyr Gly Phe Pro
        50                  55                  60

Ala His Ser Asp Glu Glu Tyr Leu Gly Ala Val Ile Pro Leu Met Lys
65                  70                  75                  80

Gln Ala Lys Val Ser Ala Leu Leu Leu Pro Gly Ile Gly Thr Val Glu
                85                  90                  95

His Leu Lys Met Ala Lys Asp Leu Gly Val Asn Thr Ile Arg Val Ala
                100                 105                 110

Thr His Cys Thr Glu Ala Asp Val Ser Glu Gln His Ile Thr Gln Ser
            115                 120                 125

Arg Lys Leu Gly Leu Asp Thr Val Gly Phe Leu Met Met Ala His Met
130                 135                 140

Ala Ser Pro Glu Lys Leu Val Ser Gln Ala Leu Leu Met Gln Gly Tyr
145                 150                 155                 160

Gly Ala Asn Cys Ile Tyr Val Thr Asp Ser Ala Gly Tyr Met Leu Pro
                165                 170                 175

Asp Asp Val Lys Ala Arg Leu Ser Ala Val Arg Ala Ala Leu Lys Pro
                180                 185                 190

Glu Thr Glu Leu Gly Phe His Gly His His Asn Leu Ala Met Gly Val
            195                 200                 205

Ala Asn Ser Ile Ala Ala Ile Glu Ala Gly Ala Thr Arg Ile Asp Ala
        210                 215                 220

Ala Ala Ala Gly Leu Gly Ala Gly Ala Gly Asn Thr Pro Met Glu Val
225                 230                 235                 240
```

```
Phe Ile Ala Val Cys Ala Arg Met Gly Ile Glu Thr Gly Val Asp Val
                245                 250                 255

Phe Lys Ile Gln Asp Val Ala Glu Asp Leu Val Val Pro Ile Met Asp
            260                 265                 270

His Val Ile Arg Ile Asp Arg Asp Ser Leu Thr Leu Gly Tyr Ala Gly
        275                 280                 285

Val Tyr Ser Ser Phe Leu Leu Phe Ala Lys Arg Ala Ser Ala Lys Tyr
    290                 295                 300

Gly Val Pro Ala Arg Asp Ile Leu Val Glu Leu Gly Arg Arg Gly Met
305                 310                 315                 320

Val Gly Gly Gln Glu Asp Met Ile Glu Asp Thr Ala Met Thr Met Ala
                325                 330                 335

Arg Glu Arg Gly Leu Thr Leu Thr Ala Ala
                340                 345

<210> SEQ ID NO 28
<211> LENGTH: 642
<212> TYPE: DNA
<213> ORGANISM: Escherichia coli

<400> SEQUENCE: 28
atgaaaaact ggaaaacaag tgcagaatca atcctgacca ccggcccggt tgtaccggtt      60
atcgtggtaa aaaactgga acacgcggtg ccgatggcaa aagcgttggt tgctggtggg     120
gtgcgcgttc tggaagtgac tctgcgtacc gagtgtgcag ttgacgctat ccgtgctatc     180
gccaaagaag tgcctgaagc gattgtgggt gccggtacgg tgctgaatcc acagcagctg     240
gcagaagtca ctgaagcggg tgcacagttc gcaattagcc cgggtctgac cgagccgctg     300
ctgaaagctg ctaccgaagg gactattcct ctgattccgg ggatcagcac tgtttccgaa     360
ctgatgctgg gtatggacta cggtttgaaa gagttcaaat tcttcccggc tgaagctaac     420
ggcggcgtga aagccctgca ggcgatcgcg ggtccgttct cccaggtccg tttctgcccg     480
acgggtggta tttctccggc taactaccgt gactacctgg cgctgaaaag cgtgctgtgc     540
atcggtggtt cctggctggt tccggcagat gcgctggaag cgggcgatta cgaccgcatt     600
actaagctgg cgcgtgaagc tgtagaaggc gctaagctgt aa                       642

<210> SEQ ID NO 29
<211> LENGTH: 1014
<212> TYPE: DNA
<213> ORGANISM: Escherichia coli

<400> SEQUENCE: 29
atgaacggta aaaactttta tatctcggac gtcacattgc gtgacggtat gcacgccatt      60
cgtcatcagt attcgctgga aaacgttcgc cagattgcca agcactgga cgatgcccgc     120 gtggattcga ttgaagtggc ccacggcgac ggtttgcaag gttccagctt aactatggt     180 ttcggcgcac atagcgacct tgaatggatt gaagcggcgg cggatgtggt gaagcacgcc     240
aaaatcgcga cgttgttgct gccaggaatc ggcactattc acgatctgaa aaatgcctgg     300
caggctggcg cgcgggtggt tcgtgtggca acgcactgta ccgaagctga tgtttccgcc     360
cagcatattc agtatgcccg cgagctcgga atggacaccg ttggttttct gatgatgagc     420
catatgacca cgccggagaa tctcgccaag caggcaaagc tgatggaagg ctacggtgcg     480
acctgtattt atgtggtgga ttctggcggt gcgatgaaca tgagcgatat ccgtgaccgt     540
ttccgcgccc tgaaagcaga gctgaaacca gaaacgcaaa ctggcatgca cgctcaccat     600
```

```
aacctgagtc ttggcgtggc gaactctatc gcggcggtgg aagagggctg cgaccgaatc    660
gacgccagcc tcgcgggaat gggcgcgggc gcaggtaacg caccgctgga agtgtttatt    720
gccgccgcgg ataaactggg ctggcagcat gggaccgatc tctatgcgtt aatggatgcc    780
gccgacgacc tggtgcgtcc gttgcaggat cgaccggtac gagtcgatcg cgaaacgctg    840
gcgctgggat acgctggtgt ttactcgagc ttcctgcgtc actgtgaaac ggcggcggcg    900
cgttatggct taagtgcggt ggatattctc gttgagctgg caaacgccg gatggttggc    960 ggccaggagg atatgatcgt tgacgtggcg ctggatctgc gcaacaacaa ataa         1014
```

<210> SEQ ID NO 30
<211> LENGTH: 331
<212> TYPE: PRT
<213> ORGANISM: Bacillus subtilis

<400> SEQUENCE: 30

```
Met Glu Tyr Thr Ser Ile Ala Asp Thr Gly Ile Glu Ala Ser Arg Ile
 1               5                  10                  15

Gly Leu Gly Thr Trp Ala Ile Gly Gly Thr Met Trp Gly Gly Thr Asp
             20                  25                  30

Glu Lys Thr Ser Ile Glu Thr Ile Arg Ala Ala Leu Asp Gln Gly Ile
         35                  40                  45

Thr Leu Ile Asp Thr Ala Pro Ala Tyr Gly Phe Gly Gln Ser Glu Glu
     50                  55                  60

Ile Val Gly Lys Ala Ile Lys Glu Tyr Gly Lys Arg Asp Gln Val Ile
 65                  70                  75                  80

Leu Ala Thr Lys Thr Ala Leu Asp Trp Lys Asn Asn Gln Leu Phe Arg
                 85                  90                  95

His Ala Asn Arg Ala Arg Ile Val Glu Glu Val Glu Asn Ser Leu Lys
            100                 105                 110

Arg Leu Gln Thr Asp Tyr Ile Asp Leu Tyr Gln Val His Trp Pro Asp
        115                 120                 125

Pro Leu Val Pro Ile Glu Glu Thr Ala Glu Val Met Lys Glu Leu Tyr
    130                 135                 140

Asp Ala Gly Lys Ile Arg Ala Ile Gly Val Ser Asn Phe Ser Ile Glu
145                 150                 155                 160

Gln Met Asp Thr Phe Arg Ala Val Ala Pro Leu His Thr Ile Gln Pro
                165                 170                 175

Pro Tyr Asn Leu Phe Glu Arg Glu Met Glu Ser Val Leu Pro Tyr
            180                 185                 190

Ala Lys Asp Asn Lys Ile Thr Thr Leu Leu Tyr Gly Ser Leu Cys Arg
        195                 200                 205

Gly Leu Leu Thr Gly Lys Met Thr Glu Glu Tyr Thr Phe Glu Gly Asp
    210                 215                 220

Asp Leu Arg Asn His Asp Pro Lys Phe Gln Lys Pro Arg Phe Lys Glu
225                 230                 235                 240

Tyr Leu Ser Ala Val Asn Gln Leu Asp Lys Leu Ala Lys Thr Arg Tyr
                245                 250                 255

Gly Lys Ser Val Ile His Leu Ala Val Arg Trp Ile Leu Asp Gln Pro
            260                 265                 270

Gly Ala Asp Ile Ala Leu Trp Gly Ala Arg Lys Pro Gly Gln Leu Glu
        275                 280                 285

Ala Leu Ser Glu Ile Thr Gly Trp Thr Leu Asn Ser Glu Asp Gln Lys
    290                 295                 300
```

```
Asp Ile Asn Thr Ile Leu Glu Asn Thr Ile Ser Asp Pro Val Gly Pro
305                 310                 315                 320

Glu Phe Met Ala Pro Pro Thr Arg Glu Glu Ile
                325                 330

<210> SEQ ID NO 31
<211> LENGTH: 329
<212> TYPE: PRT
<213> ORGANISM: Pseudomonas aeruginosa

<400> SEQUENCE: 31

Met Ser Val Glu Ser Ile Arg Ile Glu Gly Ile Asp Thr Pro Val Ser
1               5                   10                  15

Arg Ile Gly Leu Gly Thr Trp Ala Ile Gly Trp Met Trp Gly Gly
                20                  25                  30

Ala Asp Asp Ala Thr Ser Val Glu Thr Ile Arg Arg Ala Val Glu Ser
                35                  40                  45

Gly Ile Asn Leu Ile Asp Thr Ala Pro Val Tyr Gly Phe Gly His Ser
        50                  55                  60

Glu Glu Val Val Gly Lys Ala Leu Gln Gly Leu Arg Asp Lys Ala Val
65                  70                  75                  80

Ile Ala Thr Lys Ala Ala Leu Glu Trp Ser Asp Ala Gly Ile His Arg
                85                  90                  95

Asn Ala Ser Ala Ala Arg Ile Arg Arg Glu Val Glu Asp Ser Leu Arg
                100                 105                 110

Arg Leu Lys Thr Asp Arg Ile Asp Leu Tyr Gln Ile His Trp Pro Asp
                115                 120                 125

Pro Leu Val Ala His Glu Thr Ala Gly Glu Leu Glu Arg Leu Arg
130                 135                 140

Arg Asp Gly Lys Ile Leu Ala Ile Gly Val Ser Asn Tyr Ser Pro Glu
145                 150                 155                 160

Gln Met Asp Gly Phe Arg Gln Phe Ala Pro Leu Ala Ser Val Gln Pro
                165                 170                 175

Pro Tyr Asn Leu Phe Glu Arg Ala Ile Asp Ala Asp Val Leu Pro Tyr
                180                 185                 190

Ala Glu Arg Asn Gly Ile Val Val Leu Ala Tyr Gly Ala Leu Cys Arg
                195                 200                 205

Gly Leu Leu Ser Gly Arg Met Asn Ala Glu Thr Arg Phe Asp Gly Asp
210                 215                 220

Asp Leu Arg Lys Ser Asp Pro Lys Phe Gln Gln Pro Arg Phe Ala Gln
225                 230                 235                 240

Tyr Leu Ala Ala Val Ala Gln Leu Glu Glu Leu Ala Arg Glu Arg Tyr
                245                 250                 255

Gly Lys Ser Val Leu Ala Leu Ala Ile Arg Trp Ile Leu Asp Arg Gly
                260                 265                 270

Pro Thr Val Ala Leu Trp Gly Ala Arg Lys Pro Glu Gln Leu Asn Gly
                275                 280                 285

Ile Ala Asp Ala Phe Gly Trp Arg Leu Asp Asp Glu Ala Met Ala Arg
        290                 295                 300

Ile Glu Arg Ile Leu Ala Glu Thr Ile Gln Asp Pro Val Gly Pro Glu
305                 310                 315                 320

Phe Met Ala Pro Pro Ser Arg Asn Ala
                325

<210> SEQ ID NO 32
```

```
<211> LENGTH: 276
<212> TYPE: PRT
<213> ORGANISM: Bacillus halodurans

<400> SEQUENCE: 32

Met Ala Asn Asn Leu Gln Ala Thr Thr Thr Leu His Asn Gly Val Lys
1               5                   10                  15

Met Pro Trp Phe Gly Leu Gly Val Phe Lys Val Ser Glu Gly Asp Glu
            20                  25                  30

Val Ile Gln Ser Val Lys Asp Ala Ile Arg Ala Gly Tyr Lys Ser Ile
        35                  40                  45

Asp Thr Ala Ala Val Tyr Gly Asn Glu Glu Gly Val Gly Lys Ala Ile
    50                  55                  60

Ala Glu Ser Gly Val Pro Arg Glu Glu Leu Phe Ile Thr Ser Lys Val
65                  70                  75                  80

Trp Asn Ala Asp Gln Gly Phe Asp Ser Thr Ile Ser Ala Phe Asn Thr
                85                  90                  95

Ser Leu Lys Lys Leu Gly Leu Asp Tyr Leu Asp Leu Tyr Leu Val His
            100                 105                 110

Trp Pro Val Lys Gly Lys Tyr Val Glu Thr Trp Lys Ala Leu Glu Lys
        115                 120                 125

Leu Tyr Gln Asp Gly Leu Val Arg Ala Ile Gly Val Ser Asn Phe Gln
    130                 135                 140

Val His His Leu Lys Asp Val Leu Glu Ala Gly Ser Ile Val Pro Met
145                 150                 155                 160

Val Asn Gln Val Glu Tyr His Pro His Leu Thr Gln Thr Glu Leu His
                165                 170                 175

Asp Phe Cys Lys Gln Asn Lys Ile Gln Leu Glu Ala Trp Ser Pro Leu
            180                 185                 190

Lys Gln Gly Gln Leu Leu Asn Asp Pro Thr Ile Val Ala Ile Ala Glu
        195                 200                 205

Ala His Gln Lys Thr Pro Ala Gln Ile Ile Leu Arg Trp Asp Leu Gln
    210                 215                 220

Asn Glu Val Val Thr Ile Pro Lys Ser Val Lys Lys Asp Arg Ile Ile
225                 230                 235                 240

Ser Asn Ala Asp Ile Phe Asp Phe Gln Leu Thr Glu Glu Asp Met Gln
                245                 250                 255

Lys Ile Asn Glu Leu Asn Lys Asn Glu Arg Val Gly Pro Asp Pro Asp
            260                 265                 270

Asn Phe Asp Phe
        275

<210> SEQ ID NO 33
<211> LENGTH: 345
<212> TYPE: PRT
<213> ORGANISM: Pseudomonas syringae

<400> SEQUENCE: 33

Met Thr Tyr Ile Ala Ala Glu Asn Arg Tyr Lys Asp Met Pro Tyr Arg
1               5                   10                  15

Arg Thr Gly Arg Ser Gly Leu Val Leu Pro Ala Leu Ser Leu Gly Leu
            20                  25                  30

Trp His Asn Phe Gly Asp Ser Thr Pro Ile Asp Thr Gln Arg Ala Met
            35                  40                  45

Leu Arg Thr Ala Phe Asp Leu Gly Ile Asn His Phe Asp Leu Ala Asn
    50                  55                  60
```

Asn Tyr Gly Pro Pro Tyr Gly Ser Ala Glu Ile Asn Phe Gly Arg Leu
 65                  70                  75                  80

Leu Arg Glu Asp Phe Lys Arg Tyr Arg Asp Glu Leu Ile Ile Ser Ser
                 85                  90                  95

Lys Ala Gly Trp Asp Met Trp Pro Gly Pro Tyr Gly Gln Gly Gly Gly
            100                 105                 110

Ser Arg Lys Tyr Val Leu Ala Ser Leu Asp Gln Ser Leu Gln Arg Met
        115                 120                 125

Gly Leu Asp Tyr Val Asp Ile Phe Tyr Ser His Arg Phe Asp Pro Asp
130                 135                 140

Thr Pro Leu Glu Glu Thr Ala Ser Ala Leu Ala Thr Ala Val Gln Gln
145                 150                 155                 160

Gly Lys Ala Leu Tyr Ile Gly Ile Ser Ser Tyr Ser Gly Ala Lys Thr
                165                 170                 175

Arg Glu Ile Ala Ala Leu Leu Lys Glu Trp Lys Val Pro Leu Leu Ile
            180                 185                 190

His Gln Pro Ala Tyr Asn Leu Leu Asn Arg Trp Val Glu Lys Asp Leu
        195                 200                 205

Leu Asp Ala Thr Glu Glu Leu Gly Ala Gly Val Ile Ala Phe Thr Ala
210                 215                 220

Leu Ala Gln Gly Leu Leu Ser Asp Lys Tyr Leu Asn Gly Val Pro Lys
225                 230                 235                 240

Asp Ala Arg Val Asn Arg Pro Gly Gly Ser Leu Gln Ala Ser His
                245                 250                 255

Leu Ser Glu Gln Asn Ile Ala His Val Arg Ala Leu Asn Glu Ile Ala
            260                 265                 270

Gln Arg Arg Gly Gln Ser Leu Ala Gln Met Ala Leu Ala Trp Thr Leu
        275                 280                 285

Arg Asp Pro Arg Val Thr Ser Ala Leu Ile Gly Ala Ser Arg Pro Glu
290                 295                 300

Gln Ile Ile Glu Asn Val Gly Ala Leu Gln Asn Leu Ala Phe Ser Ser
305                 310                 315                 320

Glu Glu Leu Ala Glu Ile Asp Ser Phe Ala Val Glu Gly Gly Ile Asn
                325                 330                 335

Leu Trp Glu Lys Pro Ser Leu Ala Glu
            340                 345

<210> SEQ ID NO 34
<211> LENGTH: 990
<212> TYPE: DNA
<213> ORGANISM: Pseudomonas aeruginosa

<400> SEQUENCE: 34
atgagcgttg aaagcattcg catcgagggt atcgacacgc cggtctcgcg catcggcctc      60
ggcacctggg ccatcggcgg ctggatgtgg ggcggcgctg acgacgcgac gtcggtggaa     120
accatccggc gtgcggtgga atccgggatc aacctgatcg acaccgcgcc ggtctatggc     180
ttcggccatt ccgaagaggt cgtcggcaag gccttgcagg gcctgcgcga caaggcggtg     240
atcgccacca aggcggcgct ggagtggagc gacgcgggca tccaccgcaa cgcctccgcc     300
gcacgcatcc gccgggaggt cgaggactcg ctgcggcggc tgaagaccga tcgtatcgac     360
ctgtaccaga ttcactggcc ggaccccgctg gtggcgcacg aggaaaccgc cggcgaactg     420
gagcgcctgc gccgcgacgg caagatcctc gccatcggcg tgagcaacta ttcgccggaa     480

```
cagatggacg ggttccgcca gttcgctccg ctggccagcg tgcagccacc ctacaacctg    540
ttcgagcgcg ccatcgacgc cgacgtgctg ccctacgccg agcgtaacgg catcgtcgtg    600
ctggcctacg agcgctgtg ccgcggcctg ctttccggac ggatgaacgc cgagacccgc     660
ttcgatggcg acgacctgcg caagtccgac ccgaagttcc agcagcccg cttcgcccag     720 tacctggcag cggtcgcgca actggaggaa ctggctcgcg agcgctatgg caagtcggtg    780
ctggccctgg ccatccgctg gattctcgat cgcggcccta cggtggcgct gtgggggcg     840 cgcaagccgg agcagttgaa cggcatcgcc gacgccttcg gctggcgcct ggacgacgag    900
gccatggccc gcatcgagcg gatcctcgcc gagaccatcc aggatccggt cggtcccgag    960
ttcatggcgc cgcccagccg caacgcctaa                                     990
```

<210> SEQ ID NO 35
<211> LENGTH: 820
<212> TYPE: PRT
<213> ORGANISM: Escherichia coli

<400> SEQUENCE: 35

```
Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
                20                  25                  30

Val Ala Thr Val Leu Ser Ala Pro Ala Lys Ile Thr Asn His Leu Val
            35                  40                  45

Ala Met Ile Glu Lys Thr Ile Ser Gly Gln Asp Ala Leu Pro Asn Ile
        50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
                100                 105                 110

Gln Cys Pro Asp Ser Ile Asn Ala Ala Leu Ile Cys Arg Gly Glu Lys
            115                 120                 125

Met Ser Ile Ala Ile Met Ala Gly Val Leu Glu Ala Arg Gly His Asn
        130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
        275                 280                 285
```

```
Gln Ala Pro Gly Thr Leu Ile Gly Ala Ser Arg Asp Glu Asp Glu Leu
    290                 295                 300
Pro Val Lys Gly Ile Ser Asn Leu Asn Asn Met Ala Met Phe Ser Val
305                 310                 315                 320
Ser Gly Pro Gly Met Lys Gly Met Val Gly Met Ala Ala Arg Val Phe
                325                 330                 335
Ala Ala Met Ser Arg Ala Arg Ile Ser Val Val Leu Ile Thr Gln Ser
            340                 345                 350
Ser Ser Glu Tyr Ser Ile Ser Phe Cys Val Pro Gln Ser Asp Cys Val
        355                 360                 365
Arg Ala Glu Arg Ala Met Gln Glu Glu Phe Tyr Leu Glu Leu Lys Glu
    370                 375                 380
Gly Leu Glu Pro Leu Ala Val Thr Glu Arg Leu Ala Ile Ile Ser
385                 390                 395                 400
Val Val Gly Asp Gly Met Arg Thr Leu Arg Gly Ile Ser Ala Lys Phe
                405                 410                 415
Phe Ala Ala Leu Ala Arg Ala Asn Ile Asn Ile Val Ala Ile Ala Gln
            420                 425                 430
Gly Ser Ser Glu Arg Ser Ile Ser Val Val Val Asn Asn Asp Asp Ala
        435                 440                 445
Thr Thr Gly Val Arg Val Thr His Gln Met Leu Phe Asn Thr Asp Gln
    450                 455                 460
Val Ile Glu Val Phe Val Ile Gly Val Gly Val Gly Gly Ala Leu
465                 470                 475                 480
Leu Glu Gln Leu Lys Arg Gln Gln Ser Trp Leu Lys Asn Lys His Ile
                485                 490                 495
Asp Leu Arg Val Cys Gly Val Ala Asn Ser Lys Ala Leu Leu Thr Asn
            500                 505                 510
Val His Gly Leu Asn Leu Glu Asn Trp Gln Glu Glu Leu Ala Gln Ala
        515                 520                 525
Lys Glu Pro Phe Asn Leu Gly Arg Leu Ile Arg Leu Val Lys Glu Tyr
    530                 535                 540
His Leu Leu Asn Pro Val Ile Val Asp Cys Thr Ser Ser Gln Ala Val
545                 550                 555                 560
Ala Asp Gln Tyr Ala Asp Phe Leu Arg Glu Gly Phe His Val Val Thr
                565                 570                 575
Pro Asn Lys Lys Ala Asn Thr Ser Ser Met Asp Tyr Tyr His Gln Leu
            580                 585                 590
Arg Tyr Ala Ala Glu Lys Ser Arg Arg Lys Phe Leu Tyr Asp Thr Asn
        595                 600                 605
Val Gly Ala Gly Leu Pro Val Ile Glu Asn Leu Gln Asn Leu Leu Asn
    610                 615                 620
Ala Gly Asp Glu Leu Met Lys Phe Ser Gly Ile Leu Ser Gly Ser Leu
625                 630                 635                 640
Ser Tyr Ile Phe Gly Lys Leu Asp Glu Gly Met Ser Phe Ser Glu Ala
                645                 650                 655
Thr Thr Leu Ala Arg Glu Met Gly Tyr Thr Glu Pro Asp Pro Arg Asp
            660                 665                 670
Asp Leu Ser Gly Met Asp Val Ala Arg Lys Leu Leu Ile Leu Ala Arg
        675                 680                 685
Glu Thr Gly Arg Glu Leu Glu Leu Ala Asp Ile Glu Ile Glu Pro Val
    690                 695                 700
```

-continued

```
Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
            725                 730                 735

Arg Asp Glu Gly Lys Val Leu Arg Tyr Val Gly Asn Ile Asp Glu Asp
                740                 745                 750

Gly Val Cys Arg Val Lys Ile Ala Glu Val Asp Gly Asn Asp Pro Leu
            755                 760                 765

Phe Lys Val Lys Asn Gly Glu Asn Ala Leu Ala Phe Tyr Ser His Tyr
        770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815

Lys Leu Gly Val
            820

<210> SEQ ID NO 36
<211> LENGTH: 819
<212> TYPE: PRT
<213> ORGANISM: Serratia marcescens

<400> SEQUENCE: 36

Met Arg Val Leu Lys Phe Gly Gly Thr Ser Val Ala Asn Ala Glu Arg
1               5                   10                  15

Phe Leu Arg Val Ala Asp Ile Met Glu Ser Asn Ala Arg Gln Gly Gln
                20                  25                  30

Val Ala Thr Val Leu Ser Ala Pro Ala Lys Ile Thr Asn His Leu Val
            35                  40                  45

Ala Met Ile Asp Lys Thr Val Ala Gly Gln Asp Ile Leu Pro Asn Met
        50                  55                  60

Ser Asp Ala Glu Arg Ile Phe Ala Asp Leu Leu Ser Gly Leu Ala Gln
65                  70                  75                  80

Ala Leu Pro Gly Phe Glu Tyr Asp Arg Leu Lys Gly Val Val Asp Gln
                85                  90                  95

Glu Phe Ala Gln Leu Lys Gln Val Leu His Gly Val Ser Leu Leu Gly
            100                 105                 110

Gln Cys Pro Asp Ser Val Asn Ala Ala Ile Ile Cys Arg Gly Glu Lys
        115                 120                 125

Leu Ser Ile Ala Ile Met Glu Gly Val Phe Arg Ala Lys Gly Tyr Pro
130                 135                 140

Val Thr Val Ile Asn Pro Val Glu Lys Leu Leu Ala Gln Gly His Tyr
145                 150                 155                 160

Leu Glu Ser Thr Val Asp Ile Ala Glu Ser Thr Leu Arg Ile Ala Ala
                165                 170                 175

Ala Ala Ile Pro Ala Asp His Ile Val Leu Met Ala Gly Phe Thr Ala
            180                 185                 190

Gly Asn Asp Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
210                 215                 220

Ile Trp Thr Asp Val Asp Gly Val Tyr Thr Cys Asp Pro Arg Thr Val
225                 230                 235                 240

Pro Asp Ala Arg Leu Leu Lys Ser Met Ser Tyr Gln Glu Ala Met Glu
                245                 250                 255
```

```
Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Ser Asn Pro
            275                 280                 285

Gln Ala Pro Gly Thr Leu Ile Gly Lys Asp Ser Thr Asp Ala Asp Met
            290                 295                 300

Pro Val Lys Gly Ile Thr Asn Leu Asn Asn Met Ala Met Ile Asn Val
305                 310                 315                 320

Ser Gly Pro Gly Met Lys Gly Met Val Gly Met Ala Ala Arg Val Phe
                    325                 330                 335

Ala Val Met Ser Arg Ala Gly Ile Ser Val Val Leu Ile Thr Gln Ser
            340                 345                 350

Ser Ser Glu Tyr Ser Ile Ser Phe Cys Val Pro Gln Gly Glu Leu Gln
            355                 360                 365

Arg Ala Arg Arg Ala Leu Glu Glu Phe Tyr Leu Glu Leu Lys Asp
            370                 375                 380

Gly Val Leu Asp Pro Leu Asp Val Met Glu Arg Leu Ala Ile Ile Ser
385                 390                 395                 400

Val Val Gly Asp Gly Met Arg Thr Leu Arg Gly Ile Ser Ala Arg Phe
                    405                 410                 415

Phe Ser Ala Leu Ala Arg Ala Asn Ile Asn Ile Val Ala Ile Ala Gln
            420                 425                 430

Gly Ser Ser Glu Arg Ser Ile Ser Val Val Val Ser Asn Asp Ser Ala
            435                 440                 445

Thr Thr Gly Val Arg Val Ser His Gln Met Leu Phe Asn Thr Asp Gln
            450                 455                 460

Val Ile Glu Val Phe Val Ile Gly Val Gly Val Gly Gly Ala Leu
465                 470                 475                 480

Ile Glu Gln Ile Tyr Arg Gln Gln Pro Trp Leu Lys Gln Lys His Ile
                    485                 490                 495

Asp Leu Arg Val Cys Gly Ile Ala Asn Ser Arg Val Met Leu Thr Asn
            500                 505                 510

Val His Gly Ile Ala Leu Asp Ser Trp Arg Asp Ala Leu Ala Gly Ala
            515                 520                 525

Gln Glu Pro Phe Asn Leu Gly Arg Leu Ile Arg Leu Val Lys Glu Tyr
            530                 535                 540

His Leu Leu Asn Pro Val Ile Asp Cys Thr Ser Ser Gln Ala Val
545                 550                 555                 560

Ala Asp Gln Tyr Val Asp Phe Leu Ala Asp Gly Phe His Val Val Thr
                    565                 570                 575

Pro Asn Lys Lys Ala Asn Thr Ser Ser Met Asn Tyr Tyr Gln Gln Leu
            580                 585                 590

Arg Ala Ala Ala Gly Ser His Arg Lys Phe Leu Tyr Asp Thr Asn
            595                 600                 605

Val Gly Ala Gly Leu Pro Val Ile Glu Asn Leu Gln Asn Leu Leu Asn
            610                 615                 620

Ala Gly Asp Glu Leu Val Arg Phe Ser Gly Ile Leu Ser Gly Ser Leu
625                 630                 635                 640

Ser Phe Ile Phe Gly Lys Leu Asp Glu Gly Leu Ser Leu Ser Ala Ala
                    645                 650                 655

Thr Leu Gln Ala Arg Ala Asn Gly Tyr Thr Glu Pro Asp Pro Arg Asp
            660                 665                 670
```

```
Asp Leu Ser Gly Met Asp Val Ala Arg Lys Leu Leu Ile Leu Ala Arg
            675                 680                 685

Glu Ala Gly Tyr Lys Leu Glu Leu Ser Asp Ile Glu Val Glu Pro Val
690                 695                 700

Leu Pro Pro Ser Phe Asp Ala Ser Gly Asp Val Asp Thr Phe Leu Ala
705                 710                 715                 720

Arg Leu Pro Glu Leu Asp Lys Glu Phe Ala Arg Asn Val Ala Asn Ala
            725                 730                 735

Ala Glu Gln Gly Lys Val Leu Arg Tyr Val Gly Leu Ile Asp Glu Gly
            740                 745                 750

Arg Cys Lys Val Arg Ile Glu Ala Val Asp Gly Asn Asp Pro Leu Tyr
            755                 760                 765

Lys Val Lys Asn Gly Glu Asn Ala Leu Ala Phe Tyr Ser Arg Tyr Tyr
            770                 775                 780

Gln Pro Leu Pro Leu Val Leu Arg Gly Tyr Gly Ala Gly Asn Asp Val
785                 790                 795                 800

Thr Ala Ala Gly Val Phe Ala Asp Leu Leu Arg Thr Leu Ser Trp Lys
            805                 810                 815

Leu Gly Val

<210> SEQ ID NO 37
<211> LENGTH: 816
<212> TYPE: PRT
<213> ORGANISM: Buchnera aphidicola

<400> SEQUENCE: 37

Met Lys Ile Leu Lys Phe Gly Gly Thr Ser Leu Ser Asn Ser Glu Leu
1               5                   10                  15

Phe Phe His Val Ala Thr Ile Ile Glu Asn Asn Leu Asn Asn Glu Gln
                20                  25                  30

Ile Ala Ile Val Leu Ser Ala Pro Gly Asn Thr Thr Asn Leu Leu Glu
            35                  40                  45

Ile Ala Ile Asn Gln Thr Ile Asn Asn Lys Asn Ile Ile Pro Ile Val
50                  55                  60

Gln Lys Ile Glu Lys Asn Phe Leu Lys Leu Ile Asn Asp Ile Tyr Gln
65                  70                  75                  80

Val Glu Gln Lys Leu Leu Tyr Glu Lys Ile Lys Asn Asn Ile Glu Asn
                85                  90                  95

Lys Leu Leu Glu Leu Lys Asn Leu Leu Gln Gly Ile Asn Leu Leu Arg
            100                 105                 110

Gln Cys Pro Asp Lys Ile Arg Ala Lys Ile Ile Ser Ser Gly Glu Tyr
            115                 120                 125

Leu Ser Ile Ser Ile Met Asn Ser Ile Leu Ile Ser Arg Gly Tyr Asn
130                 135                 140

Thr Thr Ile Ile Asp Pro Val Lys Lys Leu Leu Thr Lys Glu Asp Thr
145                 150                 155                 160

Tyr Leu Asn Ala Thr Val Asn Ile Lys Ile Ser Lys Phe Arg Ile Leu
                165                 170                 175

Ser Met Lys Ile Pro Lys His His Ile Ile Leu Met Pro Gly Phe Thr
            180                 185                 190

Ala Gly Asn Lys Gln Gly Glu Leu Val Thr Leu Gly Arg Asn Gly Ser
            195                 200                 205

Asp Tyr Ser Ala Thr Ile Leu Ser Val Cys Leu Asn Ser Thr Met Cys
210                 215                 220
```

```
Glu Ile Trp Thr Asp Val Asn Gly Val Tyr Thr Cys Asp Pro Lys Leu
225                 230                 235                 240

Val Ser Asp Ala Lys Leu Leu Thr Ser Leu Ser Tyr Arg Glu Ala Ile
                245                 250                 255

Glu Leu Ser Tyr Leu Gly Ala Lys Ile Leu His Pro Asn Thr Ile Tyr
            260                 265                 270

Pro Ile Gln Lys Phe Lys Ile Pro Cys Thr Ile Lys Asn Thr His Asn
        275                 280                 285

Pro Ser Ser Ile Gly Thr Lys Ile Ser Cys Asn His Val Lys Asn Lys
    290                 295                 300

Asn Leu Ile Thr Gly Val Thr Tyr Leu Glu Asn Val His Met Phe Ser
305                 310                 315                 320

Ile Ser Cys Leu Tyr Ser Lys Asn Ile Glu Thr Ile Ile Pro Lys Ile
                325                 330                 335

Phe Ser Cys Met Ser Leu Ser Lys Ile Trp Ile Ile Leu Thr Ile Gln
            340                 345                 350

Thr Ser Ser Gln Asn Thr Ile Ser Phe Cys Ile Leu Lys Thr Met Thr
        355                 360                 365

Asn Thr Ala Leu His Val Leu His Lys Ala Leu Tyr Leu Glu Leu Lys
    370                 375                 380

His Lys Leu Leu Lys Pro Ile Lys Val Glu Lys Leu Thr Leu Ile
385                 390                 395                 400

Ser Val Ile Ser Ser Asp Ile Leu Asn Asn Thr Lys Ile Thr Glu Lys
                405                 410                 415

Val Phe Ser Ile Leu Lys His Val Asn Ile Asn Thr Leu Ala Ile Ser
            420                 425                 430

Lys Gly Ala Ser Lys Asn Ser Ile Ser Ile Val Val Lys His Asp Asp
        435                 440                 445

Gly Ile Leu Gly Val Arg Ala Leu His Lys Gly Ile Phe Asn Lys Asn
    450                 455                 460

Cys Thr Ala Glu Ile Phe Leu Ile Gly Ile Gly Arg Val Gly Gln Thr
465                 470                 475                 480

Phe Leu Lys Gln Ile Ile Glu Gln Lys Asn Trp Leu Lys Ser Lys Asn
                485                 490                 495

Ile Asp Leu Lys Ile Cys Gly Ile Ala Asn Ser Lys Asn Phe Ile Leu
            500                 505                 510

Asn Leu Asp Gly Ile Asn Pro Lys Asn Trp Lys Arg Asp Leu Asn Leu
        515                 520                 525

Ser Lys Lys Ser Phe Asn Phe Lys His Leu Leu Asn Ser Ile Gln Asn
    530                 535                 540

Tyr Tyr Leu Ile Asn Pro Ile Ile Val Asp Cys Thr Ser Asp Lys Asn
545                 550                 555                 560

Ile Ala Asn Gln Tyr Ile Ser Phe Ile Asn Cys Gly Phe His Ile Val
                565                 570                 575

Thr Pro Asn Lys Lys Ala Asn Thr Thr Asn Trp Lys Tyr Tyr Glu Asp
            580                 585                 590

Ile Arg Leu Ala Ala Gln Lys Glu Lys Lys Phe Phe Tyr Glu Thr
        595                 600                 605

Asn Val Gly Ala Gly Leu Pro Val Ile Glu Asn Leu Lys Asn Leu Leu
    610                 615                 620

Arg Thr Gly Asp Thr Leu Ile His Phe Lys Gly Ile Leu Ser Gly Ser
625                 630                 635                 640

Leu Ser Phe Ile Phe Gly Lys Leu Glu Asp Asn Ile Ser Leu Ser Glu
```

```
                          645                 650                 655
Ala Thr Lys Gln Ala Gln Ser Leu Gly Phe Thr Glu Pro Asn Pro Lys
                660                 665                 670

Asp Asp Leu Ser Gly Ile Asp Val Ala Arg Lys Leu Leu Ile Leu Ala
            675                 680                 685

Arg Glu Val Gly Tyr Lys Leu Glu Leu Lys Asp Ile Lys Ile Glu Pro
690                 695                 700

Leu Leu Pro Lys Glu Phe Asn Asn Ile Ser Asn Thr Thr Asp Phe Ile
705                 710                 715                 720

Thr Lys Leu Lys Glu Leu Asp Gln Ile Phe Cys Asn Arg Val Lys Lys
                725                 730                 735

Ala Arg Lys Leu Gly Lys Arg Leu Arg Phe Val Gly Ile Ile Asn Gln
            740                 745                 750

Lys Gly Asn Cys Gln Val Lys Ile Asp Glu Val Asp His Asn Asp Pro
        755                 760                 765

Leu Tyr Asn Ile Lys Asn Gly Glu Asn Ala Leu Ala Phe Tyr Ser Lys
    770                 775                 780

Tyr Tyr Gln Pro Ile Pro Leu Val Leu Arg Gly Tyr Gly Ala Gly Asn
785                 790                 795                 800

Asn Val Thr Ala Ser Gly Ile Phe Ser Asp Val Leu Arg Ile Leu Leu
                805                 810                 815

<210> SEQ ID NO 38
<211> LENGTH: 310
<212> TYPE: PRT
<213> ORGANISM: Escherichia coli

<400> SEQUENCE: 38

Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
                20                  25                  30

Gly Asp Val Val Thr Val Glu Ala Ala Glu Thr Phe Ser Leu Asn Asn
            35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
    130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205
```

```
Gly Phe Ile His Ala Cys Tyr Ser Arg Gln Pro Glu Leu Ala Ala Lys
            210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
                260                 265                 270

Pro Glu Thr Ala Gln Arg Val Ala Asp Trp Leu Gly Lys Asn Tyr Leu
                275                 280                 285

Gln Asn Gln Glu Gly Phe Val His Ile Cys Arg Leu Asp Thr Ala Gly
290                 295                 300

Ala Arg Val Leu Glu Asn
305                 310

<210> SEQ ID NO 39
<211> LENGTH: 318
<212> TYPE: PRT
<213> ORGANISM: Vibrio vulnificus

<400> SEQUENCE: 39

Met Ala Val Val Val Tyr Ala Pro Ala Ser Ile Gly Asn Val Ser Val
1               5                   10                  15

Gly Phe Asp Val Leu Gly Ala Ala Val Ser Pro Ile Asp Gly Thr Leu
                20                  25                  30

Leu Gly Asp Arg Val Met Val Lys Ala Gly Asn Glu Pro Phe Ser Leu
                35                  40                  45

Lys Thr Ala Gly Ser Phe Val Ala Lys Leu Pro Ser Asp Pro Lys Glu
50                  55                  60

Asn Ile Val Tyr Asp Cys Trp Arg Val Phe Ala Arg Glu Leu Asp Lys
65                  70                  75                  80

Lys Gly Leu Glu Leu Lys Pro Leu Glu Met Thr Leu Glu Lys Asn Met
                85                  90                  95

Pro Ile Gly Ser Gly Leu Gly Ser Ser Ala Cys Ser Ile Val Ala Ala
                100                 105                 110

Leu Asp Ala Leu Asn Gln Phe His Ala Asn Pro Leu Asp Glu Met Glu
            115                 120                 125

Leu Leu Ala Leu Met Gly Glu Met Glu Gly Gln Ile Ser Gly Gly Val
            130                 135                 140

His Tyr Asp Asn Val Ala Pro Cys Tyr Leu Gly Gly Leu Gln Leu Met
145                 150                 155                 160

Leu Glu Glu Leu Gly Ile Ile Ser Gln Glu Val Pro Cys Phe Asp Asp
                165                 170                 175

Trp Tyr Trp Val Met Ala Tyr Pro Gly Ile Lys Val Ser Thr Ala Glu
                180                 185                 190

Ala Arg Ala Ile Leu Pro Ser Gln Tyr Arg Arg Gln Asp Val Ile Ala
            195                 200                 205

His Gly Arg His Leu Ala Gly Phe Ile His Ala Cys His Ser Gly Gln
210                 215                 220

Pro Glu Leu Ala Ala Lys Met Ile Lys Asp Val Ile Ala Glu Pro Tyr
225                 230                 235                 240

Arg Glu Lys Leu Leu Pro Gly Phe Ala Asp Ala Arg Lys Tyr Ala Ala
                245                 250                 255

Ser Ala Gly Ala Leu Ala Thr Gly Ile Ser Gly Ser Gly Pro Thr Leu
                260                 265                 270
```

```
Phe Ser Ile Cys Lys Asp Gln Asp Val Ala Gln Arg Val Ala Arg Trp
        275                 280                 285

Leu Glu Gln Asn Tyr Val Gln Asn Glu Glu Gly Phe Val His Ile Cys
        290                 295                 300

Arg Leu Asp Lys Lys Gly Ser Ile Val Thr Gly Ser Glu Leu
305                 310                 315

<210> SEQ ID NO 40
<211> LENGTH: 315
<212> TYPE: PRT
<213> ORGANISM: Buchnera aphidicola

<400> SEQUENCE: 40

Met Ile Lys Ile Tyr Ala Pro Ala Ser Ile Gly Asn Val Gly Val Gly
1               5                   10                  15

Phe Asp Ile Leu Gly Ile Ala Ile Lys Pro Ile Asp Lys Thr Leu Leu
                20                  25                  30

Gly Asp Cys Ile Ser Ile Lys Pro Ser Lys Lys Phe Gln Leu Lys Asn
            35                  40                  45

His Gly Asn Phe Ser Lys Gln Leu Pro Val Asn Ile Lys Glu Asn Ile
    50                  55                  60

Ile Trp Lys Ala Trp Lys Tyr Phe Asn Lys Lys Ala Lys Lys Lys Lys
65                  70                  75                  80

Thr Val Lys Ile Val Leu Glu Lys Asn Met Pro Ile Gly Ser Gly Leu
                85                  90                  95

Gly Ser Ser Ala Ser Ser Ile Val Ala Cys Val Ile Ala Leu Asn Lys
            100                 105                 110

Phe Tyr Lys Thr Lys Leu Ser Lys Thr Lys Leu Leu Lys Ile Met Gly
        115                 120                 125

Lys Leu Glu Gly Ile Ile Ser Gly Glu Val His Tyr Asp Asn Val Ala
130                 135                 140

Pro Cys Tyr Leu Gly Gly Leu Gln Leu Ile Thr Asn Asp Gln Lys Asn
145                 150                 155                 160

Ile Thr Gln Lys Leu Pro Ile Phe Thr Asp Trp Leu Trp Val Ile Ala
                165                 170                 175

Trp Pro Gly Val Thr Leu Ser Thr Ser Gln Ala Arg Asn Ile Leu Pro
            180                 185                 190

Leu Lys Tyr Lys Lys Thr Cys Ile His Asn Ser Arg Asn Leu Ala
        195                 200                 205

Thr Phe Ile His Ala Leu Tyr Thr Lys Gln Ser Glu Leu Ala Ile Arg
210                 215                 220

Tyr Met Lys Asp Ile Ile Ala Glu Pro Tyr Arg Ile Pro Leu Ile Pro
225                 230                 235                 240

Lys Phe Leu Ile Ser Lys Lys Ile Ile Glu Leu Gly Ala Leu Thr
                245                 250                 255

Cys Asn Ile Ser Gly Ser Gly Pro Thr Leu Phe Ser Val Cys Pro Asn
            260                 265                 270

Ile Ser Ile Ala Lys Lys Val Lys Ile Trp Leu Lys Lys Asn Tyr Met
        275                 280                 285

Glu Asn Gln Thr Gly Phe Val His Ile Cys Lys Ile Asp Gln Ser Gly
        290                 295                 300

Ala Arg Lys Met Glu Lys Lys Asn Glu Ile Ile
305                 310                 315
```

```
<210> SEQ ID NO 41
<211> LENGTH: 428
<212> TYPE: PRT
<213> ORGANISM: Escherichia coli

<400> SEQUENCE: 41

Met Lys Leu Tyr Asn Leu Lys Asp His Asn Glu Gln Val Ser Phe Ala
1               5                   10                  15

Gln Ala Val Thr Gln Gly Leu Gly Lys Asn Gln Gly Leu Phe Phe Pro
            20                  25                  30

His Asp Leu Pro Glu Phe Ser Leu Thr Glu Ile Asp Glu Met Leu Lys
        35                  40                  45

Leu Asp Phe Val Thr Arg Ser Ala Lys Ile Leu Ser Ala Phe Ile Gly
    50                  55                  60

Asp Glu Ile Pro Gln Glu Ile Leu Glu Glu Arg Val Arg Ala Ala Phe
65                  70                  75                  80

Ala Phe Pro Ala Pro Val Ala Asn Val Glu Ser Asp Val Gly Cys Leu
                85                  90                  95

Glu Leu Phe His Gly Pro Thr Leu Ala Phe Lys Asp Phe Gly Gly Arg
            100                 105                 110

Phe Met Ala Gln Met Leu Thr His Ile Ala Gly Asp Lys Pro Val Thr
        115                 120                 125

Ile Leu Thr Ala Thr Ser Gly Asp Thr Gly Ala Ala Val Ala His Ala
    130                 135                 140

Phe Tyr Gly Leu Pro Asn Val Lys Val Val Ile Leu Tyr Pro Arg Gly
145                 150                 155                 160

Lys Ile Ser Pro Leu Gln Glu Lys Leu Phe Cys Thr Leu Gly Gly Asn
                165                 170                 175

Ile Glu Thr Val Ala Ile Asp Gly Asp Phe Asp Ala Cys Gln Ala Leu
            180                 185                 190

Val Lys Gln Ala Phe Asp Asp Glu Glu Leu Lys Val Ala Leu Gly Leu
        195                 200                 205

Asn Ser Ala Asn Ser Ile Asn Ile Ser Arg Leu Leu Ala Gln Ile Cys
    210                 215                 220

Tyr Tyr Phe Glu Ala Val Ala Gln Leu Pro Gln Glu Thr Arg Asn Gln
225                 230                 235                 240

Leu Val Val Ser Val Pro Ser Gly Asn Phe Gly Asp Leu Thr Ala Gly
                245                 250                 255

Leu Leu Ala Lys Ser Leu Gly Leu Pro Val Lys Arg Phe Ile Ala Ala
            260                 265                 270

Thr Asn Val Asn Asp Thr Val Pro Arg Phe Leu His Asp Gly Gln Trp
        275                 280                 285

Ser Pro Lys Ala Thr Gln Ala Thr Leu Ser Asn Ala Met Asp Val Ser
    290                 295                 300

Gln Pro Asn Asn Trp Pro Arg Val Glu Glu Leu Phe Arg Arg Lys Ile
305                 310                 315                 320

Trp Gln Leu Lys Glu Leu Gly Tyr Ala Ala Val Asp Asp Glu Thr Thr
                325                 330                 335

Gln Gln Thr Met Arg Glu Leu Lys Glu Leu Gly Tyr Thr Ser Glu Pro
            340                 345                 350

His Ala Ala Val Ala Tyr Arg Ala Leu Arg Asp Gln Leu Asn Pro Gly
        355                 360                 365

Glu Tyr Gly Leu Phe Leu Gly Thr Ala His Pro Ala Lys Phe Lys Glu
    370                 375                 380
```

```
Ser Val Glu Ala Ile Leu Gly Glu Thr Leu Asp Leu Pro Lys Glu Leu
385                 390                 395                 400

Ala Glu Arg Ala Asp Leu Pro Leu Leu Ser His Asn Leu Pro Ala Asp
            405                 410                 415

Phe Ala Ala Leu Arg Lys Leu Met Met Asn His Gln
            420                 425

<210> SEQ ID NO 42
<211> LENGTH: 425
<212> TYPE: PRT
<213> ORGANISM: Haemophilus influenzae

<400> SEQUENCE: 42

Met Asn Leu Tyr Asn Ile Lys His Pro Glu Glu Gln Val Thr Phe Ser
1               5                   10                  15

Gln Ala Val Arg Gln Gly Leu Gly Arg Asp Gln Gly Leu Phe Phe Pro
            20                  25                  30

Glu Val Ile Pro Gln Leu Asn Asn Ile Asn Glu Leu Leu Glu Leu Pro
        35                  40                  45

Leu Val Glu Arg Ser Gln Lys Ile Leu Gly Ala Leu Ile Asp Gly Glu
50                  55                  60

Leu Pro Gln Ala Thr Leu Asp Ala Met Val Lys Asn Ala Phe Thr Phe
65                  70                  75                  80

Pro Ala Pro Leu Glu Lys Val Glu Glu Asn Ile Tyr Ala Leu Glu Leu
                85                  90                  95

Phe His Gly Pro Thr Leu Ala Phe Lys Asp Phe Gly Gly Arg Phe Met
            100                 105                 110

Ala Gln Ala Leu Ala Ala Val Arg Gly Asp Gly Lys Ile Thr Ile Leu
        115                 120                 125

Thr Ala Thr Ser Gly Asp Thr Gly Ala Ala Val Ala His Ala Phe Tyr
130                 135                 140

Gly Leu Glu Asn Ile Asn Val Val Ile Leu Tyr Pro Lys Gly Lys Ile
145                 150                 155                 160

Ser Pro Leu Gln Glu Lys Leu Phe Cys Thr Leu Gly Gly Asn Ile Arg
                165                 170                 175

Thr Val Ala Ile Asn Ala Asp Phe Asp Ala Cys Gln Ala Leu Val Lys
            180                 185                 190

Gln Ala Phe Asp Asp Val Glu Leu Arg Gln Ala Ile Gly Leu Asn Ser
        195                 200                 205

Ala Asn Ser Ile Asn Ile Ser Arg Leu Leu Ala Gln Val Cys Tyr Tyr
210                 215                 220

Phe Glu Ala Val Ala Gln Leu Pro Lys Glu Lys Arg Asp Asn Val Val
225                 230                 235                 240

Val Ser Val Pro Ser Gly Asn Phe Gly Asn Leu Thr Ala Gly Leu Ile
                245                 250                 255

Ala Lys Thr Leu Gly Leu Pro Ile Lys Arg Phe Val Ala Ser Thr Asn
            260                 265                 270

Ala Asn Asp Thr Val Pro Arg Tyr Leu Lys Ser Gly Asn Trp Asp Pro
        275                 280                 285

Lys Thr Thr Val Ala Thr Leu Ser Asn Ala Met Asp Val Ser Arg Pro
290                 295                 300

Asn Asn Trp Pro Arg Val Glu Glu Leu Phe Lys Arg Asn Gly Trp Asp
305                 310                 315                 320

Leu Thr Asp Leu Gly Ser Gly Met Leu Ser Asp Ser Glu Thr Glu Asp
                325                 330                 335
```

```
Thr Leu Lys Ala Met Gln Ser Lys Gly Tyr Leu Cys Glu Pro His Gly
            340                 345                 350

Ala Ile Ala Tyr Gln Val Leu Lys Asp Gln Leu Lys Ala Ser Glu Thr
            355                 360                 365

Gly Ile Phe Leu Cys Thr Ala His Pro Ala Lys Phe Lys Glu Ser Val
        370                 375                 380

Glu Arg Ile Leu Gly Ile Gln Leu Pro Leu Pro Glu Thr Leu Asp Lys
385                 390                 395                 400

His Asn Gln Leu Pro Leu Leu Ser Asp Glu Met Asp Asn Asp Phe Ala
                405                 410                 415

Gln Leu Arg Ala Tyr Leu Leu Lys Ser
            420                 425

<210> SEQ ID NO 43
<211> LENGTH: 469
<212> TYPE: PRT
<213> ORGANISM: Pseudomonas aeruginosa

<400> SEQUENCE: 43

Met Arg Tyr Ile Ser Thr Arg Gly Gln Ala Pro Ala Leu Asn Phe Glu
1               5                   10                  15

Asp Val Leu Leu Ala Gly Leu Ala Ser Asp Gly Gly Leu Tyr Val Pro
            20                  25                  30

Glu Asn Leu Pro Arg Phe Thr Leu Glu Glu Ile Ala Ser Trp Val Gly
        35                  40                  45

Leu Pro Tyr His Glu Leu Ala Phe Arg Val Met Arg Pro Phe Val Ala
50                  55                  60

Gly Ser Ile Ala Asp Ala Asp Phe Lys Lys Ile Leu Glu Glu Thr Tyr
65                  70                  75                  80

Gly Val Phe Ala His Asp Ala Val Ala Pro Leu Arg Gln Leu Asn Gly
            85                  90                  95

Asn Glu Trp Val Leu Glu Leu Phe His Gly Pro Thr Leu Ala Phe Lys
            100                 105                 110

Asp Phe Ala Leu Gln Leu Leu Gly Arg Leu Leu Asp His Val Leu Ala
        115                 120                 125

Lys Arg Gly Glu Arg Val Val Ile Met Gly Ala Thr Ser Gly Asp Thr
130                 135                 140

Gly Ser Ala Ala Ile Glu Gly Cys Arg Arg Cys Asp Asn Val Asp Ile
145                 150                 155                 160

Phe Ile Met His Pro His Asn Arg Val Ser Glu Val Gln Arg Arg Gln
                165                 170                 175

Met Thr Thr Ile Leu Gly Asp Asn Ile His Asn Ile Ala Ile Glu Gly
            180                 185                 190

Asn Phe Asp Asp Cys Gln Glu Met Val Lys Ala Ser Phe Ala Asp Gln
        195                 200                 205

Gly Phe Leu Lys Gly Thr Arg Leu Val Ala Val Asn Ser Ile Asn Trp
    210                 215                 220

Ala Arg Ile Met Ala Gln Ile Val Tyr Tyr Phe His Ala Ala Leu Gln
225                 230                 235                 240

Leu Gly Ala Pro His Arg Ser Val Ala Phe Ser Val Pro Thr Gly Asn
                245                 250                 255

Phe Gly Asp Ile Phe Ala Gly Tyr Leu Ala Arg Asn Met Gly Leu Pro
            260                 265                 270

Val Ser Gln Leu Ile Val Ala Thr Asn Arg Asn Asp Ile Leu His Arg
```

```
            275                 280                 285
    Phe Met Ser Gly Asn Arg Tyr Asp Lys Asp Thr Leu His Pro Ser Leu
        290                 295                 300

Ser Pro Ser Met Asp Ile Met Val Ser Ser Asn Phe Glu Arg Leu Leu
    305                 310                 315                 320

Phe Asp Leu His Gly Arg Asn Gly Lys Ala Val Ala Glu Leu Leu Asp
                    325                 330                 335

Ala Phe Lys Ala Ser Gly Lys Leu Ser Val Glu Asp Gln Arg Trp Thr
                340                 345                 350

Glu Ala Arg Lys Leu Phe Asp Ser Leu Ala Val Ser Asp Glu Gln Thr
            355                 360                 365

Cys Glu Thr Ile Ala Glu Val Tyr Arg Ser Ser Gly Glu Leu Leu Asp
    370                 375                 380

Pro His Thr Ala Ile Gly Val Arg Ala Ala Arg Glu Cys Arg Arg Ser
    385                 390                 395                 400

Leu Ser Val Pro Met Val Thr Leu Gly Thr Ala His Pro Val Lys Phe
                    405                 410                 415

Pro Glu Ala Val Glu Lys Ala Gly Ile Gly Gln Ala Pro Ala Leu Pro
                420                 425                 430

Ala His Leu Ala Asp Leu Phe Glu Arg Glu Arg Cys Thr Val Leu
            435                 440                 445

Pro Asn Glu Leu Ala Lys Val Gln Ala Phe Val Ser Gln His Gly Asn
        450                 455                 460

Arg Gly Lys Pro Leu
    465

<210> SEQ ID NO 44
<211> LENGTH: 2463
<212> TYPE: DNA
<213> ORGANISM: Escherichia coli

<400> SEQUENCE: 44
atgcgagtgt tgaagttcgg cggtacatca gtggcaaatg cagaacgttt tctgcgtgtt      60
gccgatattc tggaaagcaa tgccaggcag gggcaggtgg ccaccgtcct ctctgccccc     120
gccaaaatca ccaaccacct ggtggcgatg attgaaaaaa ccattagcgg ccaggatgct     180
ttacccaata tcagcgatgc cgaacgtatt tttgccgaac ttttgacggg actcgccgcc     240
gcccagccgg ggttcccgct ggcgcaattg aaaactttcg tcgatcagga atttgcccaa     300
ataaaacatg tcctgcatgg cattagtttg ttggggcagt gccggatag catcaacgct     360 gcgctgattt gccgtggcga gaaaatgtcg atcgccatta tggccggcgt attagaagcg     420
cgcggtcaca acgttactgt tatcgatccg gtcgaaaaac tgctggcagt ggggcattac     480
ctcgaatcta ccgtcgatat tgctgagtcc accgccgta ttgcggcaag ccgcattccg     540
gctgatcaca tggtgctgat gcaggttc accgccggta atgaaaaagg cgaactggtg     600
gtgcttggac gcaacggttc cgactactct gctgcggtgc tggctgcctg tttacgcgcc     660
gattgttgcg agatttggac ggacgttgac ggggtctata cctgcgaccc cgtcaggtg     720 cccgatgcga ggttgttgaa gtcgatgtcc taccaggaag cgatggagct ttcctacttc     780
ggcgctaaag ttcttcaccc ccgcaccatt accccatcg cccagttcca gatcccttgc     840
ctgattaaaa ataccggaaa tcctcaagca ccaggtacgc tcattggtgc cagccgtgat     900
gaagacgaat taccggtcaa gggcatttcc aatctgaata acatggcaat gttcagcgtt     960
tctggtccgg ggatgaaagg gatggtcggc atggcggcgc gcgtctttgc agcgatgtca    1020
```

```
cgcgcccgta tttccgtggt gctgattacg caatcatctt ccgaatacag catcagtttc    1080
tgcgttccac aaagcgactg tgtgcgagct gaacgggcaa tgcaggaaga gttctacctg    1140
gaactgaaag aaggcttact ggagccgctg gcagtgacgg aacggctggc cattatctcg    1200
gtggtaggtg atggtatgcg caccttgcgt gggatctcgg cgaaattctt tgccgcactg    1260
gcccgcgcca atatcaacat tgtcgccatt gctcagggat cttctgaacg ctcaatctct    1320
gtcgtggtaa ataacgatga tgcgaccact ggcgtgcgcg ttactcatca gatgctgttc    1380
aataccgatc aggttatcga agtgtttgtg attggcgtcg gtggcgttgg cggtgcgctg    1440
ctggagcaac tgaagcgtca gcaaagctgg ctgaagaata acatatcga cttacgtgtc    1500 tgcggtgttg ccaactcgaa ggctctgctc accaatgtac atggccttaa tctggaaaac    1560
tggcaggaag aactggcgca agccaaagag ccgtttaatc tcgggcgctt aattcgcctc    1620
gtgaaagaat atcatctgct gaacccggtc attgttgact gcacttccag ccaggcagtg    1680
gcggatcaat atgccgactt cctgcgcgaa ggtttccacg ttgtcacgcc gaacaaaaag    1740
gccaacacct cgtcgatgga ttactaccat cagttgcgtt atgcggcgga aaaatcgcgg    1800
cgtaaattcc tctatgacac caacgttggg gctggattac cggttattga gaacctgcaa    1860
aatctgctca atgcaggtga tgaattgatg aagttctccg gcattctttc tggttcgctt    1920
tcttatatct cggcaagtt agacgaaggc atgagtttct ccgaggcgac cacgctggcg    1980
cgggaaatgg ttataccga accggacccg cgagatgatc tttctggtat ggatgtggcg    2040
cgtaaactat tgattctcgc tcgtgaaacg ggacgtgaac tggagctggc ggatattgaa    2100
attgaacctg tgctgcccgc agagtttaac gccgagggtg atgttgccgc ttttatggcg    2160
aatctgtcac aactcgacga tctctttgcc gcgcgcgtgg cgaaggcccg tgatgaagga    2220
aaagttttgc gctatgttgg caatattgat gaagatggcg tctgccgcgt gaagattgcc    2280
gaagtggatg gtaatgatcc gctgttcaaa gtgaaaaatg gcgaaaacgc cctggccttc    2340
tatagccact attatcagcc gctgccgttg gtactgcgcg gatatggtgc gggcaatgac    2400
gttacagctg ccggtgtctt tgctgatctg ctacgtaccc tctcatggaa gttaggagtc    2460
tga                                                                  2463
```

<210> SEQ ID NO 45
<211> LENGTH: 933
<212> TYPE: DNA
<213> ORGANISM: Escherichia coli

<400> SEQUENCE: 45

```
atggttaaag tttatgcccc ggcttccagt gccaatatga gcgtcgggtt tgatgtgctc    60
ggggcggcgg tgacacctgt tgatggtgca ttgctcggag atgtagtcac ggttgaggcg    120
gcagagacat tcagtctcaa caacctcgga cgctttgccg ataagctgcc gtcagaacca    180
cgggaaaata tcgtttatca gtgctgggag cgttttttgcc aggaactggg taagcaaatt    240
ccagtggcga tgaccctgga aaagaatatg ccgatcggtt cgggcttagg ctccagtgcc    300
tgttcggtgg tcgcggcgct gatggcgatg aatgaacact gcggcaagcc gcttaatgac    360
actcgtttgc tggctttgat gggcgagctg gaaggccgta tctccggcag cattcattac    420
gacaacgtgg caccgtgttt tctcggtggt atgcagttga tgatcgaaga aaacgacatc    480
atcagccagc aagtgccagg gtttgatgag tggctgtggg tgctggcgta tccggggatt    540
aaagtctcga cggcagaagc cagggctatt ttaccggcgc agtatcgccg ccaggattgc    600
```

```
attgcgcacg ggcgacatct ggcaggcttc attcacgcct gctattcccg tcagcctgag    660
cttgccgcga agctgatgaa agatgttatc gctgaaccct accgtgaacg gttactgcca    720
ggcttccggc aggcgcggca ggcggtcgcg gaaatcggcg cggtagcgag cggtatctcc    780
ggctccggcc cgaccttgtt cgctctgtgt gacaagccgg aaaccgccca gcgcgttgcc    840
gactggttgg gtaagaacta cctgcaaaat caggaaggtt ttgttcatat ttgccggctg    900
gatacggcgg gcgcacgagt actggaaaac taa                                 933
```

<210> SEQ ID NO 46
<211> LENGTH: 1287
<212> TYPE: DNA
<213> ORGANISM: Escherichia coli

<400> SEQUENCE: 46

```
atgaaactct acaatctgaa agatcacaac gagcaggtca gctttgcgca agccgtaacc     60
caggggttgg gcaaaaatca ggggctgttt tttccgcacg acctgccgga attcagcctg    120
actgaaattg atgagatgct gaagctggat tttgtcaccc gcagtgcgaa gatcctctcg    180
gcgtttattg gtgatgaaat cccacaggaa atcctggaag agcgcgtgcg cgcggcgttt    240
gccttcccgg ctccggtcgc caatgttgaa agcgatgtcg gttgtctgga attgttccac    300
gggccaacgc tggcatttaa agatttcggc ggtcgcttta tggcacaaat gctgacccat    360
attgcgggtg ataagccagt gaccattctg accgcgacct ccgtgatac cggagcggca    420 gtggctcatg ctttctacgg tttaccgaat gtgaaagtgg ttatcctcta ccacgaggc    480 aaaatcagtc cactgcaaga aaaactgttc tgtacattgg gcgcaatat cgaaactgtt    540 gccatcgacg gcgatttcga tgcctgtcag gcgctggtga agcaggcgtt tgatgatgaa    600
gaactgaaag tggcgctagg gttaaactcg gctaactcga ttaacatcag ccgtttgctg    660
gcgcagattt gctactactt tgaagctgtt gcgcagctgc cgcaggagac gcgcaaccag    720
ctggttgtct cggtgccaag cggaaacttc ggcgatttga cggcgggtct gctggcgaag    780
tcactcggtc tgccggtgaa acgttttatt gctgcgacca acgtgaacga taccgtgcca    840
cgtttcctgc acgacggtca gtggtcaccc aaagcgactc aggcgacgtt atccaacgcg    900
atggacgtga gtcagccgaa caactggccg cgtgtggaag agttgttccg ccgcaaaatc    960
tggcaactga agagctggg ttatcagcc gtggatgatg aaaccacgca acagacaatg   1020
cgtgagttaa agaactggg ctacacttcg gagccgcacg ctgccgtagc ttatcgtgcg   1080
ctgcgtgatc agttgaatcc aggcgaatat ggcttgttcc tcggcaccgc gcatccggcg   1140
aaatttaaag agagcgtgga agcgattctc ggtgaaacgt tggatctgcc aaaagagctg   1200
gcagaacgtg ctgatttacc cttgctttca cataatctgc ccgccgattt tgctgcgttg   1260
cgtaaattga tgatgaatca tcagtaa                                       1287
```

<210> SEQ ID NO 47
<211> LENGTH: 514
<212> TYPE: PRT
<213> ORGANISM: Escherichia coli

<400> SEQUENCE: 47

```
Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
```

```
              35                  40                  45
Leu Val Lys Arg Glu Asp Arg Gln Pro Val His Ser Phe Lys Leu Arg
 50                  55                  60

Gly Ala Tyr Ala Met Met Ala Gly Leu Thr Glu Gln Lys Ala His
 65                  70                  75                  80

Gly Val Ile Thr Ala Ser Ala Gly Asn His Ala Gln Gly Val Ala Phe
                 85                  90                  95

Ser Ser Ala Arg Leu Gly Val Lys Ala Leu Ile Val Met Pro Thr Ala
                100                 105                 110

Thr Ala Asp Ile Lys Val Asp Ala Val Arg Gly Phe Gly Gly Glu Val
                115                 120                 125

Leu Leu His Gly Ala Asn Phe Asp Glu Ala Lys Ala Lys Ala Ile Glu
130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
                180                 185                 190

Ala Ala Gly Val Ala Val Leu Ile Lys Gln Leu Met Pro Gln Ile Lys
                195                 200                 205

Val Ile Ala Val Glu Ala Glu Asp Ser Ala Cys Leu Lys Ala Ala Leu
210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
                260                 265                 270

Ala Met Lys Asp Leu Phe Glu Asp Val Arg Ala Val Ala Glu Pro Ser
                275                 280                 285

Gly Ala Leu Ala Leu Ala Gly Met Lys Lys Tyr Ile Ala Leu His Asn
                290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
                340                 345                 350

Leu Lys Phe Cys Gln Leu Leu Gly Gly Arg Ser Val Thr Glu Phe Asn
                355                 360                 365

Tyr Arg Phe Ala Asp Ala Lys Asn Ala Cys Ile Phe Val Gly Val Arg
                370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Asp Glu Met Ala Lys
                405                 410                 415

Leu His Val Arg Tyr Met Val Gly Gly Arg Pro Ser His Pro Leu Gln
                420                 425                 430

Glu Arg Leu Tyr Ser Phe Glu Phe Pro Glu Ser Pro Gly Ala Leu Leu
                435                 440                 445

Arg Phe Leu Asn Thr Leu Gly Thr Tyr Trp Asn Ile Ser Leu Phe His
450                 455                 460
```

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Asn Asn Pro Ala Phe Arg Phe Phe Leu
                500                 505                 510

Ala Gly

<210> SEQ ID NO 48
<211> LENGTH: 513
<212> TYPE: PRT
<213> ORGANISM: Pasteurella multocida

<400> SEQUENCE: 48

Met Val Asn Asn Leu His Ser Ala His Pro Thr Gly Ala Glu Tyr Leu
1               5                   10                  15

Lys Ala Val Leu Ser Ser Lys Val Tyr Asp Val Ala Gln Val Thr Pro
            20                  25                  30

Leu Gln Asp Met Ala Lys Leu Ser Glu Arg Leu Gly Asn Lys Val Phe
        35                  40                  45

Ile Lys Arg Glu Asp Arg Gln Pro Val His Ser Phe Lys Leu Arg Gly
50                  55                  60

Ala Tyr Ala Met Ile Ala Gly Leu Ser Ala Glu Gln Lys Ala Ser Gly
65                  70                  75                  80

Val Ile Ala Ala Ser Ala Gly Asn His Ala Gln Gly Val Ala Leu Ser
                85                  90                  95

Ala Lys His Leu Gly Leu Arg Ala Leu Ile Val Met Pro Gln Asn Thr
            100                 105                 110

Pro Ser Ile Lys Val Asp Ala Val Arg Gly Phe Gly Gly Glu Val Leu
        115                 120                 125

Leu His Gly Ala Asn Phe Asp Glu Ala Lys Ala Lys Ala Ile Glu Leu
130                 135                 140

Ala Glu Ser Lys Asn Met Thr Phe Ile Pro Pro Phe Asp His Pro Ala
145                 150                 155                 160

Val Ile Ala Gly Gln Gly Ser Ile Ala Met Glu Leu Leu Gln Gln Asn
                165                 170                 175

Ser Gln Ile Asp Arg Ile Phe Val Pro Val Gly Gly Gly Gly Leu Ala
            180                 185                 190

Ala Gly Ile Ala Val Leu Ile Lys Gln Leu Met Pro Glu Ile Lys Val
        195                 200                 205

Ile Gly Val Glu Ser Lys Asp Ser Ala Cys Leu Tyr Arg Ala Leu Lys
210                 215                 220

Ala Gly Lys Pro Ile Asp Leu Asp Arg Val Gly Leu Phe Ala Asp Gly
225                 230                 235                 240

Val Ala Val Lys Arg Ile Gly Asp Glu Thr Phe Arg Val Cys Gln Gln
                245                 250                 255

Tyr Ile Asp Asp Val Val Leu Val Asp Gly Asp Glu Ile Cys Ala Ala
            260                 265                 270

Val Lys Asp Ile Phe Glu Asn Val Arg Ala Ile Ala Glu Pro Ser Gly
        275                 280                 285

Ala Leu Ser Leu Ala Gly Leu Lys Lys Tyr Val Lys Glu His Asn Ile
    290                 295                 300

Gln Gly Glu Thr Leu Val Asn Val Leu Ser Gly Ala Asn Leu Asn Phe
305                 310                 315                 320

His Thr Leu Arg Tyr Val Ser Glu Arg Cys Glu Ile Gly Glu Gln His
            325                 330                 335

Glu Ala Leu Ala Val Thr Ile Pro Glu Gln Pro Gly Ser Phe Leu
        340                 345                 350

Lys Phe Cys His Ile Leu Gly His Val Pro Val Thr Glu Phe Lys Tyr
        355                 360                 365

Arg Tyr Ala Asp Asp Lys Gln Ala Cys Ile Phe Val Gly Val Arg Ile
        370                 375                 380

Thr Gly Gln Glu Glu Lys Gln Thr Ile Ile Asn Gln Leu Gln Gln Asn
385                 390                 395                 400

Gly Tyr Asp Leu Ile Asp Leu Ser Asn Asp Ile Ala Lys Thr His
            405                 410                 415

Val Arg Tyr Met Ile Gly Gly Arg Ser Asn Ser Pro Leu Lys Glu Arg
            420                 425                 430

Leu Tyr Ser Phe Glu Phe Pro Glu Gln Lys Gly Ala Leu Leu Lys Phe
        435                 440                 445

Leu Glu Thr Leu Gly Gln Thr His Trp Asn Ile Ser Val Phe His Tyr
        450                 455                 460

Arg Ala His Gly Ala Asp Tyr Gly Asn Val Leu Ala Gly Phe Gln Leu
465                 470                 475                 480

Asn Asp Glu Asp Leu Asp Ala Phe Asn Gln His Leu Glu Lys Leu Gly
                485                 490                 495

Tyr Val Tyr Gln Asp Val Thr Glu Ser Pro Ala Tyr Arg Tyr Phe Leu
            500                 505                 510

Val

<210> SEQ ID NO 49
<211> LENGTH: 507
<212> TYPE: PRT
<213> ORGANISM: Burkholderia multivorans

<400> SEQUENCE: 49

Met Ala Ser His Asp Tyr Leu Lys Lys Ile Leu Thr Ala Arg Val Tyr
1               5                   10                  15

Asp Val Ala Phe Glu Thr Glu Leu Glu Pro Ala Arg Asn Leu Ser Ala
            20                  25                  30

Arg Leu Arg Asn Pro Val Tyr Leu Lys Arg Glu Asp Asn Gln Pro Val
35 40 45

Phe Ser Phe Lys Leu Arg Gly Ala Tyr Asn Lys Met Ala His Ile Pro
50 55 60

Ala Asp Ala Leu Ala Arg Gly Val Ile Thr Ala Ser Ala Gly Asn His
65 70 75 80

Ala Gln Gly Val Ala Phe Ser Ala Ala Arg Met Gly Val Lys Ala Val
85 90 95

Ile Val Val Pro Val Thr Thr Pro Gln Val Lys Val Asp Ala Val Arg
100 105 110

Ala His Gly Gly Pro Gly Val Glu Val Ile Gln Ala Gly Glu Ser Tyr
115 120 125

Ser Asp Ala Tyr Ala His Ala Leu Lys Val Gln Glu Glu Arg Gly Leu
130 135 140

Thr Phe Val His Pro Phe Asp Asp Pro Tyr Val Ile Ala Gly Gln Gly
145 150 155 160

Thr Ile Ala Met Glu Ile Leu Arg Gln His Gln Gly Pro Ile His Ala
165 170 175

-continued

```
Ile Phe Val Pro Ile Gly Gly Gly Leu Ala Ala Gly Val Ala Ala
            180                 185                 190

Tyr Val Lys Ala Val Arg Pro Glu Ile Lys Val Ile Gly Val Gln Ala
            195                 200                 205

Glu Asp Ser Cys Ala Met Ala Gln Ser Leu Gln Ala Gly Lys Arg Val
210                 215                 220

Glu Leu Ala Glu Val Gly Leu Phe Ala Asp Gly Thr Ala Val Lys Leu
225                 230                 235                 240

Val Gly Glu Glu Thr Phe Arg Leu Cys Lys Glu Tyr Leu Asp Gly Val
            245                 250                 255

Val Thr Val Asp Thr Asp Ala Leu Cys Ala Ala Ile Lys Asp Val Phe
            260                 265                 270

Gln Asp Thr Arg Ser Val Leu Glu Pro Ser Gly Ala Leu Ala Val Ala
            275                 280                 285

Gly Ala Lys Leu Tyr Ala Glu Arg Glu Gly Ile Glu Asn Gln Thr Leu
            290                 295                 300

Val Ala Val Thr Ser Gly Ala Asn Met Asn Phe Asp Arg Met Arg Phe
305                 310                 315                 320

Val Ala Glu Arg Ala Glu Val Gly Glu Ala Arg Glu Ala Val Phe Ala
            325                 330                 335

Val Thr Ile Pro Glu Glu Arg Gly Ser Phe Lys Arg Phe Cys Ser Leu
            340                 345                 350

Val Gly Asp Arg Asn Val Thr Glu Phe Asn Tyr Arg Ile Ala Asp Ala
            355                 360                 365

Gln Ser Ala His Ile Phe Val Gly Val Gln Ile Arg Arg Gly Glu
            370                 375                 380

Ser Ala Asp Ile Ala Ala Asn Phe Glu Ser His Gly Phe Lys Thr Ala
385                 390                 395                 400

Asp Leu Thr His Asp Glu Leu Ser Lys Glu His Ile Arg Tyr Met Val
            405                 410                 415

Gly Gly Arg Ser Pro Leu Ala Leu Asp Glu Arg Leu Phe Arg Phe Glu
            420                 425                 430

Phe Pro Glu Arg Pro Gly Ala Leu Met Lys Phe Leu Ser Ser Met Ala
            435                 440                 445

Pro Asp Trp Asn Ile Ser Leu Phe His Tyr Arg Asn Gln Gly Ala Asp
450                 455                 460

Tyr Ser Ser Ile Leu Val Gly Leu Gln Val Pro Gln Ala Asp His Ala
465                 470                 475                 480

Glu Phe Glu Arg Phe Leu Ala Ala Leu Gly Tyr Pro Tyr Val Glu Glu
            485                 490                 495

Ser Ala Asn Pro Ala Tyr Arg Leu Phe Leu Ser
            500                 505
```

<210> SEQ ID NO 50
<211> LENGTH: 1545
<212> TYPE: DNA
<213> ORGANISM: Escherichia coli

<400> SEQUENCE: 50

| | |
|---|---|
| atggctgact cgcaacccct gtccggtgct ccggaaggtg ccgaatattt aagagcagtg | 60 |
| ctgcgcgcgc cggtttacga ggcggcgcag gttacgccgc tacaaaaaat ggaaaaactg | 120 |
| tcgtcgcgtc ttgataacgt cattctggtg aagcgcgaag atcgccagcc agtgcacagc | 180 |
| tttaagctgc gcggcgcata cgccatgatg gcgggcctga cggaagaaca gaaagcgcac | 240 |

```
ggcgtgatca ctgcttctgc gggtaaccac gcgcagggcg tcgcgttttc ttctgcgcgg      300
ttaggcgtga aggccctgat cgttatgcca accgccaccg ccgacatcaa agtcgacgcg      360
gtgcgcggct tcggcggcga agtgctgctc cacggcgcga actttgatga agcgaaagcc      420
aaagcgatcg aactgtcaca gcagcagggg ttcacctggg tgccgccgtt cgaccatccg      480
atggtgattg ccgggcaagg cacgctggcg ctggaactgc tccagcagga cgcccatctc      540
gaccgcgtat ttgtgccagt cggcggcggc ggtctggctg ctggcgtggc ggtgctgatc      600
aaacaactga tgccgcaaat caaagtgatc gccgtagaag cggaagactc cgcctgcctg      660
aaagcagcgc tggatgcggg tcatccggtt gatctgccgc gctagggct atttgctgaa       720 ggcgtagcgg taaaacgcat cggtgacgaa accttccgtt tatgccagga gtatctcgac      780
gacatcatca ccgtcgatag cgatgcgatc tgtgcggcga tgaaggattt attcgaagat      840
gtgcgcgcgg tggcggaacc ctctggcgcg ctggcgctgg cgggaatgaa aaatatatc      900 gccctgcaca acattcgcgg cgaacggctg gcgcatattc tttccggtgc caacgtgaac      960
ttccacggcc tgcgctacgt ctcagaacgc tgcgaactgg gcgaacagcg tgaagcgttg     1020
ttggcggtga ccattccgga agaaaaaggc agcttcctca aattctgcca actgcttggc     1080
gggcgttcgg tcaccgagtt caactaccgt tttgccgatg ccaaaaacgc ctgcatcttt     1140
gtcggtgtgc gcctgagccg cggcctcgaa gagcgcaaag aaattttgca gatgctcaac     1200
gacggcggct acagcgtggt tgatctctcc gacgacgaaa tggcgaagct acacgtgcgc     1260
tatatggtcg gcggacgtcc atcgcatccg ttgcaggaac gcctctacag cttcgaattc     1320
ccggaatcac cgggcgcgct gctgcgcttc ctcaacacgc tgggtacgta ctggaacatt     1380
tctttgttcc actatcgcag ccatggcacc gactacgggc gcgtactggc ggcgttcgaa     1440
cttggcgacc atgaaccgga tttcgaaacc cggctgaatg agctgggcta cgattgccac     1500
gacgaaacca taacccggc gttcaggttc tttttggcgg gttag                      1545
```

<210> SEQ ID NO 51
<211> LENGTH: 523
<212> TYPE: PRT
<213> ORGANISM: Escherichia coli

<400> SEQUENCE: 51

```
Met Ser Gln Gln Val Ile Ile Phe Asp Thr Thr Leu Arg Asp Gly Glu
1               5                   10                  15

Gln Ala Leu Gln Ala Ser Leu Ser Val Lys Glu Lys Leu Gln Ile Ala
                20                  25                  30

Leu Ala Leu Glu Arg Met Gly Val Asp Val Met Glu Val Gly Phe Pro
            35                  40                  45

Val Ser Ser Pro Gly Asp Phe Glu Ser Val Gln Thr Ile Ala Arg Gln
        50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Ser Cys Glu Asp Ala Gly
    130                 135                 140
```

```
Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
            195                 200                 205

Leu Ala Val Gly Asn Ser Leu Ala Ala Val His Ala Gly Ala Arg Gln
210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
                260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
            325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
            355                 360                 365

Gln Val Phe Asp Tyr Asp Leu Glu Ala Leu Ala Phe Ile Gly Lys Gln
370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
            405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
            435                 440                 445

Tyr Ser Leu Thr Ala Lys Gly His Gly Lys Asp Ala Leu Gly Gln Val
        450                 455                 460

Asp Ile Val Ala Asn Tyr Asn Gly Arg Arg Phe His Gly Val Gly Leu
465                 470                 475                 480

Ala Thr Asp Ile Val Glu Ser Ser Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520
```

<210> SEQ ID NO 52
<211> LENGTH: 519
<212> TYPE: PRT
<213> ORGANISM: Buchnera aphidicola

```
<400> SEQUENCE: 52

Met Lys Ser Lys Val Val Ile Phe Asp Thr Thr Leu Arg Asp Gly Glu
1               5                   10                  15

Gln Ala Leu Gln Ala Ser Leu Ser Val Lys Glu Lys Leu Gln Ile Ala
            20                  25                  30

Leu Ser Leu Glu Lys Cys Gly Ile Asp Ile Leu Glu Ile Gly Phe Pro
        35                  40                  45

Val Ser Ser Pro Gly Asp Phe Lys Ser Val Gln Thr Ile Ser Lys Asn
    50                  55                  60

Ile Lys Asn Ser Arg Ile Cys Ser Leu Ala Arg Cys Ile Glu Lys Asp
65                  70                  75                  80

Ile Asp Ala Ala Gly Glu Ala Met Ser Ser Asp Ser Phe Arg Ile
                85                  90                  95

His Ile Phe Leu Ala Thr Ser Thr Leu His Met Glu Ser Lys Leu Lys
            100                 105                 110

Lys Asn Phe Asn Glu Ile Ile Asp Met Ala Val Phe Ser Val Lys Lys
        115                 120                 125

Ala Leu Arg Tyr Thr Asp Asp Ile Glu Phe Ser Cys Glu Asp Ala Thr
    130                 135                 140

Arg Thr Thr Met Asp Asn Leu Cys Arg Ile Val Glu Thr Leu Ile Lys
145                 150                 155                 160

Ser Gly Val Lys Thr Ile Asn Ile Pro Asp Thr Val Gly Tyr Thr Val
                165                 170                 175

Pro Asn Glu Leu Ser Cys Ile Ile Lys Asn Leu Phe Glu Arg Val Pro
            180                 185                 190

Asn Ile His Lys Ser Ile Ile Ser Val His Cys His Asp Asp Leu Gly
        195                 200                 205

Met Ala Val Gly Asn Ser Ile Ser Ala Ile Gln Ala Gly Ala Arg Gln
    210                 215                 220

Ile Glu Gly Thr Ile Asn Gly Ile Gly Glu Arg Ala Gly Asn Thr Ala
225                 230                 235                 240

Leu Glu Glu Ile Ile Met Ala Ile Lys Val Arg Glu Asp Ile Leu Ser
                245                 250                 255

Val Ser Thr Asn Ile Asn Tyr Lys Glu Ile Tyr Arg Thr Ser Lys Ile
            260                 265                 270

Val Ser Gln Ile Cys Asn Met Pro Ile Pro Ser Asn Lys Ala Ile Val
        275                 280                 285

Gly Ser Asn Ala Phe Ala His Ser Ser Gly Ile His Gln Asp Gly Val
    290                 295                 300

Leu Lys Asn Arg Lys Asn Tyr Glu Ile Met Glu Pro Ser Ser Ile Gly
305                 310                 315                 320

Leu Lys Glu Val Lys Leu Asn Leu Thr Ser Arg Ser Gly Arg Ala Ala
                325                 330                 335

Val Lys His Tyr Met Asp Glu Met Gly Tyr Asn Asn Ser Asp Tyr Asn
            340                 345                 350

Ile Asp Glu Leu Tyr Thr Ala Phe Leu Lys Leu Ala Asp Lys Lys Gly
        355                 360                 365

Gln Val Phe Asp Tyr Asp Leu Glu Ala Leu Ala Phe Ile Asn Lys Gln
    370                 375                 380

Gln Asp Glu Trp Glu Tyr Phe Ser Leu Lys Phe Phe Ser Val Gln Ser
385                 390                 395                 400

Ile Ser Asn Ser Leu Ser Thr Ala Ser Val Lys Leu Leu Cys Gly Lys
                405                 410                 415
```

```
Lys Thr Tyr Thr Glu Ser Ser Thr Thr Ser Asn Gly Pro Val Asp Ala
            420                 425                 430

Ile Tyr Gln Ala Leu Asn Arg Ile Ala Cys Phe Pro Ile Ile Leu Gln
            435                 440                 445

Lys Phe Gln Leu Val Ala Lys Gly Lys Gly Lys Asp Ala Leu Gly Gln
450                 455                 460

Val Asp Ile Leu Val Glu His Lys Lys Arg Lys Phe His Gly Val Gly
465                 470                 475                 480

Leu Ala Thr Asp Ile Ile Glu Ala Ser Ala Gln Ala Met Ile Asn Val
            485                 490                 495

Leu Asn Asn Ile Trp Lys Ala Lys Gln Val Asn Lys Lys Leu Lys Ile
            500                 505                 510

Leu Lys Asp Phe Lys Lys Lys
            515

<210> SEQ ID NO 53
<211> LENGTH: 513
<212> TYPE: PRT
<213> ORGANISM: Dechloromonas aromatica

<400> SEQUENCE: 53

Met Lys Gln His Leu Val Ile Phe Asp Thr Thr Leu Arg Asp Gly Glu
1               5                   10                  15

Gln Ser Pro Gly Ala Ser Met Thr Lys Glu Glu Lys Ile Arg Val Ala
                20                  25                  30

Arg Gln Leu Glu Lys Met Arg Val Asp Val Ile Glu Ala Gly Phe Ala
            35                  40                  45

Ala Ala Ser Pro Gly Asp Phe Asp Ala Ile His Ser Ile Ala Gln Thr
        50                  55                  60

Ile Lys Asp Ser Thr Val Cys Ser Leu Ala Arg Ala Asn Glu Asn Asp
65                  70                  75                  80

Ile Arg Arg Ala Gly Glu Ala Ile Lys Pro Ala Gln Ser Gly Arg Ile
                85                  90                  95

His Thr Phe Ile Ala Thr Ser Pro Ile His Met Glu Lys Lys Leu Arg
            100                 105                 110

Met Thr Pro Asp Gln Val Val Glu Gln Ala Val Lys Ala Ile Gly Trp
        115                 120                 125

Ala Arg Glu Tyr Thr Asp Asp Ile Glu Phe Ser Ala Glu Asp Ala Gly
        130                 135                 140

Arg Ser Asp Leu Asp Phe Leu Cys Arg Ile Phe Glu Glu Val Ile Lys
145                 150                 155                 160

Ala Gly Ala Thr Thr Ile Asn Val Pro Asp Thr Val Gly Tyr Asn Ile
                165                 170                 175

Pro Ser Gln Tyr Ala Glu Thr Met Arg Gln Leu Ile Glu Arg Val Pro
            180                 185                 190

Asn Ser Asp Lys Val Val Trp Ser Val His Cys His Asn Asp Leu Gly
            195                 200                 205

Leu Ala Val Ser Asn Ser Leu Ala Ala Val Leu Cys Gly Ala Arg Gln
        210                 215                 220

Val Glu Cys Thr Ile Asn Gly Leu Gly Glu Arg Ala Gly Asn Ala Ala
225                 230                 235                 240

Leu Glu Glu Ile Val Met Ala Val Arg Thr Arg Ala Asp Val Phe Pro
                245                 250                 255

Val Glu Thr Arg Ile Asp Thr Thr Gln Ile Val Pro Ala Ser Lys Leu
```

```
                260                 265                 270
Val Ser Gln Ile Thr Gly Tyr Pro Val Gln Pro Asn Lys Ala Val Val
        275                 280                 285

Gly Ala Asn Ala Phe Ala His Glu Ser Gly Ile His Gln Asp Gly Val
        290                 295                 300

Leu Lys His Arg Glu Thr Tyr Glu Ile Met Arg Ala Gln Asp Val Gly
305                 310                 315                 320

Trp Thr Gln Asn Lys Leu Val Leu Gly Lys His Ser Gly Arg Asn Ala
                325                 330                 335

Phe Lys Asn Arg Leu Gln Glu Leu Gly Ile Glu Leu Glu Ser Asp Glu
                340                 345                 350

Ala Leu Asn Ala Ala Phe Ala Arg Phe Lys Glu Leu Ala Asp Lys Lys
                355                 360                 365

His Glu Ile Phe Asp Glu Asp Leu His Ala Leu Val Ser Asp Asp Leu
                370                 375                 380

Val Thr Pro Asp Gln Glu Tyr Tyr Lys Leu Val Tyr Ser Arg Val Cys
385                 390                 395                 400

Ser Glu Thr Gly Glu Met Pro Arg Ala Ser Val Ile Leu Asn Ile Gly
                405                 410                 415

Gly Val Glu His Lys Ala Glu Ala Asp Gly Gly Pro Val Asp Ala
                420                 425                 430

Thr Phe Lys Ala Ile Glu Ser Ile Ala Gly Ser Gly Ala Glu Leu Leu
                435                 440                 445

Leu Tyr Ser Val Asn Ala Ile Thr Thr Gly Thr Asp Ala Gln Gly Glu
                450                 455                 460

Val Thr Thr Arg Leu Ser Lys Gly Asp Arg Ile Val Asn Gly Asn Gly
465                 470                 475                 480

Ala Asp Thr Asp Ile Val Ile Ala Ser Ala Arg Ser Tyr Leu Asn Ala
                485                 490                 495

Leu Asn Lys Leu His Ser Thr Leu Asp Lys Val Lys Ala Gln Gly Gly
                500                 505                 510

Val

<210> SEQ ID NO 54
<211> LENGTH: 363
<212> TYPE: PRT
<213> ORGANISM: Escherichia coli

<400> SEQUENCE: 54

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
                20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Leu
                85                  90                  95

Pro Leu Arg Lys His Phe Lys Leu Phe Ser Asn Leu Arg Pro Ala Lys
                100                 105                 110

Leu Tyr Gln Gly Leu Glu Ala Phe Cys Pro Leu Arg Ala Asp Ile Ala
```

```
            115                 120                 125
Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Ile Glu Arg Ile Ala
                165                 170                 175

Arg Ile Ala Phe Glu Ser Ala Arg Lys Arg His Lys Val Thr Ser
            180                 185                 190

Ile Asp Lys Ala Asn Val Leu Gln Ser Ser Ile Leu Trp Arg Glu Ile
        195                 200                 205

Val Asn Glu Ile Ala Thr Glu Tyr Pro Asp Val Glu Leu Ala His Met
    210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
        275                 280                 285

Asp Ile Ala Gly Lys Asn Ile Ala Asn Pro Ile Ala Gln Ile Leu Ser
    290                 295                 300

Leu Ala Leu Leu Leu Arg Tyr Ser Leu Asp Ala Asp Asp Ala Ala Cys
305                 310                 315                 320

Ala Ile Glu Arg Ala Ile Asn Arg Ala Leu Glu Glu Gly Ile Arg Thr
                325                 330                 335

Gly Asp Leu Ala Arg Gly Ala Ala Ala Val Ser Thr Asp Glu Met Gly
            340                 345                 350

Asp Ile Ile Ala Arg Tyr Val Ala Glu Gly Val
        355                 360

<210> SEQ ID NO 55
<211> LENGTH: 358
<212> TYPE: PRT
<213> ORGANISM: Haemophilus influenzae

<400> SEQUENCE: 55

Met Gln Ser Tyr Asn Val Ala Val Leu Ala Gly Asp Gly Ile Gly Pro
1               5                   10                  15

Glu Val Met Ala Glu Ala Met Lys Val Leu Asn Lys Val Gln Glu Lys
                20                  25                  30

Phe Gly Phe Lys Leu Asn Phe Asn Glu Phe Val Gly Gly Ala Ala
            35                  40                  45

Ile Asp His Cys Gly Tyr Pro Leu Pro Ala Glu Thr Leu Lys Gly Cys
        50                  55                  60

Asp Glu Ala Asp Ala Ile Leu Phe Gly Ser Val Gly Gly Pro Lys Trp
65                  70                  75                  80

Thr Asn Leu Pro Pro Asp Gln Gln Pro Glu Arg Gly Ala Leu Leu Pro
                85                  90                  95

Leu Arg Lys His Phe Lys Leu Phe Cys Asn Leu Arg Pro Ala Thr Leu
            100                 105                 110

Tyr Lys Gly Leu Glu Lys Phe Cys Pro Leu Arg Ala Asp Ile Ala Ala
        115                 120                 125
```

```
Lys Gly Phe Asp Met Val Val Val Arg Glu Leu Thr Gly Gly Ile Tyr
    130                 135                 140

Phe Gly Gln Pro Lys Gly Arg Glu Gly Glu Gly Ser Gln Thr Lys Ala
145                 150                 155                 160

Phe Asp Thr Glu Val Tyr Tyr Lys Tyr Glu Ile Glu Arg Ile Ala Arg
                165                 170                 175

Ala Ala Phe Glu Ala Ala Met Lys Arg Asn Lys Lys Val Thr Ser Val
            180                 185                 190

Asp Lys Ala Asn Val Leu Gln Ser Ser Ile Leu Trp Arg Glu Thr Val
        195                 200                 205

Thr Glu Met Ala Lys Asp Tyr Pro Glu Val Thr Leu Glu His Ile Tyr
    210                 215                 220

Ile Asp Asn Ala Thr Met Gln Leu Ile Lys Ala Pro Glu Ser Phe Asp
225                 230                 235                 240

Val Leu Leu Cys Ser Asn Ile Phe Gly Asp Ile Ile Ser Asp Glu Ala
                245                 250                 255

Ala Met Ile Thr Gly Ser Met Gly Met Leu Pro Ser Ala Ser Leu Asn
            260                 265                 270

Glu Ala Gly Phe Gly Leu Tyr Glu Pro Ala Gly Gly Ser Ala Pro Asp
        275                 280                 285

Ile Ala Gly Lys Gly Ile Ala Asn Pro Ile Ala Gln Ile Leu Ser Ala
    290                 295                 300

Ala Met Met Leu Arg Tyr Ser Phe Asn Leu Asn Glu Ala Ala Asp Ala
305                 310                 315                 320

Ile Glu Ser Ala Val Gln Lys Val Leu Ala Ser Gly His Arg Thr Ala
                325                 330                 335

Asp Leu Ala Asp Asp Ser Thr Pro Val Ser Thr Ala Glu Met Gly Thr
            340                 345                 350

Leu Ile Thr Gln Ala Ile
        355

<210> SEQ ID NO 56
<211> LENGTH: 357
<212> TYPE: PRT
<213> ORGANISM: Xanthomonas axonopodis

<400> SEQUENCE: 56

Met Ser Lys Gln Ile Leu Ile Leu Pro Gly Asp Gly Ile Gly Pro Glu
1               5                   10                  15

Ile Met Ala Glu Ala Val Lys Val Leu Lys Arg Ile Asp Ala Gln His
            20                  25                  30

Gly Leu Gly Phe Gln Leu Val Tyr Asp Glu Leu Gly Gly Thr Ala Tyr
        35                  40                  45

Asp Lys Tyr Gly Ser Pro Leu Ala Asp Glu Thr Leu Glu Arg Ala Arg
    50                  55                  60

Gly Ala Asp Ala Val Leu Leu Gly Ala Val Gly Gly Pro Gln Trp Asp
65                  70                  75                  80

Thr Ile Asp Pro Ala Leu Arg Pro Glu Arg Gly Leu Leu Lys Ile Arg
                85                  90                  95

Ser Gln Leu Gly Leu Phe Ala Asn Leu Arg Pro Ala Leu Leu Tyr Pro
            100                 105                 110

Gln Leu Ala Asp Ala Ser Thr Leu Lys Pro Glu Val Val Ala Gly Leu
        115                 120                 125

Asp Leu Leu Ile Leu Arg Glu Leu Thr Gly Gly Ile Tyr Phe Gly Gln
    130                 135                 140
```

```
Pro Arg Gly Asn Arg Thr Leu Asp Asn Gly Glu Arg Gln Ala Tyr Asp
145                 150                 155                 160

Thr Leu Pro Tyr Ser Glu Ser Glu Ile Arg Arg Ile Ala Lys Ala Gly
                165                 170                 175

Phe Asp Met Ala Arg Leu Arg Gly Lys Lys Leu Cys Ser Val Asp Lys
            180                 185                 190

Ala Asn Val Leu Ala Ser Ser Gln Leu Trp Arg Ala Val Val Glu Glu
                195                 200                 205

Val Ala Lys Asp Tyr Pro Asp Ile Ala Leu Ser His Met Tyr Val Asp
210                 215                 220                 240

Asn Ala Ala Met Gln Leu Val Arg Ala Pro Lys Gln Phe Asp Val Ile
225                 230                 235                 240

Val Thr Asp Asn Met Phe Gly Asp Ile Leu Ser Asp Gln Ala Ser Met
                245                 250                 255

Leu Thr Gly Ser Ile Gly Met Leu Pro Ser Ala Ser Leu Asp Ala Asn
                260                 265                 270

Ser Lys Gly Met Tyr Glu Pro Cys His Gly Ser Ala Pro Asp Ile Ala
                275                 280                 285

Gly Lys Gly Ile Ala Asn Pro Leu Ala Thr Ile Leu Ser Val Ala Met
                290                 295                 300

Met Leu Arg Tyr Thr Phe Ala Arg Ala Thr Ala Ala Asp Ala Ile Glu
305                 310                 315                 320

His Ala Val Gly Lys Val Leu Asp Gln Gly Leu Arg Thr Ala Asp Ile
                325                 330                 335

Trp Ser Glu Gly Thr Thr Lys Val Gly Thr Val Ala Met Gly Asp Ala
                340                 345                 350

Val Val Ala Ala Leu
                355

<210> SEQ ID NO 57
<211> LENGTH: 466
<212> TYPE: PRT
<213> ORGANISM: Escherichia coli

<400> SEQUENCE: 57

Met Ala Lys Thr Leu Tyr Glu Lys Leu Phe Asp Ala His Val Val Tyr
1               5                   10                  15

Glu Ala Glu Asn Glu Thr Pro Leu Leu Tyr Ile Asp Arg His Leu Val
                20                  25                  30

His Glu Val Thr Ser Pro Gln Ala Phe Asp Gly Leu Arg Ala His Gly
            35                  40                  45

Arg Pro Val Arg Gln Pro Gly Lys Thr Phe Ala Thr Met Asp His Asn
50                  55                  60

Val Ser Thr Gln Thr Lys Asp Ile Asn Ala Cys Gly Glu Met Ala Arg
65                  70                  75                  80

Ile Gln Met Gln Glu Leu Ile Lys Asn Cys Lys Glu Phe Gly Val Glu
                85                  90                  95

Leu Tyr Asp Leu Asn His Pro Tyr Gln Gly Ile Val His Val Met Gly
            100                 105                 110

Pro Glu Gln Gly Val Thr Leu Pro Gly Met Thr Ile Val Cys Gly Asp
            115                 120                 125

Ser His Thr Ala Thr His Gly Ala Phe Gly Ala Leu Ala Phe Gly Ile
            130                 135                 140

Gly Thr Ser Glu Val Glu His Val Leu Ala Thr Gln Thr Leu Lys Gln
```

```
                145                 150                 155                 160
        Gly Arg Ala Lys Thr Met Lys Ile Glu Val Gln Gly Lys Ala Ala Pro
                        165                 170                 175

Gly Ile Thr Ala Lys Asp Ile Val Leu Ala Ile Ile Gly Lys Thr Gly
                        180                 185                 190

Ser Ala Gly Thr Gly His Val Val Glu Phe Cys Gly Glu Ala Ile
                        195                 200                 205

Arg Asp Leu Ser Met Glu Gly Arg Met Thr Leu Cys Asn Met Ala Ile
                        210                 215                 220

Glu Met Gly Ala Lys Ala Gly Leu Val Ala Pro Asp Glu Thr Thr Phe
        225                 230                 235                 240

Asn Tyr Val Lys Gly Arg Leu His Ala Pro Lys Gly Lys Asp Phe Asp
                        245                 250                 255

Asp Ala Val Ala Tyr Trp Lys Thr Leu Gln Thr Asp Glu Gly Ala Thr
                        260                 265                 270

Phe Asp Thr Val Val Thr Leu Gln Ala Glu Glu Ile Ser Pro Gln Val
                        275                 280                 285

Thr Trp Gly Thr Asn Pro Gly Gln Val Ile Ser Val Asn Asp Asn Ile
                        290                 295                 300

Pro Asp Pro Ala Ser Phe Ala Asp Pro Val Glu Arg Ala Ser Ala Glu
        305                 310                 315                 320

Lys Ala Leu Ala Tyr Met Gly Leu Lys Pro Gly Ile Pro Leu Thr Glu
                        325                 330                 335

Val Ala Ile Asp Lys Val Phe Ile Gly Ser Cys Thr Asn Ser Arg Ile
                        340                 345                 350

Glu Asp Leu Arg Ala Ala Ala Glu Ile Ala Lys Gly Arg Lys Val Ala
                        355                 360                 365

Pro Gly Val Gln Ala Leu Val Val Pro Gly Ser Gly Pro Val Lys Ala
                        370                 375                 380

Gln Ala Glu Ala Glu Gly Leu Asp Lys Ile Phe Ile Glu Ala Gly Phe
        385                 390                 395                 400

Glu Trp Arg Leu Pro Gly Cys Ser Met Cys Leu Ala Met Asn Asn Asp
                        405                 410                 415

Arg Leu Asn Pro Gly Glu Arg Cys Ala Ser Thr Ser Asn Arg Asn Phe
                        420                 425                 430

Glu Gly Arg Gln Gly Arg Gly Gly Arg Thr His Leu Val Ser Pro Ala
                        435                 440                 445

Met Ala Ala Ala Ala Val Thr Gly His Phe Ala Asp Ile Arg Asn
            450                 455                 460

Ile Lys
        465

<210> SEQ ID NO 58
<211> LENGTH: 466
<212> TYPE: PRT
<213> ORGANISM: Shewanella woodyi

<400> SEQUENCE: 58

Met Ala Lys Thr Leu Tyr Glu Lys Val Trp Asp Ser His Val Val
        1               5                   10                  15

Ala Asn Glu Gly Glu Ala Pro Leu Ile Tyr Val Asp Arg His Leu Val
                        20                  25                  30

His Glu Val Thr Ser Pro Gln Ala Phe Ser Gly Leu Lys Val Ala Gly
                        35                  40                  45
```

```
Arg Arg Leu Arg Ala Pro Glu Lys Thr Phe Ala Thr Met Asp His Asn
    50              55                  60
Thr Ser Thr Lys Ser Ala Ser Leu Asp Ala Leu Ser Pro Met Ala Arg
65              70                  75                  80
Ile Gln Val Glu Thr Leu Gln Asp Asn Cys Lys Glu Phe Gly Ile Lys
                85                  90                  95
Leu Tyr Asp Ile His His Lys Asn Gln Gly Ile Val His Val Met Gly
            100                 105                 110
Pro Glu Leu Gly Ile Thr Leu Pro Gly Thr Val Ile Val Cys Gly Asp
            115                 120                 125
Ser His Thr Ala Thr His Gly Ala Phe Gly Ala Leu Ala Phe Gly Ile
    130                 135                 140
Gly Thr Ser Glu Val Glu His Val Met Ala Thr Gln Thr Leu Arg Gln
145                 150                 155                 160
Asn Lys Ala Lys Thr Met Lys Ile Glu Val Lys Gly His Val Thr Pro
                165                 170                 175
Gly Ile Thr Ala Lys Asp Ile Val Leu Ala Ile Gly Lys Ile Gly
            180                 185                 190
Met Asp Gly Gly Thr Gly Tyr Val Val Glu Phe Cys Gly Glu Ala Ile
    195                 200                 205
Glu Ala Leu Ser Met Glu Gly Arg Met Thr Val Cys Asn Met Ala Ile
    210                 215                 220
Glu Met Gly Ala Lys Ala Gly Met Ile Ala Pro Asp Ala Thr Thr Ala
225                 230                 235                 240
Glu Tyr Leu Lys Gly Arg Glu Phe Ala Pro Lys Ala Glu Ser Trp Glu
                245                 250                 255
Gln Ala Ile Glu Ala Trp Ser Glu Leu Lys Thr Asp Ala Asp Ala Val
            260                 265                 270
Phe Asp Ser Thr Val Ile Leu Glu Ala Ala Asp Ile Ala Pro Gln Leu
            275                 280                 285
Thr Trp Gly Thr Asn Pro Gly Gln Val Val Ala Ile Asp Gly Val Val
    290                 295                 300
Pro Asn Pro Gln Asp Glu Pro Asn Ala Thr Val Lys Ala Ser Ile Glu
305                 310                 315                 320
Lys Ala Leu Glu Tyr Val Ala Leu Ser Ala Gly Thr Ser Met Lys Asp
                325                 330                 335
Val Ser Ile Asn Lys Val Phe Ile Gly Ser Cys Thr Asn Ser Arg Ile
            340                 345                 350
Glu Asp Leu Arg Asp Ala Ala Leu His Ala Lys Gly Lys His Val Ala
            355                 360                 365
Glu Gly Val Thr Ala Ile Val Val Pro Gly Ser Gly Leu Val Lys Glu
    370                 375                 380
Gln Ala Glu Ala Glu Gly Leu Asp Lys Ile Phe Ile Glu Ala Gly Phe
385                 390                 395                 400
Glu Trp Arg Leu Pro Gly Cys Ser Met Cys Leu Ala Met Asn Asp Asp
                405                 410                 415
Arg Leu Glu Ala Gly Asp Arg Cys Ala Ser Thr Ser Asn Arg Asn Phe
            420                 425                 430
Glu Gly Arg Gln Gly Arg Gly Ser Arg Thr His Leu Val Ser Pro Ala
            435                 440                 445
Met Ala Ala Ala Ala Val Ala Gly His Phe Val Asp Ile Arg Gln
    450                 455                 460
Thr Leu
```

<210> SEQ ID NO 59
<211> LENGTH: 469
<212> TYPE: PRT
<213> ORGANISM: Ochrobactrum anthropi

<400> SEQUENCE: 59

```
Met Ser Ala Pro Arg Thr Leu Tyr Asp Lys Ile Trp Asp His Val
1               5                   10                  15

Val Asp Gln Gln Glu Asp Gly Thr Cys Leu Leu Tyr Ile Asp Arg His
                20                  25                  30

Leu Val His Glu Val Thr Ser Pro Gln Ala Phe Glu Gly Leu Arg Met
            35                  40                  45

Ala Gly Arg Lys Val Arg His Pro Glu Lys Thr Leu Ala Val Val Asp
        50                  55                  60

His Asn Val Pro Thr Ser Pro Asp Arg Ile Asn Gly Ile Lys Asn Glu
65              70                  75                  80

Glu Ser Arg Ile Gln Val Glu Ala Leu Ala Lys Asn Ala Ala Asp Phe
                85                  90                  95

Asn Val Glu Tyr Tyr Ser Glu Arg Asp Arg Gln Gly Val Val His
            100                 105                 110

Ile Val Gly Pro Glu Gln Gly Phe Thr Leu Pro Gly Met Thr Ile Val
        115                 120                 125

Cys Gly Asp Ser His Thr Ser Thr His Gly Ala Phe Gly Ser Leu Ala
130                 135                 140

His Gly Ile Gly Thr Ser Glu Val Glu His Val Leu Ala Thr Gln Thr
145                 150                 155                 160

Leu Ile Gln Lys Lys Ala Lys Asn Met Leu Val Arg Val Glu Gly Glu
                165                 170                 175

Leu Ala Pro Gly Val Thr Ala Lys Asp Ile Thr Leu Ala Ile Ile Gly
            180                 185                 190

Glu Ile Gly Thr Ala Gly Gly Thr Gly Tyr Val Ile Glu Tyr Ala Gly
        195                 200                 205

Ser Ala Ile Arg Ser Leu Ser Met Glu Gly Arg Met Thr Val Cys Asn
        210                 215                 220

Met Ser Ile Glu Gly Gly Ala Arg Ala Gly Leu Ile Ala Pro Asp Glu
225                 230                 235                 240

Thr Thr Phe Ala Tyr Val Gln Asp Lys Pro Arg Ala Pro Lys Gly Glu
                245                 250                 255

Ala Leu Glu Gln Ala Ile Ser Tyr Trp Lys Thr Leu His Ser Asp Glu
            260                 265                 270

Gly Ala His Phe Asp Lys Ile Val Glu Leu Asp Ala Ala Lys Ile Ser
        275                 280                 285

Pro Val Val Ser Trp Gly Ser Ser Pro Glu Asp Val Val Phe Val Thr
    290                 295                 300

Asp Ile Val Pro Asn Pro Asp Glu Ile Lys Asp Thr Lys Arg Ala
305                 310                 315                 320

Ser Lys Trp Arg Ala Leu Asp Tyr Met Gly Leu Lys Pro Gly Thr Lys
                325                 330                 335

Met Thr Asp Ile Lys Ile Asp Arg Val Phe Ile Gly Ser Cys Thr Asn
            340                 345                 350

Gly Arg Ile Glu Asp Leu Arg Asp Ala Ala Arg Met Ala Ala Gly Lys
        355                 360                 365
```

```
Lys Val Ala Ala Gly Val Asn Ala Met Ile Val Pro Gly Ser Gly Leu
    370                 375                 380

Val Lys Glu Gln Ala Glu Ala Glu Gly Leu Asp Lys Ile Phe Ile Glu
385                 390                 395                 400

Ala Gly Phe Asp Trp Arg Glu Pro Gly Cys Ser Met Cys Leu Ala Met
                    405                 410                 415

Asn Asp Asp Arg Leu Lys Pro Gly Glu Arg Cys Ala Ser Thr Ser Asn
                420                 425                 430

Arg Asn Phe Glu Gly Arg Gln Gly Phe Lys Gly Arg Thr His Leu Val
            435                 440                 445

Ser Pro Ala Met Ala Ala Ala Ala Ile Ala Gly His Phe Val Asp
    450                 455                 460

Ile Arg Glu Trp Asn
465

<210> SEQ ID NO 60
<211> LENGTH: 201
<212> TYPE: PRT
<213> ORGANISM: Escherichia coli

<400> SEQUENCE: 60

Met Ala Glu Lys Phe Ile Lys His Thr Gly Leu Val Val Pro Leu Asp
1               5                   10                  15

Ala Ala Asn Val Asp Thr Asp Ala Ile Ile Pro Lys Gln Phe Leu Gln
            20                  25                  30

Lys Val Thr Arg Thr Gly Phe Gly Ala His Leu Phe Asn Asp Trp Arg
        35                  40                  45

Phe Leu Asp Glu Lys Gly Gln Gln Pro Asn Pro Asp Phe Val Leu Asn
    50                  55                  60

Phe Pro Gln Tyr Gln Gly Ala Ser Ile Leu Leu Ala Arg Glu Asn Phe
65                  70                  75                  80

Gly Cys Gly Ser Ser Arg Glu His Ala Pro Trp Ala Leu Thr Asp Tyr
                85                  90                  95

Gly Phe Lys Val Val Ile Ala Pro Ser Phe Ala Asp Ile Phe Tyr Gly
            100                 105                 110

Asn Ser Phe Asn Asn Gln Leu Leu Pro Val Lys Leu Ser Asp Ala Glu
        115                 120                 125

Val Asp Glu Leu Phe Ala Leu Val Lys Ala Asn Pro Gly Ile His Phe
    130                 135                 140

Asp Val Asp Leu Glu Ala Gln Glu Val Lys Ala Gly Glu Lys Thr Tyr
145                 150                 155                 160

Arg Phe Thr Ile Asp Ala Phe Arg Arg His Cys Met Met Asn Gly Leu
                165                 170                 175

Asp Ser Ile Gly Leu Thr Leu Gln His Asp Asp Ala Ile Ala Ala Tyr
            180                 185                 190

Glu Ala Lys Gln Pro Ala Phe Met Asn
        195                 200

<210> SEQ ID NO 61
<211> LENGTH: 199
<212> TYPE: PRT
<213> ORGANISM: Tolumonas auensis

<400> SEQUENCE: 61

Met Gln Glu Phe Lys Gln His Thr Gly Leu Ala Val Pro Leu Asp Ser
1               5                   10                  15
```

Ala Asn Val Asp Thr Asp Gln Ile Ile Pro Lys Gln Phe Leu Gln Arg
            20                  25                  30

Val Ser Lys Leu Gly Phe Gly Gln Asn Leu Phe His Asp Trp Arg Phe
        35                  40                  45

Leu Asp Glu Ala Gly Thr Gln Pro Asn Pro Glu Phe Val Leu Asn Phe
    50                  55                  60

Pro Arg Tyr Lys Gly Ala Ser Ile Leu Leu Ala Arg Glu Asn Phe Gly
65                  70                  75                  80

Asn Gly Ser Ser Arg Glu His Ala Pro Trp Ala Leu Ala Asp Tyr Gly
                85                  90                  95

Leu Lys Ala Val Ile Ala Pro Ser Phe Ala Asp Ile Phe Tyr Gly Asn
            100                 105                 110

Ser Leu Asn Asn Gly Leu Leu Val Val Arg Leu Lys Asp Asp Glu Val
            115                 120                 125

Asp Ala Leu Phe Lys Leu Val Glu Ala Asn Glu Gly Gln Asn Ile Thr
        130                 135                 140

Val Asp Leu Glu Ala Lys Glu Val Arg Ala Ala Asp Tyr Cys Phe Lys
145                 150                 155                 160

Phe Glu Ile Asp Asp Phe Arg Arg Tyr Cys Ile Met Asn Gly Leu Asp
                165                 170                 175

Asn Ile Gly Leu Thr Leu Gln His Ala Asp Ala Ile Asp Ala Tyr Glu
            180                 185                 190

Ala Lys Gln Pro Val Trp Leu
        195

<210> SEQ ID NO 62
<211> LENGTH: 194
<212> TYPE: PRT
<213> ORGANISM: Brevibacillus brevis

<400> SEQUENCE: 62

Met Asn Pro Phe Val Ile His Thr Gly Val Val Ala Pro Leu Asp Arg
1               5                   10                  15

Val Asn Val Asp Thr Asp Ala Ile Ile Pro Lys Gln Phe Leu Lys Arg
            20                  25                  30

Ile Glu Arg Ser Gly Phe Gly Gln Phe Leu Phe Tyr Glu Trp Arg Phe
        35                  40                  45

Thr Val Asp Gly Ala Pro Ile Asp Ser Phe Ile Leu Asn Thr Pro Ala
    50                  55                  60

Tyr Lys Glu Ser Thr Val Leu Leu Ala Arg Asn Asn Phe Gly Cys Gly
65                  70                  75                  80

Ser Ser Arg Glu His Ala Pro Trp Ala Leu Leu Asp Tyr Gly Phe Arg
                85                  90                  95

Cys Val Ile Ala Pro Ser Phe Ala Asp Ile Phe Tyr Asn Asn Cys Phe
            100                 105                 110

Lys Asn Gly Ile Leu Pro Ile Lys Leu Ser Glu Glu Val Asp Glu
            115                 120                 125

Leu Phe Asn Arg Ala Glu Ser Lys Pro Asn Tyr Gln Leu Thr Ile Asp
        130                 135                 140

Leu Gln Glu Gln Val Val Arg Asp Asn Glu Gly Leu Ser Tyr Pro Phe
145                 150                 155                 160

Glu Val Asp Ser Tyr Arg Arg Tyr Cys Leu Leu Asn Gly Leu Asp Asp
                165                 170                 175

Ile Gly Ile Thr Leu Gln Tyr Glu Asp Lys Ile Ala Ala Tyr Glu Ala
            180                 185                 190

Arg Arg

<210> SEQ ID NO 63
<211> LENGTH: 1572
<212> TYPE: DNA
<213> ORGANISM: Escherichia coli

<400> SEQUENCE: 63

| | | | | | |
|---|---|---|---|---|---|
| atgagccagc | aagtcattat | tttcgatacc | acattgcgcg | acggtgaaca | ggcgttacag | 60 |
| gcaagcttga | gtgtgaaaga | aaaactgcaa | attgcgctgg | cccttgagcg | tatgggtgtt | 120 |
| gacgtgatgg | aagtcggttt | ccccgtctct | tcgccgggcg | attttgaatc | ggtgcaaacc | 180 |
| atcgcccgcc | aggttaaaaa | cagccgcgta | tgtgcgttag | ctcgctgcgt | ggaaaaagat | 240 |
| atcgacgtgg | cggccgaatc | cctgaaagtc | gccgaagcct | tccgtattca | tacctttatt | 300 |
| gccacttcgc | caatgcacat | cgccaccaag | ctgcgcagca | cgctggacga | ggtgatcgaa | 360 |
| cgcgctatct | atatggtgaa | acgcgcccgt | aattacaccg | atgatgttga | attttcttgc | 420 |
| gaagatgccg | gcgtacacc | cattgccgat | ctggcgcgag | tggtcgaagc | ggcgattaat | 480 |
| gccggtgcca | ccaccatcaa | cattccggac | accgtgggct | acaccatgcc | gtttgagttc | 540 |
| gccggaatca | tcagcggcct | gtatgaacgc | gtgcctaaca | tcgacaaagc | cattatctcc | 600 |
| gtacataccc | acgacgattt | gggcctggcg | gtcggaaact | cactggcggc | ggtacatgcc | 660 |
| ggtgcacgcc | aggtggaagg | cgcaatgaac | gggatcggcg | agcgtgccgg | aaactgttcc | 720 |
| ctggaagaag | tcatcatggc | gatcaaagtt | cgtaaggata | ttctcaacgt | ccacaccgcc | 780 |
| attaatcacc | aggagatatg | cgcaccagc | cagttagtta | gccagatttg | taatatgccg | 840 |
| atcccggcaa | acaaagccat | tgttggcagc | ggcgcattcg | cacactcctc | cggtatacac | 900 |
| caggatggcg | tgctgaaaaa | ccgcgaaaac | tacgaaatca | tgacaccaga | atctattggt | 960 |
| ctgaaccaaa | tccagctgaa | tctgacctct | cgttcggggc | gtgcggcggt | gaaacatcgc | 1020 |
| atggatgaga | tggggtataa | agaaagtgaa | tataatttag | acaatttgta | cgatgctttc | 1080 |
| ctgaagctgg | cggacaaaaa | aggtcaggtg | tttgattacg | atctggaggc | gctggccttc | 1140 |
| atcggtaagc | agcaagaaga | gccggagcat | ttccgtctgg | attacttcag | cgtgcagtct | 1200 |
| ggctctaacg | atatcgccac | cgccgccgtc | aaactggcct | gtggcgaaga | agtcaaagca | 1260 |
| gaagccgcca | acgtaacgg | tccggtcgat | gccgtctatc | aggcaattaa | ccgcatcact | 1320 |
| gaatataacg | tcgaactggt | gaaatacagc | ctgaccgcca | aggccacgg | taaagatgcg | 1380 |
| ctgggtcagt | ggatatcgt | cgctaactac | aacggtcgcc | gcttccacgg | cgtcggcctg | 1440 |
| gctaccgata | ttgtcgagtc | atctgccaaa | gccatggtgc | acgttctgaa | caatatctgg | 1500 |
| cgtgccgcag | aagtcgaaaa | agagttgcaa | cgcaaagctc | aacacaacga | aaacaacaag | 1560 |
| gaaaccgtgt | ga | | | | | 1572 |

<210> SEQ ID NO 64
<211> LENGTH: 1092
<212> TYPE: DNA
<213> ORGANISM: Escherichia coli

<400> SEQUENCE: 64

| | | | | | |
|---|---|---|---|---|---|
| atgtcgaaga | attaccatat | tgccgtattg | ccggggacg | gtattggtcc | ggaagtgatg | 60 |
| acccaggcgc | tgaaagtgct | ggatgccgtg | cgcaaccgct | ttgcgatgcg | catcaccacc | 120 |
| agccattacg | atgtaggcgg | cgcagccatt | gataaccacg | ggcaaccact | gccgcctgcg | 180 |

| | |
|---|---|
| acggttgaag gttgtgagca agccgatgcc gtgctgtttg gctcggtagg cggcccgaag | 240 |
| tgggaacatt taccaccaga ccagcaacca gaacgcggcg cgctgctgcc tctgcgtaag | 300 |
| cacttcaaat tattcagcaa cctgcgcccg gcaaaactgt atcaggggct ggaagcattc | 360 |
| tgtccgctgc gtgcagacat tgccgcaaac ggcttcgaca tcctgtgtgt gcgcgaactg | 420 |
| accggcggca tctatttcgg tcagccaaaa ggccgcgaag gtagcggaca atatgaaaaa | 480 |
| gcctttgata ccgaggtgta tcaccgtttt gagatcgaac gtatcgcccg catcgcgttt | 540 |
| gaatctgctc gcaagcgtcg ccacaaagtg acgtcgatcg ataaagccaa cgtgctgcaa | 600 |
| tcctctattt tatggcggga gatcgttaac gagatcgcca cggaataccc ggatgtcgaa | 660 |
| ctggcgcata tgtacatcga caacgccacc atgcagctga ttaaagatcc atcacagttt | 720 |
| gacgttctgc tgtgctccaa cctgtttggc gacattctgt ctgacgagtg cgcaatgatc | 780 |
| actggctcga tggggatgtt gccttccgcc agcctgaacg agcaaggttt tggactgtat | 840 |
| gaaccggcgg gcggctcggc accagatatc gcaggcaaaa acatcgccaa cccgattgca | 900 |
| caaatccttt cgctggcact gctgctgcgt tacagcctgg atgccgatga tgcggcttgc | 960 |
| gccattgaac gcgccattaa ccgcgcatta agaaggca ttcgcaccgg ggatttagcc | 1020 |
| cgtggcgctg ccgccgttag taccgatgaa atgggcgata tcattgcccg ctatgtagca | 1080 |
| gaagggtgt aa | 1092 |

<210> SEQ ID NO 65
<211> LENGTH: 1401
<212> TYPE: DNA
<213> ORGANISM: Escherichia coli

<400> SEQUENCE: 65

| | |
|---|---|
| atggctaaga cgttatacga aaaattgttc gacgctcacg ttgtgtacga agccgaaaac | 60 |
| gaaaccccac tgttatatat cgaccgccac ctggtgcatg aagtgacctc accgcaggcg | 120 |
| ttcgatggtc tgcgcgccca cggtcgcccg gtacgtcagc cgggcaaaac cttcgctacc | 180 |
| atggatcaca acgtctctac ccagaccaaa gacattaatg cctgcggtga atggcgcgt | 240 |
| atccagatgc aggaactgat caaaaactgc aaagaatttg cgtcgaact gtatgacctg | 300 |
| aatcacccgt atcagggga cgtccacgta atggggccgg aacagggcgt caccttgccg | 360 |
| gggatgacca tttgtctgcg gcgactcgca tccgccaccc acggcgcgtt tggcgcactg | 420 |
| gcctttggta tcggcacttc cgaagttgaa cacgtactgg caacgcaaac cctgaaacag | 480 |
| ggccgcgcaa aaaccatgaa aattgaagtc caggcaaag ccgcgccggg cattaccgca | 540 |
| aaagatatcg tgctggcaat tatcggtaaa accggtagcg caggcggcac cgggcatgtg | 600 |
| gtggagtttt gcggcgaagc aatccgtgat ttaagcatgg aaggtcgtat gaccctgtgc | 660 |
| aatatggcaa tcgaaatggg cgcaaaagcc ggtctggttg caccggacga aaccaccttt | 720 |
| aactatgtca aaggccgtct gcatgcgccg aaaggcaaag atttcgacga cgccgttgcc | 780 |
| tactggaaaa ccctgcaaac cgacgaaggc gcaacttccg ataccgttgt cactctgcaa | 840 |
| gcagaagaaa tttcaccgca ggtcacctgg ggcaccaatc ccggccaggt gatttccgtg | 900 |
| aacgacaata ttcccgatcc ggcttcgttt gccgatccgg ttgaacgcgc gtcggcagaa | 960 |
| aaagcgctgg cctatatggg gctgaaaccg ggtattccgc tgaccgaagt ggctatcgac | 1020 |
| aaagtgttta tcggttcctg taccaactcg cgcattgaag atttacgcgc ggcagcggag | 1080 |
| atcgccaaag gcgaaaagt cgcgccaggc gtgcaggcac tggtggttcc cggctctggc | 1140 |
| ccggtaaaag cccaggcgga agcggaaggt ctggataaaa tctttattga agccggtttt | 1200 |

```
gaatggcgct tgcctggctg ctcaatgtgt ctggcgatga acaacgaccg tctgaatccg      1260
ggcgaacgtt gtgcctccac cagcaaccgt aactttgaag ccgccagggg cgcggcgggg      1320
cgcacgcatc tggtcagccc ggcaatggct gccgctgctg ctgtgaccgg acatttcgcc      1380
gacattcgca acattaaata a                                                1401
```

<210> SEQ ID NO 66
<211> LENGTH: 548
<212> TYPE: PRT
<213> ORGANISM: Lactococcus lactis

<400> SEQUENCE: 66

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Pro Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Asn Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Thr Leu Pro Ser Phe Leu Gly Ile
                245                 250                 255

Tyr Asn Gly Lys Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Ser Ile Gln Asn Phe Asp Phe
305                 310                 315                 320

Glu Ser Leu Ile Ser Ser Leu Leu Asp Leu Ser Gly Ile Glu Tyr Lys
                325                 330                 335
```

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
        370                 375                 380

Ser Ser Ile Phe Leu Lys Pro Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Glu Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Val Leu Ala Lys
        515                 520                 525

Glu Asp Ala Pro Lys Val Leu Lys Met Gly Lys Leu Phe Ala Glu
    530                 535                 540

Gln Asn Lys Ser
545

<210> SEQ ID NO 67
<211> LENGTH: 552
<212> TYPE: PRT
<213> ORGANISM: Enterobacter cloacae

<400> SEQUENCE: 67

Met Arg Thr Pro Tyr Cys Val Ala Asp Tyr Leu Leu Asp Arg Leu Thr
1               5                   10                  15

Asp Cys Gly Ala Asp His Leu Phe Gly Val Pro Gly Asp Tyr Asn Leu
                20                  25                  30

Gln Phe Leu Asp His Val Ile Asp Ser Pro Asp Ile Cys Trp Val Gly
            35                  40                  45

Cys Ala Asn Glu Leu Asn Ala Ser Tyr Ala Ala Asp Gly Tyr Ala Arg
        50                  55                  60

Cys Lys Gly Phe Ala Ala Leu Leu Thr Thr Phe Gly Val Gly Glu Leu
65                  70                  75                  80

Ser Ala Met Asn Gly Ile Ala Gly Ser Tyr Ala Glu His Val Pro Val
                85                  90                  95

Leu His Ile Val Gly Ala Pro Gly Thr Ala Ala Gln Gln Arg Gly Glu
            100                 105                 110

Leu Leu His His Thr Leu Gly Asp Gly Glu Phe Arg His Phe Tyr His
        115                 120                 125

Met Ser Glu Pro Ile Thr Val Ala Gln Ala Val Leu Thr Glu Gln Asn
    130                 135                 140

Ala Cys Tyr Glu Ile Asp Arg Val Leu Thr Thr Met Leu Arg Glu Arg

```
            145                 150                 155                 160
        Arg Pro Gly Tyr Leu Met Leu Pro Ala Asp Val Ala Lys Lys Ala Ala
                        165                 170                 175

Thr Pro Pro Val Asn Ala Leu Thr His Lys Gln Ala His Ala Asp Ser
                        180                 185                 190

Ala Cys Leu Lys Ala Phe Arg Asp Ala Ala Glu Asn Lys Leu Ala Met
                        195                 200                 205

Ser Lys Arg Thr Ala Leu Leu Ala Asp Phe Leu Val Leu Arg His Gly
                        210                 215                 220

Leu Lys His Ala Leu Gln Lys Trp Val Lys Glu Val Pro Met Ala His
        225                 230                 235                 240

Ala Thr Met Leu Met Gly Lys Gly Ile Phe Asp Glu Arg Gln Ala Gly
                        245                 250                 255

Phe Tyr Gly Thr Tyr Ser Gly Ser Ala Ser Thr Gly Ala Val Lys Glu
                        260                 265                 270

Ala Ile Glu Gly Ala Asp Thr Val Leu Cys Val Gly Thr Arg Phe Thr
                        275                 280                 285

Asp Thr Leu Thr Ala Gly Phe Thr His Gln Leu Thr Pro Ala Gln Thr
                        290                 295                 300

Ile Glu Val Gln Pro His Ala Ala Arg Val Gly Asp Val Trp Phe Thr
        305                 310                 315                 320

Gly Ile Pro Met Asn Gln Ala Ile Glu Thr Leu Val Glu Leu Cys Lys
                        325                 330                 335

Gln His Val His Ala Gly Leu Met Ser Ser Ser Gly Ala Ile Pro
                        340                 345                 350

Phe Pro Gln Pro Asp Gly Ser Leu Thr Gln Glu Asn Phe Trp Arg Thr
                        355                 360                 365

Leu Gln Thr Phe Ile Arg Pro Gly Asp Ile Ile Leu Ala Asp Gln Gly
                        370                 375                 380

Thr Ser Ala Phe Gly Ala Ile Asp Leu Arg Leu Pro Ala Asp Val Asn
        385                 390                 395                 400

Phe Ile Val Gln Pro Leu Trp Gly Ser Ile Gly Tyr Thr Leu Ala Ala
                        405                 410                 415

Ala Phe Gly Ala Gln Thr Ala Cys Pro Asn Arg Arg Val Ile Val Leu
                        420                 425                 430

Thr Gly Asp Gly Ala Ala Gln Leu Thr Ile Gln Glu Leu Gly Ser Met
                        435                 440                 445

Leu Arg Asp Lys Gln His Pro Ile Ile Leu Val Leu Asn Asn Glu Gly
        450                 455                 460

Tyr Thr Val Glu Arg Ala Ile His Gly Ala Glu Gln Arg Tyr Asn Asp
        465                 470                 475                 480

Ile Ala Leu Trp Asn Trp Thr His Ile Pro Gln Ala Leu Ser Leu Asp
                        485                 490                 495

Pro Gln Ser Glu Cys Trp Arg Val Ser Glu Ala Glu Gln Leu Ala Asp
                        500                 505                 510

Val Leu Glu Lys Val Ala His His Glu Arg Leu Ser Leu Ile Glu Val
                        515                 520                 525

Met Leu Pro Lys Ala Asp Ile Pro Pro Leu Leu Gly Ala Leu Thr Lys
                        530                 535                 540

Ala Leu Glu Ala Cys Asn Asn Ala
        545                 550

<210> SEQ ID NO 68
```

<211> LENGTH: 555
<212> TYPE: PRT
<213> ORGANISM: Mycobacterium smegmatis

<400> SEQUENCE: 68

```
Met Thr Asp Asp Gly Tyr Thr Val Gly Asp Tyr Leu Leu Asp Arg Leu
1               5                   10                  15

Ala Glu Leu Gly Val Thr Glu Val Phe Gly Val Pro Gly Asp Tyr Gln
            20                  25                  30

Leu Glu Phe Leu Asp His Val Ala His Pro Arg Ile Thr Trp Val
        35                  40                  45

Gly Gly Ala Asn Glu Leu Asn Ala Gly Tyr Ala Ala Asp Gly Tyr Gly
50                  55                  60

Arg Leu Arg Gly Met Ala Ala Leu Val Thr Thr Phe Gly Val Gly Glu
65                  70                  75                  80

Leu Ser Ala Ala Asn Ala Ile Ala Gly Ser Tyr Ala Glu His Val Pro
                85                  90                  95

Val Val His Ile Val Gly Ala Pro Ser Lys Asp Ser Gln Ala Ala Arg
            100                 105                 110

Arg Ile Val His His Thr Leu Gly Asp Gly Asp Phe Glu His Phe Leu
        115                 120                 125

Arg Met Ser Arg Glu Ile Thr Cys Ala Gln Ala Asn Leu Val Pro Ala
130                 135                 140

Thr Ala Thr Arg Glu Ile Asp Arg Val Leu Ser Glu Val His Glu Gln
145                 150                 155                 160

Lys Arg Pro Gly Tyr Leu Leu Ile Ala Thr Asp Val Ala Arg Phe Pro
                165                 170                 175

Thr Glu Pro Pro Thr Ala Pro Leu Pro Arg His Ser Gly Gly Thr Ser
            180                 185                 190

Pro Arg Ala Leu Ser Leu Phe Thr Glu Ala Ala Thr Gln Leu Ile Gly
        195                 200                 205

Glu His Arg Leu Thr Val Leu Ala Asp Phe Leu His Arg Met Gly
210                 215                 220

Cys Val Glu Ala Leu Asn Lys Leu Leu Thr Ala Asp Thr Val Pro His
225                 230                 235                 240

Ala Thr Leu Met Trp Gly Lys Ser Leu Val Asp Glu Ser Ser Pro Asn
                245                 250                 255

Phe Leu Gly Ile Tyr Ala Gly Ala Ala Ser Glu Gly Ser Val Arg Glu
            260                 265                 270

Val Ile Glu Asp Ala Pro Val Leu Val Thr Ala Gly Val Leu Phe Thr
        275                 280                 285

Asp Met Val Ser Gly Phe Phe Ser Gln Arg Ile Asp Pro Ala Arg Thr
290                 295                 300

Ile Asp Ile Gly Val Asn Gln Ser Val Val Ala Gly Gln Val Phe Ala
305                 310                 315                 320

Pro Leu Asp Met Ala Ala Ala Leu Asp Ala Leu Ala Ser Ile Leu Ala
                325                 330                 335

Glu Arg Gly Ile Glu Ser Pro Ala Leu Pro Ala Pro Ala Pro Gln
            340                 345                 350

Arg Pro Ala Pro Pro Arg Asp Ala Val Leu Thr Gln Glu Ala Leu
        355                 360                 365

Trp Asp Arg Leu Ala Glu Ala Leu Thr Pro Gly Asn Val Val Leu Ala
370                 375                 380

Asp Gln Gly Thr Ser Phe Tyr Gly Leu Ala Gly His Arg Leu Ala Ser
```

```
                385                 390                 395                 400
Gly Val Thr Phe Ile Gly Gln Pro Leu Trp Ala Ser Ile Gly Tyr Thr
                    405                 410                 415

Leu Pro Ala Ala Leu Gly Ala Gly Leu Ala Asp Arg Asp Arg Arg Thr
                420                 425                 430

Val Leu Leu Ile Gly Asp Gly Ala Ala Gln Leu Thr Val Gln Glu Leu
            435                 440                 445

Gly Ala Phe Gly Arg Glu Gly Leu Thr Pro Val Val Val Val Val Asn
        450                 455                 460

Asn Asn Gly Tyr Thr Val Glu Arg Ala Ile His Gly Val Thr Ala Arg
465                 470                 475                 480

Tyr Asn Asp Ile Thr Ala Trp Arg Trp Thr Glu Leu Pro Ala Ala Leu
                    485                 490                 495

Gly Val Pro Asp Ala Leu Thr Phe Arg Cys Ala Thr Tyr Gly Glu Leu
                500                 505                 510

Asp Asp Ala Leu Thr Val Ala Ala Glu Thr Gln Asp Arg Met Val Phe
            515                 520                 525

Val Glu Val Met Leu Glu Arg Met Asp Ile Pro Pro Leu Leu Gly Glu
        530                 535                 540

Leu Ala Gln Ser Ala Ser Ala Ala Asn Ala Lys
545                 550                 555

<210> SEQ ID NO 69
<211> LENGTH: 1647
<212> TYPE: DNA
<213> ORGANISM: Lactococcus lactis

<400> SEQUENCE: 69
atgtatacag taggagatta cctattagac cgattacacg agttaggaat tgaagaaatt      60
tttggagtcc ctggagacta taacttacaa ttttttagatc aaattatttc ccgcaaggat    120
atgaaatggg tcgaaatgc taatgaatta atgcttcttt atatggctga tggctatgct     180
cgtactaaaa aagctgccgc atttcttaca acctttggag taggtgaatt gagtgcagtt    240
aatggattag caggaagtta cgccgaaaat ttaccagtag tagaaatagt gggatcacct    300
acatcaaaag tccaaaatga aggaaaattt gttcatcata cgctggctga cggtgatttt    360 aaacactttta tgaaaatgca cgaacctgtt acagcagctc gaactttact gacagcagaa    420
aatgcaaccg ttgaaattga ccgagtactt tctgcactac taaaagaaag aaaacctgtc    480
tatatcaact accagttga tgttgctgct gcaaaagcag agaaaccctc actcccttttg    540 aaaaaagaaa atccaacttc aaatacaagt gaccaagaga ttttgaataa aattcaagaa    600
agcttgaaaa atgccaaaaa accaatcgtg attacaggac atgaaataat tagctttggc    660
ttagaaaata cagtcactca atttatttca aagacaaaac tccctattac gacattaaac    720
tttgaaaaaa gttcagttga tgaaactctc ccttcatttt taggaatcta taatggtaaa    780
ctctcagagc ctaatcttaa agaattcgtg aatcagccg acttcatcct gatgcttgga    840
gttaaactca cagactcttc aacaggagca tttacccatc atttaaatga aaataaaatg    900
atttcactga acatagacga aggaaaaata tttaacgaaa gcatccaaaa ttttgatttt    960
gaatccctca tctcctctct cttagaccta agcggaatag aatacaaagg aaaatatatc   1020
gataaaaagc aagaagactt tgttccatca aatgcgcttt tatcacaaga ccgcctatgg   1080
caagcagttg aaaaccctaac tcaaagcaat gaaacaatcg ttgctgaaca agggacatca   1140 ttcttttggcg cttcatcaat tttcttaaaa ccaaagagtc attttattgg tcaacccttta   1200
```

| | |
|---|---|
| tggggatcaa ttggatatac attcccagca gcattaggaa gccaaattgc agataaagaa | 1260 |
| agcagacacc ttttatttat tggtgatggt tcacttcaac ttacagtgca agaattagga | 1320 |
| ttagcaatca gagaaaaaat taatccaatt tgctttatta tcaataatga tggttataca | 1380 |
| gtcgaaagag aaattcatgg accaaatcaa agctacaatg atattccaat gtggaattac | 1440 |
| tcaaaattac cagaatcatt tggagcaaca aagaacgag tagtctcgaa atcgttaga | 1500 |
| actgaaaatg aatttgtgtc tgtcatgaaa gaagctcaag cagatccaaa tagaatgtac | 1560 |
| tggattgagt tagttttggc aaaagaagat gcaccaaaag tactgaaaaa atgggtaaa | 1620 |
| ctatttgctg aacaaaataa atcataa | 1647 |

<210> SEQ ID NO 70
<211> LENGTH: 1668
<212> TYPE: DNA
<213> ORGANISM: Mycobacterium smegmatis

<400> SEQUENCE: 70

| | |
|---|---|
| atgaccgatg acggctacac agtcggtgac tacctcctgg accggctcgc cgaactcggc | 60 |
| gtgaccgagg tcttcggcgt ccccggcgac tatcagctgg agttcctcga ccacgtcgtg | 120 |
| gcgcacccgc gcatcacgtg ggtcggcggc gcgaacgaac tcaacgcggg ctacgcggcc | 180 |
| gacggctacg gccggctgcg gggcatggcg gcgttggtca ccacgttcgg cgtcggtgag | 240 |
| ctctcggcgg ccaacgccat cgcaggcagc tacgccgagc acgtcccggt ggtgcacatc | 300 |
| gtcggcgcgc cgtcgaagga ttcgcaggcc gcgcggcgca tcgtgcacca cacgctgggt | 360 |
| gacggcgatt tcgagcactt cctgcgcatg agccgcgaga tcacctgcgc gcaggccaat | 420 |
| ctggtgcccg ccacgcgac ccgcgagatc gaccgcgtgc tctcggaggt gcacgagcag | 480 |
| aagcggcccg gctatctgct gatcgcgacc gacgtcgccc gcttccccac cgaaccaccg | 540 |
| accgccccgc tgccgcgcca cagcggggc accagcccac gggcgctgtc gctgttcacc | 600 |
| gaggccgcaa cgcaactcat cggcgagcac cggttgaccg tgctggccga tttcctggtg | 660 |
| caccgcatgg gatgcgtcga ggcgctcaac aagctgctga ccgccgacac cgtgccgcac | 720 |
| gccacgctga tgtggggcaa gagcctggtc gacgagagtt cgccgaactt cctgggcatc | 780 |
| tacgccggtg cggccagtga gggctcggtg cgcgaggtga tcgaggacgc gcctgtgctg | 840 |
| gtgaccgcag gtgtgctgtt caccgacatg gtcagcgggt tcttcagcca gcgcatcgac | 900 |
| ccggcacgca cgatcgacat cggggtcaac cagagcgtcg tcgccgggca ggtgttcgcg | 960 |
| ccgctggaca tggctgccgc gctcgacgcg ctcgcgtcga tcctcgccga acgcggcatc | 1020 |
| gagtcgcccg cactgccgcc ggccccgca ccgcagcggc ccgcagcgcc gccgcgtgac | 1080 |
| gcggtgctta cacaggaagc gttgtgggac aggctcgccg aggcgttgac gccgggcaac | 1140 |
| gtggtgctcg ccgaccaggg cacgtctttc tacggcctgg ccgggcaccg gctggcgtcg | 1200 |
| ggcgtgacat tcatcggtca gccgttgtgg cgtcgatcg gctacacact gcccgccgcg | 1260 |
| ctcggcgcgg gtctggccga ccgcgaccgg cgcacggtgc tgctgatcgg cgacggcgca | 1320 |
| gcgcagttga cggtcagga actcggcgcg ttcggccgcg aggggctcac gcccgtggtg | 1380 |
| gtggtcgtca acaacaacgg ctacaccgtg gagcgcgcga tccacggtgt cacggcccgc | 1440 |
| tacaacgaca tcacggcgtg gcggtggacc gagttgccgg ccgcactcgg tgtgccgat | 1500 |
| gcgctgacgt tccgctgcgc cacctacggc gaactgacg acgcgctgac cgtcgccgcc | 1560 |
| gagacgcagg accgcatggt gttcgtcgag gtgatgcttg agcgcatgga cattccgccg | 1620 | ctgctgggcg agctcgcaca gtcggcgtcg gccgccaacg ccaaatag        1668

<210> SEQ ID NO 71
<211> LENGTH: 568
<212> TYPE: PRT
<213> ORGANISM: Zymomonas mobilis

<400> SEQUENCE: 71

```
Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365
```

-continued

```
Glu Ile Ala Arg Gln Val Glu Ala Leu Leu Thr Pro Asn Thr Thr Val
        370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565
```

<210> SEQ ID NO 72
<211> LENGTH: 563
<212> TYPE: PRT
<213> ORGANISM: Saccharomyces cerevisiae

<400> SEQUENCE: 72

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175
```

Pro Ala Lys Leu Leu Gln Thr Pro Ile Asp Met Ser Leu Lys Pro Asn
        180                 185                 190

Asp Ala Glu Ser Glu Lys Glu Val Ile Asp Thr Ile Leu Ala Leu Val
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
        370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
            515                 520                 525

Asp Asn Ser Lys Ile Arg Met Ile Glu Ile Met Leu Pro Val Phe Asp
            530                 535                 540

Ala Pro Gln Asn Leu Val Glu Gln Ala Lys Leu Thr Ala Ala Thr Asn
545                 550                 555                 560

Ala Lys Gln

<210> SEQ ID NO 73
<211> LENGTH: 607
<212> TYPE: PRT

<213> ORGANISM: Arabidopsis thaliana

<400> SEQUENCE: 73

```
Met Asp Thr Lys Ile Gly Ser Ile Asp Asp Cys Lys Pro Thr Asn Gly
1               5                   10                  15

Asp Val Cys Ser Pro Thr Asn Gly Thr Val Ala Thr Ile His Asn Ser
            20                  25                  30

Val Pro Ser Ser Ala Ile Thr Ile Asn Tyr Cys Asp Ala Thr Leu Gly
        35                  40                  45

Arg His Leu Ala Arg Arg Leu Val Gln Ala Gly Val Thr Asp Val Phe
    50                  55                  60

Ser Val Pro Gly Asp Phe Asn Leu Thr Leu Leu Asp His Leu Met Ala
65                  70                  75                  80

Glu Pro Asp Leu Asn Leu Ile Gly Cys Cys Asn Glu Leu Asn Ala Gly
                85                  90                  95

Tyr Ala Ala Asp Gly Tyr Ala Arg Ser Arg Gly Val Gly Ala Cys Val
            100                 105                 110

Val Thr Phe Thr Val Gly Gly Leu Ser Val Leu Asn Ala Ile Ala Gly
        115                 120                 125

Ala Tyr Ser Glu Asn Leu Pro Leu Ile Cys Ile Val Gly Gly Pro Asn
    130                 135                 140

Ser Asn Asp Tyr Gly Thr Asn Arg Ile Leu His His Thr Ile Gly Leu
145                 150                 155                 160

Pro Asp Phe Ser Gln Glu Leu Arg Cys Phe Gln Thr Val Thr Cys Tyr
                165                 170                 175

Gln Ala Val Val Asn Asn Leu Asp Asp Ala His Glu Gln Ile Asp Lys
            180                 185                 190

Ala Ile Ser Thr Ala Leu Lys Glu Ser Lys Pro Val Tyr Ile Ser Val
        195                 200                 205

Ser Cys Asn Leu Ala Ala Ile Pro His His Thr Phe Ser Arg Asp Pro
    210                 215                 220

Val Pro Phe Ser Leu Ala Pro Arg Leu Ser Asn Lys Met Gly Leu Glu
225                 230                 235                 240

Ala Ala Val Glu Ala Thr Leu Glu Phe Leu Asn Lys Ala Val Lys Pro
                245                 250                 255

Val Met Val Gly Gly Pro Lys Leu Arg Val Ala Lys Ala Cys Asp Ala
            260                 265                 270

Phe Val Glu Leu Ala Asp Ala Ser Gly Tyr Ala Leu Ala Met Met Pro
        275                 280                 285

Ser Ala Lys Gly Phe Val Pro Glu His His Pro His Phe Ile Gly Thr
    290                 295                 300

Tyr Trp Gly Ala Val Ser Thr Pro Phe Cys Ser Glu Ile Val Glu Ser
305                 310                 315                 320

Ala Asp Ala Tyr Ile Phe Ala Gly Pro Ile Phe Asn Asp Tyr Ser Ser
                325                 330                 335

Val Gly Tyr Ser Leu Leu Leu Lys Glu Lys Ala Ile Val Val Gln
            340                 345                 350

Pro Asp Arg Ile Thr Val Ala Asn Gly Pro Thr Phe Gly Cys Ile Leu
        355                 360                 365

Met Ser Asp Phe Phe Arg Glu Leu Ser Lys Arg Val Lys Arg Asn Glu
    370                 375                 380

Thr Ala Tyr Glu Asn Tyr His Arg Ile Phe Val Pro Glu Gly Lys Pro
385                 390                 395                 400
```

```
Leu Lys Cys Glu Ser Arg Glu Pro Leu Arg Val Asn Thr Met Phe Gln
                405                 410                 415

His Ile Gln Lys Met Leu Ser Ser Glu Thr Ala Val Ile Ala Glu Thr
            420                 425                 430

Gly Asp Ser Trp Phe Asn Cys Gln Lys Leu Lys Leu Pro Lys Gly Cys
        435                 440                 445

Gly Tyr Glu Phe Gln Met Gln Tyr Gly Ser Ile Gly Trp Ser Val Gly
    450                 455                 460

Ala Thr Leu Gly Tyr Ala Gln Ala Ser Pro Glu Lys Arg Val Leu Ala
465                 470                 475                 480

Phe Ile Gly Asp Gly Ser Phe Gln Val Thr Val Gln Asp Ile Ser Thr
                485                 490                 495

Met Leu Arg Asn Gly Gln Lys Thr Ile Ile Phe Leu Ile Asn Asn Gly
            500                 505                 510

Gly Tyr Thr Ile Glu Val Glu Ile His Asp Gly Pro Tyr Asn Val Ile
        515                 520                 525

Lys Asn Trp Asn Tyr Thr Gly Leu Val Asp Ala Ile His Asn Gly Glu
    530                 535                 540

Gly Asn Cys Trp Thr Ala Lys Val Arg Tyr Glu Glu Glu Leu Val Glu
545                 550                 555                 560

Ala Ile Thr Thr Ala Thr Thr Glu Lys Lys Asp Cys Leu Cys Phe Ile
                565                 570                 575

Glu Val Ile Leu His Lys Asp Asp Thr Ser Lys Glu Leu Leu Glu Trp
            580                 585                 590

Gly Ser Arg Val Ser Ala Ala Asn Ser Arg Pro Pro Asn Pro Gln
        595                 600                 605

<210> SEQ ID NO 74
<211> LENGTH: 558
<212> TYPE: PRT
<213> ORGANISM: Bacillus cereus

<400> SEQUENCE: 74

Met Lys Thr Gln Tyr Thr Val Ser Thr Tyr Leu Leu Asp Arg Leu Ser
1               5                   10                  15

Glu Leu Gly Ile Glu His Ile Phe Gly Val Pro Gly Asp Tyr Asn Leu
            20                  25                  30

Ala Phe Leu Asp Asp Val Ile Ala His Glu Asn Val Glu Trp Ile Gly
        35                  40                  45

Asn Cys Asn Glu Leu Asn Ala Ala Tyr Ala Ala Asp Gly Tyr Ala Arg
    50                  55                  60

Ile Lys Gly Ile Ala Ala Leu Ile Thr Thr Phe Gly Val Gly Glu Leu
65                  70                  75                  80

Ser Ala Ile Asn Gly Ile Ala Gly Ser Tyr Ala Glu Asn Val Pro Val
                85                  90                  95

Ile Lys Ile Thr Gly Thr Pro Pro Thr Thr Val Met Glu Asn Gly Ala
            100                 105                 110

Leu Val His His Thr Leu Gly Asp Gly Lys Phe Asp His Phe Ser Asn
        115                 120                 125

Met Tyr Arg Glu Ile Thr Val Ala Gln Ser Lys Leu Thr Pro Glu His
    130                 135                 140

Ala Ala Glu Glu Ile Asp Arg Val Leu Arg Ala Cys Trp Ser Ala Lys
145                 150                 155                 160

Arg Pro Val His Ile Gln Leu Pro Ile Asp Val Tyr Asn Lys Pro Ile
                165                 170                 175
```

```
Asn Lys Pro Thr Glu Pro Ile Leu His Lys Pro Val Ser Asn Lys
        180                 185                 190

Asp Ala Leu Asp Lys Met Leu Leu His Ala Thr Ser Lys Ile Asn Ser
        195                 200                 205

Ala Lys Lys Pro Val Ile Leu Ala Asp Phe Glu Val Glu Arg Phe His
210                 215                 220

Ala Lys Glu Tyr Leu Tyr Gln Phe Val Glu Lys Thr Gly Phe Pro Ile
225                 230                 235                 240

Ala Thr Leu Ser Met Gly Lys Gly Ile Phe Pro Glu Lys His Pro Gln
            245                 250                 255

Phe Ile Gly Ile Tyr Thr Gly Asp Val Ser Pro Tyr Leu Arg Lys
        260                 265                 270

Arg Ile Asp Glu Ser Asp Cys Ile Ile Ser Ile Gly Val Lys Leu Thr
        275                 280                 285

Asp Thr Ile Thr Gly Gly Phe Thr Gln Gly Phe Met Lys Glu Gln Val
        290                 295                 300

Ile Glu Ile His Pro Tyr Thr Val Lys Ile Thr Asp Lys Lys Tyr Gly
305                 310                 315                 320

Pro Val Val Met Lys Asp Val Leu Gln His Leu Ser Asp Leu Ile Glu
            325                 330                 335

His Arg Asn Gly Glu Thr Leu Asp Ile Lys Pro Phe Ile Ser Glu Ser
            340                 345                 350

Leu Ser Ile Thr Glu Lys Phe Asn Pro Lys Pro Gln Met Val Thr Gln
        355                 360                 365

Lys Arg Phe Cys Gln Gln Ile Tyr His Phe Leu Gln Glu Lys Asp Val
        370                 375                 380

Leu Leu Ala Glu Gln Gly Thr Pro Phe Phe Gly Ser Ala Thr Ile Pro
385                 390                 395                 400

Leu Pro Asn Asp Thr Thr Tyr Val Ala Gln Pro Leu Trp Gly Ser Ile
            405                 410                 415

Gly Tyr Thr Leu Pro Ala Leu Leu Gly Thr Gln Leu Ala Asn Leu Ser
        420                 425                 430

Arg Arg Asn Ile Leu Ile Ile Gly Asp Gly Ser Phe Gln Leu Thr Val
        435                 440                 445

Gln Glu Leu Ser Thr Ile Leu Arg Gln Asn Leu Asn Pro Ile Ile Phe
450                 455                 460

Leu Ile Asn Asn Asn Gly Tyr Thr Val Glu Arg Ala Ile His Gly Gln
465                 470                 475                 480

Asn Glu Pro Tyr Asn Asp Ile Gln Met Trp Asp Tyr Thr Lys Leu Ala
            485                 490                 495

Asn Val Phe Gly Thr Glu Glu Lys Ser Leu Thr Cys Lys Val Glu Asn
            500                 505                 510

Glu Ile Glu Leu Gln Glu Val Leu Thr Lys Ile Ser Asn Asp Lys Asp
        515                 520                 525

Gln Leu Thr Phe Val Glu Val Met Ser Gln Gly Asp Gln Pro Glu
        530                 535                 540

Leu Leu Ala Lys Leu Gly Lys Arg Phe Gly Gln Gln Asn Ser
545                 550                 555

<210> SEQ ID NO 75
<211> LENGTH: 1707
<212> TYPE: DNA
<213> ORGANISM: Zymomonas mobilis
```

<400> SEQUENCE: 75

```
atgagttata ctgtcggtac ctatttagcg gagcggcttg tccagattgg tctcaagcat      60
cacttcgcag tcgcgggcga ctacaacctc gtccttcttg acaacctgct tttgaacaaa     120
aacatggagc aggtttattg ctgtaacgaa ctgaactgcg gtttcagtgc agaaggttat     180
gctcgtgcca aggcgcagc agcagccgtc gttacctaca gcgtcggtgc gctttccgca     240
tttgatgcta tcggtggcgc ctatgcagaa aaccttccgg ttatcctgat ctccggtgct     300
ccgaacaaca atgatcacgc tgctggtcac gtgttgcatc acgctcttgg caaaaccgac     360
tatcactatc agttggaaat ggccaagaac atcacggccg ccgctgaagc gatttacacc     420
ccggaagaag ctccggctaa aatcgatcac gtgattaaaa ctgctcttcg tgagaagaag     480
ccggtttatc tcgaaatcgc ttgcaacatt gcttccatgc cctgcgccgc tcctggaccg     540
gcaagcgcat tgttcaatga cgaagccagc gacgaagctt ctttgaatgc agcggttgaa     600
gaaaccctga attcatcgc caaccgcgac aaagttgccg tcctcgtcgg cagcaagctg     660
cgcgcagctg gtgctgaaga gctgctgtc aaatttgctg atgctctcgg tggcgcagtt     720
gctaccatgg ctgctgcaaa aagcttcttc ccagaagaaa accgcatta tcggcacc      780
tcatggggtg aagtcagcta ccgggcgtt gaaaagacga tgaaagaagc cgatgcggtt     840
atcgctctgg ctcctgtctt caacgactac tccaccactg gttggacgga tattcctgat     900
cctaagaaac tggttctcgc tgaaccgcgt tctgtcgtcg ttaacggcat tcgcttcccc     960
agcgtccatc tgaaagacta tctgacccgt ttggctcaga agttttccaa gaaaaccggt    1020
gcattggact cttcaaaatc cctcaatgca ggtgaactga gaaagccgc tccggctgat    1080
ccgagtgctc cgttggtcaa cgcagaaatc gcccgtcagg tcgaagctct tctgaccccg    1140
aacacgacgg ttattgctga aaccggtgac tcttggttca atgctcagcg catgaagctc    1200
ccgaacggtg ctcgcgttga atatgaaatg cagtggggtc acattggttg gtccgttcct    1260
gccgccttcg gttatgccgt cggtgctccg gaacgtcgca acatcctcat ggttggtgat    1320
ggttccttcc agctgacggc tcaggaagtc gctcagatgg ttcgcctgaa actgccggtt    1380
atcatcttct tgatcaataa ctatggttac accatcgaag ttatgatcca tgatggtccg    1440
tacaacaaca tcaagaactg ggattatgcc ggtctgatgg aagtgttcaa cggtaacggt    1500
ggttatgaca gcggtgctgg taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                        1707
```

<210> SEQ ID NO 76
<211> LENGTH: 528
<212> TYPE: PRT
<213> ORGANISM: Pseudomonas putida

<400> SEQUENCE: 76

```
Met Ala Ser Val His Gly Thr Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
        35                  40                  45

Cys Val Val Gly Ile Ala Asp Gly Tyr Ala Gln Ala Ser Arg Lys Pro
    50                  55                  60
```

```
Ala Phe Ile Asn Leu His Ser Ala Ala Gly Thr Gly Asn Ala Met Gly
 65                  70                  75                  80

Ala Leu Ser Asn Ala Trp Asn Ser His Ser Pro Leu Ile Val Thr Ala
                 85                  90                  95

Gly Gln Gln Thr Arg Ala Met Ile Gly Val Glu Ala Leu Leu Thr Asn
            100                 105                 110

Val Asp Ala Ala Asn Leu Pro Arg Pro Leu Val Lys Trp Ser Tyr Glu
        115                 120                 125

Pro Ala Ser Ala Ala Glu Val Pro His Ala Met Ser Arg Ala Ile His
    130                 135                 140

Met Ala Ser Met Ala Pro Gln Gly Pro Val Tyr Leu Ser Val Pro Tyr
145                 150                 155                 160

Asp Asp Trp Asp Lys Asp Ala Asp Pro Gln Ser His His Leu Phe Asp
                165                 170                 175

Arg His Val Ser Ser Val Arg Leu Asn Asp Gln Asp Leu Asp Ile
            180                 185                 190

Leu Val Lys Ala Leu Asn Ser Ala Ser Asn Pro Ala Ile Val Leu Gly
        195                 200                 205

Pro Asp Val Asp Ala Ala Asn Ala Asn Ala Asp Cys Val Met Leu Ala
210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Gly His Asp Val Val Leu Val
            260                 265                 270

Ile Gly Ala Pro Val Phe Arg Tyr His Gln Tyr Asp Pro Gly Gln Tyr
        275                 280                 285

Leu Lys Pro Gly Thr Arg Leu Ile Ser Val Thr Cys Asp Pro Leu Glu
290                 295                 300

Ala Ala Arg Ala Pro Met Gly Asp Ala Ile Val Ala Asp Ile Gly Ala
305                 310                 315                 320

Met Ala Ser Ala Leu Ala Asn Leu Val Glu Glu Ser Ser Arg Gln Leu
                325                 330                 335

Pro Thr Ala Ala Pro Glu Pro Ala Lys Val Asp Gln Asp Ala Gly Arg
            340                 345                 350

Leu His Pro Glu Thr Val Phe Asp Thr Leu Asn Asp Met Ala Pro Glu
        355                 360                 365

Asn Ala Ile Tyr Leu Asn Glu Ser Thr Ser Thr Thr Ala Gln Met Trp
370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
        435                 440                 445

Ile Phe Val Ile Met Asn Asn Gly Thr Tyr Gly Ala Leu Arg Trp Phe
    450                 455                 460

Ala Gly Val Leu Glu Ala Glu Asn Val Pro Gly Leu Asp Val Pro Gly
465                 470                 475                 480
```

```
Ile Asp Phe Arg Ala Leu Ala Lys Gly Tyr Gly Val Gln Ala Leu Lys
                485                 490                 495

Ala Asp Asn Leu Glu Gln Leu Lys Gly Ser Leu Gln Glu Ala Leu Ser
            500                 505                 510

Ala Lys Gly Pro Val Leu Ile Glu Val Ser Thr Val Ser Pro Val Lys
        515                 520                 525

<210> SEQ ID NO 77
<211> LENGTH: 547
<212> TYPE: PRT
<213> ORGANISM: Lactococcus lactis

<400> SEQUENCE: 77

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335
```

```
Gly Gln Tyr Ile Asp Lys Gln Tyr Glu Glu Phe Ile Pro Ser Ser Ala
                340                 345                 350

Pro Leu Ser Gln Asp Arg Leu Trp Gln Ala Val Glu Ser Leu Thr Gln
            355                 360                 365

Ser Asn Glu Thr Ile Val Ala Glu Gln Gly Thr Ser Phe Phe Gly Ala
        370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Val Asn Arg Met Tyr Trp Ile Glu Leu Val Leu Glu Lys
        515                 520                 525

Glu Asp Ala Pro Lys Leu Leu Lys Lys Met Gly Lys Leu Phe Ala Glu
    530                 535                 540

Gln Asn Lys
545

<210> SEQ ID NO 78
<211> LENGTH: 1587
<212> TYPE: DNA
<213> ORGANISM: Pseudomonas putida

<400> SEQUENCE: 78
atggcttcgg tacacggcac acatacgaa ctcttgcgac gtcaaggcat cgatacggtc      60
ttcggcaatc ctggctcgaa cgagctcccg tttttgaagg actttccaga ggactttcga     120
tacatcctgg ctttgcagga agcgtgtgtg gtgggcattg cagacggcta tgcgcaagcc     180
agtcggaagc cggctttcat taacctgcat tctgctgctg gtaccggcaa tgctatgggt     240
gcactcagta acgcctggaa ctcacattcc ccgctgatcg tcactgccgg ccagcagacc     300
agggcgatga ttggcgttga agctctgctg accaacgtcg atgccgccaa cctgccacga     360
ccacttgtca aatggagcta cgagcccgca agcgcagcag aagtccctca tgcgatgagc     420
agggctatcc atatgcaag catggcgcca caaggccctg tctatctttc ggtgccatat     480
gacgattggg ataaggatgc tgatcctcag tccaccacc ttttgatcg ccatgtcagt      540
tcatcagtac gcctgaacga ccaggatctc gatattctgg tgaaagctct caacagcgca     600
tccaacccgg cgatcgtcct gggcccggac gtcgacgcag caaatgcgaa cgcagactgc     660
gtcatgttgg ccgaacgcct caaagctccg gtttggttg cgccatccgc tccacgctgc     720
ccattcccta cccgtcatcc ttgcttccgt ggattgatgc cagctggcat cgcagcgatt     780
tctcagctgc tcgaaggtca cgatgtggtt ttggtaatcg gcgctccagt gttccgttac    840
```

| | |
|---|---|
| caccaatacg acccaggtca atatctcaaa cctggcacgc gattgatttc ggtgacctgc | 900 |
| gacccgctcg aagctgcacg cgcgccaatg ggcgatgcga tcgtggcaga cattggtgcg | 960 |
| atggctagcg ctcttgccaa cttggttgaa gagagcagcc gccagctccc aactgcagct | 1020 |
| ccggaacccg cgaaggttga ccaagacgct ggccgacttc acccagagac agtgttcgac | 1080 |
| acactgaacg acatggcccc ggagaatgcg atttacctga acgagtcgac ttcaacgacc | 1140 |
| gcccaaatgt ggcagcgcct gaacatgcgc aaccctggta gctactactt ctgtgcagct | 1200 |
| ggcggactgg gcttcgccct gcctgcagca attggcgttc aactcgcaga acccgagcga | 1260 |
| caagtcatcg ccgtcattgg cgacggatcg gcgaactaca gcattagtgc gttgtggact | 1320 |
| gcagctcagt acaacatccc cactatcttc gtgatcatga acaacggcac ctacggtgcg | 1380 |
| ttgcgatggt ttgccggcgt tctcgaagca gaaaacgttc ctgggctgga tgtgccaggg | 1440 |
| atcgacttcc gcgcactcgc caagggctat ggtgtccaag cgctgaaagc cgacaacctt | 1500 |
| gagcagctca agggttcgct acaagaagcg cttctctgcca aaggcccggt acttatcgaa | 1560 |
| gtaagcaccg taagcccggt gaagtga | 1587 |

<210> SEQ ID NO 79
<211> LENGTH: 1644
<212> TYPE: DNA
<213> ORGANISM: Lactococcus lactis

<400> SEQUENCE: 79

| | |
|---|---|
| atgtatacag taggagatta cctgttagac cgattacacg agttgggaat tgaagaaatt | 60 |
| tttggagttc ctggtgacta taacttacaa tttttagatc aaattatttc acgcgaagat | 120 |
| atgaaatgga ttggaaatgc taatgaatta aatgcttctt atatggctga tggttatgct | 180 |
| cgtactaaaa aagctgccgc atttctcacc acatttggag tcggcgaatt gagtgcgatc | 240 |
| aatggactgg caggaagtta tgccgaaaat ttaccagtag tagaaattgt tggttcacca | 300 |
| acttcaaaag tacaaaatga cggaaaattt gtccatcata cactagcaga tggtgatttt | 360 |
| aaacacttta tgaagatgca tgaacctgtt acagcagcgc ggactttact gacagcagaa | 420 |
| aatgccacat atgaaattga ccgagtactt tctcaattac taaagaaaag aaaaccagtc | 480 |
| tatattaact taccagtcga tgttgctgca gcaaaagcag agaagcctgc attatcttta | 540 |
| gaaaaagaaa gctctacaac aaatacaact gaacaagtga ttttgagtaa gattgaagaa | 600 |
| agtttgaaaa atgcccaaaa accagtagtg attgcaggac acgaagtaat tagttttggt | 660 |
| ttagaaaaaa cggtaactca gtttgtttca gaaacaaaac taccgattac gacactaaat | 720 |
| tttggtaaaa gtgctgttga tgaatctttg ccctcatttt taggaatata taacgggaaa | 780 |
| ctttcagaaa tcagtcttaa aaattttgtg gagtccgcag actttatcct aatgcttgga | 840 |
| gtgaagctta cggactcctc aacaggtgca ttcacacatc atttagatga aaataaaatg | 900 |
| atttcactaa acatagatga aggaataatt ttcaataaag tggtagaaga ttttgatttt | 960 |
| agagcagtgg tttcttcttt atcagaatta aaaggaatag aatatgaagg acaatatatt | 1020 |
| gataagcaat atgaagaatt tattccatca agtgctccct tatcacaaga ccgtctatgg | 1080 |
| caggcagttg aaagtttgac tcaaagcaat gaaacaatcg ttgctgaaca aggaacctca | 1140 |
| tttttttggag cttcaacaat tttcttaaaa tcaaatagtc gttttattgg acaacctta | 1200 |
| tggggttcta ttggatatac ttttccagcg gctttaggaa gccaaattgc ggataaagag | 1260 |
| agcagacacc tttatttat tggtgatggt tcacttcaac ttaccgtaca agaattagga | 1320 |
| ctatcaatca gagaaaaact caatccaatt tgttttatca taaataatga tggttataca | 1380 |

```
gttgaaagag aaatccacgg acctactcaa agttataacg acattccaat gtggaattac    1440
tcgaaattac cagaaacatt tggagcaaca gaagatcgtg tagtatcaaa aattgttaga    1500
acagagaatg aatttgtgtc tgtcatgaaa gaagcccaag cagatgtcaa tagaatgtat    1560
tggatagaac tagttttgga aaagaagat gcgccaaaat tactgaaaaa aatgggtaaa     1620
ttatttgctg agcaaaataa atag                                          1644

<210> SEQ ID NO 80
<211> LENGTH: 842
<212> TYPE: DNA
<213> ORGANISM: Paraburkholderia xenovorans

<400> SEQUENCE: 80
atgaagctag aaggcaaaaa agtcaccgtc cacgacatga cgctgcgcga cggcatgcac      60
cccaagcgcc accagatgac gctggagcaa atgaaatcca tcgcctgcgg cctggatgcc    120
gcgggcatcc cgctgatcga agtcaccac ggcgacggcc tgggcggctc ctccgtcaac     180
tacggctttc cggcgcacag cgacgaggaa tacctgggcg ccgtgattcc gttgatgaag    240
caggccaagg tcagtgccct gctcttgccc ggcatcggca ccgtcgaaca cctgaagatg    300
gccaaggacc tgggcgtgaa caccatccgc gtggccaccc actgcaccga agccgatgtg    360
tcggagcagc acatcaccca atcgcgcaag ctgggtctgg acaccgtggg ctttttgatg    420
atggcgcaca tggccagccc agaaaagctg gtcagccagg cactcttgat gcaaggctac    480
ggcgccaact gcatctacgt caccgactcg gccggctaca tgctgcctga cgacgtgaaa    540
gcgcgcctga gtgccgtgcg tgccgcgctc aaacccgaaa ccgagttggg cttttcacggc   600 catcacaacc tggccatggg cgtcgccaac tcgatcgccg cgatcgaggc cggggccacc    660
cgcatcgatg ccgctgccgc tggcctgggt gccggcgccg gcaacacgcc gatggaggtg    720
ttcatcgccg tatgcgcgcg catggggatc gaaaccggag tcgatgtgtt caagatccag    780
gacgtggccg aagacctggt ggtgccgatc atggaccatg tcatccgcat cgaccgcgac    840
tc                                                                   842

<210> SEQ ID NO 81
<211> LENGTH: 789
<212> TYPE: DNA
<213> ORGANISM: Escherichia coli

<400> SEQUENCE: 81
atggaaaaca gttttaaagc ggcgctgaaa gcaggccgcc gcagatcgg attatggctg       60 gggctgagta gcagttacag cgcagagtta ctggccggag caggattcga ctggttgttg    120
atcgacggta acacgcgcc gaataacgtg caaaccgtgc tcacccagct acaggcgatt     180
gcgccctacc ccagtcagcc agtggtacgc ccatcgtgga cgatccggt gcaaatcaaa    240 caactgctgg acgtcggcac acaaaccttg ctggtgccga tggtacaaaa cgctgacgaa    300
gcccgtgaag cggtacgcgc caccccgttat ccccccgccg gtattcgcgg tgtgggcagt    360
gcgctggccc gcgcctcgcg ctggaatcgt attcctgatt acctgcaaaa agccaacgat    420
caaatgtgcg tgctggtgca gatcgaaacg cgtgaggcaa tgaagaactt accgcagatt    480
ctggacgtgg aaggcgtcga cggcgtgttt atcggcccgg cggatctgag cgccgatatg    540
ggttatgccg gtaatccgca gcacccggaa gtacaggccg ccattgagca ggcgatcgtg    600
cagatccgtg aatcgggcaa agcgccgggg atcctgatcg ccaatgagca actggcaaaa    660
```

```
cgctatctgg aactgggcgc gctgtttgtc gccgtcggcg ttgacaccac cctgctcgcc    720
cgcgccgctg aagcgctggc agcacggttt ggtgcgcagg ccaccgccgt gaagcccggc    780
gtgtattaa                                                            789
```

<210> SEQ ID NO 82
<211> LENGTH: 606
<212> TYPE: DNA
<213> ORGANISM: Escherichia coli

<400> SEQUENCE: 82

```
atggcagaga aatttatcaa acacacaggc ctggtggttc cgctggatgc cgccaatgtc     60
gataccgatg caatcatccc gaaacagttt ttgcagaaag tgacccgtac gggttttggc    120
gcgcatctgt ttaacgactg gcgttttctg gatgaaaaag ccaacagcc aaaccccggac    180 ttcgtgctga acttcccgca gtatcaggcc gcttccattt tgctggcacg agaaaacttc    240
ggctgtggct cttcgcgtga gcacgcgccc tgggcattga ccgactacgg ttttaaagtg    300
gtgattgcgc cgagttttgc tgacatcttc tacggcaata gctttaacaa ccagctgctg    360
ccggtgaaat taagcgatgc agaagtggac gaactgtttg cgctggtgaa agctaatccg    420
gggatccatt tcgacgtgga tctggaagcg caagaggtga aagcgggaga gaaaacctat    480
cgctttacca tcgatgcctt ccgccgccac tgcatgatga acggtctgga cagtattggg    540
cttaccttgc agcacgacga cgccattgcc gcttatgaag caaaacaacc tgcgtttatg    600
aattaa                                                               606
```

<210> SEQ ID NO 83
<211> LENGTH: 262
<212> TYPE: PRT
<213> ORGANISM: Escherichia coli

<400> SEQUENCE: 83

```
Met Glu Asn Ser Phe Lys Ala Ala Leu Lys Ala Gly Arg Pro Gln Ile
1               5                   10                  15

Gly Leu Trp Leu Gly Leu Ser Ser Tyr Ser Ala Glu Leu Leu Ala
            20                  25                  30

Gly Ala Gly Phe Asp Trp Leu Leu Ile Asp Gly Glu His Ala Pro Asn
        35                  40                  45

Asn Val Gln Thr Val Leu Thr Gln Leu Gln Ala Ile Ala Pro Tyr Pro
    50                  55                  60

Ser Gln Pro Val Val Arg Pro Ser Trp Asn Asp Pro Val Gln Ile Lys
65                  70                  75                  80

Gln Leu Leu Asp Val Gly Thr Gln Thr Leu Leu Val Pro Met Val Gln
                85                  90                  95

Asn Ala Asp Glu Ala Arg Glu Ala Val Arg Ala Thr Arg Tyr Pro Pro
            100                 105                 110

Ala Gly Ile Arg Gly Val Gly Ser Ala Leu Ala Arg Ala Ser Arg Trp
        115                 120                 125

Asn Arg Ile Pro Asp Tyr Leu Gln Lys Ala Asn Asp Gln Met Cys Val
    130                 135                 140

Leu Val Gln Ile Glu Thr Arg Glu Ala Met Lys Asn Leu Pro Gln Ile
145                 150                 155                 160

Leu Asp Val Glu Gly Val Asp Gly Val Phe Ile Gly Pro Ala Asp Leu
                165                 170                 175

Ser Ala Asp Met Gly Tyr Ala Gly Asn Pro Gln His Pro Glu Val Gln
            180                 185                 190
```

Ala Ala Ile Glu Gln Ala Ile Val Gln Ile Arg Glu Ser Gly Lys Ala
        195                 200                 205

Pro Gly Ile Leu Ile Ala Asn Glu Gln Leu Ala Lys Arg Tyr Leu Glu
        210                 215                 220

Leu Gly Ala Leu Phe Val Ala Val Gly Val Asp Thr Thr Leu Leu Ala
225                 230                 235                 240

Arg Ala Ala Glu Ala Leu Ala Ala Arg Phe Gly Ala Gln Ala Thr Ala
                245                 250                 255

Val Lys Pro Gly Val Tyr
            260

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggtcaactaa tccttaactg atcg                                            24

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
aagcaaatca tcaccgcact gac                                             23

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caggcttagc gcaacaaacg                                                 20

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggttgcgcct acactaagc                                                  19

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

```
tccacttaag aaggtaggtg ttac                                              24

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aaagttgccg ctttacgggg aaa                                               23
```